US008585753B2

(12) United States Patent
Scanlon et al.

(10) Patent No.: US 8,585,753 B2
(45) Date of Patent: Nov. 19, 2013

(54) FIBRILLATED BIODEGRADABLE PROSTHESIS

(76) Inventors: John James Scanlon, Wilmington, DE (US); Catherine Ann Scanlon, Wilmington, DE (US)

( * ) Notice: Subject to any disclaimer, the term of this patent is extended or adjusted under 35 U.S.C. 154(b) by 924 days.

(21) Appl. No.: 11/713,361

(22) Filed: Mar. 3, 2007

(65) Prior Publication Data

US 2007/0207186 A1      Sep. 6, 2007

Related U.S. Application Data

(60) Provisional application No. 60/779,128, filed on Mar. 4, 2006.

(51) Int. Cl.
    *A61F 2/06*      (2013.01)
(52) U.S. Cl.
    USPC ............................................. 623/1.42
(58) Field of Classification Search
    USPC ............. 623/1.13, 1.35, 1.39, 1.4, 1.42–1.46, 623/1.54, 1.15, 1.28; 606/1.35, 1.39, 1.4, 606/1.42–1.46
    See application file for complete search history.

(56) References Cited

U.S. PATENT DOCUMENTS

| | | |
|---|---|---|
| 3,953,566 A | 4/1976 | Gore |
| 3,962,153 A | 6/1976 | Gore |
| 4,096,227 A | 6/1978 | Gore |
| 4,110,392 A | 8/1978 | Yamazaki |
| 4,187,390 A | 2/1980 | Gore |
| 4,596,837 A | 6/1986 | Yamamoto |
| 4,739,762 A | 4/1988 | Palmaz |
| 4,985,296 A | 1/1991 | Mortimer |
| 5,449,373 A | 9/1995 | Pinchasik |
| 5,476,589 A | 12/1995 | Bacino |
| 5,716,660 A * | 2/1998 | Weadock et al. ............ 427/2.25 |
| 5,718,973 A * | 2/1998 | Lewis et al. .................. 623/1.32 |
| 5,753,358 A | 5/1998 | Korleski |
| 5,827,327 A | 10/1998 | McHaney |
| 6,025,044 A | 2/2000 | Campbell |
| 6,048,484 A | 4/2000 | House |
| 6,517,570 B1 | 2/2003 | Lau |

(Continued)

OTHER PUBLICATIONS

Linda Johnson, "Johnson & Johnson to cut 4820 jobs," Associated Press, Aug. 1, 2007, USA.

(Continued)

*Primary Examiner* — Ryan Severson
*Assistant Examiner* — Tin Nguyen

(57) ABSTRACT

The present invention is a more durable expanded material that enables thinner wall thicknesses and a more flexible reinforcement suitable for stenting. The present invention is especially useful in the construction of grafts, stents, and stent-grafts which are used, for example, in repairing or replacing blood vessels that are narrowed or occluded by disease, aneurismal blood vessels, or other medical treatments. The inventive material and configurations allow expansion or contraction in size or adjustment in size in an incremental manner so that the optimum size, shape, and fit with other objects can be obtained. The present invention is also optionally capable of more accurately delivering one or more active ingredients such as drugs over longer periods of time. The present invention optionally includes surface modifications and additives that increase the surface adhesion of active ingredients, coatings, or combinations thereof. Finally, the present invention optionally includes growing cells on the inventive material so that the expanded material, reinforcement, or combinations thereof are useful, for example, in producing lab-grown blood vessels or organs.

31 Claims, 11 Drawing Sheets

(56) References Cited

U.S. PATENT DOCUMENTS

| | | | |
|---|---|---|---|
| 6,517,571 B1* | 2/2003 | Brauker et al. | 623/1.13 |
| 6,551,350 B1 | 4/2003 | Thornton | |
| 6,558,414 B2 | 5/2003 | Layne | |
| 6,673,102 B1 | 1/2004 | Vonesh | |
| 6,852,122 B2 | 2/2005 | Rush | |
| 2002/0042645 A1* | 4/2002 | Shannon | 623/1.13 |
| 2002/0198588 A1* | 12/2002 | Armstrong et al. | 623/1.13 |
| 2003/0074049 A1* | 4/2003 | Hoganson et al. | 623/1.13 |
| 2003/0198769 A1* | 10/2003 | Jing et al. | 428/36.91 |
| 2004/0024442 A1* | 2/2004 | Sowinski et al. | 623/1.13 |
| 2004/0044397 A1* | 3/2004 | Stinson | 623/1.15 |
| 2004/0049264 A1* | 3/2004 | Sowinski et al. | 623/1.28 |
| 2004/0219185 A1* | 11/2004 | Ringeisen | 424/423 |
| 2005/0025799 A1* | 2/2005 | Hossainy et al. | 424/423 |
| 2005/0033417 A1* | 2/2005 | Borges et al. | 623/1.46 |
| 2006/0200233 A1* | 9/2006 | Kujawski | 623/1.49 |

OTHER PUBLICATIONS

Associated Press, "FDA to probe safety of popular heart stents," Dec. 4, 2006, USA.

Angioplasty.org, "Problems resurface about drug eluting stents," Sep. 9, 2006, USA.

American Heart Association, "Patients who receive drug-eluting stents should continue anti-platelet medications," Jan. 16, 2007, USA.

Lawrence K. Altman, M.D., "Doctors look for source of Stent Complications," The New York Times, Nov. 18, 2003, USA.

Amy Barrett and John Carey, "In a Bind Over Stents," Business Week, Aug. 8, 2005, USA.

Fluon, The process of PTFE coagulated dispersion powders, Technical Service Note F3/4/5, AGC Chemicals Americas, Inc., Sep. 2002.

Technical Information Sheet, Coagulated Dispersion Grade CD123 & CD127, AGC Chemicals Americas, Inc., Feb. 2007.

* cited by examiner

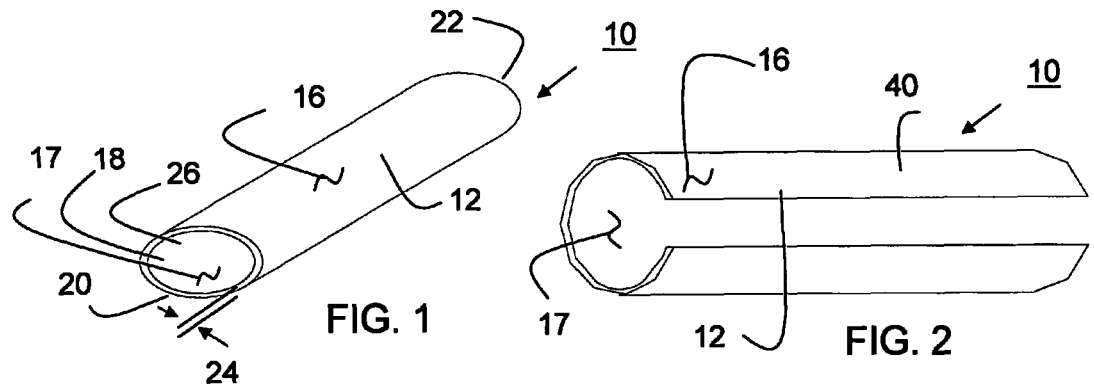
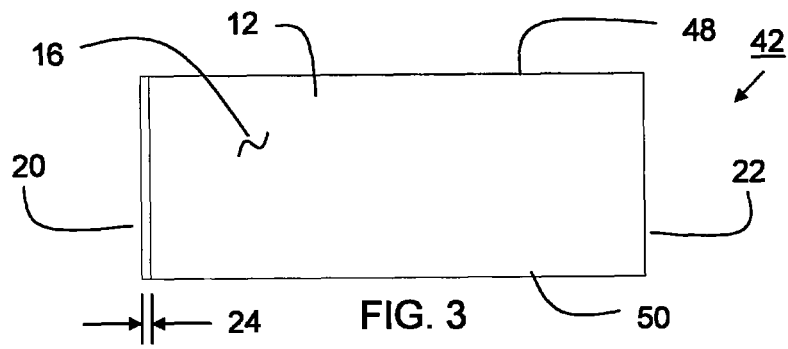
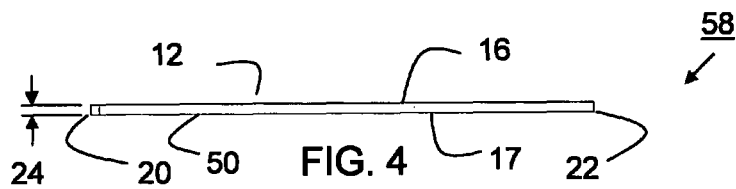
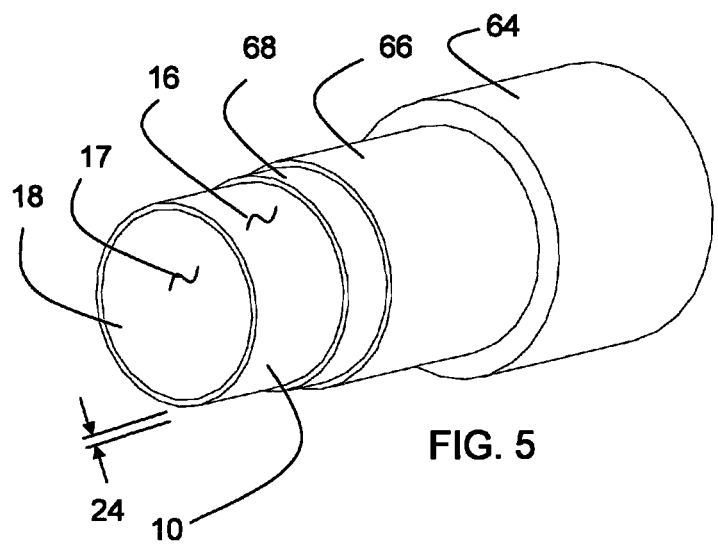

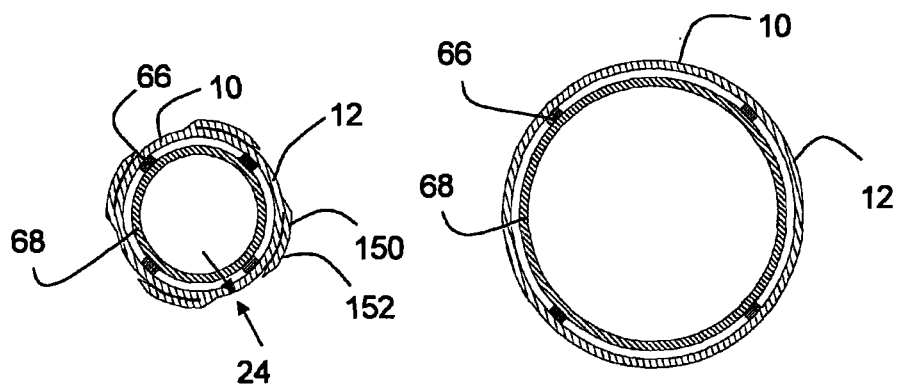
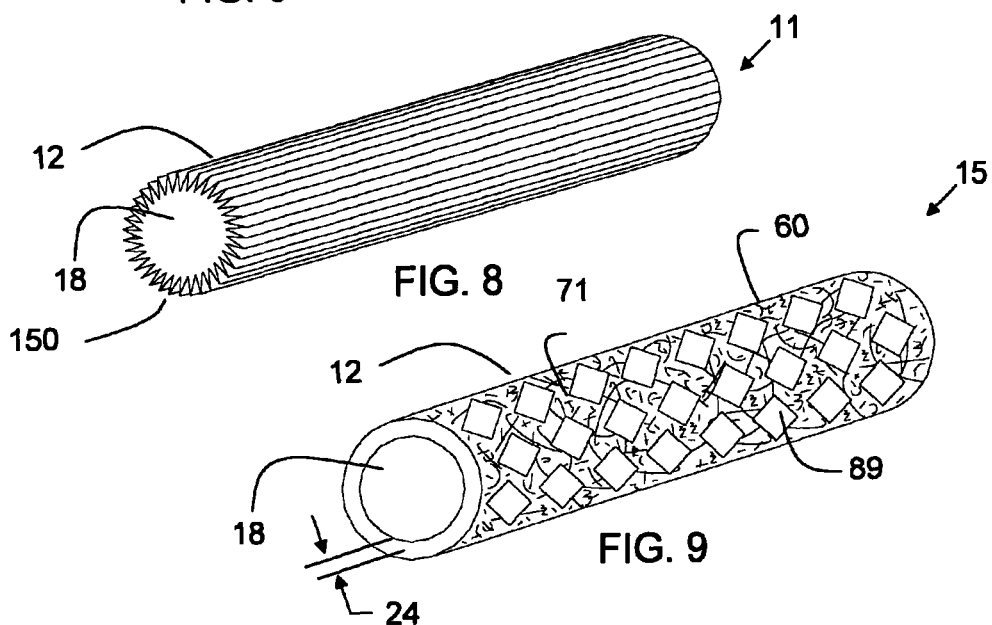
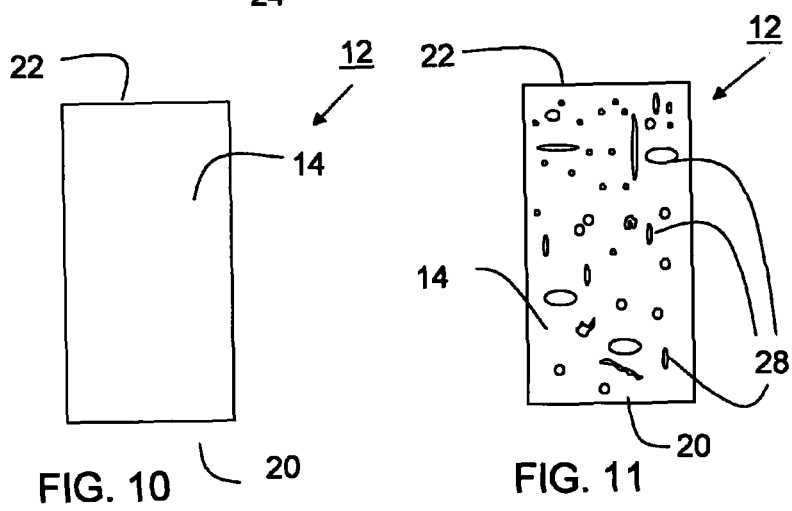

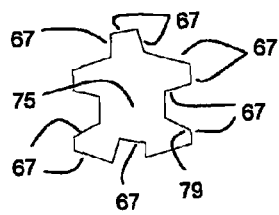
FIG. 38
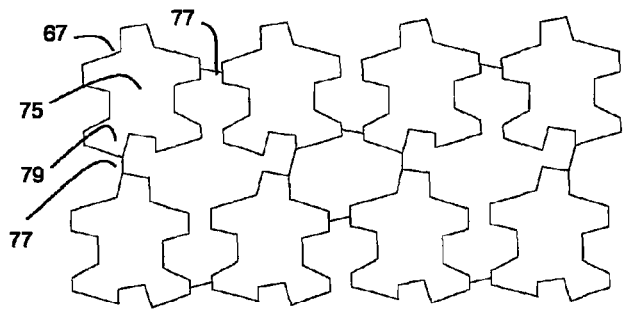
FIG. 48
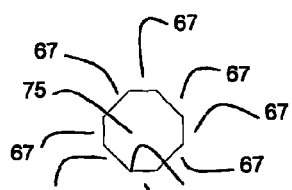
FIG. 39
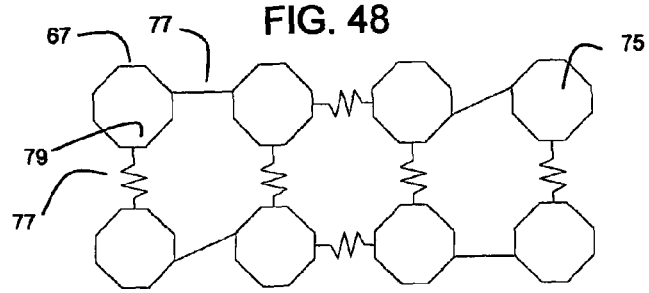
FIG. 49
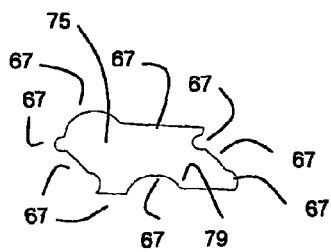
FIG. 40
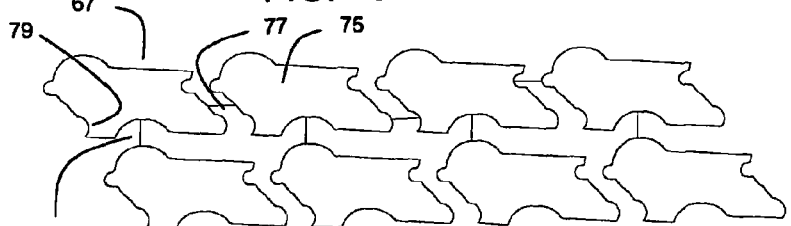
FIG. 50
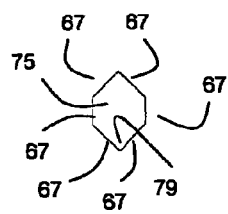
FIG. 41
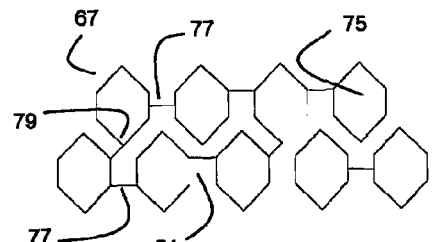
FIG. 51
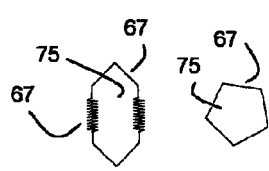
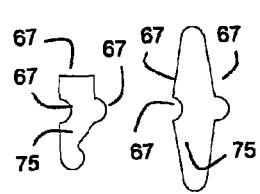
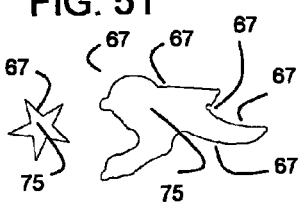
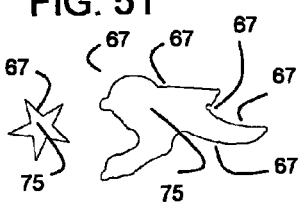
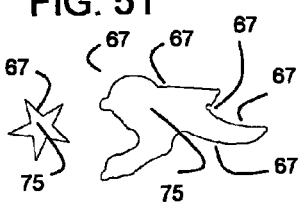
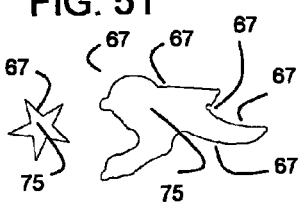
FIG. 42   FIG. 43   FIG. 44   FIG. 45   FIG. 46   FIG. 47

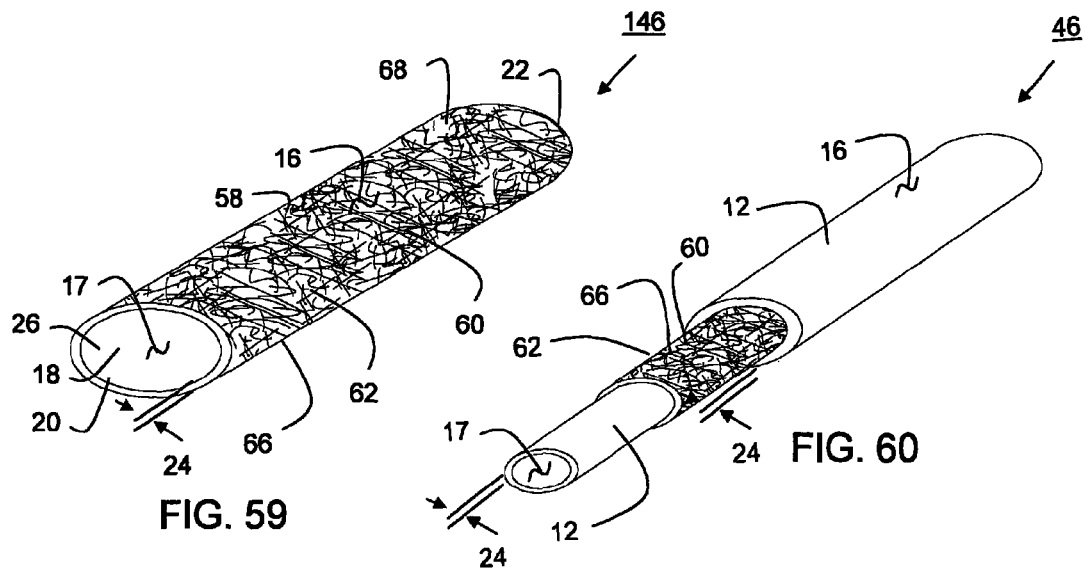
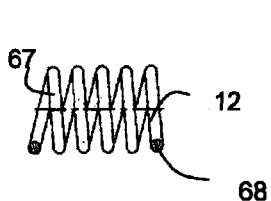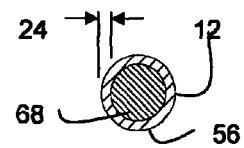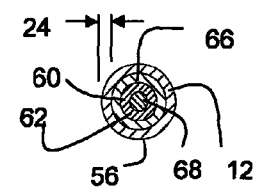
FIG. 61  FIG. 62  FIG. 63
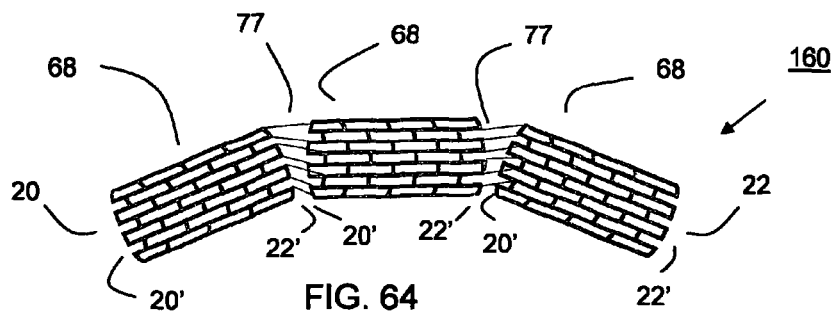
FIG. 64
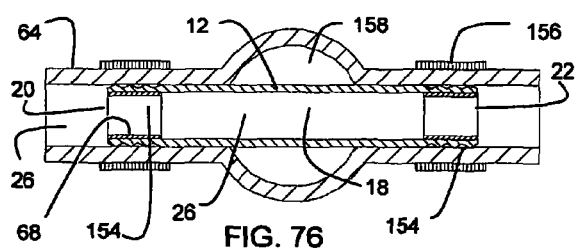
FIG. 76

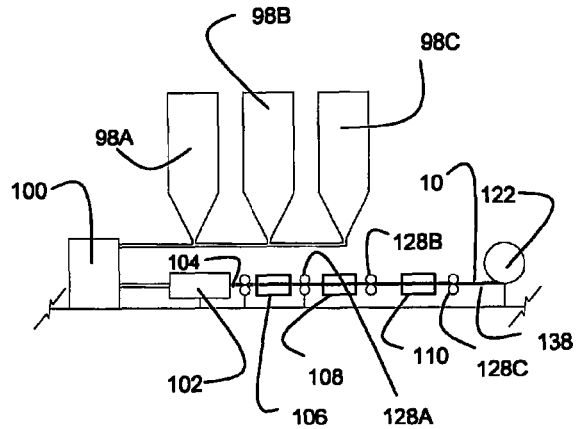
FIG. 77
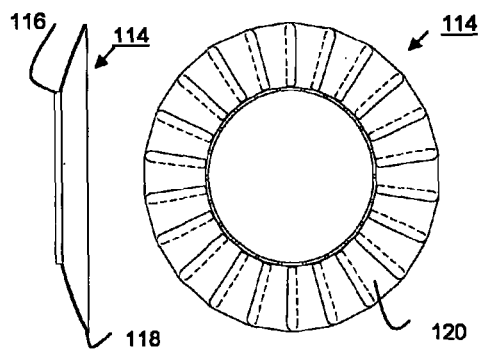
FIG. 79  FIG. 80
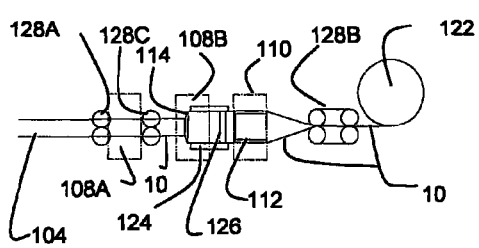
FIG. 78
FIG. 81
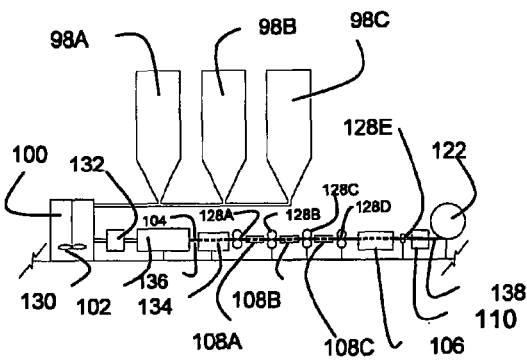
FIG. 82
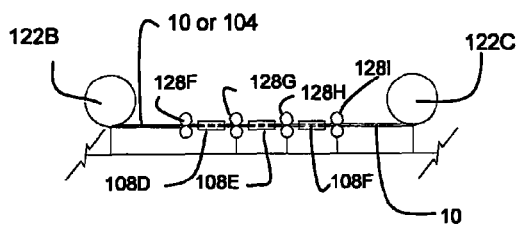
FIG. 83

FIBRILLATED BIODEGRADABLE PROSTHESIS

RELATED APPLICATION

This application claims benefit of Provisional Patent Application Ser. No. 60/779,128 filed 04 Mar. 2006.

FIELD OF INVENTION

The present invention relates to improved materials and configurations for use in the manufacturing of medical devices such as expandable intraluminal stents, grafts, stent-grafts, surgical fabrics, suppositories, transdermal patches, or oral medications that optionally deliver active ingredients within a living body.

BACKGROUND OF INVENTION

The prior art describes a variety of grafts that are used for the replacement of diseased passageways in a living body. In addition, the prior art teaches several metallic reinforcements used for stenting to hold open constricted passageways in a living body. Moreover, there exists in the prior art stent-grafts which are generally a combination of these two separate components which are commonly used to repair aneurismal vessels.

The prior art includes grafts manufactured of materials such a textiles, polytetrafluoroethylene, expanded polytetrafluoroethylene, platinum, and gold. Due to the limitations of the materials employed, these prior art grafts have relatively large wall thicknesses that limit the bore size in cylindrical embodiments which results in a restriction or a pressure drop as contents such as blood flow through the graft. The heavy wall thickness also increases the possibility of the living body rejecting the foreign graft. Furthermore, the prior art expanded polytetrafluoroethylene materials have inferior physical properties such as strength and abrasion resistance which are important properties for safe installation and providing long service life. In particular, the prior art grafts offer significant room for improvement in suture retention and tear resistance. These prior art grafts also require the use of a separate component to hold open the bore of cylindrical shaped grafts. Exemplary patents of grafts include: U.S. Pat. No. 6,025,044 to Campbell (2000); U.S. Pat. No. 6,038,484 to House (2000); and U.S. Pat. No. 6,517,571 to Brauker (2003). Exemplary patents for producing expanded polytetrafluoroethylene include: U.S. Pat. No. 3,953,566 to Gore (1976); U.S. Pat. No. 3,962,153 to Gore (1976); U.S. Pat. No. 4,096,227 to Gore (1978); and U.S. Pat. No. 4,197,390 to Gore (1980).

The prior art reinforcements used for stenting are typically manufactured completely of materials such as stainless steel, tantalum, and nickel-titanium alloys. These stents are usually transported to the location of installation in a reduced size where they are subsequently dilated to come into contact with the interior surface of the passageway in which they are being installed. Despite attempts to make stents more flexible through the use of a large variety of configurations, the reinforcements used for stenting made of these prior art materials are sometimes difficult to install in small or curved passageways. In addition, due to size limitations a surgeon normally needs over two stents on average to complete a stenting procedure. Furthermore, the reinforcements used for stenting are generally of the uniform thickness from first end to second end which creates a stress concentration at the notch between the passageway in which it is installed and the end of the stent. This stress concentration can result in failure of fragile passageways such as human arteries or veins. Exemplary patents of metallic reinforcements used for stenting include: U.S. Pat. No. 4,739,762 to Palmaz (1988); U.S. Pat. No. 5,102,417 to Palmaz (1992); U.S. Pat. No. 5,449,373 to Pinchasik (1995); U.S. Pat. No. 5,972,018 to Israel (1999); and U.S. Pat. No. 6,884,260 to Kugler (2005).

In the prior art there are also grafts and stents which include bioactive materials. Coated medical devices have experienced problems with the coating flaking off or causing the recipient to have an allergic reaction when in-vivo. Pathologists have also found that drug eluting metallic stents have problems with delayed healing so that the endothelial layer of cells that would normally cover the members of the stent was non-existent or uneven thereby resulting in thrombosis which resulted in patient death. It was unexpected that the present invention provides potential for a more consistent and even growth of the endothelial layer of cells by providing a more accurate and controlled release of active ingredients over time.

The prior art drug eluting stents also require a longer term antiplatelet therapy than bare metal stents. Since the surfaces of the bare metal stents are thrombogenic, the drug eluting stents are designed to inhibit or slow cell growth in an attempt to eliminate restenosis. The active ingredients included in the drug eluting stents, however, require that the patients be given an antiplatelet therapy for a longer period of time while the artery heals and a thin layer of endothelial cells grows over the members of the stent to reduce the risk of thrombus. Due to this phenomenon the Federal Drug Administration (FDA) recommends that the period of therapy be increased from 6 weeks for bare metal stents to 3-6 months for use with drug eluting stents and in some cases doctors prescribe some medications for longer periods of time such as for life. This therapy adds substantial daily expense for the patient and in many cases the patients are allergic to the medications and they cause the patients to have unwanted side effects like illness and a higher risk of uncontrolled bleeding during future surgical procedures.

There is also a significant problem of attaching active ingredients to the prior art medical devices like grafts and stent-grafts that have polymeric surfaces. It was surprising how significant of an improvement of adhesion of active ingredients and coatings could be achieved to the medical devices comprised of polymers in the present invention by including additives in the polymers. This improvement was especially noticeable when the additives partially or fully protruded from the surface of the polymer because the additives appear to mechanically lock the active ingredients, coating, or combinations thereof to the polymeric surface.

The prior art drug delivery mechanisms also can also provide the patient with imprecise drug dosage and modified release characteristics especially when employed over long periods of time. For drug eluting stents the imprecision of the dosage is related to the difficulty of evenly dispersing active ingredients in coatings, obtaining a uniform dry coating film on partially vertical surfaces like those found on stents, and inconsistent delivery related to poor adhesion of coating to the stent's surface. Furthermore, for a graft the imprecision is primarily related to the heterogeneous structure of the prior art materials like found in expanded polytetrafluoroethylene and the poor adhesion to polymeric surfaces. The highly uniform structure of the expanded material of the present invention and the improved adhesion enables a significant improvement in the precision of active ingredient delivery over time. Moreover, the active ingredients showed potential to significantly improve patency by positioning the active ingredients between layers of expanded material instead of on the surface or in coatings on surface.

Due to the high shear stress that develops during bending of a stent-graft while sliding it through the torturous path of the human anatomy, there is a significant risk in the prior art stent-grafts that the graft will tear at the connection points between the stent and graft. This risk is increased as the wall thickness of the graft is reduced. It is highly beneficial to patient safety to increase the graft wall strength and to minimize the wall thickness of the graft to minimize pressure drop through the graft and to enable the use of grafts in smaller sizes. If the graft separates from the stent there is risk the graft will collapse causing a restriction in flow or worse yet a life threatening leak. In the prior art there are attempts to reduce tearing by modifying the mechanical design of the connections but this often results in a larger than necessary wall thickness that causes unnecessary restrictions in flow or lack of flexibility of the stent-graft. In the present invention, there are tear arresting additives which enable thinner wall thicknesses without tearing regardless of mechanical design.

The large wall thicknesses of the prior art grafts comprised of expanded polytetrafluoroethylene employ paste extrusion techniques using relatively large particle size raw materials. The fine powder polytetrafluoroethylene [PTFE] of the prior art such as Asahi Glass Co. Fluon® CD-123 has an average particle size of about 475 microns, Asahi Glass Co. Fluon® CD-1 has an average particle size of about 550 microns, Dupont 601A has an average particle size of about 570 microns, and Dupont 610A has an average particle size of about 470 microns. It was surprising to discover in the present invention that potential exists for thinner wall thicknesses by using smaller particle size polytetrafluoroethylene raw materials. Moreover, these wall thicknesses could be substantially more durable and have increased adhesion characteristics by including additives and nano size articles.

The present invention addresses the aforementioned limitations of the prior art by providing: a novel material that is suitable for use in a prosthesis deployed in a living body that is incrementally expandable from a first size to a second size through deformation or self-expansion; a prosthesis that is substantially more flexible and capable of conforming to the natural curvatures of passageways in a living body when installed using, for example, noninvasive surgery techniques such as those employing a catheter or a balloon catheter; a prosthesis that can have a variable wall thickness to reduce creating a stress concentration between the prosthesis and the passageway in which it is installed, a prosthesis that has minimal drag against the interior wall of a passageway in a body when inserted through the passageway; a prosthesis material and manufacturing process that enables the production of very small sizes and a large variety of sizes so that surgeons can, for example, repair very small blood vessels and use less prostheses per procedure; a prosthesis having a relatively thin wall thickness that substantially increases the size of the bore in tubular embodiments increasing flow and reducing pressure drop; a prosthesis that is self-expanding from a first size to a second size that undergoes relaxation to manage the outward radial pressure applied to a supporting passageway such as blood carrying artery, a prosthesis that more accurately delivers the dosage of active ingredients like drugs with or without a coating especially over long periods of time; a prosthesis that includes surface treatments, additives, or combinations thereof that substantially minimizes the risk of coatings or active ingredients from flaking-off the surface of the prosthesis and can sometimes assist in maintaining the original position of the prosthesis after deployment, and a prosthesis that can include biological cells grown in vivo or vitro that can be implanted into a body as, for example, a blood carrying vessel or organ to replace unrepairable portions of the anatomy.

SUMMARY OF THE INVENTION

Accordingly, it is an object of the present invention to provide an improved material, reinforcement, or combination thereof for use in medical applications.

One more object of the present invention is to provide an improved material, reinforcement, or combination thereof that has improved performance in stents, grafts, stent-grafts, bifurcated stents, bifurcated grafts, bifurcated stent-grafts, sutures, hernia patches, oral grafts, drug delivery devices, surgical fabrics, cosmetic surgery materials, oncology treatments, dental floss, implants, filters, joint replacement or repair, shunts, wound care, oral tablets, oral capsules, suppositories, or transdermal patches.

It is another object of the present invention to provide an expanded material for medical applications that includes strengthening and abrasion resisting additives so that a thinner wall thicknesses is possible; the adhesion of coatings, active ingredients, and combinations thereof to polymeric surfaces is improved; the potential of tearing of the graft wall at its connection points to the stent is substantially reduced, and the suture retention strength is increased.

Yet another object of the present invention is to provide a drug delivery system that is capable of substantially more precisely delivering active ingredients over relatively long periods of time.

An additional object of the present invention is to provide an active ingredient delivery system that improves the healing process and substantially more consistently enables the endothelial layer of cells to line a stent, graft, or stent-graft and to minimize the length of time of antiplatelet therapy after installation.

One more object of the present invention is to provide an improved material in configurations selected from the group of tubular, sheet, fiber, woven, nonwoven, or combinations thereof.

A further object of the present invention is to provide a reinforcement material suitable for stenting that has improved flexibility; a less complex manufacturing process; a wall thickness of varying thickness to reduce stress concentrations at the juncture between the stent and the passageway in which it is installed; and an ability to be easily produced in a large variety of sizes so that less stents are required by procedure.

It is one more object of the present invention to provide a scaffold for growing living cells so that lab grown blood vessels and organs can be manufactured if a synthetic prosthesis is not a viable replacement for damaged or diseased vessels or organs.

A still further object of the present invention is to provide a material and reinforcement that are suitable for use individually or in combination that are substantially more effective in medical applications.

BRIEF DESCRIPTION OF THE DRAWING FIGURES

The advantages of the present invention will become more apparent upon consideration of the following detailed disclosure of the invention, particularly when taken in conjunction with the accompanying figures wherein:

FIG. 1 illustrates an expanded material in the form of an expanded tubular profile.

FIGS. 2 and 3 illustrate the expanded tubular profile of FIG. 1 wherein the tubular profile is slit longitudinally and converted to a sheet of expanded material.

FIG. 4 illustrates an expanded material in the form of one of many possible embodiments of an expanded fiber.

FIG. 5 illustrates an exploded assembly drawing of one embodiment of the expanded material (in the form of the expanded tubular profile), reinforcement, connecting material, and supporting member.

FIGS. 6 and 7 illustrate an expanded material (in the form of an expanded tubular profile) including folds with reinforcement, connecting material, and supporting member in cross sectional end view.

FIG. 8 illustrates an embodiment of expanded material that is in the form of an expanded tubular profile that includes pleats to reduce its size.

FIG. 9 illustrates an expanded material in the form of an expanded tubular profile that includes deformable elements which maintain size and shape, additives which increase strength, and thru holes which serve as open cells.

FIG. 10 shows a top view of the expanded material according to the present invention under magnification having solid wall thickness.

FIG. 11 is an illustration in top view of expanded material according to the present invention under magnification having a porous wall thickness including voids.

FIG. 21A-D are schematic diagrams that illustrate two round shaped expanded tubular profiles of the present invention in end view that are being flattened and formed into a multilayer wall thickness.

Figure 22A:
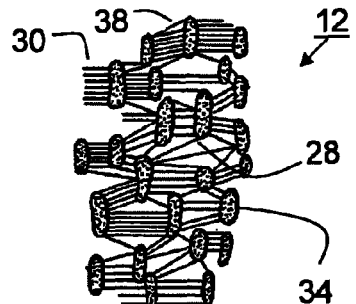
Figure 22B:
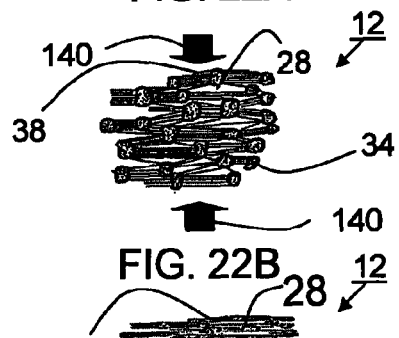
Figure 22C:

FIGS. 22A-C are schematic diagrams that illustrate expanded material according to the present invention under magnification being densified.

Figure 23:
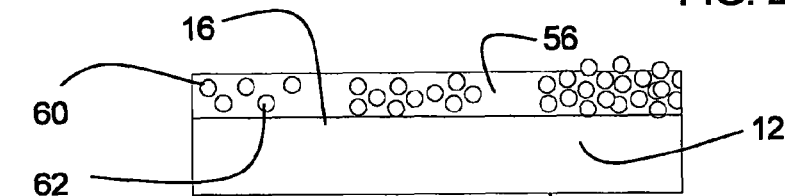

FIG. 23 is a schematic diagram that illustrates in cross sectional end view an expanded material of the present invention including a covering and additives on outside surface.

FIGS. 24-32 are schematic diagrams that illustrate embodiments of the expanded material of the present invention in under magnification including additives, nano size articles, or combinations thereof.

Figure 33:
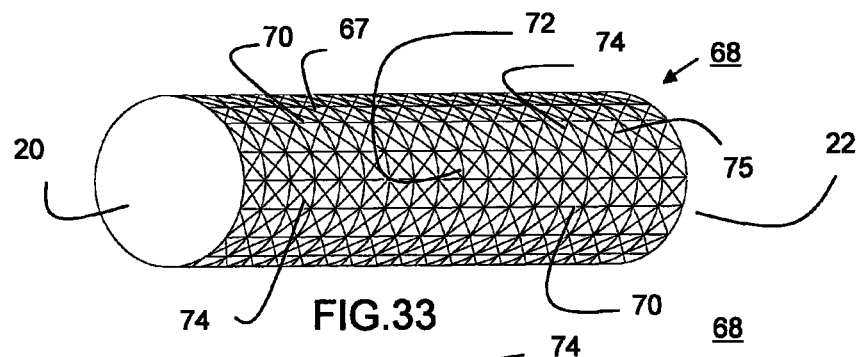
Figure 34:
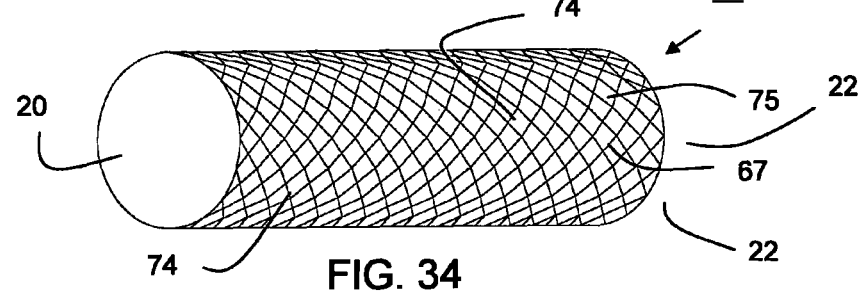

FIGS. 33-34 are illustrations of tubular shaped embodiments of reinforcements in isometric view.

Figure 35:
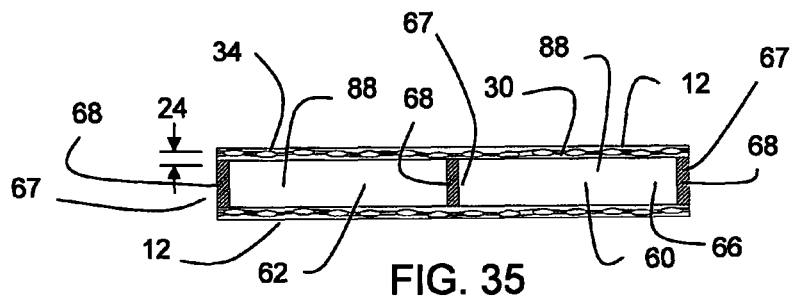

FIG. 35 is an illustration in cross sectional view of two layers of expanded material having reinforcement, additives, and nano size articles between the layers of the expanded material.

Figure 36:
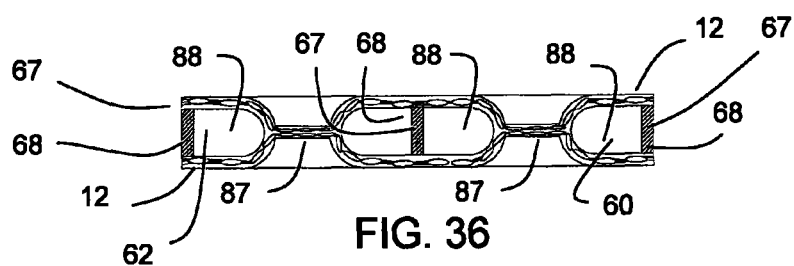

FIG. 36 is an illustration in cross sectional view of two layers of the expanded material including an interconnection located between the member segments of the reinforcement.

Figure 37:
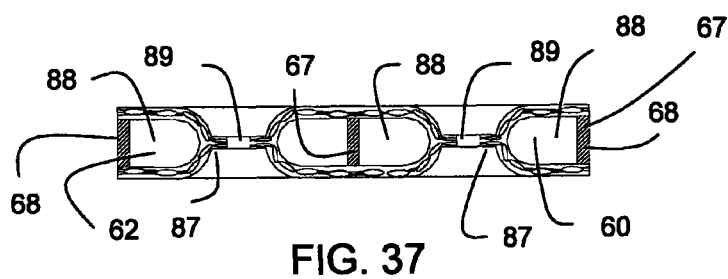

FIG. 37 is an illustration in cross sectional view of two layers of expanded material including a thru hole in the interconnection located between the member segments of the reinforcement.

FIGS. 38-47 illustrate a variety of possible shapes of open cells in the reinforcement or the expanded material.

FIGS. 48-51 illustrate a variety of possible patterns of groups of open cells used in the reinforcement or expanded material.

Figures 52, 53:
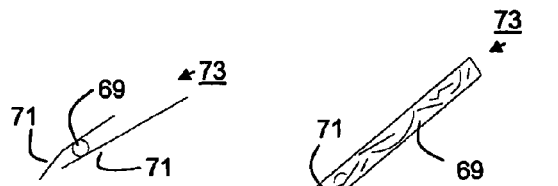

FIG. 52 illustrates two deformable elements connected by a binder.

FIG. 53 illustrates a group of deformable elements encapsulated by a binder.

Figure 54:
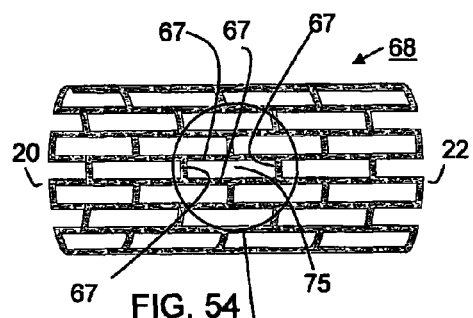
Figure 55:
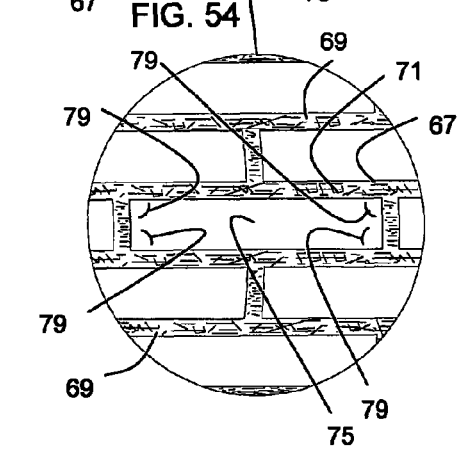

FIGS. 54-55 illustrate an example of the reinforcement in the first size wherein FIG. 55 is a close-up view.

Figure 57:
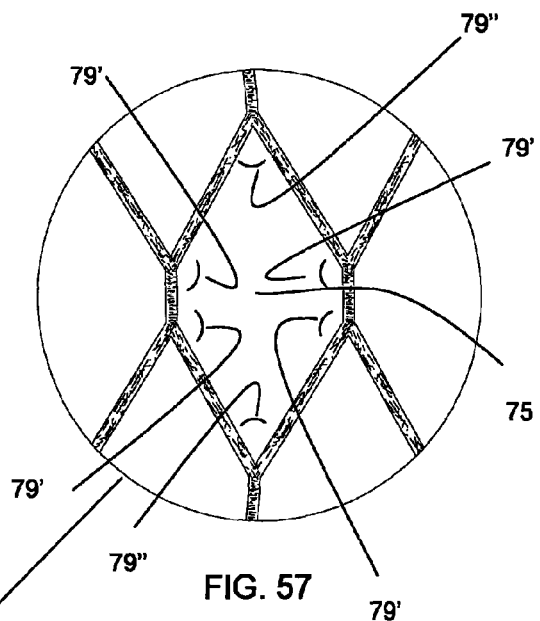
Figure 56:
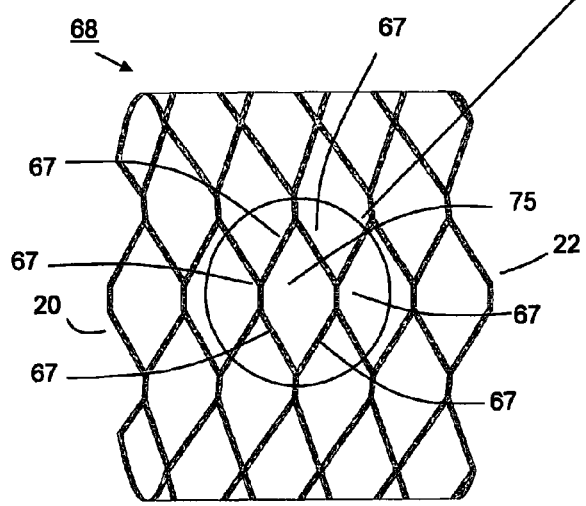

FIGS. 56-57 illustrate an example of the reinforcement of FIG. 54 in second size wherein FIG. 57 is in close-up view.

Figure 58:
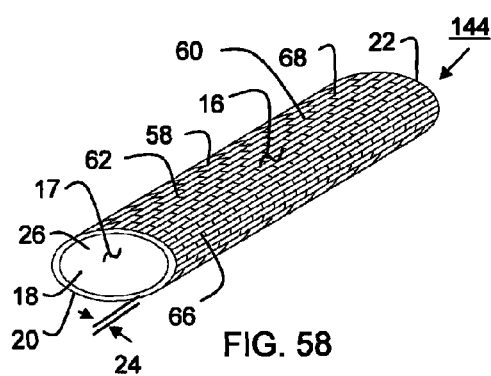

FIG. 58 is an illustration a tubular profile manufactured of woven expanded fiber.

FIG. 59 is an illustration a tubular profile manufactured of nonwoven expanded fiber.

FIG. 60 is an illustration in exploded isometric view of two expanded tubular profiles encapsulating a connecting member, fiber additives, and nano size articles.

FIG. 61 shows in side view a coil shaped reinforcement with expanded material encapsulating the reinforcement.

FIG. 62 shows a cross sectional end view of the coil shaped reinforcement and expanded material of FIG. 61.

FIG. 63 shows in cross sectional end view the coil shaped reinforcement of FIG. 61 further including a connecting member, additives, nano size articles, and covering.

FIG. 64 is an illustration of an articulated reinforcement comprised of multiple reinforcement segments connected by somewhat flexible connecting members.

Figure 65:
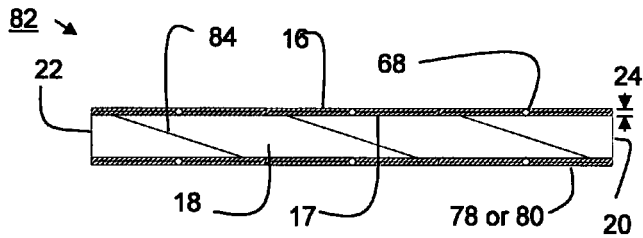

FIG. 65 is an illustration of a tubular profile in cross sectional side view having a wall thickness made of a spirally wrapped flattened expanded tubular profile.

Figure 66:
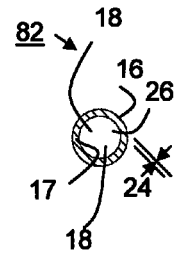

FIG. 66 shows the tubular profile of FIG. 65 in cross sectional end view.

Figure 67:
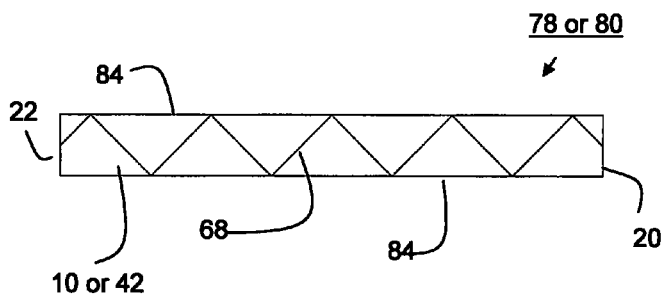

FIG. 67 is an illustration of a length of the flattened expanded tubular profile in top view including a zigzag shaped reinforcement located in bore that is suitable for formation into the wall thickness of another tubular profile.

Figure 68:
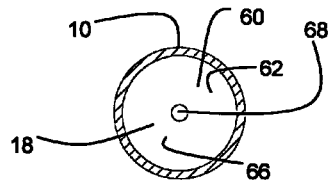

FIG. 68 is an illustration in cross sectional end view of unflattened expanded tubular profile with a reinforcement located in bore.

Figure 69:
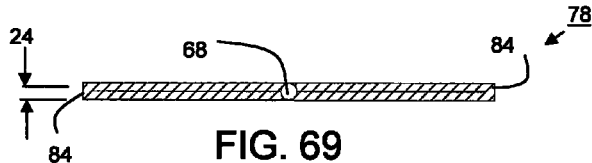

FIG. 69 shows the expanded tubular profile of FIG. 68 that has been flattened.

Figure 70:
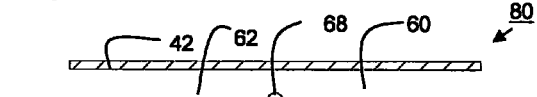

FIG. 70 is an illustration in cross sectional end view of a reinforcement positioned between two layers of expanded sheet.

Figure 71:
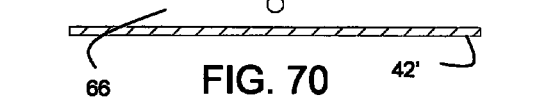

FIG. 71 is an illustration of the two layers of expanded sheet of FIG. 70 that has been flattened.

Figure 72:
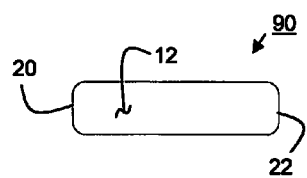

FIG. 72 is an illustration of a casing in top plan view of expanded tubular profile where ends are sealed closed to contain contents.

Figure 73:
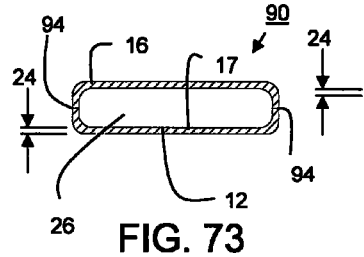

FIG. 73 is an illustration in cross sectional side view of the casing of FIG. 72.

Figure 74:
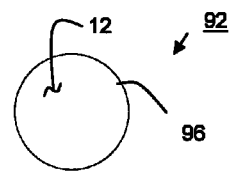

FIG. 74 is an illustration of a shell in top plan view of expanded sheet where perimeter is sealed closed to contain the contents.

Figure 75:
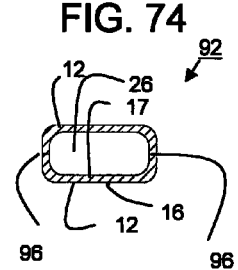

FIG. 75 is an illustration in cross sectional side view of the shell of FIG. 74.

FIG. 76 is an illustration of a supporting member having an enlarged bore with an expanded tubular profile installed therein so that annular-seals direct the contents through expanded tubular profile in the enlarged area.

FIG. 77 illustrates one example manufacturing process for producing the stretched expanded material of the present invention.

FIG. 78 illustrates the manufacturing process of FIG. 77 with an axial stretching step preceding the circumferential stretching step.

FIGS. 79-80 illustrate one embodiment of an adjustable mandrel used for circumferential stretching.

FIG. 81 illustrates a tab of the adjustable mandrel of FIGS. 79 and 80.

FIG. 82 illustrates a second example manufacturing process for producing the stretched expanded material of the present invention having multiple stretching steps.

FIG. 83 illustrates an example of an off-line process for producing the stretched expanded material of the present invention.

These figures merely schematically illustrate the invention and are not intended to indicate relative size and dimensions of actual product or manufacturing systems or components thereof.

While the present invention will hereinafter be described in connection with the preferred embodiments and methods of use thereof, it will be understood that it is not intended to limit the invention to these embodiments and methods of use. Instead, it is intended to cover all alternatives, modifications, and equivalents as may be included within the spirit and scope of the invention as defined in the appended claims.

| REFERENCE NUMERALS IN DRAWINGS | |
|---|---|
| 10. | Expanded tubular profile |
| 11. | Pleated expanded tubular profile |
| 12. | Expanded material |
| 14. | Material |
| 15. | Perforated tubular profile |
| 16. | Outside surface |
| 17. | Inside surface |
| 18. | Bore |
| 20. | First end |
| 22. | Second end |
| 24. | Wall thickness |
| 26. | Contents |
| 28. | Voids |
| 30. | Axial fibrils |
| 32. | Circumferential fibrils |
| 34. | Nodes |
| 36. | Angled fibrils |
| 38. | Bent fibrils |
| 40. | Slit |
| 42. | Expanded sheet |
| 44. | Seamed tubular profile |
| 46. | Multi layer tubular profile |
| 48. | Third end |
| 50. | Fourth end |
| 52. | Multi layer wall thickness |
| 54. | Densified expanded material |
| 56. | Covering |
| 58. | Expanded fibers |
| 60. | Additives |
| 62. | Nano size articles |
| 64. | Supporting member |
| 66. | Connecting material |
| 67. | Member segment |
| 68. | Reinforcement |
| 69. | Binder |
| 70. | Longitudinal member segment |
| 71. | Deformable element |
| 72. | Radial member segment |
| 73. | Formable composite |
| 74. | Angled member segment |
| 75. | Open Cell |
| 76. | Undercuts |
| 77. | Connecting member |
| 78. | Flattened tubular profile |
| 79. | Internal angle |
| 80. | Layered flat profile |
| 81. | Open member segment |
| 82. | Self-supporting tubular profile |
| 84. | Edge |
| 86. | Blunt-end |
| 87. | Interconnection |
| 88. | Pocket |
| 89. | Thru hole |

| REFERENCE NUMERALS IN DRAWINGS -continued | |
|---|---|
| 90. | Casing |
| 92. | Shell |
| 94. | End seal |
| 96. | Top/Bottom seal |
| 98. | Silo |
| 100. | Blend tank |
| 102. | Extruder |
| 104. | Unexpanded tubular profile |
| 106. | Extraction device |
| 108. | Temperature controlled area |
| 110. | Thermal treatment zone |
| 112. | Barrel |
| 114. | Mandrel |
| 116. | Leading edge |
| 118. | Trailing edge |
| 120. | Tab |
| 122. | Coiler |
| 124. | Constraint |
| 126. | Support seal |
| 128. | Puller |
| 130. | Agitator |
| 132. | Intensive mix tank |
| 134. | Quench tank |
| 136. | Air gap |
| 138. | Adaptation zone |
| 140. | Compressive force |
| 142. | Circumferential force |
| 144. | Woven tubular profile |
| 146. | Nonwoven tubular profile |
| 148. | Sharp end |
| 150. | Fold |
| 152. | Extra wall thickness |
| 154. | Annular-seal |
| 156. | Collar |
| 158. | Sac |
| 160. | Articulated Reinforcement |

DESCRIPTION OF THE PREFERRED EMBODIMENTS

The present invention includes an expanded material 12, a reinforcement 68, or combinations thereof that are optionally installed with a supporting member 64. The individual components or combinations thereof optionally further include a covering 56, additives 60, nano size articles 62, or combinations thereof. The additives 60 and nano size articles 62 are optionally partially or fully one or more active or inactive ingredients that are delivered to the surroundings.

The expanded material 12 of the present invention is comprised of an outside surface 16, an inside surface 17, a first end 20, a second end 22, and at least one layer of a wall thickness 24. The expanded material 12 is obtained by at least partially stretching the material 14. The structure of the expanded material 12 is optionally made substantially permanent or locked-in after stretching by thermal treatment. The expanded material 12 preferably has a uniform structure that is optionally obtained by at least partially stretching the material 14 in the circumferential direction.

The expanded material 12 can be in any configuration but it is generally in the form of an expanded tubular profile 10 (FIG. 1), an expanded sheet 42 (FIG. 3), or an expanded fiber 58 (FIG. 4).

A typical embodiment of the expanded tubular profile 10 is shown in FIG. 1 in isometric view. It is comprised of the outside surface 16, the inside surface 17, a bore 18, the first end 20, the second end 22, and at least one layer of the wall thickness 24. The wall thickness 24 is partially or fully comprised of the expanded material 12. The bore 18 optionally includes one or more contents 26. The structure of the wall thickness 24 of the expanded material 12 can be designed to partially or fully contain the contents 26 such as those in the bore 18.

As shown in FIG. 2, the expanded tubular profile 10 optionally includes at least one slit 40 that is opened to convert the expanded tubular profile 10 into the expanded sheet 42 as shown in FIG. 3. The expanded sheet 42 of the present invention is any sheet, film, membrane, thin layer, skin or anything that is thin in comparison to its length and width. The expanded sheet 42 is comprised of the outside surface 16, the inside surface 17 (not shown), the first end 20, the second end 22, a third end 48, a fourth end 50, and at least one layer of the wall thickness 24. The wall thickness 24 is partially or fully comprised of the expanded material 12.

The expanded sheet 42 is preferably produced by slitting the expanded tubular profile 10. However, the expanded sheet 42 can also be made in sheet or film configuration but this generally produces a less uniform product when stretched. Producing the expanded sheet 42 from the expanded tubular profile 10 produces a much more uniform product having a substantially more uniform structure across its entire width when compared to an expanded sheet stretched in sheet configuration. An expanded sheet 42 manufactured from an expanded tubular profile 10 also significantly reduces wasted material 14 when compared to expanded sheet stretched in sheet configuration because the heterogeneous, damaged, unstretched, or combinations thereof portions found in the prior art near the ends 48 and 50 do not have to be trimmed off. The manufacturing process of the present invention also consumes significantly less energy when compared to the prior art.

The expanded fiber 58 is preferably produced by slitting one or more layers of the expanded sheet 42 into relatively narrow strips of any size. However, the expanded fiber 58 can also be made in filament, rod, or tape configurations but this generally produces a less uniform product when stretched and the material 14 can only be stretched in one direction. The expanded sheet 42 optionally includes a plurality of additional slits 40 that convert the expanded sheet 42 into the expanded fiber 58 as shown in FIG. 4. The expanded fiber 58 is generally comprised of the outside surface 16, the inside surface 17, the first end 20, the second end 22, the third end 48 (not shown), the fourth end 50, and at least one layer of the wall thickness 24. The wall thickness 24 is partially or fully comprised of the expanded material 12. The expanded fiber 58 is alternatively produced of a small diameter expanded tubular profile 10 or a flattened small diameter expanded tubular profile 10. These expanded fibers 58 can also be subsequently transformed into other articles such as yarns, sutures, fabrics, ropes, braided rods, threads, casings, etc. The expanded fiber 58 of the present invention can also be subsequently chopped into shorter fibers and, for example, converted into felts, papers, nonwovens, etc.

The expanded material 12 (such as the expanded tubular profile 10, expanded sheet 42, expanded fiber 58, or combinations thereof) optionally includes a supporting member 64, a connecting material 66, a reinforcement 68, or combinations thereof. The supporting member 64, reinforcement 68, or combinations thereof are positioned either on or near the outside surface 16, inside surface 17, or combinations thereof. The reinforcement 68 is alternatively positioned within the wall thickness 24, between two wall thicknesses 24, or between wall thicknesses 24 comprised of two or more layers of the expanded material 12. The connecting material 66 is optionally positioned between two or more layers of the expanded material 12, between two or more wall thicknesses 24, between the expanded material 12 and the reinforcement 68, between the reinforcement 68 and the supporting member 64, between the expanded material 12 and the supporting member 64, or combinations thereof. An embodiment of one of the possible combinations in tubular configuration is shown in FIG. 5 in exploded isometric view.

The supporting member 64 is a host or passageway that works in cooperation with or receives the expanded material 12, reinforcement 68, or combinations thereof. The optional connecting material 66 partially or fully attaches the expanded material 12 to: another layer of the expanded material 12; a wall thicknesses 24, the supporting member 64; the reinforcement 68; or combinations thereof. The connection is either permanent or temporary. The connecting material 66 can also optionally partially or fully attach the reinforcement 68 to the supporting member 64. The reinforcement 68, for example, provides additional strength, support, structure, shape, shape recovery, size recovery, shape memory, size memory, or combinations thereof to the expanded material 12. The reinforcement 68 can also be used independently to, for example, hold open a constricted supporting member 64.

As an example is shown in FIG. 6 in cross sectional end view, the expanded material 12 (such as the expanded tubular profile 10) is optionally reduced in size by including one or more folds 150 in the wall thickness 24 of the expanded material 12. The fold 150, for example, is a wall thickness 24 that is bent over, intertwined, or doubled up so that at least one part lies on another part. The fold 150 temporarily or permanently stores an extra wall thickness 152. The fold 150 can be optionally partially or fully tacked down with, for example, an adhesive material or other means to keep the fold 150 at least temporarily positioned. As illustrated in FIG. 7, in cross sectional end view, the expanded material 12 (such as the expanded tubular profile 10) can be unfolded up to its original size or larger. Alternatively, as shown in FIG. 8, the optional folds 150 are obtained by temporarily or permanently pleating the wall thickness 24. The optional pleats can be of uniform or varying size and shape. The pleats can be oriented around the circumference as shown in FIG. 8 to, for example, reduce the diameter; the pleats can be oriented longitudinally (not shown) to, for example, reduce its length, or combinations thereof.

As shown if FIG. 9, the size and shape of the expanded material 12 (such as in the form of the expanded tubular profile 10) can be optionally retained when in first size and shape or in second size and shape by use a plurality of deformable elements 71 when they are included in the material 14, between layers of expanded material 12, within the wall thickness 24, on the inside surface 17, on the outside surface 16, or combinations thereof. The preferred deformable elements 71 that provide this functionality, for example, enable the expanded material 12 to be self-expandable, formable, deformable, or combinations thereof in a way that the second size and shape is substantially retained after installation. The expanded material 12, for instance, can be maintained in a reduced size and shape by the plurality of deformable elements 71 and subsequently maintained in a larger second size and shape after dilation by the plurality of deformable elements 71. The expanded material 12 (such as the expanded tubular profile 10) also optionally includes one or more thru holes 89 in the wall thickness 24 as also shown in FIG. 9 to form a perforated tubular profile 15. The thru holes 89 can be of any size and shape such as the examples schematically shown in FIGS. 38-47. The size and shape of the thru holes 89 can be uniform or varying within an embodiment. Likewise the remaining expanded material 12 left between the thru holes 89 can be of any shape or pattern that provides the functionality described herein.

The structure of the expanded material 12 that comprises the wall thickness 24 is either solid or porous. A solid structure as shown in FIG. 10 is comprised substantially of the material 14. A porous structure as shown in FIG. 11 is comprised of the material 14 that includes one or a plurality of voids 28. The void 28 is an open space or gap in the material 14. Although it is shown differently in FIG. 11, it is preferred that the voids 28 be substantially uniform in size and distribution. A porous wall thickness 24 can be partially or fully permeable or impermeable to gases, liquids, or combinations thereof.

Figure 12:
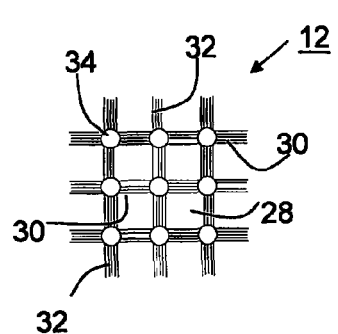
FIGS. 12-19 are schematic diagrams that illustrate in top view the expanded material according to the present invention under magnification having a porous wall thickness having voids, nodes, fibrils, or combinations thereof.
Figure 13:
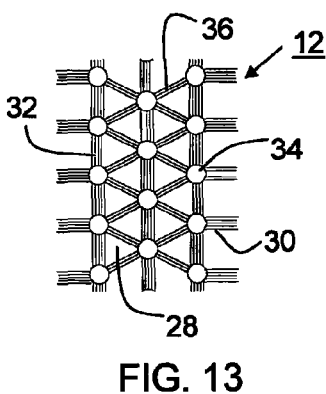
Figure 14:
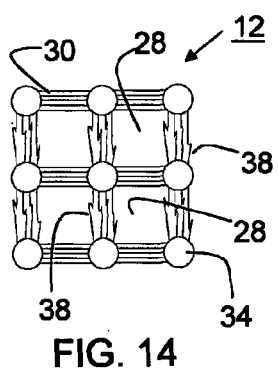
Figure 15:
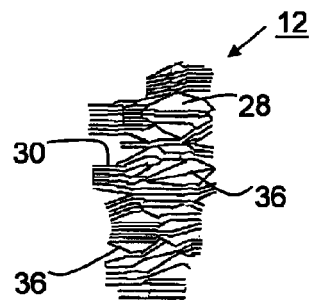

As shown in FIGS. 12-14, which are schematic illustrations of the structure of the expanded material 12 in top plan view under magnification, the porous structure optionally includes one or a plurality of voids 28, nodes 34, axial fibrils 30, circumferential fibrils 32, angled fibrils 36, bent fibrils 38, or combinations thereof. The fibrils can be substantially straight or they can include curves, bends, or other non-straight forms. The fibrils, voids, and nodes are sometimes created during the stretching of the material 14. Under some manufacturing conditions, as schematically shown in FIG. 15, it is possible to have a node-free porous structure that is comprised of the axial fibrils 30, circumferential fibrils 32, angled fibrils 36, bent fibrils 38, voids 28, or combinations thereof. The structure including a plurality of fibrils can have a web-like appearance under magnification.

Figure 16:
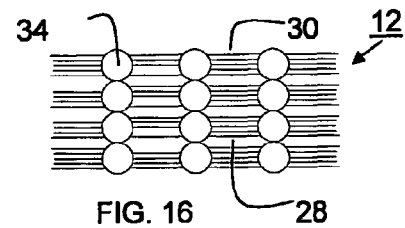
Figure 17:
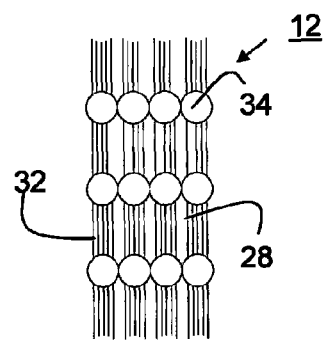
Figure 19:
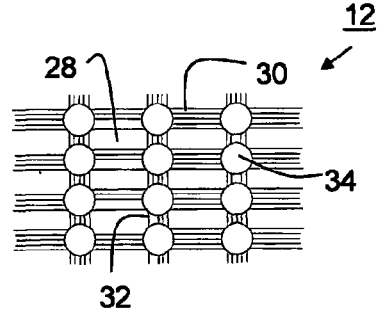
Figure 18:
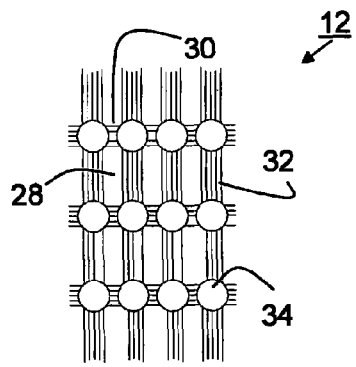
Figure 21A:
Figure 21B:
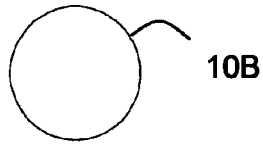
Figure 21C:
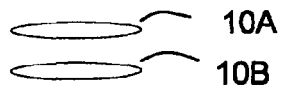
Figure 21D:

As schematically illustrated in FIG. 16 the axial fibrils 30 which are substantially oriented in the axial direction are generally created by stretching the material 14 in the axial direction. As schematically shown in FIG. 17, the circumferential fibrils 32 which are substantially oriented in the circumferential direction are generally created by stretching the material 14 in the circumferential direction. As shown in FIG. 13, the angled fibrils 36 are generally formed by stretching the material 14 in the axial and circumferential direction concurrently. The expanded material 12 that partially or fully contains bent fibrils 38 is generally more stretchable than the expanded material 12 comprised of mostly or totally unbent fibrils. As shown in FIG. 14, the bent fibrils 38 are usually formed by stretching the material 14 and allowing it to at least partially shrink back to about its original size before partially or fully locking-in the structure with, for example, thermal treatment. As schematically shown in FIGS. 18 and 19, the length of the fibrils can be customized by, for example, modifying the amount of stretching in the axial or circumferential direction.

Figure 20:
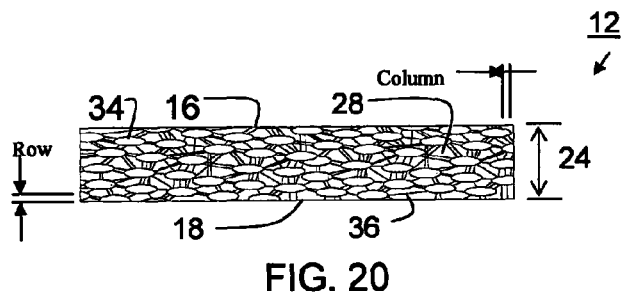
FIG. 20 is a schematic diagram that illustrates in cross sectional end view of one of many possible embodiments of the expanded material of the present invention under magnification.

As an example is schematically illustrated in FIG. 20, which is a cross sectional view of the expanded material 12, the wall thickness 24 of the porous structure is generally comprised of one or more partial or full rows of voids 28, nodes 34, fibrils such as 30, 32, 36, 38 or combinations thereof. The rows and columns of voids 28, nodes 34, fibrils such as 30, 32, 36, 38, or combinations thereof can be arranged randomly but it is preferred that they are organized in a somewhat repeating pattern.

As an example is schematically illustrated in FIGS. 21A-D, which are illustrations of the expanded tubular profile 10 in end view, one way of many possible ways of manufacturing a multi layer wall thickness 52 is to flatten one or more expanded tubular profiles 10 of the same or different structures. The multi layer wall thickness 52 can also be fabricated by assembling two or more expanded sheets 42 of the same or different structure. It is also possible to create a multiple layer expanded tubular profile 10 by assembling two or more expanded tubular profiles 10 of the same or different structure. One more way of producing a multi layer wall thickness 52 is to assemble two or more wall thickness 24 of unstretched material 14 in any configuration such a tubular or sheet and then stretch the assembly to convert the assembly into a wall thickness 24 of multiple layers of the expanded material 12. The multi layer wall thickness expanded tubular profile 10, of course, can be optionally converted into the expanded sheet 42 or expanded fiber 58.

As just discussed, the wall thickness 24 or the multi layer wall thickness 52 can be comprised of one or more layers of expanded material 12 of the same or different structure. For example, one layer can be more porous than another. Moreover, the fibril size, fibril orientation, fibril straightness, void size, node size, density, thickness, permeability, porosity, or combinations thereof can be varied from layer to layer. The multi layer wall thickness 52 optionally includes the connecting material 66 or other means to facilitate partially or fully holding the layers together. Alternatively, the multiple layers can be partially or fully attached mechanically, thermally, ultrasonically, welding, compression, etc. The multi layer wall thickness can be optionally quilted so that pockets formed contain additives 60, nano size articles 62, or combinations thereof such as active ingredients.

A multi layer wall thickness 52 optionally includes one or more additives 60, nano size articles 62, or combinations thereof between the layers. The additives 60, nano size articles 62, or combinations thereof are, for example, optionally a particle, tube, or a fiber shape. The additives 60, nano size articles 62, or combinations thereof are optionally partially or fully an active ingredient. The nano size articles 62 are optionally useful in delivering the active ingredients. The active ingredients are optionally microencapsulated. There are also optionally different concentrations or types of additives 60, nano size articles 62, or combinations thereof such as active ingredient from one layer of the expanded material 12 to another layer of the expanded material 12. There are also optionally different types of connecting material 66 from one layer of the expanded material 12 to another layer of the expanded material 12. Inactive ingredients, connecting material 66 concentration, or combinations thereof are also sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is optionally through the voids 28 in the expanded material 12. The delivery is at constant rate, ascending rate, descending rate, changing rate, or combinations thereof. The delivery is immediate, time delayed, modified release, sustained, or combinations thereof. The uniformly expanded material 12 of the present invention provides an unusually accurate dosage of the active ingredients especially when delivered over extended periods of time.

As schematically illustrated in FIGS. 22A-C, the expanded material 12 is optionally densified so that its specific gravity or density is partially or fully increased. Moreover, the densification can substantially reduce or eliminate the porosity of the expanded material 12 if desired. The expanded material 12 can be fully densified or partially densified. The undensified expanded material 12, shown in FIG. 22A, is for, example, densified by utilizing a compressive force 140, thermal treatment, or combinations thereof as shown in FIG. 22B, to partially or fully reduce the void 28 content of the expanded material 12 as shown in FIG. 22C.

The expanded material 12 is optionally densified when it includes one or more additives 60, nano size articles 62, connecting material 66, or combinations thereof. The densification process partially or fully retains the additives 60, nano size articles 62, or combinations thereof. The optional connecting material 66 can partially or fully retain the densified structure with or without thermal treatment. The additives 60, nano size articles 62, or combinations thereof are, for example, optionally a particle, tube, or fiber shape. The additives 60, nano size articles 62, or combinations thereof are optionally partially or fully an active ingredient. The nano size articles 62 are optionally useful in delivering the active ingredients. The active ingredients are optionally microencapsulated. Inactive ingredients, connecting material 66 concentration, or combinations thereof are also sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or a combinations thereof. The delivery is optionally through the voids 28 in the expanded material 12. The delivery is at constant rate, ascending rate, descending rate, changing rate, or combinations thereof. The delivery is immediate, time delayed, modified release, sustained, or a combinations thereof.

As schematically illustrated in FIG. 23, the expanded material 12 (such as the expanded tubular profile 10, expanded sheet 42, expanded fiber 58, or combinations thereof) optionally includes one or more layers of a covering 56. The covering 56 optionally partially or fully covers the inside surface 17, outside surface 16, ends 20, 22, 48, 50, or combinations thereof. For example, the covering 56 can optionally only partially or fully cover the first end 20 and second end 22 to provide a more durable area where sutures are used to connect the expanded material 12 to another object. Alternatively, the covering 56 optionally partially or fully covers the surfaces of the individual voids 28, fibrils 30, 32, 36, 38, nodes 34, or combinations thereof. The covering 56 is substantially permanent or erodible. The covering 56 can also optionally partially or fully fill the voids 28.

The covering 56 optionally includes one or a plurality of additives 60, nano size articles 62, or combinations thereof. The inside surface 17, outside surface 16, or any surface of the expanded material 12 can be treated to increase adhesion of the covering to these surfaces. The additives 60, nano size articles 62, or combinations thereof are, for example, optionally a particle, tube, or fiber shape. The covering 56 can optionally partially or fully evaporate or otherwise partially or fully disappear leaving behind additives 60, nano size articles 62, or combinations thereof such as active ingredients on the surface of the expanded material 12. The additives 60, nano size articles 62, or combinations thereof are optionally partially or fully an active ingredient. The nano size articles 62 are optionally useful in delivering the active ingredients. The active ingredients are optionally microencapsulated. There can optionally also be different concentrations or types of the additives 60, nano size articles 62, or combinations thereof such as the active ingredient from one layer of the covering 56 to another layer of the covering 56. There can also optionally be different types of covering 56 from layer of covering 56 to layer of covering 56. Inactive ingredients, the covering 56 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery, for example, is constant rate, ascending rate, descending rate, changing rate, or combinations thereof. The delivery is, for example, immediate, time delayed, modified release, sustained, or combinations thereof.

As schematically illustrated in FIGS. 24-32, which illustrate the expanded material 12 in top plan view under magnification, the material 14 or expanded material 12 optionally includes one or a plurality of additives 60, nano size articles 62, or combinations thereof. The additives 60, nano size articles 62, or combinations thereof are, for example, optionally a particle, tube or fiber shape. The additives 60, nano size articles 62, or combinations thereof are included with the material 14 or the expanded material 12 before, during, or after extrusion, processing, or stretching. The additives 60, nano size articles 62, or combinations thereof optionally modify the properties or functionality of the expanded material 12. These additives 60, nano size articles 62, or combinations thereof are optionally positioned within the material 14, within the wall thickness 24 of the expanded material 12, between layers of the expanded material 12, on the inside surface 17, on the outside surface 16, or combinations thereof. As schematically shown in FIGS. 24-27, the additives 60, nano size articles, or combinations thereof can also be optionally positioned between one or more voids, 28, one or more fibrils 30, 32, 36, 38, nodes 34, or combinations thereof. The additives 60, nano size articles 62, or combinations thereof can optionally at least partially protrude from the inside surface 17 or the outside surface 16. The protruding additives 60, nano sized articles 62, or combinations thereof can help immobilize the expanded material 12 or prevent by-pass of the contents 26 around the expanded material 12 upon final positioning. These additives 60, nano size articles 62, or combinations thereof can also be positioned partially or fully within or on the surface of the voids 28, nodes 34, fibrils 30, 32, 36, 38, or combinations thereof. Due to the typical small dimensions of the voids 28, nodes 34 and fibrils 30, 32, 36, 38, it is sometimes desirable to use a very small form of the additives 60 that are herein referred to as nano size articles 62. Moreover, one or more of layers of the covering 56, connecting material 66, or combinations thereof can be applied underneath or over the additives 60 or the nano size articles 62.

The additives 60, nano size articles 62, or combinations thereof when included in the material 14 or the expanded material 12 are optionally partially or fully an active ingredient. The nano size articles 62 are optionally useful in delivering the active ingredients. The active ingredients are optionally microencapsulated. Inactive ingredients, material 14 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, at constant rate, ascending rate, descending rate, changing rate, or any combinations thereof. The delivery is, for example, immediate, time delayed, modified release, sustained, or combinations thereof.

The reinforcement 68 of the present invention has a partially or fully solid wall thickness. An example of a solid wall thickness is illustrated in FIG. 5 and a partially solid wall thickness is illustrated in FIGS. 33 and 34. The reinforcement 68 is optionally expandable or contractible from a first size and shape to a second size and shape.

As schematically illustrated in a tubular embodiment in FIGS. 33-34, the reinforcement 68 optionally includes a plurality of member segments 67. The member segments 67 are of uniform or varying thickness and can be of any cross sectional shape. The reinforcement 68 can optionally, for example, include one or more longitudinal member segments 70, radial member segments 72, angled member segments 74, helical member segments, curved member segments, angled member segments, or combinations thereof. Although not necessary, the reinforcement 68 preferably forms a mesh or lattice structure. The open area between the member segments 67 is an open cell 75. The open cells 75 can be of any shape as a few examples are schematically shown in FIGS. 38-47. The shapes of the open cells 75 can be of a uniform or varied pattern within one embodiment to customize the flexibility, manage the longitudinal shrinkage or expansion upon changing size and shape, minimize drag within a passageway, modification of other properties, or combinations thereof. As a few examples are shown in FIGS. 48-51, the open cells 75 are typically organized in groups of the open cells 75 that are in repeating, non-repeating, meandering, or combinations thereof patterns down the length, circumference, width, or combinations thereof of the reinforcement 68. As also shown, in FIGS. 48-51, the open cells 75 are optionally interconnected with other open cells 75 with one or more member segments 67 or connecting members 77. The open cells 75 are optionally fully or partially surrounded by the member segments 67. FIG. 48 illustrates an example of wherein the open cells 75 are fully surrounded with the member segments 67 and FIG. 51 shows an example wherein a few of the open cells 75 are partially surrounded by the member segments 67 so that there is at least one open member segment 81.

As previously described, the reinforcement 68 of the present invention optionally includes one or more layers of the expanded material 12 (such as the expanded tubular profile 10, expanded sheet 42, expanded fiber 58, or combinations thereof), connecting material 66, covering 56, or combinations thereof. These supplementary materials can be positioned on the inside surface, outside surface, surfaces of the member segments 67, or combinations thereof of the reinforcement 68. When the reinforcement 68 is disposed between two wall thicknesses 24 or layers of the expanded material 12, the first end 20, the second end 22, or both of the expanded material 12 are optionally partially or fully sealed to partially or fully encapsulate the reinforcement 68. If the reinforcement 68 is a sheet or fiber configuration the third end 48 and the fourth end 50 are also optionally partially or fully sealed.

The previously mentioned member segments 67, connecting members 77, or combinations thereof are single or multiple strands. The strands are optionally woven, nonwoven, knitted, zigzagged, wound, bent, helical, serpentine, twisted, braided, curved, or combinations thereof. The reinforcement 68 optionally includes one or a plurality of expansion means that enable the reinforcement 68 to be reduced or enlarged in size. Furthermore, the reinforcement 68 optionally includes one or a plurality of stress relief features to prevent breakage of the member segments 67 or connecting members 77 during manufacturing, size reduction, installation, enlargement, usage, or combinations thereof. The reinforcement 68 is optionally self-enlarging, spring-like, or mechanically enlargeable. The reinforcement 68 is optionally partially or fully bendable to one or more bends of any radius or curvature in one or more planes preferably without substantial kinking or fully collapsing the bore 18.

As shown in FIGS. 54 and 55, the reinforcement 68 in first size typically has first shaped open cells 75 and first size internal angles 79. As shown in FIGS. 56 and 57, upon deformation or self-expansion the reinforcement 68 optionally changes to second size and shape resulting in the open cells 75 and internal angles 79 also changing to a second size and shape. In this example of the inventive functionality, the reinforcement 68 is increased in size from first diameter to second diameter that results in the internal angles also changing. In addition, the shape of the open cells 75 changes from a rectangular shape to a polygonal shape.

As an example is illustrated in FIG. 64, the reinforcement 68 is optionally divided into two or more connected or disconnected segments to allow the reinforcement 68 to conform to tighter radiuses. For example, the individual reinforcement segments 68 can be attached to each other with one or more substantially more flexible connecting members 77 that increase the overall flexibility of the articulated reinforcement 160. A reinforcement 68 as shown in FIG. 64 that is comprised of multiple segments to form an articulated reinforcement 160 can be optionally changed from first size and shape to second size and shape so that, for example, the size of the individual segments are different. Thus the reinforcement 68 can have a variable size from the first end 20 to the second end 22 where each segment has a different size and shape. Moreover, each segment can have a different ending shape from first end 20' to second end 22' so that an optimal fit is obtained for each individual segment with the supporting member 64.

The member segments 67 of the reinforcement 68 are optionally of varying or uniform cross sectional dimension, thickness, stiffness, flexibility, or combinations thereof to minimize stress concentrations. Stress concentrations can result in failure of the supporting member 64 at the junction of the supporting member 64 and the reinforcement 68 and/or expanded material 12 when there is, for example, a change in wall thickness, stiffness, or a notch. The reinforcement 68 is capable of compressing or holding the expanded material 12 against the supporting member 64.

The reinforcement 68 of the present invention can be of any material that provides the functionality described herein. However, it is preferred that the reinforcement 68 is comprised of a formable composite 73 that includes a plurality of substantially discontinuous deformable elements 71 that are partially or fully interconnected as shown in FIG. 52 or encapsulated as shown in FIG. 53 with one or more binders 69. The binder 69 partially or fully holds the deformable elements 71 substantially together as a pair or group of deformable elements 71. The deformable elements 71 for the most part are capable of retaining the first size and shape until after deformation or after self expansion wherein they retain the second size and shape. The binder 69 optionally includes one or more of the additives 60, nano size articles 62, or combinations thereof. The additives 60, nano size articles 62, or combinations thereof can optionally partially or fully protrude from the inside surface, outside surface, or combinations thereof of the reinforcement 68 or any surface of the member segments 67. The additives 60, nano size articles 62, or combinations thereof are, for example, optionally a particle, tube, or fiber shape. The additives 60, nano size articles 62, or combinations thereof are optionally partially or fully an active ingredient. The nano size articles 62 are optionally useful in delivering the active ingredients. The active ingredients are optionally microencapsulated. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

The reinforcement 68 optionally includes one or a plurality of somewhat sharp ends to partially or fully attach the reinforcement 68 to the supporting member 64, expanded material 12, or combinations thereof so that they do not substantially move once positioned. The reinforcement 68 also optionally includes one or a plurality of blunt ends 86 to at least partially prevent the reinforcement 68 from damaging or snagging the supporting member 64. The blunt end 86 can, for example, be in the form of any eyelets, rings, bent portions, or curved portions. The blunt end 86 can also be used, for example, to place the reinforcement 68, expanded material 12, or combinations thereof in tension or compression to change their size and/or shape. Once the tension or compression is removed, the reinforcement 68, expanded material 12 (such as the expanded tubular profile 10), or combinations thereof can optionally change from first size and shape to second size and shape or the shape of nearby constraints.

The reinforcement 68 optionally includes one or more layers of the covering 56. The inside surface, outside surface, or any surface of the reinforcement 68 such as the surfaces of the member segments 67 can be optionally treated to increase adhesion of the covering 56 to these surfaces. The covering 56 partially or fully covers the reinforcement 68. The covering 56 is substantially permanent or erodible. The covering 56 optionally includes one or more additives 60, nano size articles 62, or combinations thereof. The covering 56 can optionally partially or fully evaporate or otherwise partially or fully disappear leaving behind additives 60, nano size articles 62, or combinations thereof such as active ingredients on the surface of the reinforcement 68. The additives 60, nano size articles 62, or combinations thereof are, for example, optionally a particle, tube, or fiber shape. The additives 60, nano size articles 62, or combinations thereof are optionally partially or fully an active ingredient. The nano size articles 62 are optionally useful in delivering the active ingredients. The active ingredients are optionally microencapsulated. There are also optionally different concentrations or types of the additives 60, nano size articles 62, or combinations thereof such as the active ingredients from one layer of the covering 56 to another layer of the covering 56. There can also optionally be different types of covering 56 from one layer of the covering 56 to another layer of the covering 56. Inactive ingredients, the covering 56 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, time delayed, modified release, sustained, or combinations thereof.

FIG. 35 illustrates an example in cross sectional view of how the reinforcement 68 is optionally positioned between two or more wall thicknesses 24 of one or more layers of the expanded material 12 (such as the expanded tubular profile 10, expanded sheet 42, expanded fiber 58, or combinations thereof) to form a partially or fully enclosed reinforcement 68. One or more pockets 88 are optionally positioned between the member segments 67 or the struts of the reinforcement 68. The pockets 88, which are the optional open spaces located between the member segments 67 of the reinforcement 68 and the top and bottom layers of the expanded material 12, serve as reservoirs and are optionally filled with one or more additives 60, nano size articles 62, connecting materials 66, or combinations thereof. The additives 60, nano size articles 62, connecting material 66, or combinations thereof can be positioned before or after assembly. The additives 60, nano size articles 62, or combinations thereof are optionally partially or fully an active ingredient. The nano size articles 62 are optionally useful in delivering the active ingredients. The active ingredients are optionally microencapsulated. Inactive ingredients, connecting material 66 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof. The delivery is optionally possible through the voids 28 in the wall thickness 24 of the expanded material 12. The uniformly expanded material 12 of the present invention provides an unusually accurate dosage of active ingredients especially when delivered over extended periods of time.

FIG. 36 illustrates in cross sectional view that the top and bottom layers of the expanded material 12 that are located between the member segments 67 of the reinforcement 68 of FIG. 35 can be optionally partially or fully connected or sealed to create an interconnection 87. The expanded material 12 in this type of embodiment is optionally capable of partially or fully encapsulating each member segment 67 of the reinforcement 68. The expanded material 12 in this type of embodiment is also capable of partially or fully encapsulating the optional additives 60, nano size articles 62, connecting material 66, or combinations thereof such as the active ingredients that are optionally positioned in the optional pockets 88. The connecting material 66, ultrasonics, laser, or thermal treatment, for example, can be optionally utilized to attach the layers of the expanded material 12 to form the interconnection 87. The additives 60, nano size articles 62, or combinations thereof such as the active ingredients that are optionally located in the pockets 88 or between the layers of the expanded material 12 are optionally delivered to the surroundings as already described herein. The uniformly expanded material 12 of the present invention provides an unusually accurate dosage of the active ingredients especially when delivered over extended periods of time.

FIG. 37 illustrates that the interconnection 87 of FIG. 36 optionally includes one or more thru holes 89. The thru holes 89 are locations where there is little or no interconnection 87 so that the expanded material 12 between the member segments 67 of the reinforcement 68 is partially or fully non existent. Therefore, each member segment 67 of the reinforcement 68 is individually encapsulated with one or more layers of the expanded material 12 and the space between the member segments 67 is partially or fully open. The layers of the expanded material 12 can be optionally positioned with the reinforcement 68 when the reinforcement 68 is in first size and shape. Because of the optional flexibility of the reinforcement 68, expanded material 12, or combinations thereof they can be changed to a second size and shape when assembled as described herein. The additives 60, nano size articles 62, or combinations thereof such as the active ingredients that are optionally located in the pockets 88, on the reinforcement 68, or between the layers of the expanded material 12 are optionally delivered to the surroundings.

The encapsulated additives 60 or nano size articles 62 such as the active ingredients can also be adapted so that one or a plurality of additives 60 or nano size articles 62 (or group thereof) are delivered through the top layer of the expanded material 12 and another (or group thereof) is delivered through the bottom layer of expanded material 12. For example, in a vascular stent-graft, an immunosuppressive agent can elute through the outside surface 16 in contact with the vessel and an anti-clotting agent can elute through the inside surface 17 that contacts the blood. It is also possible to regulate the amount of active ingredient delivered by the use of different structures such as the porosity of the expanded material 12. The delivery can also be additionally regulated through the use of the covering 56 on the expanded material 12, the amount of densification of the expanded material 12, microencapsulation, or combinations thereof. When installed, for example, in a blood carrying vessel the endothelium can partially or fully grow through the thru holes 89 to partially or fully line the inside surface of the assembly.

To overcome the potential problem of the coverings 56, additives 60, nano size articles 62, connecting materials 66, or combinations thereof from separating from the surfaces of the expanded material 12, reinforcement 68, or combinations thereof it is preferred that the outside surface 16, the inside surface 17, surfaces of the member segments 67, or combinations thereof are optionally treated or include one or a plurality of undercuts 76 to increase adhesion. The surface treatment or undercuts 76 which increase adhesion can also overcome the problem of delamination of multiple layers of the expanded material 12 or separation between the reinforcement 68 or the supporting member 64 and the expanded material 12. Without intent on limiting, the treatment is, for example, achieved by etching (e.g., glycol diethers, ethylene glycol dimethyl ether or monoglyme, diethylene glycol dimethyl ether or diglyme, tetraethylene glycol dimethyl ether or tetraglyme), chemical treatment, abrasion, thermal degradation, laser, corona treatment, plasma processing (e.g., oxygen, argon, nitrogen, ammonia), priming, etc. or combinations thereof.

Although it is preferred to manufacture the expanded material 12 (such as in the form of the expanded tubular profile 10) of indefinite length without seams, it is also possible within the scope of the present invention to produce other embodiments of tubular profiles from the expanded fiber 58, expanded sheet 42, or combinations thereof. As shown in FIG. 58, a woven tubular profile 144 can be partially or fully fabricated from the expanded fiber 58 of the same or different structure, for example, by weaving, felting, or knitting the expanded fiber 58 or yarn of continuous or discontinuous lengths into a tubular shape of one or more layers of the wall thickness 24. Weaving of the fiber 58 can be achieved by interlacing or interweaving one or more threads, strands, monofilaments, fiber bundles, or strips of the expanded fiber 58 of, for example, the weft and the warp on a loom. The woven tubular profile 144 can optionally include one or more strands of continuous or discontinuous lengths of the reinforcement 68 that are woven with the expanded fiber 58. Moreover, the woven expanded tubular profile 144 can optionally include one or more layers of the expanded sheet 42 or expanded tubular profile 10 of the same or different structures or supplementary reinforcements 68 of one or more segments positioned on or near the inside surface 17, the outside surface 16, or combinations thereof. The expanded fiber 58 can also optionally be woven into sheet configurations.

In addition, a nonwoven tubular profile 146 can be partially or fully fabricated from continuous or discontinuous lengths of the expanded fiber 58 of the same or different structure by nonwovens means as illustrated in FIG. 59. The nonwoven tubular profile 146 can also optionally include one or more strands of the reinforcement 68 that are continuous or discontinuous lengths. The nonwoven tubular profile 146 comprising the expanded fiber 58, reinforcement 68, or combinations thereof are typically held in tubular configuration by thermal treatment, by use one or more of the connecting materials 66, binder 69, or combinations thereof. Moreover, the nonwoven expanded tubular profile 146 can optionally include one or more layers of the expanded sheet 42, expanded fibers 58, expanded tubular profile 10 of the same or different structures or supplementary reinforcements 68 of one or more segments positioned on or near the inside surface 17, the outside surface 16, or combinations thereof. The expanded fiber 58 can also optionally be nonwoven into sheet configurations.

A seamed tubular profile 44 (not shown) is produced of one or more layers of the expanded material 12 by forming one or more expanded sheets 42 of the same or different structures into a tubular profile. For example, the first layer can have fibrils oriented axially and the second layer can have fibrils oriented circumferentially or multiaxially. The tubular profiles constructed of the expanded sheet 42 are generally held in tubular configuration with seams. The seams can be radial, helical, or longitudinal configurations, for example. A seam is formed by any means know by those skilled in the art of creating seams such as welding, baking, mechanical connection, electric discharge, hot plate or wire, magnetism, flame, heat, sewing, taping, gluing, fusion, welding, ultrasonics, etc. The seams can abut or overlap. Moreover, the seamed tubular profile 44 can optionally include one or more layers of the expanded sheet 42, expanded fiber 58 or expanded tubular profile 10 of the same or different structure or supplementary reinforcements 68 of one or more segments positioned on or near the inside surface 17, the outside surface 16, or combinations thereof.

The woven tubular profile 144, nonwoven tubular profile 146, or seamed tubular profile 44 can be optionally folded or pleated to temporarily or permanently change their sized and shape. Furthermore, they can be deformable or self-expanding from first size and shape to second size and shape.

The woven tubular profile 144, nonwoven tubular profile 146, seamed tubular profile 44, woven sheets, nonwoven sheets, or combinations thereof optionally include one or more additives 60, nano size articles 62, connecting material 66, or combinations thereof. The additives 60, nano size articles 62, or combinations thereof are optionally located on the inside surface 17, within the wall thickness 24, between layers, on the outside surface 16, or combinations thereof. The additives 60, nano size articles 62, or combinations thereof are optionally partially or fully an active ingredient. The nano size articles 62 are optionally useful in delivering active ingredients. The active ingredients are optionally microencapsulated. Inactive ingredients, connecting material 66 concentration, or combinations thereof are sometimes employed to dilute the active ingredients to achieve the desired dosage. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is constant rate, ascending rate, descending rate, changing rate, or combinations thereof. The delivery is immediate, time delayed, modified release, sustained, or combinations thereof.

The woven tubular profile 144, nonwoven tubular profile 146, seamed tubular profile 44, woven sheets, nonwoven sheets, or combinations thereof optionally include one or more layers of the covering 56 that partially or fully covers the inside surface 17, outside surface 16, or combinations thereof. Alternatively, the covering 56 optionally partially or fully covers the surfaces of the individual voids 28, fibrils 30, 32, 36, 38, nodes 34, or combinations thereof. The covering 56 is substantially permanent or erodible. The covering 56 optionally includes one or more additives 60, nano size articles 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. There are also optionally different concentrations or types of the active ingredient from one layer of the covering 56 to another layer of covering 56. There can also be different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is constant rate, ascending rate, descending rate, changing rate, or combinations thereof. The delivery is time delayed, modified release, sustained, or combinations thereof.

FIG. 60, which is illustrated in exploded isometric view, shows that a tubular profile is optionally constructed of two or more wall thicknesses 24 of one or more layers of the expanded material 12 such as the expanded tubular profile 10, expanded sheet 42, expanded fiber 58, woven tubular profile 144, nonwoven tubular profile 146, seamed tubular profile 44, or combinations thereof. In addition, FIG. 60 shows that the multiple wall thicknesses 24 optionally include one or more additives 60, nano size articles 62, connecting material 66, or combinations thereof disposed between the wall thicknesses 24. The wall thicknesses 24 are optionally comprised of one or more layers of the expanded material 12 of the same or different structure. The additives 60, nano size articles 62, or combinations thereof can also be optionally located within the wall thicknesses 24, on the outside surface 16, on the inside surface 17, or combinations thereof. The additives 60, nano size articles 62, or combinations thereof are optionally partially or fully an active ingredient. The nano size articles 62 are optionally useful in delivering the active ingredients. The active ingredients are optionally microencapsulated. Inactive ingredients, connecting material 66 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof. The delivery is optionally possible through the voids 28 in the wall thickness 24 of the expanded material 12. The uniformly expanded material 12 of the present invention provides an unusually accurate dosage of active ingredients especially when delivered over extended periods of time.

The multi layer tubular profile 46 like the one in FIG. 60 optionally includes one or more layers of the covering 56. The covering 56 is substantially permanent or erodible. The covering 56 partially or fully covers the inside surface 17, the outside surface 16, or combinations thereof. Alternatively, the covering 56 optionally partially or fully covers the surfaces of the individual voids 28, fibrils 30, 32, 36, 38, nodes 34, or combinations thereof. The covering 56 optionally includes one or more additives 60, nano size articles 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. There are also optionally different concentrations or types of the active ingredients from one layer of the covering 56 to another layer of the covering 56. There can also be different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, time delayed, modified release, sustained, or combinations thereof.

The expanded material 12 (such as the expanded tubular profile 10, expanded sheet 42, expanded fiber 58), reinforcement 68, or combinations thereof are optionally partially or fully cured-in-place such as in-vivo or in-vitro. The expanded material 12 can be cured-in-place independently or when assembled with the supporting member 64, reinforcement 68, or combinations thereof. It is possible that the expanded material 12 is partially or fully made of a material 14 that is curable-in-place. Alternatively, it is possible the expanded material 12 is adapted with a one or more curable coverings 56, connecting material 66, additives 60, nano size articles 62, or combinations thereof. The desirable curable material 14, covering 56, connecting material 66, additive 60, nano size article 62, or combinations thereof of the present invention is any material that provides flexibility for insertion, positioning, shaping, sizing, or combinations thereof and can be strengthened, hardened or otherwise modified to substantially maintain the best possible configuration, properties, and performance upon final location.

Again referring to FIG. 60, as an example of a tubular profile that is curable in place, the connecting material 66 is a light, temperature, radiation, moisture, microwave, ultrasonic, peroxide, or chemical reaction curable resin, material, or polymer. In this example, the curable connecting material 66 is disposed between two or more wall thicknesses 24 of the expanded material 12. The connecting material 66 is optionally contained in the expanded material 12 by at least partially connecting or sealing the two wall thicknesses 24 of the expanded material 12 at the ends 20 and 22. The uncured or partially cured connecting material 66 enables the tubular profile to be flexible so that it can be easily shaped, sized, and positioned. Upon achieving its ultimate configuration and location, the resin or polymer is cured-in-place so that it substantially maintains this configuration and location during its service life. An optional at least partially translucent expanded material 12 can facilitate the use of light curable materials. The connecting material 66, expanded material 12, or combinations thereof optionally include additives 60, nano size articles 62, or combinations thereof. It is preferred to include at least one fiber shaped additive 60, nano size article 62, or combinations thereof of any shape in a cure-in-place embodiment to provide additional strength. The expanded material 12 substantially protects the connecting material 66 against chemical or biological attack to maintain a substantially long service life. Optionally one or more layers of a barrier material, for example, in the form of another film or foil that is disposed anywhere between the connecting material 66 and the outside surface 16 and/or inside surface 17 can also be used to provide additional protection against degradation of the connecting material 66 and further extend the service life. Instead of using a curable connecting material 66, in the present invention a curable covering 56, material 14, additive 60, binder 69, or combinations thereof can also be utilized. The cure-in-place tubular profile can be a single or multiple wall thickness 24 of expanded material 12. A cure-in-place tubular profile is a useful alternative to utilizing a metallic stent or stent-graft to, for example, prop open a blood carrying vessel or repair an aneurismal vessel.

As other examples of cure-in-place expanded material 12, and without intent on limiting, it is possible within the scope of the present invention to partially or fully cover the outside surface 16, inside surface 17 or fill the voids 28 of the expanded material 12, or combinations thereof with a curable resin, material, or polymer. The resin, material, or polymer can be partially cured to eliminate surface tackiness prior to positioning. The covered or filled expanded material 12 can be, for example, collapsed in size and inserted into the supporting member 64. Upon positioning, sizing, and shaping to obtain the optimum configuration, the covered or filled expanded material 12 is cured-in-place to substantially maintain the customized fit obtained.

In a cure-in-place embodiment that uses a chemically reactive connecting material 66, additives 60, nano size articles 60, covering 56, or combinations thereof, the reactive components can be optionally temporarily separated by microencapsulation or nanoencapsulation of the reactive components. Therefore, the expanded material 12 can be easily positioned, sized, shaped, or combinations thereof and then cured-in-place by combining the reactive materials by, for example, breaking, dissolving, or melting the microencapsulation to release the reactive materials.

FIGS. 61 and 62 show an example of another embodiment of the expanded material 12 of the present invention. The coil shaped reinforcement 68 can have a helical member segment 67 that is straight as shown in FIG. 61 or the coil shaped reinforcement can optionally include a member segment 67 that contains, for example, one or more additional shapes such as curved, bent, helical, zig-zag, portions. The reinforcement 68 can be of any cross sectional shape that is of uniform or varying thickness. The coil shaped reinforcement 68, which is shown in side view in FIG. 61 and in cross sectional end view in FIG. 62, is covered with one or more layers of the expanded material 12 (that is in the form of the expanded tubular profile 10, the expanded sheet 42, the expanded fiber 58, or combinations thereof). The ends 20 and 22 of the expanded material 12 are optionally partially or fully closed or sealed to partially or fully encapsulate the reinforcement 68. The ends of the coil shaped reinforcement 68 can be optionally welded or otherwise connected to the last coil. The weld or connection can be optionally deburred and/or polished or otherwise blunted. The member segment 67 itself can be covered with expanded material 12 as shown in FIG. 62 or the inside surface, outside surface, or combinations thereof of the entire coil shaped reinforcement 68 can be covered with the expanded material 12 (not shown).

FIG. 63, which is another embodiment of a cross sectional end view of the coil shaped reinforcement 68 in FIG. 61, shows that the coil shaped reinforcement 68 optionally includes the covering 56, additives 60, nano size articles 62, connecting material 66, or combinations thereof. The additives 60, nano size articles 62, connecting members 66, or combinations thereof are optionally disposed within the expanded material 12, on the inside surface 17, on the outside surface 16, between the layers of the expanded material 12, or as shown in FIG. 63 between the reinforcement 68 and the expanded material 12, or combinations thereof. The additives 60, nano size articles 62, or combinations thereof are optionally partially or fully an active ingredient. The nano size articles 62 are optionally useful in delivering the active ingredients. The active ingredients are optionally microencapsulated. Inactive ingredients, connecting material 66 concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof. The delivery is optionally possible through the voids 28 in the wall thickness 24 of the expanded material 12. The uniformly expanded material 12 of the present invention provides an unusually accurate dosage of active ingredients especially when delivered over extended periods of time.

The coil shaped reinforcement 68 optionally includes one or more layers of the covering 56 that partially or fully covers its surface. The covering 56 is substantially permanent or erodible. The covering 56 optionally includes at least one additive 60, nano size article 62, or combinations thereof. The additives 60, nano size articles 62, or combinations thereof are optionally partially or fully an active ingredient. The nano size articles 62 are optionally useful in delivering active ingredients. The active ingredients are optionally microencapsulated. There are optionally different concentrations or types of active ingredients from one layer of the covering 56 to another layer of the covering 56. There can also be different types of covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

The outside surface 16, inside surface 17, or combinations thereof of the expanded material 12 optionally covering the coil shaped reinforcement 68 also optionally contains one or more layers of the covering 56. The covering 56 is substantially permanent or erodible. The covering 56 partially or fully covers the outside surface 16 or the inside surface 17. Alternatively the covering 56 partially or fully covers the surfaces of the individual voids 28, fibrils 30, 32, 36, 38, nodes 34, or combinations thereof. The covering 56 optionally includes at least one additive 60, nano size article 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. There are optionally different concentrations or types of active ingredients from one layer of the covering 56 to another layer of the covering 56. There can also be different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

FIGS. 65 and 66 show yet another embodiment of a tubular profile of the present invention. FIG. 65, which illustrates the tubular profile in cross sectional side view, and FIG. 66, which illustrates the tubular profile of FIG. 65 in cross sectional end view, show a tubular profile having a wall thickness 24 that is partially or fully comprised of a flattened tubular profile 78. The flattened tubular profile 78 optionally includes the reinforcement 68 disposed in the bore 18 of the flattened expanded tubular profile 78 as shown in FIG. 69. The reinforcement 68 optionally includes the previously described sharp end, the blunt end, or combinations thereof. The reinforcement 68 can slide within the wall thickness 24 or be immovable. The reinforcement 68 optionally has size memory, shape memory, or combinations thereof. The reinforcement 68 is optionally self-expanding, mechanically expandable, spring-like, bendable to any curvature, or combinations thereof. The tubular profile of FIGS. 65-66 can be optionally augmented with one or more other reinforcements 68 of one or more segments as previously described that are disposed on or near the inside surface 17 or outside surface 16 of the tubular profile.

To fabricate the tubular profile having the wall thickness 24 comprising the flattened tubular profile 78, the unflattened expanded tubular profile 10, as shown in FIG. 68, is partially or fully flattened as shown in FIG. 69. Referring back to FIGS. 65 and 66, the flattened tubular profile 78 is formed into a tubular shape and a plurality of edges 84 are partially or fully connected to maintain the flattened tubular profile 78 in the tubular shape. Connecting the edges 84 optionally forms a seam that is partially or fully leak-proof in the wall thickness 24 of the tubular profile. As shown in FIGS. 68 and 69, the flattened tubular profile 78 optionally includes the reinforcement 68 disposed in the bore 18. When the flattened tubular profile 78 includes one or more strands of the reinforcement 68, the tubular profile can be a self-supporting tubular profile 82. As shown in FIG. 67, which is shows the flattened tubular profile 78 in plan view, the reinforcement 68 that is disposed in the bore 18 of the flattened tubular profile 78 can be a zigzag shape. Alternatively, the reinforcement 68 can be any shape such as straight, bent, curved, criss-cross, etc. The reinforcement 68 can also be of one or more strands that are single segment, multiple segments, woven, nonwoven, knitted, twisted, braided, mesh, or combinations thereof.

The flattened tubular profile 78 shown in FIGS. 65-66 can be alternatively substituted in this embodiment with a layered flat profile 80 shown in FIG. 71. As shown in FIGS. 70 and 71, which are shown in cross sectional view, the layered flat profile 80 is fabricated by partially or fully attaching two or more layers of the expanded sheet 42 of the same or different structure. The layered flat profile 80 optionally includes the reinforcement 68.

The tubular profile comprising the wall thickness 24 that is a flattened tubular profile 78 or layered flat profile 80 can optionally include one or more additional layers of expanded material 12 (that are comprised of the expanded tubular profile 10, the expanded sheet 42, the expanded fiber 58, or combinations thereof) of the same or different structure. These other layers can be disposed on or near the inside surface 17, the outside surface 16, or combinations thereof. Furthermore, the wall thickness 24 of this type of tubular profile can optionally further include one or more additional layers of flattened tubular profile 78, layered flat profile 80, supplementary reinforcements 68 of one or more segments, or combinations thereof disposed on or near the inside surface 17, outside surface 16, or combinations thereof.

The flattened tubular profile 78 or the layered flat profile 80 optionally includes one or a plurality of additives 60, nano size articles 62, connecting members 66, or combinations thereof. The additives 60, nano size articles 62, or combinations thereof are optionally partially or fully an active ingredient. The nano size articles 62 are optionally useful in delivering active ingredients. The active ingredients are optionally microencapsulated. Inactive ingredients, connecting material 66 concentration, or combinations thereof are sometimes employed to dilute the active ingredients to achieve the desired dosage or dosage distribution. The additives 60, nano size articles 62, or combinations thereof such as the active ingredients are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof. The delivery is optionally possible through the voids 28 in the wall thickness 24 of the expanded material 12. The uniformly expanded material 12 of the present invention provides an unusually accurate dosage of active ingredients especially when delivered over extended periods of time.

The tubular profile having a wall thickness 24 of the flattened tubular profile 78 or the layered flat profile 80 optionally includes one or more layers of the covering 56. The covering 56 partially or fully covers the outside surface 16, inside surface 17, or combinations thereof. The covering 56 is substantially permanent or erodible. The covering 56 optionally includes one or a plurality of additives 60, nano size articles 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. There are optionally different concentrations or types of the active ingredients from one layer of covering 56 to another layer of covering 56. There can also be optionally different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano sized articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

The reinforcement 68 disposed in the flattened tubular profile 78 or layered flat profile 80 optionally includes one or more layers of the covering 56. The covering 56 is substantially permanent or erodible. The covering 56 optionally includes at least one additive 60, nano size article 62, or combinations thereof. The additives 60, nano size articles 62, or combinations thereof are optionally partially or fully an active ingredient. The nano size articles 62 are optionally useful in delivering active ingredients. The active ingredients are optionally microencapsulated. There can also be optionally different concentrations or types of active ingredients from one layer of the covering 56 to another layer of the covering 56. There can also be optionally different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano sized article 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

FIGS. 72 and 73 show one more embodiment of the expanded material 12 of the present invention that is a casing 90. The casing 90 is shown in top plan view in FIG. 72 and in cross sectional side view in FIG. 73. The casing 90 is formed of any size and shape when one or more layers of the expanded material 12 (such as the expanded tubular profile 10, expanded sheet 42, expanded fiber 58, or combinations thereof) of the same or different structure are in a tubular shape that has the first end 20 and the second end 22 partially or fully closed with an end seal 94 to partially or fully encapsulate the contents 26. The casing 90 can be of any size or shape.

Alternatively, the contents 26 can be encapsulated with a shell 92 of any size or shape. The shell 92 is shown in top plan view in FIG. 74 and in cross sectional side view in FIG. 75. The shell 92 is formed of two or more layers of the expanded material 12 of the same or different structure such as the expanded sheet 42, expanded fiber 58, or combinations thereof. The shell 92 partially or fully encapsulates the contents 26 by partially or fully connecting the top layer to the bottom layer of the expanded material 12 around the perimeter of the shell 92 with a top/bottom seal 96.

As shown in FIGS. 73 and 75, the casing 90 or the shell 92 optionally includes one or more of the contents 26, the connecting material 66, binder, vehicle, or combinations thereof. The contents 26, connecting material 66, binder, vehicle, or combinations thereof can be positioned before, during, or after assembly of the casing 90 or the shell 92. The contents 26 are additives 60, nano size articles 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. Inactive ingredients, connecting material 66 concentration, vehicle concentration, binder concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof. The delivery is optionally possible through the voids 28 in the wall thickness 24 of the expanded material 12. The uniformly expanded material 12 of the present invention provides an unusually accurate dosage of active ingredients especially when delivered over extended periods of time. The delivery is also possible through the end seal 94 or the top/bottom seal 96.

The casing 90 or the shell 92 optionally includes one or more layers of the covering 56. The covering is substantially permanent or erodible. The covering 56 partially or fully covers the outside surface 16, inside surface 17, or combinations thereof. Alternatively, the covering 56 partially or fully covers the individual voids 28, fibrils 30, 32, 36, 38, nodes 34, or combinations thereof. The covering 56 optionally includes at least one additive 60, nano size article 62, or combinations thereof. The additives 60, nano size articles 62, or combinations thereof are optionally partially or fully an active ingredient. The nano size articles 62 are optionally useful in delivering the active ingredients. The active ingredients are optionally microencapsulated. There are optionally different concentrations or types of the active ingredients from one layer of the covering 56 to another layer of the covering 56. There can also be different types of the covering 56 from one layer of the covering 56 to another layer of the covering 56. Inactive ingredients, covering 56 concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

It is possible within the scope of the present invention to nest one or more casings 90 or shells 92 within other casings 90 or shells 92 of like or different construction or structure. Furthermore, the contents 26 can be coated or otherwise encapsulated (e.g. microencapsulation) in discrete or aggregated forms. The expanded material 12, coverings 56, or combinations thereof of the casings 90 or shells 92 can be partially or fully indigestible, non-biodegradable, biodegradable or digestible material 14 depending on the requirements of the end-use application.

The casing 90 and the shell 92 are useful for, but not limited to, the administration or storage of active ingredients such as medications. For instance, the casings 90 or shells 92 can be orally ingested, temporarily or permanently medically implanted, positioned on the skin or inserted through the rectum, vagina, ureter, sinus, or other orifices as a suppository for humans or other mammals.

FIG. 76 illustrates that the expanded material 12 (in the form of the expanded tubular profile 10) optionally includes an annular seal 154 which can cover the entire expanded material 12 or be limited to being only on first end 20, second end 22, (e.g. at or near orifices) or combination thereof. The annular seal 154, for example, creates a seal between the outside surface 16 of the expanded tubular profile 10, reinforcement 68, or combinations thereof and the inside surface of the supporting member 64. The annular seal 154 is, for example, comprised of sealing surfaces such as protrusions, curved protrusions, angular protrusions, o-rings, cuffs, gaskets, grooves, or combinations thereof. The first end 20, second end 22 or combinations thereof optionally include barbs or other means that mechanically grab or hold the annular seal 154 with the supporting member 64 in a substantially leak-proof position. The annular seal 154 is optionally held in compression against the supporting member 64 by the reinforcement 68 which can partially or fully cover the length of the expanded material 12. The supporting member 64 is optionally supported by a collar 156 that is somewhat rigid and maintains the end seal 154 in compression to maintain a substantially leak-proof seal during service life, especially when the supporting member 64 is comprised of a pliable material. The collar 156 is optionally hinged and/or contains clamping means to allow the cuff to be opened and secured around the supporting member 64. The annular seal 154 preferably directs the contents 24 that are, for example, flowing in the supporting member 64 to flow into the bore 18 of the expanded material 12 (such as the expanded tubular profile 10), reinforcement 68, or combinations thereof without bypassing the expanded tubular profile 10 and filling a sac 158. If, for example, the supporting member is a blood carrying vessel, it is preferable to have little or no endo leakage into the sac. It is optionally possible to insert the expanded material 12 (such as the expanded tubular profile 10) in a folded configuration or reduced size into the supporting member 64 through an incision in the sac so that the sac is taken out of service after installation and the area between the expanded tubular profile's 10 outside surface 16 and the supporting member's 64 sac 158 is unpressurized. Of course, the expanded tubular profile 10 can also be inserted upstream or downstream of the sac 158 or wherever possible.

DETAILED DESCRIPTION OF THE PREFERRED EMBODIMENTS

The expanded material 12 such as the expanded tubular profile 10, expanded sheet 42, expanded fiber 58, or combinations thereof can be any shape. In addition to the round shaped expanded tubular profile 10, as shown in FIG. 1, a few other examples of shapes include oval-shaped, rectangular-shaped, square-shaped, octagon-shaped, hexagon-shaped, triangular-shaped, pleated, multilobal, concave polygon-shaped, decagon-shaped, diamond-shaped, dodecagon-shaped, elliptical-shaped, isogon-shaped, nonagon-shaped, parallelogram-shaped, pentagon-shaped, polygonal-shaped, quadrangle-shaped, quadrilateral-shaped, rhombus-shaped, spherical polygon-shaped, star-shaped, trapezoid-shaped, undecagon-shaped, or combinations thereof, etc. Moreover, in some cases, like when the wall thickness 24 is thin, the shape can be somewhat amorphous. In addition, the shape may contain other functional, decorative, ornamental or architectural details.

The length of the expanded material 12 such as the expanded tubular profile 10, expanded sheet 42, expanded fiber 58, or combinations thereof from first end 20 to second end 22 can be definite or indefinite. The optional contents 26 can flow from first end 20 to second end 22 or be motionless.

Although it may be less uniform, if the end-use application requires, the expanded material 12 (like the expanded tubular profile 10) can be optionally adapted to be tapered, for example, from first end 20 to second end 22. For example, the expanded tubular profile 10 can be larger on first end 20 than on second end 22. Alternatively, it can be larger or smaller on the ends than at the middle section.

The outside surface 16 and inside surface 17 of the expanded material 12 can be partially or completely smooth or rough. Furthermore, its wall thickness 24 can be partially or completely opaque, translucent, or transparent.

Although some of the illustrations in the figures show the structure of the expanded material 12 such as the fibrils 30, 32, 36, 38, voids 28, and nodes 34 as essentially identical in size and in shape, they can in practice have an infinite variety of shapes and sizes within the scope of the present invention. Moreover, the optional nodes 34 can sometimes or always be clumped together, attached to one another, or be hollow.

The fibrils 30, 32, 36, 38 of the present invention can be of any length that meets the requirements of the end-use application, but they are preferably in the range of about 0 to 25,000 microns, more preferably in the range of about 0 to 500 microns, and most preferably in the range of about 0 to 250 microns. The fibrils 30, 32, 36, 38 can be of any cross sectional size but are generally in the range of about 0 to 10 microns, more preferably in the range of about 0.0005 to 5 microns, and most preferably less than 0.5 micron. The cross sectional size of the fibrils 30, 32, 36, 38 can also vary across the length of the fibrils. The voids 28 in material 14 can range from about 0 to 99 volume percent. The voids 28 can be any size that meets the requirements of the end-use application, but it is preferable to have a nominal void 28 size in the range of about 0.05 to 0.4 microns for the expanded material 12 when used in high efficiency filtration end-use applications. The nodes 34 can be any size that meets the requirements of the end-use application, but they are preferably in the range of about 0 to 2,500 microns, more preferably in the range of about 0 to 500 microns, and most preferably in the range of about 0 to 50 microns. The size and shape of the fibrils, voids, and nodes can vary from embodiment to embodiment, but it is preferable to minimize this variation within an embodiment to produce a uniformly expanded material 12.

The expanded material 12 of the present invention is obtained by stretching or drawing any material 14 during the manufacturing process in the axial direction, circumferential direction, or combinations thereof. As previously indicated, the expanded material can also be produced by stretching in sheet configuration but this produces a less uniform product. This is achieved, for example, by stretching the material 14 during or after the extrusion process at an elevated temperature. Optionally, blending of the material 14 to be expanded with any solvent, lubricant or another aid prior to stretching the material 14 can facilitate the expansion process.

Circumferential stretching is imparted on the unexpanded tubular profile 104 by stretching the unexpanded tubular profile 104 in any way from its first diameter D1 to a second larger diameter D2. Increasing the diameter through a circumferential force 142 increases the circumference of the unexpanded tubular profile 104 making it larger. The expanded tubular profile 10 can be optionally stretched a second time to take its diameter from a second diameter D2 to a third diameter D3 . In fact, the tubular profile can be stretched circumferentially an infinite amount of times in vary degrees and/or rates of expansion. For illustration purposes only and without intent on limiting, the tubular profile has a first diameter D1 of 50.8 mm (2 inches), a second diameter D2 of 101.6 mm (4 inches) and a third diameter D3 of 203.2 mm (8 inches). Therefore, the first stretch is 100% or 2:1. Likewise, the second stretch is 100% or 2:1. To achieve a uniformly expanded tubular profile 10 having a uniform structure, it is important to carefully control the expansion from first diameter to subsequent diameters. Alternatively, an unexpanded sheet can be optionally stretched from first width to second width, third width and so on if produced in sheet form.

To achieve a uniformly expanded material 12 (such as the expanded tubular profile 10) the final circumference and/or diameter preferably does not vary in size from first end 20 to second end 22 more than about 200%, preferably no more than the range of about 0-50% and most preferably no more than the range of about 0-15%.

Axial stretching is imparted on the unexpanded tubular profile 104 by stretching the unexpanded tubular profile 104 from its first length L1 to its second length L2. The expanded tubular profile 10 can be optionally stretched a second time to take its length from a second length L2 to a third length L3. The tubular profile can be axially stretched an infinite amount of times in varying degrees and/or rates of expansion. For illustration purposes only and without intent on limiting, the tubular profile has a first length L1 of 152.4 mm (6 inches) a second length L2 of 304.8 mm (12 inches) and a third length L3 of 609.6 mm (24 inches). Therefore, the first stretch is 100% or 2:1. Likewise, the second stretch is 100% or 2:1. To achieve a uniformly expanded tubular profile 10 having uniform cross section, it is important to carefully control the expansion from first length to subsequent length.

The material 14 or the expanded material 12 of the present invention can be stretched circumferentially, axially, or any combinations thereof an infinite amount of times at any rate of stretch, change in size, temperature, or combination thereof up to the point of substantially breaking the wall thickness 24. In addition, the stretching can alternate between circumferential and axial stretching in an infinite amount of combinations.

The present invention of stretching the material 14 or the expanded material 12 in tubular configuration also has the advantage of manufacturing the expanded sheet 42 utilizing far less space. For example, to produce an expanded sheet 42 that is 1 meter (39.37 inches) wide as described in the prior art requires a machine that is at least that wide. In contrast, the preferred process of the present invention only requires equipment about 0.32 meters (12.53 inches) wide. This represents a reduction in space requirements of 68 percent. A smaller manufacturing space and equipment also consume far less energy during processing.

The expanded sheet 42 of the present invention has a significantly more uniform wall thickness 24, structure, and density across its entire width from third end 48 to fourth end 50 when compared to the heterogeneous expanded sheets described in the prior art. According to the prior art, the sheets are normally gripped at the third end 48 and fourth end 50 when stretching in the cross direction. Due to a phenomena frequently referred to as necking-down, when the sheet of the prior art is stretched by gripping at or near the third end 48 and fourth end 50 it is much thinner around the center and thicker or denser around the third end 48 and fourth end 50 after stretching. The areas near the third end 48 and fourth end 50 of the expanded sheet produced according to the prior art can also be damaged or punctured from gripping. In fact, it appears as though a significant amount of the material 14 is rendered waste when using the process of the prior art because the inconsistent or damaged ends near third end 48 and fourth end 50 have to be trimmed off. The wasted material 14 of the prior art substantially increases the cost of producing the stretched expanded material 12.

The prior art method of producing porous expanded material 12 in sheet configuration also has the disadvantage of being more permeable or porous at the center section and less permeable or porous at the areas near third end 48 and fourth end 50 where it can be thicker or denser. Therefore, the porous expanded material 12 of the present invention that is produced in tubular configuration and then slit into a sheet configuration is far more uniformly expanded producing essentially more uniform void size, void distribution, node size, node distribution, fibril size, fibril distribution, or combinations thereof. The net result is a higher quality, lower cost material that is suitable for many end-use applications.

It is possible to examine the uniformity of the expanded material 12 by measuring the void size, void distribution, fibril length, node size, node distribution, strength, or permeability. To have a uniformly expanded material 12 there should be minimal variation around the circumference of an expanded tubular profile 10 or from third end 48 to fourth end 50 on an expanded sheet 42 without trimming off unexpanded or partially expanded sections. For example, the mean length of fibrils 30, 32, 36, 38 located at or near the center of the expanded sheet 42 preferably vary less than about 50 percent, more preferably less than about 25 percent, and most preferably less than about 15 percent when compared to fibrils 30, 32, 36, 38 located at or near the third end 48 or fourth end 50 of the expanded sheet 42.

The expanded material 12 such as the expanded tubular profile 10, expanded sheet 42, or expanded fiber 58 can be any size and thickness. Typically its width or diameter will range from under about 0.0127 mm (0.0005 inch) to about 3.7 m (144 inch) or larger. The wall thickness 24 of the expanded material 12 of the present invention ranges from under about 0.000254 mm (0.00001 inch) to about 101.6 mm (4 inches) thick or larger. Preferably, the expanded material 12 has a wall thickness 24 of under about 0.00127 mm (0.00005 inch) to about 50.8 mm (2 inches thick) and most preferably from about 0.00127 mm (0.00005 inch) or under to about 6.4 mm (0.25 inch) thick or larger. The wall thickness 24, however, varies according to the size of the expanded material 12 (such as the expanded tubular profile 10, expanded sheet 42, or expanded fiber 58) and the design requirements of the end-use application. For example, very small diameter tubular profiles used in medical applications or treatments can require even thinner wall thicknesses. The optimum wall thickness 24 can be experimentally determined by those skilled in the art of engineering. In addition, the dimensions can be regulated by governmental or industry codes and standards.

Although it depends on size, in general for vascular grafts and stent-grafts the preferred wall thickness 24 of the expanded material 12 is less than about 1 mm (0.039 inch), more preferably less than about 0.5 mm (0.019 inch), and most preferably less than about 0.2 mm (0.007 inch). The mean fibril length is preferred to be in the range of about 0 to 0.15 mm (0 to 0.0059 inch), more preferably in the range of about 0 to 0.09 mm (0 to 0.0035 inch), and most preferably in the range of about 0 to 0.03 mm (0 to 0.0011 inch). The preferred void 28 size is preferably less than about 0.01 mm (0.0004 inch), more preferably less than about 0.005 mm (0.0002 inch), and most preferably less than about 0.003 mm (0.0001 inch).

Without intent of limiting, the expanded material 12 (such as the expanded tubular profile 10, expanded sheet 42, expanded fiber 58), reinforcement 68, or combinations thereof are useful in any medical applications or treatments such as, for example,: abdominal aortic aneurysms; aneurysm repair; AAA (Abdominal Aortic Aneurysm) grafts; abrasion resistant gum grafts; actinic keratoses; acute inferior-wall myocardial infarction; acute nonlymphocytic leukemia; acute promyelocytic leukemia; adipose tissue; administration of drugs (orally; through skin; internally; implantation; suppository; etc); alcoholism; allergies; allografts; allograft substitutes; alloplastic materials; alveolar bone regeneration; ana plastic cancers; anastomosis devices; anastomosis of the ureter; anemia; aneurismal vessels; aneurysms; aneurysm in the iliac arteries; angioplasty; angioplasty/stenting; angioplasty/stenting in the kidneys; angioplasty/stenting in blood carrying passageways; angioplasty/stenting in the legs; angioplasty balloon; angioplasties of graft-artery anastomotic strictures; animal implants; anorexia; anxiety; aortic aneurysms; aortic therapy; aortic vessels; appetite suppressants; artificial pancreas; arteries; artery and vein tissue; articular cartilage tissue; asthma; atrial septal defects; arterial atherosclerotic lesions; atherectomy; atherosclerosis; autogenous grafts; autografts; autoimmune diseases; baldness; balloon catheters; bandages; bariatric surgical procedures; basal cell carcinoma; basilar trunk aneurysm; bifurcated stents; bifurcated grafts; bifurcated stent-grafts; bifurcated endoprosthesis; bioabsorbable grafts; bioabsorbable stents; bioabsorbable stent-grafts; biliary ducts; biliary stent; biliary stent-grafts; biliary grafts; biluminal endovascular grafts; bioactive coils; biopsy channels; biomedical products; birth control; bladder; bladder cancer; bladder tissue; blepharoplasty; blood; blood disorders; blood testing; blood vessels; body lumens; body weight reduction; bone graft; bone graft containment; bone augmentation; bone metastases; bone substitutes; bone tissue; bones; bowel anastomosis; bowels; bowel stenting; brain; brain [stem] implants; brain cancer; brain tumors; breast; breast cancer; breast enlargement; breast grafts; breast implants; breast reshaping; brow lifts; burns; bypass grafts; cachexia; canthoplasty; cancellous bone; cancer; cancer fighting drugs; cancer in postmenopausal women; cancer of oral cavity; cancer of the adrenal cortex; cancer of the endometrium; cancer of the larynx (voice box); cancer of the pancreas; cancer of the parathyroid; cancer of the thyroid gland; cancer of tissues of the lip or mouth (e.g.; tongue; gums; lining of cheeks; bottom of mouth; hard & soft palate; retromolar trigone); cancers; cancers of the blood; cancers of the nasal cavity; candidiasis; capsules; carcinoid syndrome; carcinoid tumors; cardiovascular disease (CVD); cardiovascular patches; carotid artery stenting (CAS); casts; catheters; cells; cervical cancer; choriocarcinoma; chronic myeloid leukemia (CML); chronic or acute inflammation; cloning; colesterol lowering drugs; colitis; collagen vascular disease; colon; colon cancers; colon grafts; colon stenting; colorectal cancers; colostomy bag attachment devices; condyloma acuminata; congenital heart disease; connective tissue disorders; constipation; contact lenses; contraceptives; controlled onset capsules; controlled onset grafts; controlled onset stent-grafts; controlled onset stents; controlled onset tablets; cortical bones; cornea; colon stents; colon grafts; coronary arteries; coronary artery bypass grafts (CABG); cosmetic surgery; cutaneous T-cell lymphoma; cyanotic congenital heart disease; cytomegalovirus (CMV); de novo lesions; decreasing anxiety; decreasing seizures; deep venous thrombosis (DVT); defibrillators; delayed release capsules; delayed release grafts; delayed release stent-grafts; delayed release stents; delayed release tablets; dental; dental and oral surgery articles; dental floss; dentistry; dermal applications; devices or medications that regulate heart (rate; beat; flow; pressure; etc.); diabetes; dialysis access applications; dialysis equipment; dialysis grafts; diarrhea; diet; digestive tract; diseases; diseases of the thoracic aorta; diseases of the superficial femoral artery; diseases of the bone marrow; drug containing dental floss; drug delivery devices; drug-eluting dental floss; drug-eluting grafts; drug-eluting implants; drug-eluting sutures; drug-eluting stents; DTP/IPV/Hib & Men C; Duke's Stage C colon cancer; ear tubes; embolic filters; electrophysiology devices; endometrial cancer; endoprosthesis; endografts; endoscopes; endoprosthesis stent-grafts; endovascular aneurysm repair (EVAR); endografts; endovascular grafting; endovascular stent-grafts; endovascular therapy; Epstein-Barr virus; erectile dysfunction; esophageal stenting; eustachian tube dysfunction; eliminate or reduce danger of occlusion caused by flaps resulting from intimal tears associated with angioplasty; extended release capsules; extended release grafts; extended release stent-grafts; extended release stents; extended release tablets; eyes; face lifts (SMAS); fertilization; femoral closures; femoral-popliteal stents; forehead lifts; filling void after tooth extraction; flu; flu vaccines; follicular cancers; Fontan Procedure; fracture fixation; fractionated dose chemotherapy; fungal and protozoal infections; gastric bypass and banding; gastroepiploic artery (GEA); gastrointestinal stromal tumors (GIST); gene therapy; germ cell cancers; glioblastoma multiforme (GBM); gout; grafts; gram-negative and gram-positive bacteria; guided tissue regenerative devices; gum grafts; gums; haemophilus influenzae type b (Hib); hair implants or replacements; hairy cell leukemia; head and neck cancer; healthcare articles; heart; heart conditions; heart beat regulation and management; heart disease; heart tissue; heart valves; hematologic diseases; hemorrhoids; hemostatic barriers; hepatectomy; hernia; hernia repair; hernia plug; herpes simplex; herpes viruses; herpes zoster (shingles); hip replacement; high blood pressure; HIV/AIDS fighting drugs; Hodgkin's disease; homografts; hormonal abnormalities; human body diseases; human or animal implants; human or animal joints; human or animal oral medications; hyaline cartilage tissue; hypercalcemia (high calcium level in the blood); hypertension; hypertrophy of the prostate gland; iliac stents and stent-grafts; immunizations; immunotherapy; implantable pumps; implants; implants generating electrical impulse; implants that influence body functions or movements; impotence; inactivated polio vaccine (IPV); increase metabolism; incontinence implants; infection (e.g. in the lungs; throat; sinuses; kidneys; bladder; abdomen; and skin); infections of female reproductive organs; infections of the urinary and lower respiratory tract; infections of throughout the body (septicemia); inflammatory bowel disease (e.g., Crohn's disease); interatrial defects; influenzas; injuries; insomnia; internal thoracis artery grafts (ITA, mammary artery); interventional devices; intestinal grafts; intestinal surgery; intestinal tissue; intestinal tracts; intestinal grafts; intestinal stents; intestinal stent-grafts; intimal smooth muscle cell hyperplasia; intracranial aneurysms; intravascular delivery devices; intravascular radiation delivery devices; intraluminal devices; intraluminal grafts; intralumincal grafts; intraocular lenses; intracranial atherosclerotic disease (ICAD); ischemic disease; joint replacement; kaposi's sarcoma (KS); keratoconus; kidney cancer; kidney grafts; kidney disease; knee replacement; laboratory testing; laryngotracheal stenting; laxative; leads for pace makers and implantable defibrillators; LITA-LAD grafts; left main coronary artery; glaucoma; lesions; lesions at a bifurcation; lesions in coronary arteries; lesions located in saphenous vein; leukemia; leukemia in the spinal fluid; ligament reconstruction; ligament tissue; limb kinking; limb occlusion; limb thrombosis; liver; liver cancer; liver disease; living tissue; lower blood pressure; lung; lung cancer; lymphoblastic leukemia (ALL); lymphocytic leukemia; lymphoma; malar, chin & nasal reconstruction; melanoma; malignant melanoma; malignant pleural mesothelioma; mastectomy; measles; mumps & rubella (MMR); medical devices; medications; medullar cancers; meningococcal C vaccine (Men C); mental disorders; mesh; metastatic breast cancer; metastatic cancers; metastatic ovarian cancer; microarterial anastomoses; minimally invasive treatments; micro stents; micro grafts; mitral valve prolapse; modified release grafts; modified release stent-grafts; modified release stents; modified release capsules; modified release casings;

modified release shells; Modified Blalock-Taussig and Blalock-Taussig shunts; molecular targeted therapy; multiple myeloma; multiple sclerosis; multiple vessels; coronary disease; muscle; muscle relaxants; muscle tissue; mycosis fungoides; myelocytic leukemia; myelodysplastic syndromes; myelogenous leukemia; myeloid leukemia; myeloma; myocardial infarction; nasal grafts; nasopharyngeal cancer; nasal reconstruction; nausea and vomiting; nausea and vomiting caused by chemotherapy; neck cancer; nerve repair; nervous system; neurosurgery; neurologic disease; neurofibromatosis arterial stenoses; neuropathic pain; nephroureteral stenting; neurological devices; non-Hodgkin's lymphoma; nonlymphocytic leukemia; non-small cell lung cancer (NSCLC); oncologogy; occluded superficial femoral artery (SFA); ophthalmic procedures; oral capsules; oral surgery; oral tablets; organs; orthopedics; orthopedic prostheses; ossicular reconstruction; osteoarthritis; osteogenic sarcoma; osteoporosis; ostial lesions; ostomy appliances; ovarian cancer; pacemakers; pancreatic stenting; pancreatic cancer; pancreas; pancreatitis; papillary cancers; paranasal sinuses cancer (including the frontal sinuses above the nose; the maxillary sinuses in the upper part of either side of the upper jawbone; the ethmoid sinuses just behind either side of the upper nose; and the sphenoid sinus behind the ethmoid sinus in the center of the skull and nasal cavity); patches; Parkinson's disease; percutaneous coronary revascularization (PCR); percutaneous coronary interventions (PCI); percutaneous balloon dilation of elastic vascular stenoses or blockages through use of a catheter mounted angioplasty balloon; percutaneous angioplasty of Takayasu arteritis; penile implants; peripheral vascular stents and stent-grafts; periodontal tissue; periodontal tissue regeneration; peripheral nerve injuries; peripheral vascular disease (PVD); periodontal & bone defects; peritoneovenous shunts; Peyronie's disease; pharmaceuticals; pharynx cancer (including the hypopharynx; nasopharynx and oropharynx; throat); pills; polycythemia vera anemia; popliteal aneurysm; porto-biliary fistula; positioning in urethral lumen; prevention of motion sickness; promyelocytic leukemia; prophylactic medications; prostate cancer; prostate enlargement; prosthesis; prosthetics; prostrate; psychotic illnesses; pulmonary conditions; radial artery grafts; reconstructive breast surgery; reconstructive surgery; rectal cancers; rectal grafts; rectal stents and stent-grafts; rectal tissue; reduction or shrinkage of aneurismal (sac); regrow nerve fibers or organs; reinforce collapsing structures; reinforce collapsing structures in respiratory tracts, digestive tracts, blood vessels, and biliary tracts; rectus sheath grafts; relaxing blood vessels; relaxing vessels; renal cell cancer; renal cell carcinoma (RCC) tumors; renal impairment; renal grafts; renal stents and stent-grafts; renal transplants; renal transplants; repair of aneurysms; repair of living cells; tissues or organs; replacement of living vessels, tissues or organs; repairs; replacement; repair of ligaments (e.g. anterior cruciate ligament [ACL], posterior cruciate ligament [PCL]); repair of tendons; reproduction of life; reproduction system; reproductive system implants; respiratory tracks; restenosis; retinoblastoma; revascularization procedures; rheumatoid arthritis; rotating joints; saphenous vein grafts; scaffolds; schizophrenia; seizures; shunts; shunts for hydrocephalus; sickle cell anemia; sinus grafts; sinus stenting; skin; skin grafts; skin cancer; skin lesions; skin tissue; skin tumors; small cell lung cancer; soft tissue repair; soft tissue suspension, augmentation, or recontouring; somatic cell nuclear transfer (SCNT); spinal cord; staphylococcal ("staph") infections; stenosis; spinal repair; stenosis of the renal artery (e.g., at ostium); stent-grafts; stenting; stents; stents in femoral ateries; stomach; stomach graft; stomach tissue; stomach cancer; stroke; subcutaneous augmentation material; suppositories; surgical implants; surgical meshes; surgical procedures; sustained release; sustained release capsules; sustained released grafts; sustained release stent-grafts; sustained release suppositories; sustained release tablets; suture anchors; sutures; symptomatic peripheral arterial disease (e.g., superficial femoral artery lesions); synthetic vascular grafts; tablets; tamoxifen therapy; targeted delivery; T-cell lymphoma of the skin (mycosis fungoides); Td/IPV; teeth whitening strips; Temporo-Mandibular Joint (TMJ) disorders; tendon tissue; testicular cancer; tissue engineering; thoracic endoprosthesis; thoracic aortic disease; thoracic aneurysm repair; thrombosis; thrombotic conditions; thyroid overactivity (Hyperthyroidism; thyrotoxicosis); thyroid cancer; thyroid therapy; tissue coaptation ties; tissue; tissue excluding material; tissue penetrable materials; tissue scaffolds; tooth implants; tortuous aneurysms; transdermal patches; transdermal systems; transjugular intrahepatic portosystemic shunt (TIPS); translumenial procedures; trauma; triple vaccine—Diphtheria; tetanus & pertussis (DTP); tubes to drain ears; tympanostomy tubes; underactivity of the thyroid gland (hypothyroidism); ureter; uretro-ureterostomies; ureteral stenting; urinary tracts; urologic diseases; urology; uterine fibroids and endometriosis; uterine cancer; vaccines; valves; valvuloplasty; various types of dressings; vascular disease; vascular grafts; vascular implants; vascular stenoses caused by neointimal fibrosis; vascular system; veins; vein grafts; ventricular shunts; vein stents; vein stent-grafts; vertebral disks; vulvar cancer; warts; wound care; wound dressings; wounds; xenografts; treatment of other diseases, cells, tissue, organs, bones, referenced in Gray's Anatomy and disorders (herein incorporated in its entirety as a reference); or combinations thereof, for example.

The expanded material 12 (such as the expanded tubular profile 10, expanded sheet 42, expanded fiber 58), reinforcement 68, or combinations thereof of the present invention can operate at low, ambient, or elevated temperatures. Without intent on limiting, it preferably operates in the temperature range of about below −268 to above 315° C. (−450 to 600° F.). Moreover, the expanded tubular profile 10 can be un-pressurized, pressurized or under a vacuum. The expanded material 12 (such as the expanded tubular profile 10, expanded sheet 42, expanded fiber 58), reinforcement 68, or combinations thereof can be utilized in end-use applications under no load, under tension or under compression.

Inside the expanded material 12 (such as the expanded tubular profile 10), reinforcement 68, or combinations thereof there are the optional contents 26 that are any liquid, gas or solid. The solids can be optionally fluidized. Without intent of limiting, a few examples of the contents 26 are acids, the additives 60, active ingredients, air, blood, biological cells, blood cells, body fluids, binder, brine, carbon dioxide, caustics, cells, chemicals, chemical compounds, coated active ingredients, crude oil, diesel fuel, discharge, drainage, drugs, electricity, electric signals, flakes, food, fuel oil, gasoline, grains, hydrocarbon fuels, hydrogen, hydrogen sulfide, inactive ingredients, juice, kerosene, magnetic signals, medications, metals, modified release active ingredients, microencapsulated active ingredients, microbes, milk, minerals, mixtures, the nano size articles 62, natural gas, nitrogen, oil, oxygen, partially or fully digested food, personal care products, pharmaceuticals, powders, plastics, radioactive materials, resins, sewage, signals, sludge, slurries, solutions, solvents, steam, suspensions, urine, vehicles, water or other materials.

The contents 26 can be optionally active ingredients (e.g. bioactive), inactive ingredients (e.g. inert), or combinations thereof. The active ingredients, for example, are at least one chemical, chemical compound, biological, biological compound, or combinations thereof that work with the human or animal bodies or any surroundings. Without intent on limiting, the active ingredients in medical applications or treatments can furnish pharmacological activity; bring the relief of symptoms; effect the diagnosis, cure, mitigation, treatment, or prevention of disease; or affect the structure or any function of the body of humans or animals. Inactive ingredients have very little or no effect on its surroundings. The contents 26 can optionally partially or fully invoke a biological or chemical response, block a biological or chemical response, modulate a biological or chemical response, or combinations thereof from the surroundings.

The content 26 that is a fluidized solid is a solid material capable of movement by force such as pumping, blowing, gravity, pouring, etc. Fluidized solids come in a variety of forms such as powders, pellets, and flakes, to name a few. Liquid contents can be of any viscosity that meets the requirements of the end-use application, including gels.

The expanded material 12 (such as the expanded tubular profile 10, expanded sheet 42, expanded fiber 58), reinforcement 68, or combinations thereof of the present invention is installed or utilized in any way such as those known by those skilled in the art of installing or utilizing piping systems, industrial products, consumer products, medical devices or medications. A few examples include adhering, assembling, clamping, direct burial, dilating, implanting, ingesting, grafting, laminating, sewing, plowing, planting, pulling-in, pushing-in, directional drilling, sewing, slipling, surgically, swallowing, inserting, submerging, trenchless rehabilitation, surface positioning, suspending, transplanting, etc.

The expanded material 12 (such as the expanded tubular profile 10, expanded sheet 42, expanded fiber 58), reinforcement 68, or combinations thereof can be anchored in place by any means that meets the requirements of the end-use application. They can be, for example, bonded, sewn in place, attached with electric discharge, taped in place, thermally fused in place, glued in place, screwed in place, riveted in place, tacked in place, grafted, ultrasonically attached, united, spot welded, interference fit, cell in-growth, surgically attached, held in place with magnetism, held in place with biological means, tissue in-growth, or held in place mechanically (e.g. staples, clamping, sutures, couplings, tunicate, etc). The anchoring means can be temporary or permanent. The expanded material 12 (such as the expanded tubular profile 10), reinforcement 68, or combinations thereof can optionally include a stab connection (i.e., any gripping means) or barbed connection that seals and/or grips at joints or other connections.

The expanded material 12 (such as the expanded profile 10, expanded sheet 42, expanded fiber 58), reinforcement 68, or combinations thereof can also contain any marker, locating or identification means to, for example, facilitate positioning or locating. This can involve, for example, physical, electric, magnetic, radioactive, ultrasonic, ultrasound, angiography, radiopaque olives, thermal signals, etc. identification means. This feature is especially useful when inserting the expanded material 12, reinforcement 68, or combinations thereof into the supporting member 64, underground, or when implanting. A signal or material imbedded in the expanded material 12, reinforcement 68, or combinations thereof, for example, can be very useful for locating a medical device in a human body. Furthermore, the signal can be useful for determining information about an implanted or buried device like the date of manufacture, lot number, serial number, product code, contents, etc. while the expanded material 12, reinforcement 68, or combinations thereof is installed.

The expanded material 12 (such as the expanded tubular profile 10, expanded sheet 42, expanded fiber 58), reinforcement 68, or combinations thereof of the present invention can be joined to other profiles, sheets, fibers, or other objects of the same, different or similar materials by any means such as through bonding; cement; adhesives; electric discharge; heat; magnetism; mechanical fittings; mechanical joints; fusion; ultrasonic welding; welding; spot welding; thermal fusion; radiation; rivets; solvent bonding; sutures; sewing; staples; tape or other means known by those skilled in the art of joining. Furthermore, the expanded material 12, reinforcement 68, or combinations thereof can optionally contain eyelets for connection to another material or object. The eyelets, areas of sutures, or other connection locations can be adapted to minimize or prevent leakage of the contents 26. When lateral connections are encountered such as a tee fitting, at least one hole can be made in the expanded material 12 (such as the expanded tubular profile 12), reinforcement 68, or combinations thereof to allow the contents 26 to flow into the lateral systems.

The expanded material 12 (such as the expanded tubular profile 10, expanded sheet 42, expanded fiber 58), reinforcement 68, or combinations thereof of the present invention can be adapted to be a tee, bifurcated, single branch, multiple branch, "Y" or elbow configuration. For example, these configurations can be created by connecting two or more of the tubular profile embodiments described herein together and tapping a hole in the wall of the first tubular profile to allow the contents 26 to flow into the second tubular profile. Alternatively, the second tubular profile can include a mitered end that is connected to a first tubular profile. The expanded material 12, reinforcement 68, or combinations thereof are optionally partially or fully assembled in-vivo (inside a living organism) or in-vitro (outside a living organism). The tubular profile can also be optionally wrapped internally (e.g. on inside surface 17) or externally (e.g. on outside surface 16) with one or more layers of the expanded material 12 of the same or different structure. The wrapped assembly can be assembled, for example, utilizing the connecting material 66, adhesives, fusion, ultrasonics, or by heating the assembly to partially or fully connect the layers together. Joints or connections can be also reinforced with tape or other means.

A molded tee fitting or branch fitting of the same or different material can also optionally serve as a center piece or divider in such branched embodiments. The ends of the tubular profile embodiments described herein such as the expanded material 12, reinforcement 68, or combinations thereof can be attached to the open ends of the fitting by any means to fabricate such an embodiment. It is possible, for example, to butt or socket fuse one or more tubular profiles to the fitting. Conversely, other connection means can be utilized such as bonding, fusion, mechanical, electric discharge, crimping, magnetism, spot welding, solvent, adhesives, sewing, ultrasonic, thermal, welds, etc.

The expanded material 12 (such as expanded tubular profile 10, expanded sheet 42, expanded fiber 58), reinforcement 68, or combinations thereof of the present invention can be rigid or flexible. They can also be optionally stretchable. When flexible they can be optionally rolled into very long spools or coils for storage. Furthermore, when flexible they can be temporarily or permanently flattened or otherwise folded to take up less space. Moreover, a reduction in size allows insertion into small or curved places. Flexibility and stretchability can also facilitate handling, improves feel and comfort of the expanded material 12, reinforcement 68, or combinations thereof.

It is optionally possible to form the expanded material 12 (such as the expanded tubular profile 10, expanded sheet 42, expanded fiber 58), reinforcement 68, or combinations thereof into shaped articles within the scope of the present invention by use of a mold. For example, the unexpanded tubular profile 104, expanded tubular profile 10, expanded sheet 42, expanded fiber 58, or combinations thereof can be expanded through the use of pneumatic or hydraulic pressure or a vacuum to take on the shape of a surrounding mold. The mold, for instance, could include ribs, pleats, dimples, or an accordion shape like the one example shown in FIG. 8. The wall thickness can also optionally be, for example, corrugated so that it includes folds or ridges and grooves. The ribs, folds, pleats, etc. can be positioned around the circumference, length, width, or combinations thereof of the expanded material 12, reinforcement 68, or combinations thereof. The mold can be optionally heated and/or cooled to retain the desired shape. It is also possible within the scope of the present invention to take uniformly expanded material 12 and form it into a shape by utilizing a male and/or female die set.

The expanded material 12 such as the expanded tubular profile 10, expanded sheet 42, expanded fiber 58 or combinations thereof of the present invention can also be optionally annealed or stress relieved after stretching. Annealing the expanded material 12 can significantly reduce or eliminate the voids 28.

The expanded material 12 (such as the expanded tubular profile 10, expanded sheet 42, expanded fiber 58), reinforcement 68, or combinations thereof of the present invention can be optionally designed to retain a memory. For example, they can be designed to at least partially shrink back to or grow from a first size and shape to a second size and shape.

Furthermore, the expanded material 12 such as the expanded tubular profile 10, expanded sheet 42, expanded fiber 58, or combinations thereof can be optionally laminated to any backing material such as a polymer, thermoplastic polymer, thermoset polymer, barrier material, porous material, ceramic, paper, glass, resin, elastomer, metal, or combinations thereof, for example. The backing material optionally includes the additives 60, nano size articles 62, or combinations thereof such as active ingredients. The backing material can be permeable, semi permeable, impermeable, or combinations thereof. These materials can be in a variety of forms such as a solid, sheet, particle, foil, film, web, gel, foam, fleece, knitted fabric, netting, fabric, felt, lattice, interlocking fibers, fibers, spun bond, scrim, spun-bonded, spun lace, woven fabric, non-woven, yarn, or combinations thereof. A backing material of the correct composition can, for example, optionally render the expanded material 12 such as the expanded tubular profile 10, expanded sheet 42, expanded fiber 58, or combinations thereof of the present invention substantially impervious, even to highly penetrating gases like hydrogen or other chemicals or biologically active materials. A laminate of expanded material 12 and a backing material is also useful, for example, as clothing, filter media, or other end-uses described herein.

Without intent on limiting, the preferred barrier materials for the expanded material 12 such as the expanded tubular profile 10, expanded sheet 42, expanded fiber 58, or combinations thereof of the present invention include, for example, polyamide [nylon], ethylene vinyl alcohol copolymer [EVOH], polyvinylidene chloride [PVDC], PCTFE fluoropolymer, metal foils, silicone, nitrile [AN-MA] copolymers, thermoplastic polyesters, perfluoroelastomers FFKM [Kalrez™], fluoroelastomer FKM [Viton™], fluorinated ethylene propylene [FEP], metal foils, cyclic olefin copolymer [COC], liquid crystal polymers [LCP], or combinations thereof. Preferred barrier coatings include silicon oxide, plasma treatment, aluminum oxide or inorganic platelet.

As already explained, the expanded material 12 (such as the expanded tubular profile 10, expanded sheet 42, expanded fiber 58), reinforcement 68, or combinations thereof optionally includes one or more layers of the covering 56. The covering 56 can optionally serve as a drug resinate or an ion exchange resin.

Any covering 56 is suitable in the present invention that meets the requirements of the end-use application. Food and Drug Administration (FDA) or German Federal Institute for Risk Management (BfR) approved coverings 56 are, for example, especially preferred for end-uses involving medical applications, devices, or treatments. The covering 56 is optionally water-borne (aqueous), solvent-borne, or combinations thereof. The covering 56 is optionally applied, for example, as a liquid, aerosol, powder, or combinations thereof. The covering 56 optionally forms a continuous or discontinuous film through, for example, drying, chemical bonding, chemical reaction, application of heat, U.V curing, chemical reaction curing, visible light curing, light curing, moisture curing, radiation curing, thermal curing (e.g., thermosetting), multi-component (e.g. two or more components) curing, or by other means known by those skilled in the art of coatings.

The covering 56 is any substance that is capable of partially or fully covering the surfaces of the expanded material 12, reinforcement 68, or combinations thereof. The covering 56 can be any layer, coating, droplet, veneer, finish, varnish, glaze, membrane, blanket, patina, paint, plating, dusting, crust, film, sheet, skin, mist, or combinations thereof that meets the requirements of the end-use application. Without intent of limiting, the types of coverings 56 of the present invention that are particularly useful are at least partially manufactured of, for example, acacia; acrylate copolymers; acrylates; acrylic copolymers; acrylic-based; acrylics; acrylic rubber; adhesives; agar; albumin; alcohols; albumin; aliphatic polycarbonates; alloys; alkyd copolymers; alkyds; anionic surfactants; aqueous latex polymeric emulsion of vinylidenefluoride and hexafluoropropolyene; aspartame; bioabsorbable polymers; biodegradable coverings; bioadsorbable materials; biocompatible metals; biostable polymers; biopolymers; bioelastomer; bioerodible hydrogels; biodegradable polymers; calcium carbonate; calcium metaphosphate; calcium phosphate; calcium stearate; carnauba wax; cationic surfactants; chondroitin sulfate; collagen (e.g., types 1-13); chitosan; collagen; colloidal silicon dioxide; copolymers of PGA/PLA; copolymers of VeoVA; crospovidone; cross linkable biological solutions; dendritic coatings; egg white; elastomers; emulsion polymers; elastin; epoxy; epoxy copolymers; erodible coverings; ethylene vinyl acetate; fast eroding coverings (<48 hours); flavorings; fluorinated ethylene propylene (FEP); fluorine rubber; fluorinated ethylene propylene copolymers; fluoroelastomers; fluorosurfactants; fluoropolymers; fibrin; fibronectin; fruit-based polymers; functional polymers, gelatin; gold; hexafluoropropolyene; high MW polylactide; homopolymer of glycolic acid; hyaluronic acid; hydroxyapatite ceramic; hypromellose; hydroxyapatite matrix; immobilization agents; lactide; lactose; laminin; latex; light curing acrylics; light curing polymers, light curing resins; low surface tension liquids; light curing elastomers; magnesium stearate; magnesium sulfate; mannitol; melamine formaldehyde resins; melamine-based; malleable metals; materials that degrade or dissolve by enzymatic hydrolysis or exposure to water; metals; metal platings; methylphenidate; microcrystalline cellulose; microcrystalline wax; modified acrylates; moisture curing resins; moisture curing polymers, multi component coatings; natural rubbers; Nitinol; nickel-titanium alloys; non-erodible coverings; non-biodegradeable coverings; olefin polymers; olefins; osmotic gradient; osmotically active materials; partially or full cross linked materials; parylene; parylene C; PEBAX; petroleum-based polymers; phospholipids; plating materials; pluronics; plant-based polymers; polyamides; poly(alpha-hydroxy acid); polyacrylamide; poly (amino acids); poly(peptides); poly(anhydrides); poly dioxanone; poly n-butyl methacrylate (PBMA); poly(DL-lactide); poly(ethylene teraphthalate); poly(hydroxy-ethyl methacrylate); poly(lactideglycolide) copolymers; poly-.alpha.-hydroxy vinylalcohol; polyacrylic acid; polyaldehydes; polyalkylene glycols; polyamides (nylon); polybutylene teraphthalate (PBT); polycaprolactone (PCL); polycarbonates; polyethers; polylactic acid-polyethylene oxide copolymers; poly(L-lactide-co-glycolide); polydioxanone; poly-DL-lactic acid (DL-PLA); polyesters; polyester containing glycolate ester linkages; polyester copolymers; polyether block amides (PEBA); poly(ether-b-amide) [Pebax™]; polyethylenes; polyethylene glycol; polyethylene oxide; polyethylene teraphtholate (PET); polyethylene co vinyl acetate (PEVA); polyethylenes; polyglycolic acids (PGA); polygluconate; polyhydroxybutyrate; polyiminocarbonates; polylactic acid (PLA); polylactic acids; poly-L-lactic acid (L-PLA); polymers containing enzymes; polyolefins; polyacrylic acid; polyorthoesters; poly(lactide-co-glycolide); polyphophoesters; polyphosphazenes; polyethylene oxide; polyethylene glycol, polyethylenimine; polypropylene; polystyrene; polysulfones; phospholipids; polytetrafluoroethylenes (PTFE); polyureas; polyurethanes; polyvinyl acetate; polyvinyl acetate homopolymers; polyvinyl acetates (PVA); polyvinyl pyrrolidone; polyvinyl alcohol; polyvinylamine; polyvinyl chlorides (PVC); povidone; proteins; saccharides; saline; semipermeable membranes; sericin; silica gel; silicone; silicone rubbers; silicone-urethane copolymers; siloxanes; silk fibroin; slowly erodible coverings (>48 hours); sodium arginate; sodium dodecyl sulfate; sodium benzoate; sodium citrate; sodium starch glycolate; starch; stainless steel; styrene acrylics; styrene-based polymers; styrene-butadiene copolymers; styrene-butadiene copolymers ethylene vinyl acetate; styrene-isobutylene based block copolymer; styrenes; sucrose; sugar-based; synthetic rubbers; surfactants; talc; tantalum; tridodecylmethyl ammonium chloride; thermally curing resins; thermally curing polymers, thermoplastic urethane (having polybutadiene polyols, polyether polyols, polyester polyols); thermoplastics; thermoset polymers; tri-calcium phosphate; ultra violet (UV) light curing resins; urethane-based; urethanes; urethane copolymers; urethane rubbers; utra violet light cure cyanoacrylates (UVCA); VA/VeoVA copolymers; vegtable-based polymers; very fast erodible coverings (<less than 1 day); medium time erodible coverings (=>1 day to =<30 days); very slow erodible coverings (>30 days); vinyl acetate ethylenes (VAE); vinyl acetates (VA); vinyl acrylics; vinyl versatates (VeoVA); vitronectin; vinylidenefluoride; vinyl's; wax; wetting agents; xanthan gum; their substantially functional equivalents; derivatives, or combinations thereof. Adhesives such as pressure sensitive adhesives can also be coated onto the expanded material 12 such as the expanded tubular profile 10, expanded sheet 42, expanded fiber 58, reinforcement 68, or combinations thereof.

The covering 56 optionally includes any substances or compounds that meet the requirements of the end-use application such as the additives 60, nano size articles 62, or combinations thereof such as those described herein. Furthermore, one or more additives 60, nano size articles 62, or combinations thereof can be dissolved, dispersed, or suspended in a solvent with or without a binder and applied as the covering 56 in the present invention.

The covering 56 can be optionally soft ($T_g$<20° C.) or hard ($T_g$>20° C.). Moreover the covering 56 can be transparent, translucent or opaque. The covering 56 can be permeable, semi permeable, substantially impermeable, or completely impermeable. The covering 56 can be of any thickness. The thickness of the covering 56 can be controlled through multiple applications or layers of the covering 56, solids content, polymer volume concentration, viscosity, or combinations thereof. The type of the covering 56, additives 60, nano size articles 62, active ingredients, or combinations thereof can vary from one layer of the covering 56 to another layer of the covering 56.

The covering 56 can be applied by any means that meets the requirements of the end-use application. Without intent of limiting, a few examples of preferred methods of applying the covering 56 to the expanded material 12, reinforcement 68, or combinations thereof include activated reactive evaporation, aerosolization, atomization, bath, brush, chemical vapor deposition, diff lusion, dip, electroplating, electrostatic, fumed, immersion, ion implantation, ion plating, mechanical plating, painting, molecular beam epitaxy (MBE), physical vapor deposition, powder coating, plating, pulsed laser surface deposition, printing, rolling, sherardising, spray, sputter deposition, thermal spraying, tumbling, vapor, or combinations thereof.

Adhesion of the covering 56 to the expanded material 12, reinforcement 68, or combinations thereof can be very critical in some end-use applications of the present invention. For example, in medical applications, it is sometimes undesirable to have the covering 56 flake-off the surface of the expanded material 12, reinforcement 68, or combinations thereof. A relatively long lasting covering 56 can be difficult to achieve in combination with materials 14 like, for example, polytetrafluoroethylene (PTFE) or polyethylene. The surface treatments such as those described herein dramatically improve the adhesion of the covering 56. Moreover, the additives 60, nano size articles 62, or combinations thereof that are partially or fully located on the surface are useful for increasing adhesion. In the present invention, it is preferred that the surface treatments or additives extend the life of the covering 56 on the surface of the expanded material 12, reinforcement 68, or combinations thereof preferably by more than about 5 percent, more preferably by more than about 30 percent, and most preferably more than about 200 percent when compared to untreated expanded material 12, reinforcement 68, or combinations thereof. One method of measuring the relative life of the covering 56 is by scrub cycles utilizing a modified version of ASTM D 2486. For example, when one sheet of the covered expanded material 12 including a surface treatment or additives is compared to another covered expanded material 12 excluding a surface treatment or additives, the covering 56 on the expanded material 12 including the surface treatment or additives lasts substantially more scrub cycles without substantial erosion of the covering 56 from the surface of the expanded material 12 or substrate. When using scrub cycles as an indicator of the covering 56 life, care must be taken to isolate the performance of the covering 56 in end-use conditions and to minimize, for example, the influence of the substrate and brush (bristles, contact pressure, speed, etc.).

The coverings 56 can optionally include film formers that cause the plurality of discrete polymer particles normally found in emulsion polymers to coalesce and form a continuous or partially continuous film. The size of the discrete polymer particles in, for example, the emulsion polymers of the present invention can be any size, but they are preferably less than about 10 microns and more preferably less than about 5 microns. The covering 56 can also be optionally being cross linked.

The covering 56 is either a continuous or discontinuous layer on the expanded material 12, reinforcement 68, or combinations thereof. The covering 58 can also be optionally applied in any pattern such as a dot or cross hatch pattern. The amount of delivery, rate of delivery, or combinations thereof of the additives 60, nano size articles 62, or combinations thereof such as the active ingredients can be somewhat regulated by the selection of the covering 56 type or by the amount of covering 56 on the additives 60, nano size articles 62, or combinations thereof. It is also possible to regulate the delivery or release by the concentration of the additives 60, nano size articles 62, or combinations thereof such as the active ingredients in the covering 56. The permeability of the covering 56 or expanded material 12 are also useful means for regulating the amount of delivery, rate of delivery, or combinations thereof of the additives 60 or nano size articles 62 such as the active ingredients. The time it takes to partially or fully erode the covering 56 is also useful for managing the amount of delivery, rate of delivery, or combinations thereof.

The additives 60, nano size articles 62, or combinations thereof such as the active ingredients can be of any concentration in the covering 56 that meets the requirements of the end-use application. However, the concentration preferably ranges from about 0-98 percent, more preferably 0-50 percent, and most preferably 0-25 percent. Likewise, the concentration or type of the additives 60, nano size articles 62, or combinations thereof such as the active ingredients can vary from one layer of the covering 56 to another layer of the covering 56. The type of substance that comprises the covering 56 can also be optionally varied from one layer of covering 56 to another layer of covering 56.

The covering 56 can be substantially permanent or engineered to erode, biodegrade, melt, crack, decompose, dissolve, or otherwise partially or fully disappear with time so that it is partially or completely removed from the expanded material 12, reinforcement 68, additives 60, nano size articles 62, or combinations thereof. If there are multiple layers of the covering 56 they can be, for example, engineered to erode or dissolve at different rates. The covering 56 can also crack in-vivo to partially or fully release, for example, the additives 60, nano size article 62, or combinations thereof such as the active ingredients. The covering 56, the structure of the expanded material 12, structure of the binder 69, densification of the expanded material 12, or combinations thereof can provide functionality that is, for example, immediate release, controlled-release, controlled on-set release, extended release, delayed release, sustained-release, modified release, prolonged release, or combinations thereof. Therefore, the covering 56, structure of the expanded material 12, structure of the binder 69, densification of the expanded material 12, use of inactive ingredients, or combinations thereof are, for example, ways of managing the delivery, pharmacokinetics, association, absorption, plasma concentration profile, drug concentration, biopharmaceutical performance, dose proportionality, pharmacodynamics, rate of absorption, extent of absorption, activity, tissue binding, protein binding, bioavailability, metabolism, buccal dissolution, GI dissolution, reactivity, interactivity (activity), or combinations thereof as well as duration of activity of these materials with their surroundings. Additives 60, nano size articles 62, or combinations thereof such as the active ingredients that are time-released can provide any dosage over any period of time that meets the requirements of the end-use application.

The modified release or sustained-release embodiments of the expanded material 12, reinforcement 68, or combinations thereof of the present invention preferably result in the delivery of the additives 60, nano size articles 62, or combinations thereof such as active ingredients over any period of time ranging from about immediate release to about 50 years or more. The delivery can also be over shorter or longer periods of time, for example, within the range of about: immediate release to under 1 hour; immediate release to under 4 hours; immediate release to under 24 hours; immediate release to under 1 month; immediate release to under 6 months; immediate release to under 1 year; immediate release to under 5 years; immediate release to under 10 years; immediate release to under 25 years; immediate release to under 75 years, and so on. The delivery can be optionally at a constant rate, ascending rate, changing rate, or descending rate over time. In the case of delivering a drug or medication, this feature is useful in achieving the optimum drug concentration striking a balance between effectiveness of treatment and minimizing negative side effects.

The partial or full disappearance of the covering 56 when used in a human body, animal body or other processes can be facilitated through the separate or combined introduction of other chemicals or compounds into the process. For example, the acidity of the body or process can be changed to partially or fully remove the covering 56. Surfactants, dispersants, or other vehicles can also be utilized to facilitate the transportation of the additives 60, nano size articles 62, or combinations thereof such as the active ingredients.

The additives 60, nano size articles 62, or combinations thereof such as active ingredients can be microencapsulated or nanoencapsulated. Microencapsulation is the process of enclosing a substance such as the active ingredients inside a miniature capsule or nanocapsule. The substance inside the capsule is any solid, liquid, gas, or combinations thereof. The microencapsulation optionally includes the covering 56 such as, for example, gelatin, wax, or other natural or plastic substances. The microencapsulation can rupture, melt, dissolve, or combinations thereof over time to deliver the additives 60, nano size articles 62, or combinations thereof. The microencapsulation may have one wall or multiple walls arranged in a strata of varying thicknesses around the core.

The microencapsulation, for example: enables the release of the additives 60, nano size articles 62, or combinations thereof such as active ingredients over longer periods of time; can deliver one or more reactive products; mask a taste; release the additives 60, nano size articles 62, or combinations thereof such as active ingredients at a specific location in the body; or combinations thereof.

The microencapsulation of the present invention can be by any process that encloses a substance like the additives 60, nano size articles 62, or combinations thereof such as the active ingredients in a relatively miniature capsule or nanocapsule. The microencapsulation can be achieved by any chemical or physical process. For example and without intent of limiting, the microencapsulation can be achieved by: chemical complex coacervations; air-suspension coating; vibrational nozzle; interfacial polymerization (IPF); polymer-polymer incompatibility (phase separation); in situ polymerization; glow discharge; centrifugal force processes; submerged nozzle processes; spray drying processes; fluid bed coating; Wurster process; pan coating method; centrifugal extrusion; matrix polymerization; rotational suspension separation; spinning disk method; or combinations thereof.

The material 14 used to manufacture the expanded material 12 of the present invention is preferably a polymer but it can be any natural or synthetic material capable of formation into a tubular profile, sheet, fiber, or combinations thereof. The most preferred materials 14 for partial or full composition of the expanded material 12 are polytetrafluoroethylene [PTFE], fluoropolymers; polyamides [nylons]; polyesters [Dacron™]; polyethylenes [PE, LDPE, LLDPE, VLDPE, MDPE, HDPE, UHMWPE, HDXLPE, PEX, etc]; polyethylene terephthalate [PET]; polypropylenes; polystyrenes; polyurethanes; polyvinylchlorides [PVC]; silicone; biopolymers and urethanes or their, precursors, derivatives, homopolymers, monomers, co-polymers, terpolymers, or combinations thereof. In addition to polytetrafluoroethylene [PTFE], also included in the class of previously mentioned preferred fluoropolymers materials 14 for at least partial composition of expanded material 12 are: any copolymer of tetrafluoroethylene, copolymers of tetrafluoroethylene (TFE) and perfluoro methyl vinyl ether, highly crystalline poly(tetrafluoroethylene), any type polytetrafluoroethylene [PTFE] suitable for paste extrusion (forming), any fine powder polytetrafluoroethylene [PTFE], any ultra fine powder polytetrafluoroethylene [PTFE] preferably having an average particle size less than 500 microns, fluorinated ethylene propylene [FEP], copolymers of tetrafluoroethylene [TFE] and per fluoro (propyl vinyl ether) [PFA], copolymers of tetrafluoroethylene and (perfluorobutyl) ethylene, copolymers of tetrafluoroethylene [TFE] and fluorinated comonomers, copolymers of tetrafluoroethylene [TFE] and ethylene, copolymers of tetrafluoroethylene [TFE] and chlorotrifluoroethylene, copolymers of tetrafluoroethylene [TFE] and hexafluoropropylene, homopolymers of polychlorotrifluoroethylene [PCTFE], and its copolymers with TFE, ethylene-chlorotrifluoroethylene (ECTFE), copolymers of ethylene-tetrafluoroethylene (ETFE), polyvinylidene fluoride (PVDFE), and polyvinyl fluoride (PVF). It is also preferable to employ polytetrafluoroethylene (PTFE) that minimizes or eliminates the use of C-8, perfluorooctanoic acid (PFOA), perfluorooctane sulfate (PFOS), ammonium salts, or ammonium perfluorooctanoate (APFO) to minimize negative health and environment impact.

Other preferred substances, polymers, homopolymers, copolymers, terpolymers that are useful materials 14 for partial or full composition of the expanded material 12 of the present invention include, for example: 1,3-propanediol [PDO] (Sorona™—available from DuPont); 1,3 propanediol terephthalate (3GT); acetal; acrylates; acrylics; acrylonitrile butadiene styrene (ABS); acrylonitrile styrene acrylate (ASA); aldehyde polymers; alginic polymers; alloys; anhydride modified polyethylene; anhydride modified polypropylene; anhydride modified vinyl acetate; aramids; biodegradable polymers; bio-based polymers; biopolymers; carbon; carbonized polymeric materials; cellulose nitrate; cellulose acetate; chlorinated polyvinyl chloride [CPVC]; chitosan; condensation polymers; copolymers of ethylene-tetrafluoroethylene [ETFE]; copolymers of tetrafluoroethylene [TFE]; copolymer of tetrafluoroethylene (TFE) and perfluoromethyl vinyl ether (PMVE); corn-based polymers; cross-linkable polymer; degradable polymers; degradable poly carbonate; degradable polycarboxylate; elastomers; ethylene butyl acrylate; ethylene chlorotrifluoroethylene [ECTFE]; ethylene methyl acrylate; ethylene tetrafluoroethylene [ETFE]; ethylene vinyl acetates [EVA]; ethylene vinyl alcohols; ethylene-chlorotrifluoroethylene copolymer; ethylene-tetrafluoroethylene [ETFE]; fluorocarbons; fluoroelastomers FKM [Viton™]; fluoropolymers; fruit-based polymers; glass; glutens; homopolymers; homopolymers of polychlorotrifluoroethylene [PCTFE]; hydrolysable polyesters [e.g. polyactic acid and polyglycolic acid]; liquid crystal polymers [LCP]; parylene; metals; methacrylates; modified polyphenylene oxides [PPO]; poly (ethylene oxide); non-highly cross-linked collagen; non highly cross-linked hyaluronic acid; nylons [e.g., 6, 46, 66, 6-3, 69, 610, 612, 11, 12]; per fluoro (alkyl vinyl ethers) [PAVE]; perfluoro (propyl vinyl ethers) [PPVE]; perfluoroalkoxyethylene [PFA]; perfluoroelastomers FFKM (Kalrez™); poly(amino acids); polyanhydrides; polmers made by dispersion polymerization; polymers made by suspension polymerization; poly (L-lactide-co-glycolide); poly (alpha-hydroxy acid); poly-L-lactide (PLLA); poly-DL-lactide (PDLLA); polydioxanone; perfluoroethylene-propylene copolymer; per fluoro methyl vinyl ether; phenolics; plant-based polymers (capable of substantially maintaining structure greater than 24 hours after installation); poly-3-hydroxybutrate; polylactic acid; poly-1-lactic acid [PLLA]; polycaprolactone [PCL]; polyglycolic acid [PGA]; polyethersulfone [PES]; poly(alkyl-p-hydroxybenzoate)s; poly (benzimidazole)s; poly(benzoxazole)s; poly(benzthiazole)s; poly-(p-phenylene benzbisoxazole)s; poly-(p-phenylene benzbis-thiazole)s; polyacetals; poly(ethylene glycol)-terephthalate-poly(butylene terephthalate) [PEGT/PBT] block co-polymer; polyacrylamides; polyacrylonitrile; polyamide imide; polyamides; polyamids; polyanhydrides; polyarylamides; polyarylate; polyarylene ether; polyaryletherketone [PAEK]; polyarylsulfone [PAS]; polybenzimidazole; polybenzoates; polybutylene; polybutylene terephthalate [PBT]; polycaprolactone; polycarbonate; polychlal; polychlorotrifluoroethylene [PCTFE]; polyester; polyester thermoplastic elastomer; polyether; poly(ether-b-amide); polyether block amide [PEBA]; polyether ester elastomer; polyetheretherketone [PEEK]; polyetherimide; polyetherketoneetherketoneketone [PEKEKK]; polyethersulfone [PES]; polyethylene [e.g., PE, LDPE, LLDPE, MDPE, HDPE, etc]; polyethylene ethyl acrylate; polyethylene naphthalate [PEN]; polyglycolic acid [PGLA]; polyethylene terephthalate [PET]; poly glycolide:trimethylene carbonate [PGA:TMC]; polygluconate; polylactic acid-polyethylene oxide copolymers; poly hydroxyl butyrate; polyphosphoesters; polyimide; polyketone; polymers based on corn-derived chemical; polymers containing enzymes; polymethyl-pentene [PMP]; poly(methyl methacrylate) [PMMA]; polyolefins; polyorthoesters; polyperfluoroalkoxyethylene; polyperfluoroalkoxy ethylene; polyphenols; polyphenylene ether; polyphenylene sulfide (PPS); polyphenylsulfone; polyphthalamide; polypropylene; polysaccharides; polysiloxanes; polystyrene; polysulfides; polysulfones; polytetrafluoroethylene [PTFE]; polytetrafluoroethylene [PTFE] having average particle size less than 600 microns; polytetrafluoroethylene [PTFE] having average particle size less than 500 microns; polytetrafluoroethylene [PTFE] having average particle size less than 400 microns; polytetrafluoroethylene [PTFE] having average particle size less than 10 microns; polytetrafluoroethylene [PTFE] having average particle size less than 5 microns; polytetrafluoroethylene [PTFE] having average particle size less than 1 micron; polytrimethylene terephthalate [PTT]; polyurea; polyurethane; polyvinyl acetate [PVAC]; polyvinyl dichloride [PVDC]; polyvinyl fluoride [PVF]; polyvinylidene fluoride [PVDF]; polyvinylchloride [PVC]; polyvinylfluoride; siloxane-based polyurethane; silicone polyurethane; styrene; styrene acrylonitrile [SAN]; styrene butadiene; styrene butadiene styrene [SBS]; styrene maleic anhydride [SMA]; styrenic elastomer [TES]; syndiotactic polystyrene [SPS]; tetrafluoroethylene [TFE]; thermoplastics; thermoplastic olefinic elastomer [TPO]; thermoplastic polyurethane [TPUR]; thermosets; vegetable oil-based polymers; vegetable-based polymers; vinyl; vinylon; their precursors, derivatives, copolymers, homopolymers, monomers, terpolymers, or combinations or compounds thereof.

To change the properties or functionality of the expanded material 12 it can be optionally tailored to meet the requirements of the end-use application: by material 14 selection; changing the molecular structure of material 14; through cross linking; through grafting; through co-polymerization; through densification; through molecular orientation; through the use of one or more additives 60, nano size articles 62, or combinations thereof. Moreover, the material 14 or the expanded material 12 can be produced from or include a resin utilizing core shell technology wherein the resin or polymer particle's outside surface has different characteristics than its inside. For example, the outside surface can be harder or softer than its core.

As already mentioned, the material 14, expanded material 12, binder 69, connecting material 66, covering 56, reinforcement 68, or combinations thereof optionally include the additives 60. The additives 60 can be any solid, liquid, gas, or combinations thereof. The additive 60 can be of any size. The smaller additives 60 are herein referred to as nano size articles 62. The additives 60, nano size articles 62, or combinations thereof included with the material 14, expanded material 12, binder 69, covering 56, connecting member 66, reinforcement 68, or combinations thereof can be in the range of about 0-99 percent. The additives 60, nano size articles 62, or combinations thereof can be discrete, agglomerated, partially agglomerated, unagglomerated, or combinations thereof.

The additives 60, nano size articles 62, or combinations thereof can modify any property or functionality of the expanded material 12 (such as the expanded tubular profile 10, expanded sheet 42, expanded fiber 58), binder 69, covering 56, connecting member 66, reinforcement 68, or combinations thereof such as, for example, improving or modifying: abrasion resistance (e.g. scrub cycles), adhesion, anti-clotting, anti-restenosis, anti-static, anti-stenosis, anti-thrombosis, anti-inflammatory, bioactivity, biodegradability, blocking resistance, buckle resistance, chemical resistance, circumferential stiffness, cleanability, color, compressive strength, conductivity, connectivity (e.g. bonding, fusion, sewing, electrical, etc.), crush resistance, curability, cut resistance (e.g. Ashland cut Protection Performance Test), density, dielectric strength, digestibility, durability, elasticity, energy absorption, external loading, feel, flame retardancy, flexibility, hardness, human body acceptance, human body acceptance as implant, hydrolytic stability, hydrophilicity, hydrophobicity, impact resistance, imperviousness, implant acceptance, infrared absorption, insulating properties, intumescence, kink resistance, locate ability, longitudinal stiffness, mar resistance, memory, microbial resistance, mildew resistance, permeability, photo stability, pressure carrying capability, puncture resistance, quietness, radiation absorption, reactivity, reduce shrinkage, resiliency, resistivity, reflectivity, rigidity, rodent repellency, scratch resistance, shape, shape recovery, size recovery, shielding, sound absorption, spring-likeness, stability, stain resistance, stiffness, strength, surface energy, surface tension, suture retention strength, tear resistance, tensile strength, thermal conductivity, thermal stability, tissue exclusion, tissue growth, tissue in-growth; toughness, UV stability, washability, weather ability, or combinations thereof. The additives 60, nano size articles 62, or combinations thereof can be optionally adapted with a coating or plating.

The additives 60, nano size articles 62, or combinations thereof are optionally partially or fully active ingredients (e.g. bioactive, chemically active, etc.) or inactive ingredients (e.g. inert). The active ingredients are at least one chemical, chemical compound, biological, or biological compound that works with human or other animal bodies or any other surroundings. Without intent on limiting, for medical end-use applications or treatments the active ingredients can furnish pharmacological activity; bring the relief of symptoms; effect the diagnosis, cure, mitigation, treatment, or prevention of disease; or affect the structure or any function of the body of humans or animals. Inactive ingredients have relatively little or no effect on its surroundings. The additives 60, nano size articles 62, or combinations thereof such as the active ingredients can be micro-encapsulated or nanoencapsulated to modify the release of the active ingredients. The additives 60, nano size articles 62, or combinations thereof such as the active ingredients can optionally at least partially invoke a biological response, block a biological response, modulate a biological response, or combinations thereof from the surroundings. The active ingredients of the present invention can be optionally developed or modified to, for example, suppress, prevent, or kill future (presently unknown) strains or variations of bacteria, viruses, diseases, etc.

The nano size articles 62 optionally include active ingredients. The nano size articles 62, for example, can include one or more antibodies, proteins, or combinations thereof that are attached to the nano sized articles 62. The antibodies, proteins, or combinations thereof can, for example, target cancer cells to selectively kill them with or without damaging healthily cells. They can be optionally engineered to attach to a specific cell's receptor. For example, a carbon nano tube can be coated with a protein that seeks out and attaches to a cancer cell.

The additives 60, nano size articles 62, or combinations thereof can be optionally exploded in vivo (within a living organism). The nano size articles 62 can be, for example, nanobombs that upon delivery to the targeted area are exploded with, for example, a light (laser), radiation, thermal treatment, ultrasound, magnetic field, chemical reaction, electric charge, biological response, or combinations thereof. The explosion can, for example, modulate the growth of or partially or fully destroy unhealthy cells; modulate the growth of healthy cells; modulate the growth of or partially or fully destroy bacteria or viruses; mitigate or destroy blood clots or artery clogging plaque or lesions; partially or fully sever blood vessels; or combinations thereof.

The additives 60, nano size articles 62, or combinations thereof can be included with the material 14 or the expanded material 12 before, during or after stretching. The additives 60, nano size articles 62, or combinations thereof can be included with the material 14, expanded material 12, binder 69, connecting material 66, reinforcement 68, covering 56, or combinations thereof during, for example, polymerization, compounding, blending, mixing, extrusion, stretching, heating, cooling, coating, densification, lamination, adaptation, or in other subsequent processes. Sometimes it is desirable to employ more than one additive 60 or nano size article 62 at a time in the present invention to obtain, for example, a synergistic effect or multi-capability/multi-functionality. Use of inactive additives 60, nano size articles 62, or combinations thereof can also dilute the active additives 60, nano size articles 62, or combinations thereof used with the expanded material 12, binder 69, connecting material 66, reinforcement 68, covering 56, or combinations thereof to obtain the correct dosage or distribution of, for example, active ingredients.

The additives 60 or nano size articles 62 can be any configuration, aspect ratio, morphology, or shape that meets the requirements of the end-use application. For example, they can be particle, tube, or fiber shaped. They can also be, for example, a shape of a block, helix, torus, sphere, hollow sphere, angled member, elongated member, etc. as some embodiments are shown if FIG. 25. In some end-use applications it is useful to employ additives 60, nano size articles 62, or combinations thereof that bloom to the surface of the material 14, expanded material 12, reinforcement 68, covering 56, binder 69, or combinations thereof. The additives 60 or nano size articles 62 can be absorbent and/or porous to hold other materials or additives 60, nano size articles 62, or combinations thereof that are, for example, active ingredients. One or a plurality of additives 60, nano size articles 62, or combinations thereof can be utilized to carry or deliver another or plurality of additives 60, nano size articles 62, or combinations thereof such as active ingredients. For instance, a nano size particle can be coated with an active ingredient so that the active ingredient can be, for example, delivered to very difficult to reach areas of the human body upon release.

The additives 60, nano size articles 62, or combinations thereof can be positioned in a uniform, heterogeneous, or random distribution. Furthermore, a binding material can be used to attach the additives 60 or nano size articles 62 to each other or to the structure of the material 14, expanded material 12, voids 28, fibrils 30, 32, 36, 38, nodes 34, wall thickness 24, reinforcement 68, covering 56, or combinations thereof.

The additives 60, nano size articles 62, or combinations thereof can be optionally attached to the expanded material 12, reinforcement 68, binder 69, covering 56, or combinations thereof thermally. For example, the additives 60, nano size articles 62, or combinations thereof can be attached to any surface of the expanded material 12, reinforcement 68, binder 69, covering 56, or combinations thereof when they are at an elevated temperature and still at least partially tacky. A tacky surface enables the additives 60, nano size articles 62, or combinations thereof to be thermally attached and substantially difficult to remove after the expanded material 12, reinforcement 68, covering 56, or combinations thereof cool. Conversely, the additives 60, nano size articles 62, or combinations thereof can be heated and applied to the expanded material 12, reinforcement 68, or combinations thereof. The additives 60, nano size articles 62, or combinations thereof can cover the surface of the expanded material 12, reinforcement 68, or combinations thereof in the range of about 0 to 100 percent. The thermally attached additives 60, nano size articles 62, or combinations thereof can provide a good bonding surface for additional layers of the covering 56, additives 60, nano size articles 62, or combinations thereof. The strength or durability of the attachment of the additives 60, nano size articles 62, the covering 56, or combinations thereof to the expanded material 12, reinforcement 68, or combinations thereof can be, for example, measured by scrub cycles.

The additives 60, nano size articles 62, or combinations thereof are optionally applied to the material 14, expanded material 12, reinforcement 68, binder 69, covering 56, or combinations thereof in one or more layers in any way that meets the requirements of the end-use application. Without intent of limiting, a few examples of preferred methods of applying additives 60, nano size articles 62, or combinations thereof include adhesion, aerosol, activated reactive evaporation, bath, bonding, brush, coating, chemical vapor deposition, chemical reaction, chemical bonding, diffusion, dip, electroplating, electrostatic, fusion, fumed, grafting, immersion, ion implantation, ion plating, mechanical plating, molecular beam epitaxy (MBE), painting, physical vapor deposition, pulsed laser surface deposition, powder coating, plating, rolling, sherardising, spray, sputter deposition, thermal spraying, tumbling, vapor, or combinations thereof.

The nano size articles 62 are a particularly useful form of the additives 60 in the present invention because they can optionally fit partially or substantially fully within the nodes 34 and/or very small fibrils 30, 32, 36, 38. The nano size articles 62 can be of any substance, material or compound and without intent on limiting are preferably those with one or more dimensions having a nominal size substantially less than about 1000 nanometers, more preferably those with nominal size substantially less than about 500 nanometers, and most preferably those less than about 200 nanometers. The nano size articles 62 sometimes, for example, like carbon nano tubes can be several nanometers in diameter but several millimeters or centimeters or more in length. The nano size articles 62 can be of any shape such as particles, fibers, spheres, bent, curved, helical, tube, crystals, etc. In addition to those mentioned elsewhere in this specification and without intent on limiting, a few examples of the nano size articles 62 of the present invention include, for example: alloy nano particles; nano particles; armchair; nanotubes; bent nano tubes; bucky badgers; boron nitride nanotubes; carbon nanotubes (CNT); cobalt nanowires; copper nanowires; core-shell nanoparticles; dendritic forms of nano particles; double-walled carbon nanotubes (DWNT); filled nano tubes; fullerites; fullerene derivative (bucky balls); germanium nanotubes; gold nanowires; inorganic nanotubes; manganese oxide nanotubes; liposome nanoparticles; multi-wall carbon nanotubes (MWNTs); nanobombs; nanocrystalline silicon; nano crystals; nano cups; nano drops; nano elastomers; nano fibers; nano gels; nano horns; nano particles; nano particles with metal core and oxide shell; nano pillars; nano ribbons; nano rings; nano scale materials; nano rods; nano tubes; nanotorus; nano wafers; nano wires; polymerized single walled nanotubes (P-SWNT); quantum dots; quantum wells; quantum wires; silicon nanotubes; silicon nanowires; single-wall nanotubes (SWCNTs); vanadium oxide nanotubes; or combinations thereof. The nano size articles 62 can be a single component or multi component such as a composite. The large relative surface area of nano size articles 62 provides unusual properties to the expanded material 12, reinforcement 68, covering 56, binder 69, or combinations thereof.

Positioning the nano size articles 62 partially or substantially within the material 14, nodes 34, fibrils 30, 32, 36, 38, reinforcement 68, covering 56, binder 69, connecting member 66, or combinations thereof can make the aforementioned components very strong, abrasion resistant, or have properties mentioned herein that are much different than the virgin material that does not contain the nano size articles 62. For example, incorporating the nano size articles 62 with the expanded material 12 can dramatically increase abrasion resistance as demonstrated by measuring scrub cycles. A modified version of ASTM D 2486 can be useful in measuring the improvement in abrasion resistance of the present invention. For example, if one sheet of the expanded material 12 containing the nano size articles 62 and another excluding the nano size articles 62 are laminated to a board and scrubbed with a brush, the expanded material 12 containing the nano size articles 62 lasts substantially more scrub cycles without substantially tearing or abrading when compared to the expanded material 12 excluding the nano size articles 62. The nano size articles 62 also can also permit stretching the material 14 without substantially breaking the wall thickness 24.

The nano size articles 62 optionally enable the production of the expanded material 12 having very thin wall thicknesses

24 of unusual strength. For example, and without intent on limiting the very thin wall thickness 24 can be produced in the range of about 0 to 0.10 mm (0 to 0.0039 inch) and even as thin as in the range of about 0 to 0.01 mm (0 to 0.00039 inch). The additives 60, nano size articles 62, or combinations thereof also optionally enable the material 14, the expanded material 12, reinforcement 68, or combinations thereof to be much stronger than the material 14, expanded material 12, reinforcement 68, or combinations thereof excluding the additives 60, nano size articles 62, or combinations thereof. For example, the tensile strength or hoop strength of the expanded material 12, reinforcement 68, or combinations thereof is without intent on limiting preferably increased in the range of about 0 to 10%, more preferably in the range of about 10 to 100%, and most preferably increased greater than about 100% vs. the expanded material 12, reinforcement 68, or combinations thereof excluding the additives 60, nano size articles 62, or combinations thereof. The material strengthening additives of the present invention include any additives 60 or nano size articles 62 that have a tensile strength or hardness substantially greater than the material 14 in which the expanded material 12 is comprised of. In addition to the nano size articles 62 mentioned elsewhere in this specification and without intent on limiting, some of the most preferred nano size articles 62 for increasing the strength of the expanded material 12, reinforcement 68, or combinations thereof include carbon nano tubes, multi-wall carbon nano tubes, single-wall nanotubes, silicon nanotubes, carbon nano fiber, ceramic particles, ceramic fiber, nano crystalline silicon, glass particles, glass nano fiber, or combinations thereof.

The nano size articles 62 of the present invention can have any activity, aspect ratio, size distribution, degree of agglomeration, crystallinity, porosity, homogeneity, stoichiometry, symmetry, surface properties, surface coating, absorption, purity, etc. that meets the requirements of the end-use application. Without intent on limiting, preferably the nano size articles 62 are optionally synthesized, for example; by using laser ablation, condensation from vapor, thermal decomposition, wet chemical reduction of metal salts, arc discharge, chemical vapor deposition (CVD), plasma-enhanced CVD, electrochemical deposition, electric glow discharge, wet chemical colloidal processes, flame pyrolysis methods, high temperature evaporation, plasma synthesis, microwave plasma, mechanical processes (e.g. grinding, alloying, milling, etc.), colloidal or liquid phase methods (e.g. chemical reactions in solvents that lead to formation of colloids), furnace flow reactors, laser induced pyrolysis, laser vaporization, sonochemistry, therma plasma, sputtering, droplet evaporation, or any process know by those skilled in the art of manufacturing nano size articles.

The voids, dimples, or indentations like the under cuts 76 within the expanded material 12 (such as the expanded tubular profile 10, expanded sheet 42, expanded fiber 58), reinforcement 68, covering 56, or combinations thereof can also be packed with additives 60, nano size articles 62, or combinations thereof such as active ingredients so that, for example, the voids 28 or the open spaces between fibrils and/or nodes are partially or fully filled. A binder, adhesive, or other material can be optionally employed to hold the additives 60, nano size articles 62, or combinations thereof in place or attach the filling to the expanded material 12, reinforcement 68, or combinations thereof. The additives 60, nano size articles 62, or combinations thereof can also be partially or fully locked into the voids 28 or open spaces by densifying the expanded material 12 after the additives 60, nano size articles 62, or combinations thereof are positioned with the expanded material 12.

Figure 24:
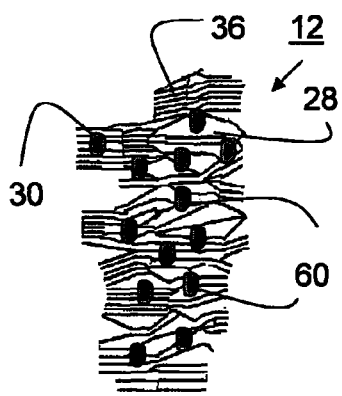
Figure 25:
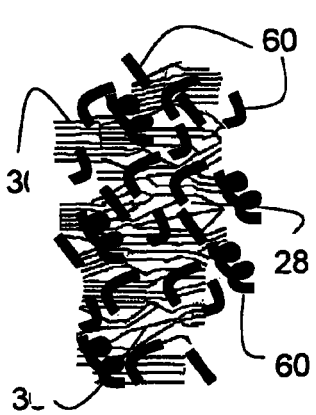

FIG. 24 illustrates an embodiment of a plurality of additives 60 that are particle shaped within wall thickness 24 so that they are in and/or between the fibrils 30, 36 and voids 28. FIG. 25 illustrates an embodiment of a plurality of additives 60 that are fiber shaped of varying configurations within wall thickness 24 so that they are in and/or between the fibrils 30, 36 and voids 28. Furthermore, it is within the scope of the present invention to have a combination of a plurality of additives 60 that are particle shaped and fiber shaped or of any shape within the wall thickness 24. The additives 60, nano size articles 62, or combinations thereof can also optionally partially or fully protrude from the inside surface 17, outside surface 16, or combinations thereof of the expanded material 12, reinforcement 68, or combinations thereof. The protruding additives 60, nano size articles 62, or combinations thereof can be useful for maintaining the position of the expanded material 12, reinforcement 68, or combinations thereof by substantially minimizing or reducing slippage potential when they are installed, for example, in the supporting member 64. The protrusions can also be useful for holding other additives 60, nano size articles 62, or combinations thereof such as active ingredients. After installation of the expanded material 12, reinforcement 68, or combinations thereof the additives 60, nano size articles 62, or combinations thereof are optionally delivered or released from these components.

Figure 26:
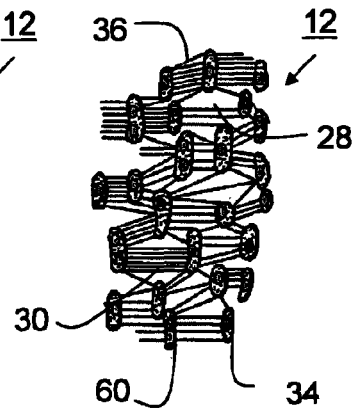
Figure 27:
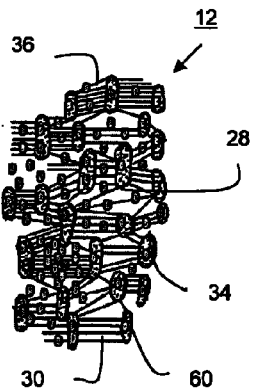
Figure 28:
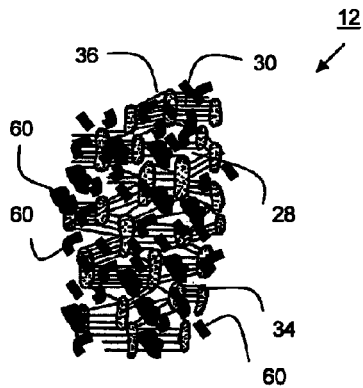

FIG. 26 illustrates an embodiment of a plurality of additives 60 that are particle shaped within wall thickness 24 of the expanded material 12 so that they are partially or fully inside the nodes 34. Although not shown, the nodes 34 can also partially or fully contain fiber, tube, or other shaped additives 60. FIG. 27 illustrates an embodiment of a plurality of additives 60 that are particle shaped within wall thickness 24 so that they are located at least partially inside the nodes 34 and in-between the nodes 34 so that they also are at least partially in the fibrils 30, 36 and voids 28. FIG. 28 illustrates an embodiment of a plurality of additives 60 that are fiber shaped of varying configurations within wall thickness 24 of expanded material 12 so that they are at least partially inside nodes 34 and in-between the nodes 34 so that they also are at least partially in fibrils 30, 36 and voids 28.

Figure 29:
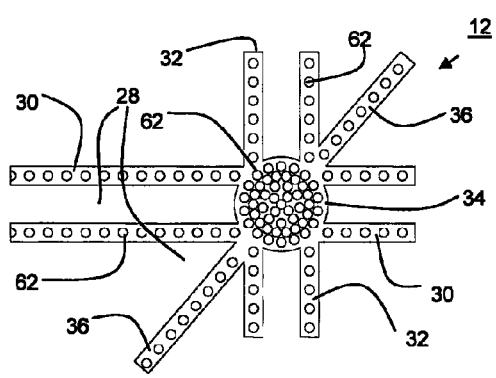

FIG. 29 illustrates an embodiment of a plurality of the additives 60 that are nano size. The nano size articles 62 as shown in FIG. 29 are so small that they can fit substantially in the axial fibrils 30, circumferential fibrils 32, angled fibrils 36, node 34, or combinations thereof. Although, it is not shown the nano size articles 62 can also fit in the bent fibrils 38. The nano size articles 62 can be densely or sparingly packed into the material 14 or expanded material 12 in random or uniform distribution. The nano size articles 62 can be at any concentration that meets the requirements of the end-use application preferably ranging from about 0 to 98 percent, more preferably about 0 to 50 percent.

Figure 30:
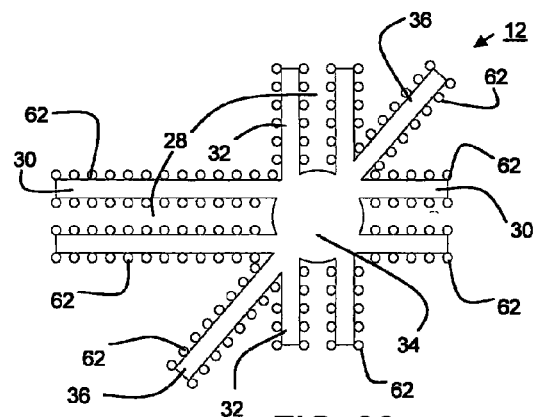
Figure 31:
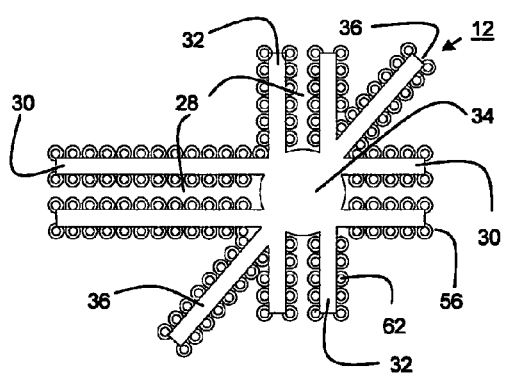

FIG. 30 illustrates another embodiment of the expanded material 12 wherein the plurality of nano size articles 62 are located substantially on the outside surface of the node 34 and the fibrils 30, 32, 36 in a substantially uniform pattern. The surface can be fully or partially covered in a uniform or heterogeneous pattern with one or more layers of nano size articles 62. One or more coverings 56 as shown in FIG. 31 can partially or fully cover these nano size articles 62 and/or the expanded material 12.

Figure 32:
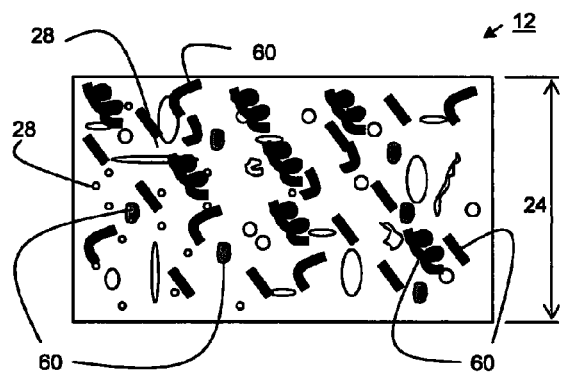

FIG. 32 illustrates an embodiment of a porous wall thickness 24 of expanded material 12 having a plurality of additives 60 that are particle and fiber-shaped. Although not illustrated, an embodiment of solid wall thickness 24 of expanded material 12 can also include a plurality of additives 60, nano size articles 62, or combinations thereof.

Additives 60, nano size articles 62, or combinations thereof can also give the expanded material 12 (such as the expanded tubular profile 10, expanded sheet 42, expanded fiber 58), reinforcement 68, or combinations thereof pigmentation and/or magnetic signal characteristics. Moreover, other additives 60 or nano size articles 62 can be used as extenders or fillers to reduce the cost of the expanded material 12, reinforcement 68, covering 56, connecting member 66, binder 69, or combinations thereof by partially substituting a lower cost material for the material 14, covering 56, or binder 69. The additives 60, nano size articles 62, or combinations thereof optionally included with the material 14, expanded material 12, binder 69, covering 56, or combinations thereof can be any materials known by those skilled in the art of additives or fillers that achieve the requirements of the end-use application or provide the properties or functionality described herein. By way of example, and without intending on limiting, the additives 60 and nano size articles 62 of the present invention can be partially or fully comprised of, for example: 2,2,6,6-tetramethylpiperidine chemical structures; 1-; 1-[4-(2-hydroxyethoxyphenyl)]-2-hydroxy-2-methylpropan-1-one; 2,2,6,6-tetrametylpiperidine chemical structures; 2-hydroxybenzophenones; 2-hydroxyethyl-N-maleimide; 2-hydroxy-phenyl benzotriazoles; absorbents; acid catalysts; acid scavengers; acids; acetone; acrylates; acrylonitrile-butadiene copolymers, actinium; activated carbon; active ingredients; acylphosphine oxides; adenine; additives that minimize tear propagation; agagrose; adhesion promoters; agents; alcohols; aldehyde polymers; algaecides; alginic polymers; alkyds; alkyl acrylate co polymer or acrylic rubbers (ACM); alkyl sulfosuccinates; alloys; alpha.-diketone; alumina powders; alumina trihydrates; aluminas; aluminum; aluminium nitrides; aluminum oxides; aluminum potasium silicates; aluminum silicates; aluminum trihydroxides (Al(OH)$_3$); aluminum oxide ceramic; americium; amines; amino acids; amino alcohols; amorphous carbon; amorphous fused silicas; amorphous graphite; amphoteric surfactants; anatase titanium dioxide; anhydrous clays; anionic surfactants; anisotropic substances; anti-crawing agents; anti-foaming agents; anti-fouling agents; antimicrobials; antimony; antimony oxides; antimony trioxides; antioxidants; antiseptics; anti-settling agents; anti-skinning agents; anti slip; antistatic; aramids; arsenic; aryliodonium salt; asbestos; ash; astatine; attapulgite clays; azoles; bactericides; bacteriostats; baking soda; balsa; barites; barium; barium oxide; barium sulfates; barium titanates; barrier coatings; beads; berkelium; bentone organophillic clay ; bentonite clay; benzoin; benzothonium chloride; berylliums; biocatalysts; biochemical agents; biocides; biocompatible materials; biologically active agents; biopolymers; biostabilizers; bis(1,2,2,6,6-pentamethyl-4-piperidinyl) sebacate; bismuth; bismuth oxide; bohrium; borides; boron; boron carbides; boron nitrides; boron steel; brass; brighteners; bromine-based additives; bromine-based FR; bromines; bronzes; bubbles; buckminsterfullerene; bucky balls; burnish-resistant additives; cadmium; caesium; calcined aluminum oxides; calcined clays; calcium carbonates (CaCo3); calcium oxide; californium; camphor quinine; carbamates (such as 3-1odo-2-propynlbutyl carbamate [IPBC] and dithiocarbamates: copper or sodium or zinc pyrithione); carbides; carbinol-functional silicone polyether copolymers; carbon blacks; carbon steels; carbonates; carbon; carnauba wax; catalysts; cationic surfactants; cellular plastics; celluloses; ceramics; cerium; cerium ammonium nitrate (IV); cerium oxides; chalcogenides; charcoal; chelators; china clays; chlorine; chlorine-based additives; chlorine-based FR; chlorosulphonated polyethylene (CSM); chromate compounds; chromes; chromium; cis-polyisoprene; clays; coated additives; cobalt; cobalt strontium ferrites; coinitiators such as di-2-hydroxyethylmethylamine; colloidal fillers; colloidal silicon dioxide; colloids; colorants; condensation polymers; conductive materials; copper dioxides; coppers; cork; corrosion inhibitors; cotton; coupling agents (promote adhesion between dissimilar compounds); craze-resistant additives; crosslinking agents, crystalline vein graphite; cubic zirconium oxides; curing agents; curium; cytosine; darmstadtium; deaerators; deflocculants; defoamers; degassing agents; demineralized bone; denaturants; desiccants; diamond; diatomaceous earth; diglycol carbonates; diluents; dioxides; diphenyl oxide compounds; dispersents; drier stabilizers; dubnium; dysprosium; einsteinium; elastomers; electroconductive additives; emulsifiers; emulsion polymers; enzymes; epoxides; epoxy/functional silanes; erbium; europium; ester alcohols [e.g., Taxanol™]; ethylene acrylate; ethylene copolymers and terpolymers; ethylene octene copolymer; ethylene propylene copolymer, terpolymer or ethylene propylene rubbers (DPM, EPDM) ethylene tetrafluoroethylene (ETFE); ethylene vinyl acetate (EVA); ethylene vinyl alcohol copolymer; ethylene chlorotrifluoroethylenes (ECTFE); ethylene vinyl acetate; ethylene vinyl alcohol copolymer; expanded and unexpanded micro spheres; ethanol; extenders; fatty acid esters; fatty acids; fatty oils; feldspar; ferrocenium salt; fibers; fillers; fisheye preventer; flake graphite; flakes; flame retardants (FR); flatting agents; flocculants; flock; fluorinated ethylene propylene (FEP); fluoroaluminosilicate glass; fluoro elastomers; fluoropolymers; foam control agents; foaming agents; francium; free radical scavengers; fumed materials; fumed silica; fused silica; fungicides; fungistats; gadolinium; gallium; gallium arsenide; gallium oxides; geranium; germanium dioxides; germanium oxides; glass; glass beads; glass bubbles; glass ionomer fillers; gloss improvers; glycols; glycol ethers [e.g., Butyl Carbitol™]; gold; graphites; guanine; guayule; gums; gypsums; halides; halogenated compounds; halogenated organics; hardeners; hassium; heat stabilizers; helium; herbicides; hevea latex; hindered amine light stabilizers (HALS); hollow micro spheres; holmium; honeycombs; hyaluronan; hyaluronic acid; hybrid (organic-inorganic) materials; hydrated calcium sulfates; hydrogen; hydrolases; hydrophilic modifiers; hydrophobic modifiers; hydroscopic surfactants; hydrous aluminum silicates; hydrous kaolin extenders; hydrous magnesium silicates; hydroxides; hydroxyalk yl substituted benzophenone; hydroxyapatite; hydroxyapatite ceramic; hydroxyphenyl-s-triazines; hypoallergenic materials; impact modifiers; inactive ingredients (or inerts); indiums; indole-3-carbinol; inorganic fillers; inorganic platelets; inorganics; intumescent flake graphite; intumescents; iodine; iodonium salts (e.g., a diaryliodonium salt); ion exchange resins; iridium, iron; iron oxides; iron-nickels; isobutylene isoprene copolymer or butyl rubber (IIR); isoprene; isopropylthioxanthen-9-one; kaolins; krypton; lanthanum; lanthanum oxide; latex; lawrencium; lead; lewis acid; light absorbents; light or UV-light (UVA, UVB) cured resins; light scattering particles; light stabilizers; lime; lithium; living organisms, lubricants; luminescent additives; lustrants; lutetium; magnesium carbonate; magnesium dioxides; magnesium hydroxide Mg(OH)$_2$; magnesium oxides; magnesium silicates; magnesium sulfate; magnesium; manganese; materials having a Moss Hardness Value greater than 3; materials having a Moss Hardness Value greater than 5; materials having a Moss Hardness Value greater than 9; materials useful for visualizing location or configuration of expanded material under fluoroscopy (e.g. bismuth, barium, gold, platinum, tantalum); meitnerium;

melamines; mercaptobenzothiazoles (MBT); mercury; metal alloys; metal carbides; metal nitrides; metal oxides; metal phosphates; metal silicates; metal silicides; metal sulfates; metal sulfides; metal doped silicas; metallic soaps; metals; methacrylate functional silicone polyether copolymers; methacrylates; micas; microbes; micro balloons; micro-crystalline silica; micro spheres (e.g. acrylonitrile, glass, ceramic, phenolics); mildewcides; milled glass fibers; mineraloids; minerals; moisture scavengers; molecular sieves; molecular sieves; molybdenum; monacyl glycerides; mono disperse non agglomerating spheres; montmorillonite bentonite clay; multi-component additives; natural calcium carbonate (CaCO3); neodymium; near-IR photoinitiator systems; neodymium; nepheline syenite; neptunium; neurotoxins; nickels; niobium; niobium oxides; nitrides; nitrile (AN-MA) copolymers; nitrile rubber; nitrogenenous heterocyclic base (purine or pyrimidine); nonionic surfactants; non-reactive HALS (NOR-HALS); nonylphenol ethoxylates; nutrients; nylon; odorants; oils; oligomers; optical brighteners; orange peel preventers; organic anti fungi; organic solids; organics; organo-clays; organophillic clay; organophosphorous hydrolase; orgno functional silanes; ortho-Phenylphenol (OPP); osmium; oxalic anilides; oxazolidines; oxides; oxyamino phosphate; palladium; paraffin wax; particles; PCTFE fluoropolymer; peptides; peptites; per fluoro proply vinyl ethers; perfluoro elastomers (FFKM), perfluoroalkoxy copolymer (PFA); performance enhancers; peroxides; preservatives; persulfates; pesticides; pharmaceuticals; pH-controling agents; phenolic micro balloons; phenolics; phospate groups; phosphate esters; phosphates; phosphides; phosphorous; phosphorous-based additives; phosphorous-based FR; photocatalytic titanium oxide; photoinitiator compositions; photoinitiators, photoreactive dyes; photosensitive aromatic sulfonium; photosensitizers; phthalates; plant-based additives; plasticizers; plastics; plated additives; platelets; platinum; plutonium; pnictides; polonium; polyacetals; polyacids; polyacrylates; polyacrylamide; polyacrylonitriles; polyamides; polyanhydrides; polybutadiene; polycarbonates; polychlorophren; polychloroprene (CR); polychlortrifluoroethylenes (PCTFE); polycrystalline alumina oxide; polyesters; polyethylene wax; polyethylenes; polyimides; polypropylenes; polysaccharides; polysiloxanes; polysulfides; polysulfones; polytetrafluoroethylene (PTFE) wax; polyureas; polyurethanes; polyvinyl acetate; polyvinyl alcohol; polyvinyl chlorides; polyvinylfluorides (PVF); polyvinylidene chloride; polyvinylidene fluorides (PVDFE); potassium; potassium titanate; powders; praseodymium; precipitated calcium carbonate (CaCO3); preservatives; processing aids; promethium; protactinium; proteins; proteolipid; pulps; purified bone morphogenic protein; pyrolytic carbon; Q-cells (inorganic hollow spheres); quantum dots; quartz; radioactive additives; radiopaque fillers; radium; reactable HALS; reactive fibers; reactive fillers; reactive glass; reactive particles; recycled materials; red lead; rhenium; rhodium; roentgenium; rubbers; rubidium; ruthenium; rutile titanium dioxide; salts; saline; salts of dodecylnathalenesulfonic acids, salts of magnesium; sand; scandium; seaborgium; selenium; samarium; semiconductors; semi-metals; silanes; silanol; silica gels; silica glass spheres; silica oxides; silica-based fillers; silicas; silicates; silicides; silicon; silicon carbides; silicon nitrides; silicon oxides; silicon rubber; silicone; silicone (and fluorosilicone) rubber (MQ, VMQ, PMQ, FMQ); silicone oils; silver; silver-chloride/titanium dioxide (AgCL/TiO2); single-component additives; Sm2CO17; Samarium; SMCO5; soaps; sodium; sodium aluminum potassium silicates; sodium alginate sol; sodium carbonates; so-gels; solid glass spheres; solid spheres; glass spheres; stabilizers; stainless steels; starches; steels; strontium; strontium oxide; strontium titanates; styrene acrylics; styrenes; sulfates; sulfides; sulfur, surface active compounds; surface treated fibers; surface treated particles; surfactants; synthetic cis-polyisoprene; synthetic graphite; synthetic mica; synthetic silicas; talc; tantalum; technetium; tellurium; terbium; tetrachloroisophalonitriles; tetra-fluoroethylene/propylene (FEPM); tetragonal zirconium oxide; terefluoroethylenes (TFE); tetragonal zirconia polycrystal ceramics; thallium; thermoplastic polyesters; thermoplastic urethanes; thermoplastic urethanes based on polyesters; thermoplastic urethanes based on polyethers; thorium; thulium; thymine; tin oxide; tins; titanates; titania, titanium dioxides (TiO2); titanium, titanocene derivatives; tolytriazole; tri-calcium phosphate; triclossan; trihydroxides; tumescent systems; tungsten; tungsten carbides; ultraviolet light absorbers (UVAs); ultraviolet light screeners; ununbium; ununhexium; ununnilium; ununoctium; ununpentium; ununquadium; ununseptium; ununtrium; unununium; uracil; uranium; UV quenchers; UV stabilizers; vaccines; vanadium; vegetable based additives; vermiculite; vinyls; vinyl acetates; water soluble calcium salts; water-dispersible lecithin; wax; wetting agents; whiskers; wood flour; woods; xenon; yeasts; ytterbium oxide; ytterbium; yttrium; yttrium oxides; zeolites; zirconates; zirconia; zerconia powders; zirconium; zirconium titantates; zinc; zinc oxide; zinc phosphates; zinc sulfide; zinc/iron phosphate; zinc, zirco aluminates; zirconates; zirconia aluminas; zirconias; zirconium; zirconium carbides; zirconium nitrates; zirconium oxides; their derivatives, their substantially functional equivalents, or combinations thereof. It is possible to use these additives 60 or nano size articles 62 in combination with other additives 60 or nano size articles 62 like the ones mentioned herein.

The preferred additives 60, nano size articles 62, or combinations thereof that are suitable for any end-use application but preferably for optionally retaining a magnetic signal in the material 14, expanded material 12, binder 69, covering 56, reinforcement 68, binder 69, or combinations thereof partially or fully include, for example, any material capable of retaining a signal, such as ferrite, alnico, iron, iron-nickel, Nd2Fe14B, Nd—B—Fe, NdFeB, SmCo, their substantially functional equivalents, or combinations thereof. A magnetic signal can be useful in imbedding any codes, personal information, serial numbers, lot numbers, dates of manufacture, date of installation, model numbers, contents, etc, or combinations thereof. Alternatively, for example, radiopaque gold bands or functionally equivalent materials can be incorporated to assist in location and positioning.

The preferred additives 60, nano size articles 62, or combinations thereof that are suitable for any end-use application but preferably to optionally adapt the material 14, expanded material 12, reinforcement 68, binder 69, covering 56, or combinations thereof optionally neutron absorbing partially or fully include, for example, cadmium, boron steel, hafnium, gadolinium, their substantially functional equivalents, or combinations thereof. Furthermore, the material 14, expanded material 12, binder 69, covering 56, or combinations thereof can serve as a radiation shield through the inclusion of preferred additives like lead, barium, bismuth, tungsten, other heavy metals, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof antimicrobial partially or fully include, for example, algaecide/algicide, bactericide, bacteriostat, biocide, fungicide, fungistat, mildewcides, or combinations thereof. Algaecide/algicides are chemical agents used to destroy algae. Bactericides are compounds used to kill bacteria. Bacteriostats are substances that control, prevent or slow the growth of bacteria. Biocides are chemical agents capable of killing organisms responsible for microbiological degradation. Fungicides are chemical agents that destroy, retard, or prevent the growth of fungi and spores. Fungistats are compounds that inhibit the growth of fungus or prevent the germination of its spores. Mildewcides are chemical agents that destroy, retard, or prevent the growth of mildew.

The preferred additives 60, nano size articles 62, or combinations thereof that are suitable for any end-use application but preferably to optionally adapt the material 14, expanded material 12, binder 69, covering 56, reinforcement 68, or combinations thereof biostable or antimicrobial partially or fully include, for example, silver ions, triclosan, organic antifungi, colloidal silver, nano silver, AgCl/TiO2, silver ceramic, sodium silver zirconium phosphate, silver zeolite, silver glass, their substantially functional equivalents, or combinations thereof. In contrast, it is possible to use additives 60, nano size articles 62, or combinations thereof to render the material 14, expanded material 12, covering 56, binder 69, reinforcement 68, or combinations thereof of the present invention at least partially biodegradable.

Other preferred additives 60, nano size articles 62, or combinations thereof that are suitable for any end-use application but preferably to optionally adapt the material 14, expanded material 12, reinforcement 68, binder 69, covering 56, or combinations thereof with biocide partially or fully include, for example, formaldehyde donors; ortho-phenylphenol (OPPs); isothiazolinone derivatives (such as 2-n-octyl-4-isothiazolin-3-one[OPIT]); guanides and giguanides (such as PHMB or polyhexamethylene biguanide); carbamates (such as 3-iodo-2-propynlbutyl carbamate [IPBC] and dithiocarbamates; copper or sodium or zinc pyrithione; benzimidazoles; n-haloalkylthio compounds; 1-(3-chloroallyl)-3,5,7-tri-aza-1-azonia-adamantane chloride; tetrachloroisophthalonitriles; cis[1-(3-chloroallyl)-3,5,7-tri-aza-1-azonia-adamantane] chloride and 2,2-dibromo-3-nitrilopropionamide (DBNPA); quaternary ammonium compounds, DCOIT-4,5-dichloro-2-n-octyl-4-isothiazolin-3-one, their substantially functional equivalents, or combinations thereof. These are a few examples of the many agents available. Depending on the end-use applications or region utilized other agents may be more suitable. It is also advantageous in some instances to use blends of agents to have an impact on a broader spectrum of biologicals. Optimization of agent selection can be obtained by those skilled in the art by testing effectiveness against target biologicals.

The preferred additives 60, nano size articles 62, or combinations thereof that are suitable for any end-use application but preferaby for optionally toughening the material 14, expanded material 12, binder 69, covering 56, reinforcement 68, or combinations thereof partially or fully include, for example, acrylic rubber, butyl rubber, chlorinated polyethylene (CPE), epichlorhydrin (CO), ethylene propylene rubber (DPM, EPDM), hydrogenated nitrile rubber (HNBR), butadiene rubber (BR), chlorobutyl (CIIR), chorosulphonated polyethylene, ethylene acrylic (AEM), fluoroelastomers, isoprene rubber, natural rubber, perfluoro elastomers (FFKM), polynorbornene rubber (PNB), polyurethane rubber (AU, EU), styrene butadiene rubber (SBR), nitrile rubber (NBR), poylchlorophren, polysulphide rubber (TR), silicone (and fluorosilicone rubber), tetra-fluoroehtylene/propylene, the substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof of the present invention with incressed strength, abrasion resistant, cut resistant, tear resistance, or combinations thereof partially or fully include, for example, alumina, ceramics, glass, metal alloys, metal oxides, metal carbides, metal nitrides, metal sulfides, metal silicates, metal silicides, metal sulfates, metal phosphates, metal borides, silica, silica glass spheres, specialty glass spheres, tungsten, tungsten carbide, colloidal silicon dioxide, alumina, aluminum oxide, semimetals, silicon dioxide, silicon carbide, titanium dioxide, calcined alumina, iron, nickel, stainless steel, metal alloys, metal, colloidal silica, fumed silica, clays, their substantially functional equivalents, or combinations thereof. These additives are also useful in articles partially or fully comprising of the expanded material 12, for example, in the production of cut resistant gloves, fibers, or ropes.

The preferred additives 60, nano size articles 62, or combinations thereof that are suitable for any end-use application but preferably to optionally adapt the material 14, expanded material 12, covering 56, or combinations thereof for dental floss partially or fully include, for example, acetyl trimethyl ammonium bromide, adrenaline, alum, aminocaproic acid, analgesics, antibacterial agents, antibiotic agents, anti-caries agents, antifungal agents, anti-inflammatory agents, antiplaque agents, anti-tartar agents, benzethonium chloride, blood factors that initiate the coagulation cascade, calcium carbonate, cetyl pyridinium chloride, chlorhexidine, dipotassium phosphate, disodium phosphate, hemisodium phosphate, hemostatic agents, hexachlorophene, immunological agents, iron salts, calcium alginate, lysozymes, magnesium carbonate, monopotassium phosphate, monosodium phosphate, noradrenaline, othophosphoric acid, remineralizing agents, sanguinaria, sodium acid pyrophosphate, sodium fluoride, sodium monofluorophosphate, stannous fluoride, tetracycline, tetrapotassium pyrophosphate, tetrasodium pyrophosphate, tranexamic acid, triclosan, ureases, vitamin K, water soluble calcium salts, whitening agents, zinc chloride, their substantially functional equivalents, or combinations thereof. It is also possible to use these additives 60 or nano size articles 62 in combinations with other additives 60 or nano size articles 62 like the ones mentioned herein. Inactive ingredients for dental floss optionally at least partially include, for example, latex, microcrystalline wax, microcrystalline wax, microcrystalline wax, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof for applications like human or animal implanting; grafting; cell cloning; organ cloning; tissue cloning; xenotransplantation; or combinations thereof partially or fully include, for example, acidic FGF; adult stem cells; agents that promote fibroblast proliferation; agents that promote angiogenesis; agents that promote fibroblast migration; agents that promote the growth of endothelial cells; agents that are effective against HIV and hepatitis; amino acids; animal cells; anti coagulants; anti inflamatory drugs; anti interleukins; anti viral drugs; antibiotics; anti coagulants; anti septics; antivirals; anti-transforming growth factors; basic fibroblast growth factor (bFGF or FGF-2); bacterial plasmids; bacterial artificial chromosomes (BAC); birth control drugs; blastocyst cells, blood stem cells; blood factors that initiate the coagulation cascade; lood elements; blood carrying vessel or artery cells; bone marrow; bone marrow cells; brain cells; cloning vectors; cancer fighting drugs; cancer eradicating drugs; chondrocytes; chemotherapy; coagulants; collagen (e.g., Types 1-13); collagen sponge; colon cells; connective tissue growth factor (CTGF); controlled release drugs; corticosterone; cosmids; corrected copies of faulty genes; culture media; cytostatic drugs; deoxyribonucleic acid (DNA); deoxyribose acid; deoxyribose nucleic acid (DNA); dexamethasone [Dalalone, Decadron, Hexadrol phosphate™]; donor cells; drugs; eggs; embryonic stem cells; endothelial growth factor (EGF); endothelial cells; enzymes, epidermal growth factor (EGF); erythromycin; erythropoietin (Epo); estrogen; eukaryotic cells; fibroblast growth factors (FGFs); feeder cells; fibroblast cells; animal fibroblasts; genes; genetic information; genetic instructions; growth hormones; enucleated eggs; hair follicles; heart muscle cells; hematopoietic cells; hematopoietic stem cells; hormones; human or animal cells; human or animal organs; human or animal tissue; IGF-2; immunosupressives; instructions; insulin; insulin-like growth factor-1 (IGF-1); insulin-like growth factor (IGF-II), intereukins (1 thru 22); interleukin 1 (Il-1); intestinal cells; inner cell mass; ionomycin; liver cells; living cells; living organisms; macrophage colony stimulating factor (MCSF); mammalian cells; mesenchymal stem cells; messages; microbes; minerals, morphine; molecular complexes; multipotent stem cells; murine cells; muscle cells; naive stem cells; nerve cells; nucleic acids; nucleotides; nutrients; organ cells; organ tissue; osteopontin VEGF; pain killers; pancreas cells; para-thyroid hormone (PTH); pentose sugar; peptides; polypeptides; pharmacological agents; platelet derived growth factor (PDGF); platelets; pluripotent stem cells; prednisolone; preservatives; prostaglandin; prostaglandin E-1; prostaglandin E-2; proteins; primordial germ cells; purified bone morphogenic protein; red blood cells; ribonucleic acid (RNA); RNA messages; saline; salts; skin; skin cells; skin stem cells; sperm; spermacides; somatic cells; stem cells; stem cells from bone marrow; stem cells from umbilical cord; steroids; stomach cells, substances that target cells or organs; testosterone; tetracycline; tissue; tissue transplants; totipotent stem cells; transforming growth factors-.alpha. (TGF-.alpha., TGF-beta); transforming tumor growth factors-beta (TGF-beta); transcription factors; trophectoderm; necrosis factor alpha (TNF-.alpha.); undifferentiated embroyonic stem cells; urothelial cells; unspecialized stems cells; unspecified stem cells; vascular cells; uterine tissue; yeast; yeast artificial chromosomes (YACs); vascular endothelial cell growth factor (VEGF); viruses, vitamin K; vitamins, white blood cells, etc. or combinations thereof. It is also possible to use these additives 60 or nano size articles 62 in combinations with other additives 60 or nano size articles 62 such as active ingredients like the ones mentioned herein.

The expanded material 12, reinforcement 68, or combinations thereof of the present invention are useful in growing, dividing, or proliferating any new cells, tissue, or organs such as those described in Gray's Anatomy (herein incorporated in its entirety). The new cells, tissue, or organs can be partially or fully grown in-vivo (within a living organism) or in-vitro (in an artificial environment outside the living organism). For example, a lab-grown blood vessel can be utilized to replace an aneurismal vessel; a lab-grown colon can be utilized to replace or repair a section of colon destroyed by cancer, or a lab-grown liver can be utilized to replace a liver destroyed by cirrhosis. Without intent on limiting, a few other examples of cloning cells, organs or tissue for transplantation include: skin, bone (skeleton), muscle, smooth muscle, cartilage, hair, joints, blood-vascular system, lymphatic system, nervous system, organs, organs of digestion, organs of voice and respiration, urinary organs, organs of generation, endoderm, mesoderm, ectoderm, etc. can be produced by partially or fully including the expanded material 12, reinforcement 68, or combinations thereof. Although not necessary, preferably the lab-grown cells, tissue, or organs are a substantially close genetic match to those of the recipient to substantially reduce the risk of rejection by the recipient. More preferably, but not necessarily, the lab grown cells, tissue, or organ optionally include corrected faulty genes if present.

The expanded material 12, reinforcement 68, or combinations thereof are useful by serving as a scaffold, host, scrim, structure, shape, or combinations thereof for growing, reproduction, propagation of cells, tissue, or organs; transforming undifferentiated cells to specific cells; conveyance of cells; or partial or full containment of cells. For example, stem cells can be reproduced or transformed in the presence of expanded material 12, reinforcement 68, or combinations thereof into skin, kidney, cartilage, gastrointestinal epithelium, GI tract, urinary tract, bone cells, blood vessels, nerve cells, etc. while on or nearby the expanded material 12. DNA, RNA, chromosomes or genetic material can also be optionally used in combination of these cells and expanded material 12, reinforcement 68, or combinations thereof to personalize or match the cells, tissue, organs, etc. of the recipient so that they are not rejected by the recipient. The assembly of these cells, tissue, organs or combinations thereof and the expanded material 12, reinforcement 68, or combinations thereof can be implanted in a human or animal body for research; improving health; cell, tissue, or organ substitution; or cell, tissue, or organ augmentation. The expanded material 12 optionally serves as a scaffold that holds and/or shapes the cells and/or tissue so that they can be implanted in the targeted area. Other additives 60, nano size articles 62, or combinations thereof such as active ingredients can be optionally utilized to impede infection, improve acceptance, manage the immune system, reduce inflammation, reduce pain, manage blood clotting, manage tissue ingrowth, and manage cell mobility and growth once implanted.

The expanded material 12, reinforcement 68, or combinations thereof are useful in any cloning process. For example, one possible process involves the steps of DNA being extracted from the person in need and inserted into an enucleated egg. After the egg containing the recipient's DNA starts to divide, the embryonic stem cells capable of being transformed into any type of tissue are harvested. The stem cells are used in combinations with the expanded material 12, reinforcement 68, or combinations thereof to generate a new tissue or organ that is a substantially genetic match to the recipient. The new tissue or organ is transplanted to the recipient substantially reducing the risk of tissue or organ rejection. Lab-grown cells, tissue, or organs significantly reduces the need for organ donors. A few example cloning processes include: recombinant DNA technology or DNA cloning; reproductive cloning; therapeutic cloning; somatic cell nuclear transfer (SCNT); molecular cloning; gene cloning; or combinations thereof.

When the expanded material 12 (such as the expanded tubular profile 10, expanded sheet 42, expanded fiber 58), reinforcement 68, or combinations thereof of the present invention are employed as an implant of any type, it is possible for cells or tissue to grow, divide, proliferate, or combinations thereof into and around the expanded material 12, reinforcement 68, or combinations thereof. The additives 60, nano size articles 62, or combinations thereof such as active ingredients are optionally used to accelerate, enhance, minimize, or control this phenomenon.

Additives 60, nano size articles 62, or combinations thereof that are suitable for any end-use application but preferably to optionally adapt the material 14, expanded material 12, binder 69, covering 56, reinforcement 68, or combinations thereof for medical end-use applications such as cardiovascular implants, implants, grafts, stents, stent-grafts, prosthesis, etc. partially or fully include, for example, agents; 'TOR' (target of rapamycin) inhibitors; 2-chlorodeoxyadenosine [cladribine]; 2-choloro-deoxyadenosine; AGI-1067 (available from AtheroGenics or Astra Zeneca); Abbott ABT-578; abciximab [RHEOPRO™; ABT-587; acenocoumarol; acetaminophen; actinomycetes; actinomycin; adenosine reuptake inhibitors; adriamycin; agents that affect the proliferation of both T cells and B cells; agents that are particle bound; agents that are protein bound; agents that promote formation of fibrotic tissue; agents that enhance endotheliazation; agents that improve cellular infiltraton; agents that improve blood compatibility; agents that promote natural tissue ingrowth; agents that block the action of NK cells and T-cell-mediated toxicities; agents that have shown block T-cell activation and proliferation; agents that inhibit platelet aggregation; agents that inhibit smooth muscle cell proliferation; agents that inhibit T lymphocytes; agents that inhibit the activity of the protein mTOR; agents that inhibit the proliferation of vascular smooth muscle cells in vivo; agents that interfere with the synthesis of nucleic acid, agents that interrupts IL-2 synthesis and signaling; agents that lower the rate of aneurysm recanalization; agents that prevent or reduce blood clotting; agents that partially or fully remove or soften relatively incompressible plaque associated with arterial atherosclerotic lesions; agents that partially or fully eliminate the elastic recoil of stenotic lesions or other mechanically dilated passageways including fissuring, flaps, or tears; agents that promote healing of passageways; agents that manage tissue ingrowth; agents that prevent or reduce local allergic inflammation reactions; agents that prevent or reduce long term clotting (>1 year); agents that prevent or reduce rejection of implant; agents that prevent or reduce short term clotting (<1 year); agents that accelerate the healing process; agents that promote a more exuberant scarring and retraction of the aneurysm and repair of the vessel wall; agents that promote healing; agents that promote vessel elasticity; agents that promote vessel relaxation; agents that encourage tissue ingrowth; agents that reduce vascular hyperplasia; agents that suppress the activity of the lymphocytes; agents that suppress the production of antibodies; agents with immunosuppressive properties; alkylating agents; alkyl sulfonates; aminoglycosides; ampicillin; aminoglutethimide [Cytadren, Elipten™]; angiogenic agents; angiopeptin; anti-angiogenic polypeptides; anitsense agents; antimitotics; antineoplastic agents; antiproliferatives; anti-angiogenic agents; angiotensin receptor blockers; angiopeptin; anti-infective agents; anti-scarring agents; anisindione [Miradon™]; anistreplase [Eminase™]; anthracyclines; anti-allergy agents; antiangiogenics; antibiotics; antibodies; anti-CD3 antibody; anti-CTGF; anticoagulants; anti-inflammatory agents; antimetabolites; anti-migratory agents; antimitotic agents; anti-neoplastics; antiplatelet agents; antiproliferative agents; antiproliferative/antimitotic alkylating agents; antiproliferative/antimitotic antimetabolites; anti-scarring agents; antisecretory; antisense oligonucleotides; anti-thrombogenics; argatroban; acetylsalicylic acid [aspirin]; aurothioglucose; AY-22989; azactam; azathioprine [Imuran™]; bacitracin; Bactrim (sulfonamide and trimethoprim); bacteriostatic agents; bactericidal and antiviral agents; basiliximab [Simulect™]; batimistat; BCP671; benzothiazine derivatives and oxicams; betamethosone; bivalirudin [Angiomax™]; bleomycins [Blenoxane™]; breveldin; busulfan; C MYC antisense; C51H79NO13; calcineurin inhibitors; carboplatin [Paraplatin™]; carmustine (BCNU) and analogs; cefazolin; cell cycle inhibitors; cephamandol; cephazolin; cephalosporins; chlorambucil [Leukeran™]; chondroitin sulfate; charonin sulfate; chitosan; chloromycetin; citric acid; cilostazol (PLETAL™); cisplatin [Platinol™]; cladribine [2-CdA, Leustatin™]; clindamycin; clopidogrel; clopidogrel bisulfate [C16H16C1 NO2S.H2SO4, PLAVIX™]; collagens [all types, 27 types]; colchicines; collagen fibers; Connective Tissue Growth Factor (CTGF); compounds with anti-angiogenic effect; compounds that block thrombin; corticosteroids (Prednisone and others); C-preteinase Inhibitors; Cox-2 inhibitors; cyclin/CDK inhibitors; cyclophosphamide and analogs; cyclospoine-A; cyclosporin; cyclosporine; cyclosporine A; cytarabine; cytochalasin; cytokines; cytostatics; cytotoxic agents; cytotoxic antibiotics; cytochalasin; cultured cells; cytovene [gancyclovir]; DNA; daclizumab [Zenapax™]; dactinomycin [Cosmegen™]; daunorubicin [Cerubidine, Daunomycin™]; dexamethasone; dextrans; dexamethasone; diclofenac [DICLOFENAC SODIUM, VOLTAREN™]; fluconazole [Diflucan™]; dipryridamole [Persantine); dipyridamole [Aggrenox™]; doxorubicin [Adriamycin™]; dipyridamole; endogenous glucocorticoids; Endothelin-1; Enhanced Healing Factors; enzymes; enoxacin; EPC antibodies; epidipodophyllotoxins; epipodophyllotoxins; eptifibatide [Integrilin™]; erythromycins; estradiols; estrogen; estradiol; ethylenimines; ethyleneimines; etodalac , [Lodine™]; etoposide [VePesid, VP-16, Etophophos™]; everolimus [Certican™]; exogenous agents; fenamates; fibrin sealant; fibrinogen; fibrinolytic agents; fibronectin; floxuridine [Fluorodeoxyuridine, FUDR™]; fluorouracil [5-FU, Adrucil, Efudex, Fluorouracil™]; folic acid [MONOPRIL™]; FTY 720; folic acid analogues [e.g.,methotrexate]; fungal peptides; G(GP) II.sub.b/III.sub.a inhibitors; gentamicin; glycoprotein IIb/IIIa receptor antagonists; gold sodium thiomalate; groth factors; glucocorticoids; growth factor receptor signal transduction kinase inhibitors; gusperimus [15-deoxyspergualin, Spanidin™]; gusperimus hydrochloride; halofunginone; heparin; heparin sodium; heteroaryl acetic acids; heterologous polyclonal antibodies; hexamethylmelamine; hirudin; hydrogels; HMG co-enzyme reductase inhibitors (statins); hormones; hydroxyurea [Hydrea™]; idarubicin [Idamycin™]; ibuprofen; indomethacin; indoleacetic acid derivatives; insoluble collagen; IL-2 receptor directed antibodies; immune modulators; immunosuppressants; immunosuppressives; indene acetic acids; indoles; indomethacin [Indocin, Indotech™]; inhibitors of DNA synthesis; inhibitors of thrombin; inhibitors of GPIIb/IIa; interferon; Interleukin-2 [Aldesleukin, Proleukin™]; intereukins [IL-1], IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23]; ion implantation; ISAtx247; ketorolac; ketorolac tromethamine [Toradol™]; KDR/flk-1; lacZ DNA; lantrunculin D; lamin; L-asparaginase; L-asparaginase which systemically metabolizes L-asparagine and deprives cells which do not have the capacity to synthesize their own asparagines; leflunomide; leflunomide metabolite; Lepirudin [Refludan™]; levafloxacin [Levaquin™]; ligands; lymphocyte immune globulin [Atgam™]; macrocyclic lactone; mechlorethamine; Medi-507; melagatran; macrocyclic triene antibiotics; macrolide lactones; materials which provide denucleation; materials which modify the hydrophobicity of the expanded material; materials which create an environment for endothelial cells to migrate to and to colonise endovascular surface; matrix production inhibitory; melphalan [Alkeran™]; mercaptopurine [6-MP, Purinethol™]; metal salts of nalidixic acid derivative; migration Inhibitors; methotrexate [amethopterin]; methylmelamines; mithramycin; mitomycin [Mitomycin C, Mutamycin™]; mitotane [Lysodren™];

mitoxantrone [Novantrone™]; mizoribine; mitmycine; mitramycin; monoclonal antibodies; M-Prednisolone; mTOR inhibitors; muromonabco3 [ORTHOCLONE OKT™3]; clotrimazole [Mycelex™]; mutamycin; mycophenolate mofetil [CellCept™]; mycophenolic acid; neomycin; nystatin [mycostatin™]; nucleic acids; NSAIDs; nitrosoureas; nitric oxide donors; nitrogen mustards; ketoconazole [Nizoral™]; NO donor compounds; non-peptide antagonists of the platelet glycoprotein (GP) IIb/IIIa receptor; P-32.10-14; paclitaxel [Taxol™]; norfloxacin; para-aminophenol derivatives; PCNA Ribozyme; pentostatin [Nipent™]; oxaliplatin [Eloxatin™]; painkillers; peptides; perfloxacin; penicillins; phenindione; phosphodiesterase III inhibitors; phosphorylcholine; phosphorylcholine chloride calcium; pipemidic acid; piromidic acid; plasminogen activator; platinum compounds; platinum coordination complexes; plicamycin [Mithracin, Mithramycin™]; polyethylene glycol and derivatives; polylysine; polymyxin B; pravastatin; protamine; probucol; procarbazine [Matulane™]; prostaglandins; prolyl hydrosylase inhibitors; pyrrolacetic acids; pyridylacetic acids; epoprostenol sodium [Flolan™ prostacyclin]; prostacyclin analogs; propionic acid and derivatives; protease inhibitors; protein; protein synthesis inhibitors; purine analogs and related inhibitors; purine analogues [e.g., azathioprine, mercaptopurine]; pyrimidine analogs; quinolones; radiation emitting materials; RestenASE; restenosis inhibiting drugs; retenoids; ribozymes; saline;salicylates; siplizumab [Medi-507]; sirolimus [rapamycin™, NSC-226080, NSC 606698, rapamune™]; sirolimus acting synergistically with cyclosporine; sirolimus acting synergistically with clopidogrel bisulfate [plavix™]; sirolimus acting synergistically with ticlopidine hydrochloride [Ticlid™]; silver; silver norfloxacin; silver salts; statins; saterinone; streptokinase [Streptase™]; streptomycin; streptomyces hygroscopicus; streptomyces tsukubaensis; streptozocin [Zanosar™]; sulfinpyrazone [Anturane™]; sulindac [Clinoril™]; surface receptors; sulfinpyrazone; synthetic heparin salts; tacrolimus [Prograf™, FK-506]; tirofiban [Aggrastat™]; tetracycline; T-cell receptor directed antibodies; teniposide [VM-26, Vumon™]; thrombolytic agents [e.g., Abbokinase™, Activase™; Eminase™, Retavase™, Streptase™]; thioguanine [6-TG, 6-Thioguanine, Tabloid™]; thiotepa [Thioplex, Triethylenethiophosphoramide™]; thrombin inhibitors; thrombolytics; tobramycin; topical anaesthesia; ticlopidine; ticlopidine hydrochloride [Ticlid™]; tissue plasminogen activator [tPA]; tobramycin; tolmetin [Tolectin™]; tranilast; transforming growth factor-beta (TGF-beta) [1]; trazenes-dacarbazinine (DTIC); triazenes; triene macrolide antibiotics; type I collagen; urokinase [Abbokinase]; turbostratic carbon; turbostatic carbon; valgancyclovir HCL [Valcyte™]; vancomycin [Vancocin™]; vascular endothelial growth factor (VEGF); vinblastine [Velban™]; vinca alkaloids (e.g. vincristine, vinblastine, podophyllins); vincristine [Oncovin™]; vinorelbine [Navelbine™]; vitronectin; vitronectin receptor antagonists; vitreous carbon; viomycin; warfarin sodium [Coumadin™]; ximelagatran [Exanta™, H 376/95]; zenapax; their substantially functional equivalents, or combinations thereof. It is also possible to use these additives 60 or nano size articles 62 in combinations with other additives 60 or nano size articles 62 mentioned herein.

The preferred additives 60, nano size articles 62, or combinations thereof that are suitable for any end-use application but preferably for optionally adapting the material 14, expanded material 12, binder 69, covering 56, reinforcement 68, or combinations thereof for any medical end-use application such as for oncology or treatment of cancer, tumors, malignant neoplasms, partially or fully include, for example, 5-fluorouracil; 90 Y ibritumomab tiuxetan; 9-aminocamptothecin (9-ac); abarelix [Plenaxis ™]; ABX-EGF [Panitumumab]; acridinyl anisidide [AMISA, AMSA, Amsacrine™]; acyclovir; adrenal steroid inhibitors; agents that affect the central nervous system (CNS); agents that attract immune system to kill cancer cells; agents that bind to receptors; agents that block estrogen; agents that block histamine; agents that block prostaglandins or synthesis of them; agents that block the action of a protein that recycles used proteins in the cell; agents that blocks adenomatous polyposis (FAP); agents that blocks growth signals in cancer cells; agents that blocks the action of the hormone testosterone; agents that cause a cell's communication system to break down; agents that cause cancer cells to die; agents that compete for hormone receptor sites on a cell; agents that control and stimulate the growth of white blood cells; agents that control cancer cell growth and division; agents that damage cell's DNA; agents that decrease blood calcium levels; agents that decrease uric acid; agents that dilate blood vessels; agents that directly or indirectly stop neurotransmitter activity in the brain; agents that have radioactive substance (e.g., iodine 131) attached to it; agents that help the (pluripotent) bone marrow stem cells grow and stimulates the growth and release of white blood cells and platelets; agents that increase the amount of serotonin and norepinephrine in the brain or nerve endings; agents that increases the tone of the smooth muscle in the intestines; agents that inhibits (blocks) the Bcr-Abl protein tyrosine kinase; agents that intefere with cell division; agents that interfere with bacterial DNA so that the cells cannot reproduce; agents that interfere with the growth of blood vessels; agents that interfere with the synthesis of nucleic acids; agents that interferes with protein synthesis so that the bacteria are unable to reproduce; agents that minimize the risk of allergic reaction; agents that modulate the cell cycle; agents that modulate/mitigate uncontrolled or unwanted cell proliferation; agents that prevent bacteria from manufacturing their cell wall; agents that prevent bone from breaking down; agents that prevent dividing cells from making DNA and RNA; agents that prevent, interfere, or minimize metastases; agents that kill or prevent reproduction of viruses; agents that prevents bacteria from making more DNA; agents that prevents fungus from making its cell wall; agents that prevents the bacterial cell from making protein so the cell dies; agents that prevents the body's adrenal glands and ovaries from making estrogen; agents that prevents the kidneys from reabsorbing sodium and chloride; agents that provide muscle relaxation; agents that reduce anxiety; agents that reduce pain; agents that reduces the number of polyps in the colon; agents that regulates the production of FSH (follicle-stimulating hormone) and LH (luteinizing hormone); agents that repair genes; agents that slows intestinal smooth muscle; agents that stimulate T-cell activation and help myeloid stem cells differentiate so they can make white blood cells; agents that facilitate stem cells in differentiation; agents that stimulate the immune system; agents that stimulate the production of immune cells (monocytes and macrophages); agents that stimulates the body's bone marrow to make more neutrophils; agents that stimulates the body's immune system to work better; agents that stop cancer cells that depend on male hormone (e.g., androgen); agents that stop cell division; agents that stop folic acid synthesis; agents that stop the growth of cancer cells; agents that stop or minimize vascular endothelial growth factor (VEGF); agents that stops bacteria from making their protein cell wall; agents that stops cytomegalovirus (CMV) growth; agents that synthesize prostaglandins; agents that tell the plasma cells to make more antibodies; agents that tell the body to stop making testosterone or estrogen; agents that increase the neutrophils (white blood cells) in the blood; agents that turn off the production of proteins (e.g., Bcl-2); agents that target enzymes like kinases that control cell growth; agents that starve tumors by for example cutting off blood vessels; agents to prevent or treat anemia (low red blood cell count); alcohol, alemtuzumab; alitretinoin; alkylating agents; alprazolam; altretamine; amifostine; amikacin sulfate; aminoglutethimide; aminoglycosides; amoxicillin; amoxicillin with clavulanate; amphotericin B, ampicillin sodium combined with sulbactam sodium, anastrozole; androgen hormone antagonists; androgens; angiogenesis inhibitors; antagonist of the gonadotropin-releasing hormone (GnRH) [also known as luteinizing hormone-releasing hormone (LHRH)™]; anthracycline antibiotics; antiadrenergic agents; antiangiogenesis drugs; anti anxiety drugs; antibiotics; antidepressants; antiestrogens; antifungal drugs; antihistamines; antimetabolites; antineoplastics; antiparasitics; antiviral agents, antiproliferative agents; aprepitant; arsenic trioxide; asparaginase; acetylsalicylic acid [Aspirin]; ATRA (All-Trans-Retinoic Acid); azacitidine; azithromycin [Zithromicin™], azole class drugs; aztreonam; benzodiazepines; bevacizumab; bexarotene; bicalutamide; biologic response modifiers; bisphosphonates; bleomycin; bortezomib; bupropion hydrochloride; buserelin acetate; buspirone hydrochloride; busulfan; butyrophenones; calcitonin-salmon; calcium-lowering agents; cannabinoids; capecitabine; carbenicillin indanyl sodium; carboplatin; carnustine [BiCNU]; caspofungin; cefaclor; cefamandole nafate; cefazolin sodium; cefdinir; cefepime; cefixime; cefoperazone sodium; cefotaxime sodium; cefoxitin sodium; cefpodoxime proxetil [Vantin™]; cefprozil; ceftazidime; ceftibuten; ceftriaxone sodium; cell cycle inhibitors; celecoxib; cephalosporin broad-spectrum antibiotics; cephalosporins; cephradine; cetuximab [Erbitux™]; chemotherapy drugs; chemotherapy sensitizers; chlorambucil; choline magnesium trisalicylate; cidofovir; cinacalcet hydrochloride; ciprofloxacin; cisplatin; citalopram hydrobromide; cladribine [2-CdA, Leustatin™]; clindamycin phosphate; clofarabine [Clolar™]; clonazepam [Klonopin]; clonidine hydrochloride; codeine; co-trimoxazole (trimethoprim and sulfamethoxazole); cyclophosphamide; cytarabine (cytosine arabinoside); cytoprotective agents; dacarbazine; dactinomycin; darbepoetin alfa; daunorubicin; daunorubicin citrate liposome, demeclocycline hydrochloride; denileukin diftitox; desipramine hydrochloride; dexamethasone; dexrazoxane; diazepam; dicloxacillin sodium; diethylstilbestrol; diphenhydramine hydrochloride; diphenoxylate hydrochloride [Lomotil™]; atropine; diphtheria toxin; docetaxel; dolasetron mesylate; doxepin hydrochloride; doxorubicin hydrochloride; doxorubicin hydrochloride liposome; dronabinol; droperidol; echinocandins; enzyme inhibitors; epidermal growth factor receptor (EGFR); tyrosine kinase inhibitors; epidermal growth factor receptor-tyrosine kinase inhibitors (EGFR-TKI); epirubicin hydrochloride; epoetin alfa; erlotinib; erythromycin; erythropoietin; estradiol phosphate; estramustine; estrogen; estrogen receptor downregulators; etanidazole; etidronate disodium; etoposide; exemestane; extended-spectrum penicillins; famciclovir, fentanyl [DURAGESIC™]; fentanyl citrate; filgrastim; floxuridine; fluconazole; flucytosine; fludarabine phosphate; fludarabine therapy; fluoroquinolones; fluorouracil; fluosol da (e.g., 20%); fluoxetine hydrochloride; flutamide; foscarnet sodium; ftorafur]; fulvestrant; furosemide; fusion proteins; gabapentin; gallium nitrate; ganciclovir; gefitinib; gemcitabine; gemtuzumab ozogamicin; gene therapy; gentamicin sulfate; glucocorticoid steroids; glycerine; goserelin acetate; granisetron hydrochloride; growth factor proteins; haloperidol; herbals; histrelin acetate; hormones; hormone and hormone-blocking drugs; hormone antagonists; hydromorphone; hydroxyurea; hypocalcemic agents; hypnotic class drugs; hypoxic radiosensitizers; ibuprofen; idarubicin; idoxifene; ifosfamide; imatinib mesylate; imipenem/cilastatin sodium; imipramine pamoate; imiquimod; immunomodulating agents; immunotherapy agents; indole-3-carbinol; indomethacin; interferon alfa; interleukin-2 (IL-2); interleukin-3; interleukin-6; interleukins 1 thru 23; irinotecan; itraconazole; kanamycin sulfate; ketoconazole; ketorolac tromethamine; lactulose; laxatives; lenalidomide (CC-5013); letrozole; leucovorin calcium; leuprolide acetate; levamisole hydrochloride; levofloxacin; levorphanol tartrate; linezolid; liposomal tretinoin; lomustine; loperamide hydrochloride; lorazepam; benzodiazepines; macrolide antibiotics; magnesium citrate; manmade or naturally-made substances that are biological response modifiers; mechlorethamine hydrochloride; medications; megestrol acetate; melphalan hydrochloride; menogaril; meperidine hydrochloride; mercaptopurine; mesna; metabolites; methadone; methotrexate; methyl-ccnu; metoclopramide [Reglan™]; metronidazole hydrochloride; mezlocillin sodium; micafungin sodium [FK-463]; miconazole nitrate; minocycline hydrochloride; mirtazapine; mitomycin; mitotic inhibitors; mitoxantrone [Novantrone, DHAD, DHAQ™]; molecular targeted therapy; monoclonal antibodies; monoclonal medicines; morphine; muscle relaxants; nafcillin sodium; nefazodone hydrochloride; nilutamide; nitrogen mustards; nitrosoureas; nonopioid analgesics; pain relievers; nonsteroidal antiandrogen; nonsteroidal anti-inflammatory drugs (NSAIDs); nortriptyline hydrochloride; nystatin; oblimersen sodium (G3139); octreotide acetate; oncology drugs; ondansetron hydrochloride; opioid analgesics; opium agents; oprelvekin; oxacillin sodium; oxaliplatin; oxazepam; oxazolidinones; oxycodone; paclitaxel; paclitaxel protein-bound particles [Abraxane™]; palifermin; palonosetron hydrochloride; pamidronate disodium; paroxetine hydrochloride [Paxil™]; pegfilgrastim; pemetrexed; penicillin g; penicillins; pentostatin; perphenazine [and amitriptyline]; phenothiazines; piperacillin sodium; piperacillin sodium combined with tazobactam sodium; plant (vinca) alkaloids; platelets; platinum chemotherapy; platinum-based and docetaxel chemotherapy; plicamycin; prednisone; procarbazine hydrochloride; prochlorperazine; promethazine hydrochloride [Phenergan™]; proteins; protein cytokines; protein-tyrosine kinase inhibitors; quinupristin and dalfopristin; radioimmunotherapy agents; raloxifene hydrochloride; raltitrexed; recombinant human keratinocyte growth factor; red blood cells; retinoids; rituximab; salicylates; salsalate; sargramostim; scopolamine; sedatives; selective estrogen receptor modulators (SERMs); semisynthetic penicillins; serotonin antagonists; sertraline hydrochloride [Zoloft™]; steroids; stool softeners; streptogram class of antibiotics; streptomycin sulfate; streptozocin; substances called biological response modifiers; sulfa drugs; synthetic antiestrogen; synthetic opioid analgesics; synthetic version of the body's luteinizing hormone-releasing hormone (LHRH); tamoxifen; tamoxifen citrate; tarceva; targeted therapies; taxanes; temozolomide; teniposide; tetracycline hydrochloride; thalidomide; thiethylperazine; thioguanine; thiotepa; thyroid hormone; ticarcillin disodium; tobramycin sulfate; topoisomerase inhibitors; topotecan hydrochloride; toremifene citrate; tositumomab; transmucosal fentanyl; trastuzumab; trazodone hydrochloride; tretinoin; tricyclic antidepressants; trimetrexate; trovafloxacin; tumor necrosis factor; uft (ftorafur and uracil) [Tegafur and Uracil™]; valcyclovir hydrochloride; valspodar; vancomycin hydrochloride; venlafaxine hydrochloride [Effexor™]; vinblastine; vincristine; vindesine; vinorelbine tartrate; vitamins; white blood cells; ziconotide; zoledronate; zoledronic acid; zolpidem tartrate; their substantially functional equivalents, or combinations thereof. It is also possible to use these additives 60 or nano size articles 62 in combinations with other additives 60 or nano size articles 62 like the ones mentioned herein.

Other additives 60, nano size articles 64, or combinations thereof that are suitable for any end-use application but preferably to adapt the material 14, expanded material 12, binder 69, covering 56, reinforcement 68, or combinations thereof for any medical end-use application partially or fully include, for example, 5-androstenediol [Neumune™]; 14-hydroxydihydrocodeinone [Oxycodone HCl]; 17 adihydroequilin; 4'-hydroxyacetanilide; 5-hydroxytryptaminel receptor subtype agonists; 9-aminocamptothecin (9-ac); a2-adrenergic agonists; abacavir sulfate; ACE inhibitors; adrenergic (vasoconstrictor) agents; adrenergic receptor blocking agents; adrenocortical steroids; agents administered in gastrointestinal tract; agents having hypolipidemic activity upon exposure to the cell; agents that act as an antagonist for hormones upon exposure to the cell; agents that block the formation of angiotensin II; agents that can modulate the balance between coagulation and fibrinolysis; agents that convert the androgen testosterone into 5-dihydrotestosterone (DHT); agents that decrease insulin resistance, agents that dissolve blood clots; agents that have apoptotic activity upon exposure to the cell; agents that impede pregnancy; agents that increase insulin sensitivity; agents that inhibit 3-hydroxy-3-methylglutaryl-coenzyme A (HMG-CoA) reductase; agents that inhibit cytokines; agents that inhibit gastric acid secretion; agents that inhibit osteoclast-mediated bone resorption; agents that inhibit the cysteinyl leukotriene CysLT1 receptor; agents that inhibit vitamin K-dependent coagulation factors; agents that lower blood pressure; agents that lower blood pressure by relaxing vessels; agents that lower cholesterol; agents that modulate and/or inhibit cell proliferation; agents that modulate and/or kill pain; agents that modulate and/or prevent build up of fibrin; agents that modulate bone metabolism; agents that modulate macrophage function; agents that modulate the generation of a-thrombin; agents that modulate and/or inhibit activity of protein kinases; agents that are used to suppress fast rhythms of the heart [cardiac arrhythmias]; agents that prevent the ovaries from releasing eggs (ovulation); agents that raise good (HDL) cholesterol levels; agents that reduce the rate at which plaque builds up in the arteries; agents that reduce triglycerides; agents that reduces the work that the heart must do to pump blood through the arteries and veins; agents that slow the heart rate; agents that stop HIV from infecting uninfected cells in the body; agents that suppress immune system (e.g., Helper T cells, Killer T cells, Suppressor T cells, T4 cells); agents that thickens cervical mucus; agents that widen blood vessels; agents the modulate and/or prevent restriction of blood flow in a vessel; agents which bind to and modulate the activity of nerve growth factor (NGF); albuterol sulfate [salbutamol sulfate]; aldosterone antagonists; alendronate sodium [Fosamax™]; alkaloids; allopurinol [Zyloprim™]; alpha-1-selective adrenoceptor blocking agents; alpha-2 adrenergic agonists; Alpha2 Agonists; alpha-blockers, alprazolam (Xanax™); alprostadil (Caverject, Muse); amiodarone hydrochloride; amprenavir [Agenerase™]; amlodipine besylate [Lotrel™, NORVASC™]; amoxicillin sodium; potassium clavulanate; amphetamine aspartate monohydrate [ADDERALL™]; amphetamine mixed salts; aminoglycoside; amphotericin; amphetamines; ampicillins; angiotensin converting enzymes (ACE) inhibitors; angiotensin II receptor (type AT1) antagonists; angiotensin II receptor antagonists; antagonists of alpha1 A adrenoceptors in the prostate; anti blood clotting agents; anti HIV agents; anti-inflammatorys; antianginal drugs; antiarrhythmic agents [sodium channel blockers (Class I), beta-adrenergic blockers (Class II), astemizole; drugs that prolong repolarization (Class III), calcium channel blockers (Class IV), adenocard, lanoxin]; anti-artherosclerosis agents; antiarthritics; antiasthmatics; antiallergics; antibodies that recognize tumor-specific antigens; anticholinergic agents; antidiabetic agents; antidiarrheals; antiepileptic drugs (AED); antifungal agents; antihyperlipidemic agents; antihypertensive agents; anti-malarials; antimigraines; antimycotic polyene antibiotics; antinausea medicines; antineoplastic agents; antiparkinsonisms; antiprotozoal agents; antipruritic agents; antipsychotics; antipyretics; anti-restenosis agents; antispasmodics, antispastics, antitussive agents; anxiolytics; apoptotic agents; appetite suppressants; aripiprazole [ABIL1FY™]; arylacetic acid; azelastine HCl [astelin™]; atenolol [Tenormin™]; atomoxetine HCl [STRATTERA™]; atorvastatin [Caduet™]; atorvastatin calcium [LIPITOR™]; atropine; atropine sulfate; alovudine; AUGMENTIN™; clavulanate potassium; azalides; baclofen [Lioresal™]; barbiturates; B-complex vitamins; benazepril hydrochloride [Lotensin™]; benzonatate [Tessalon™]; benztropine mesylate [Cogentin™]; beta blockers [beta-adrenergic blocking agents]; beta1-adrenoreceptor blocking agents; beta1-selective (cardioselective) adrenoceptor blocking agents; beta1-selective (cardioselective) hydrophilic blocking agents; beta2-adrenergic bronchodilators; beta-adrenergic receptor blocking agents; betamethasone dipropionate; bile acid sequestrants; bisoprolol fumarate [Zebeta™]; bisulfan; blood factors that initiate the coagulation cascade; blood pressure drugs; blood-glucose-lowering drugs; bone-morphogenic proteins; brimonidine tartrate; broad-spectrum antibiotics; broad-spectrum cephalosporin antibiotics; budesonide [RHINOCORT™]; butalbital; butyraldehyde; caffeine; calcitonin [Calcimar™]; calcium antagonists; calcium blockers; calcium channel blockers; calcium ion antagonists; calcium ion cellular influx inhibitors; calanolide A; calcium ion influx inhibitors; candesartan cilexetil [Atacand™]; captopril [Capoten™]; carbencillin; carbamazepine [Tegretol™]; carbidopa [Sinemet™]; carisoprodol [SOMA™]; carvedilol [Coreg™]; cefazolin; cephalosporin; central nervous system (CNS) stimulants; central nervous system depressants; cephalexin [Keflex™]; cetirizine HCl [Zyrtec™]; chemicals that stop HIV from infecting uninfected cells in the body; chiorambucil; chlorhexidine gluconate; chlorpheniramine polistirex; chloramphenicol; chlorthalidone; cholesterol lowering agents; cholestyramine resin; cimetidine [Tagamet™](or other ucer drugs); clemastine; ciprofloxacin hydrochloride [CIPRO™]; clarithromycin [Biaxin™]; clindamycin hydrochloride [Cleocin™]; clobetasol propionate [Olux™]; clindamycin; codeine phosphate; coichicine; colesevelam hydrochloride [WelChol™]; combination HIV treatment (also known as HAART); simvistatin/ezetimibe [Vytorin™]; lamivudine/zidovudine [Combivir™]; conjugated estrogens [Premphase™]; connective tissue growth factor (CTGF); contraceptives; cyclobenzaprine hydrochloride [FLEXERIL™]; DPP-4 inhibitors; DPC 083; DPC 961; DPC 963; dapivirine; decongestants; desloratadine [CLARINEX™]; desogestrel; dextroamphetamine saccharate [ADDERALL™]; dextroamphetamine sulfate; delavirdine mesylate [Rescriptor™]; dibenzoxepin tricyclic compounds; dicyclomine hydrochloride [Bentyl™]; didanosine [Videx™]; digoxin [Lanoxin™]; diltiazem hydrochloride [Tiazac™]; diuretics; divalproex sodium [Depakote™]; dmphetamine sulfate; DNA-damaging agents;

docusate sodium; donepezil hydrochloride [ARICEPT™]; dopamine; dorzolamide hydrochloride; doxazosin mesylate [CARDURA™]; doxycycline hyclate; doxycyclines; drospirenone; emtricitabine [Emtriva™ or FTC]; enalapril maleate [Vasotec™]; endothelial growth factor (EGF); epimers; lamivudine [Epivir™ or 3TC]; equilins; erythromycin; ezetimibe [Zetia™]; escitalopram oxalate [Lexapro™]; esomeprazole magnesium [Nexium™]; estrogen receptor modulators (SERM); Efavirenz [Sustiva™]estrogenic compounds; estrogens; estrones; eszopiclone [LUNESTA™]; etodolac [Lodine™]; ethinyl estradiol (EE); famotidine [PEPCID™]; felodipine [PLENDIL™]; fenofibrate [TRICOR™]; ferrous sulfate; fexofenadine hydrochloride [ALLEGRA™]; finasteride [PROSCAR™]; fluoride; fluticasone propionate; fluvastatin sodium [Lescol™]; gemfibrozil [Lopid™]; gentamicin; griseofulvin; GW695634; GW8248; glimepiride [AMARYL™]; glipizide [GLUCOTROL™]; glucocorticoids; glyburide [Micronase™]; glycosides; H1-receptor antagonists; histamine H1-receptor antagonists; histamine H2-receptor antagonists; HLA-B2702 peptide; HMG-CoA reductase inhibitors; human insulin isophane; hydrochlorothiazide [HydroDIURIL™]; hydrochloride (HCL); triamterene [DYAZIDE™]; hydrocodone bitartrate [Vicodin™]; hydrocodone polistirex ; hydroxychloroquine [Plaquenil™]; hydroxyzine hydrochloride [Atarax™]; hyoscyamine sulfate [LEVSIN™]; hypnotic agents; imidzopyridines; immune globulins; immunoconjugates; Interferon alfacon-1 [Infergen™]; immunomodulators; immunosuppresives; immunosuppressors; indapamide [Lozol™]; indazole compounds; infliximab [Remicade™]; inhibitors of 3 hydroxy-3-methylglutaryl-coenzyme A (HMG-CoA) reductase; inhibitors of A.P. induced platelet aggregation; inhibitors of angiotensin I-converting enzyme (ACE); inhibitors of aromatic amino acid decarboxylation; inhibitors of cyclic guanosine monophosphate (cGMP)-specific phosphodiesterase type 5 (PDE5); inhibitors of osteoclast-mediated bone resorption; inhibitors of steroid Type II 5-reductase; inhibitors of the alpha1 subtype of alpha adrenergic receptors; insulin (e.g., human recombinant) [Humulin™]; Indinavir [Crixivan™]; insulin glargine [rDNA origin] [Lantus™]; insulin lispro (human analog) [HUMALOG™]; saquinavir [Invirase™]; irbesartan [AVAPRO™]; iron; isosorbide mononitrate [Dilatrate™]; kanamycin; labetalol hydrochloride [TRANDATE™]; zidovudine [AZT, Retrovir]; lamotrigine [LAMICTAL™]; lansoprazole [Prevacid™]; latanoprost [Xalatan™]; leukotriene receptor antagonists; levalbuterol [Xopenex™]; levodopa; levonorgestrel [Plan B™]; levothyroxine sodium [Levoxyl™]; lincomycin [Lincocin™]; lipid-lowering agents; lipid-lowering compounds; lisinopril [PRINIVIL™]; lithium carbonate [Eskalith™]; loratadine [Claritin™]; losartan potassium [COZAAR™]; lovastatin [Advicor™, Mevacor™]; macrophage colony stimulating factor (MCSF); magnesium carbonate; MIV 150; meclizine HCl [Antivert™]; medroxyprogesterone [acetoxymethylprogesterone]; meloxicam [MOBIC™]; meperidine [Demerol™]; mephenesin carbamate, mestranol; metaxalone [SKELAXIN™]; metformin hydrochloride [RIOMET, GLUCOPHAGE™]; methocarbamol [Robaxin™]; Medi-500 (formerly T10B9); methylphenidate; [methylphenidate HCl, CONCERTA™, Ritalin™]; methylprednisolone [Medrol™]; methylxanthines; metoprolol succinate [Toprol™]; metoprolol tartrate [Lopressor™]; minerals; mometasone furoate monohydrate [Nasonex™]; montelukast sodium [Singular™]; morphine [morphine sulfate]; moxifloxacin hydrochloride [AVELOX™]; MT103 family of chemicals; multivitamins [e.g., Vitamin A, Vitamin C, Vitamin D, Vitamin E, Thiamin, Riboflavin, Niacin, Vitamin B6, etc.]; mupirocin [Bactroban™]; muscarinic receptor antagonists; nabumetone [Relafen™]; nafcillin; naproxen [Aleve™, naproxen sodium, Naprelan™]; narcotics; nateglinide [StarliX™]; nelfinavir [Viracept™]; nicotinic acid [NIASPAN™]; nevirapine [Viramune™]; niacin/lovastatin; nifedipine [Procardia™]; nitrofurantoin [Nacrobid™]; nitroglycerin [Nitrostat™]; nitrosoureas; nonbenzodiazepine; nicotine; non-nicotine quit smoking aids; non-nucleoside reverse transcriptase inhibitors; nonopiates, non-salicylate analgesics; nonselective β-adrenergic blocking agents; nonsteroidal anti-inflammatory agents; nonsulfhydryl angiotensin-converting enzyme inhibitors; norelgestromin; norepinephrine reuptake inhibitors; norethindrone; novobiocin; nucleoside analogs (NRTIs); nucleoside reverse transcriptase inhibitors; nucleotide reverse transcriptase inhibitors; olanzapine [ZYPREXA™]; olmesartan medoxomil [BENICAR™]; olopatadine [PATANOL™]; omeprazole [Prilosec™]; opioid agonists; oxcarbazepine [Trileptal™]; oxybutynin chloride [DITROPAN™]; oxycodone hydrochloride [OxyContin™]; pain relievers; pantoprazole sodium [PROTONIX™]; papaverine hydrochloride; parasympathomimetics; para-thyroid hormone (PTH); penicillin; penicillin V potassium; peptides that targets a tumor cell; perindopril; phenazopyridine hydrochloride [Pyridium™]; phenobarbital; phentermine hydrochloride [Fastin™]; phentolamine [Rogitine™]; phenytoin sodium [Dilantin™]; physiologically acceptable salts; pimecrolimus [Elidel™]; pioglitazone hydrochloride [ACTOS™]; plicomycin; polymyxin; polyamines; polyethylene glycol [Miralax™]; polypeptide hormones; potassium chloride [micro K™]; pravastatin sodium [Pravachol™]; progestational compounds; progesterone [PROMETRIUM™]; progestin; propoxyphene hydrochloride; propoxyphene napsylate [Darvocet™]; propranolol hydrochloride [Inderal™]; prostaglandin F2a analogues; prostaglandins; protein kinase family of enzymes; protein-based therapies; proteins; pseudoephedrine HCl; psychotherapeutic agents; psychotropic agents; pyranocarboxylic acids; pyrazolopyrimidine class of drugs; quetiapine fumarate [SEROQUEL™]; quinapril hydrochloride [Accupril™]; quinine sulfate; R-and S-enantiomers; rabeprazole sodium [ACIPHEX™]; racemic compounds; ramipril [ALTACE™]; ranitidine hydrochloride [ZANTAC™]; receptor (type AT1) antagonists; refampin; renin-angiotensin blockers; regulatory proteins; risedronate sodium [ACTONEL™]; ritonavir [Norvir™]; risperidone [RISPERDAL™]; ritalin hydrochloride; rofecoxib [VIOXX™]; rosiglitazone maleate [AVANDIA™]; rosuvastatin calcium [CRESTOR™]; salmeterol xinafoate [SEREVENT™]; selective AT1 subtype angiotensin II receptor antagonists; selective glucocorticoid receptor agonists (SEGRAs); selective serotonin re-uptake inhibitors (SSRIs); sildenafil citrate [Viagra™]; simvastatin [butanoic acid, ZOCOR™]; sitagliptin phosphate [Januvia™]; slow channel blockers; sodium equilin sulfate [e.g, PREMARIN™]; sodium estrone sulfate; spironolactone [Aldactone™]; β-lactamase inhibitors; streptomycin; substances with selective alpha1-adrenergic and nonselective beta-adrenergic receptor blocking actions; sulfonamide; sulfamethoxazole [Septra™]; sumatriptan succinate [Imitrex™]; sympathomimetics; synthetic hormones; synthetic peptides, synthetic peptide derivatives; TMC278; T3 liothyronine; T4 levothyroxine; tadalafil [Cialis™]; TAFI (thrombin activatable fibrinolysis inhibitors); tamsulosin hydrochloride [Flomax™]; temazepam [Restoril™]; tenofovir disoproxil fumarate [Viread™]; terazosin hydrochloride [HYTRIN™]; terbinafine hydrochloride [Lamisil™]; trifenagrel; terfenadine; tetracyclines [Sumycin™]; theophylline [Theodur™]; therapeutic drugs; timolol maleate;

tizanidine hydrochloride [Zanaflex™]; tolterodine tartrate [DETROL™]; topiramate [TOPAMAX™]; tramadol hydrochloride [ULTRAM™]; tranquilizers; transforming growth factor-.alpha. (TGF-.alpha.); transplatinum; trastuzumab [Erceptin™]; trazodone hydrochloride [DESYREL™]; trimethoprim; triamcinolone acetonide; triprolidine; triazolam [Halcion]; trimethoprim [Proloprim™]; sulfamethoxazole; tri-sprintec; trizivir [abacavir, lamivudine, zidovudine]; tumor necrosis factor (TNFα) inhibitors; ulcer drugs; valdecoxib [BEXTRA™]; valsartan [Diovan™]; vancomycin; vardenafil [Levitra]; vasodilators; verapamil [Calan™]; vincristin; vincristine [Oncovin™]; vildagliptin [Galvus™, LAF237]; water soluble calcium salts; xanthine oxidase inhibitors; yohimbine hydrochloride; zaleplon [Sonata™]; zafirlukast [Accolate™]; zolpidem tartrate [Ambien™]; β2-adrenergic receptor agonists; their substantially functional equivalents, or combinations thereof. It is also possible to use these additives 60 or nano size articles 62 in combinations with other additives 60 or nano size articles 62 like the ones mentioned herein.

As previously mentioned, the expanded material 12, reinforcement 68, or combinations thereof optionally include the supporting member 64. The supporting member 64 optionally serves as a host to the expanded material 12, reinforcement 68, or combinations thereof. For example, a blood carrying artery in a human body can be the supporting member 64. Another example of the supporting member is an underground pipe. In either of these examples, the expanded material 12 (such as one that is in the form of the expanded tubular profile 10), reinforcement 68, or combinations thereof can be inserted into the bore of the blood carrying artery or the underground pipe and can be positioned, for example, so that they cover a weak spot or a constricted area. The expanded material 12, reinforcement 68, or combinations thereof in these examples can at least partially reinforce or line the inside surface of the supporting member 64 or host, especially in the area of the weakened or constricted area. The expanded material 12 (such as in the form of an expanded tubular profile 10), reinforcement 68, or combinations thereof can also hold open the bore of a constricted supporting member 64 so that the contents 26 can flow through the bore.

The expanded material 12 (such as the expanded tubular profile 10), reinforcement 68, or combinations thereof can also be positioned between two supporting members 64. For example, a section of the supporting member 64 can be removed and replaced with a section of the expanded material 12 (such as the expanded tubular profile 10), reinforcement 68, or combinations thereof as a spool piece. The areas of connection between the expanded material 12 (such as the expanded tubular profile 10) and the supporting member 64 can optionally be sealed to prevent, for example, the contents 24 from leaking out of the bore 18. The expanded material 12, reinforcement 68, or combinations thereof can also be an extension to the supporting member 64.

The expanded material 12, reinforcement 68, or combinations thereof are optionally positioned with the supporting member 64 by any means know by those skilled in the art of assembly. They can be, for example, assembled, inserted, wrapped, ingested, swallowed, co-extruded, insert molded, injection molded, blow molded, an extension, cut-in, vacuum molded, rotary molded, transfer molded, pressure formed, cast (to form), pulled, pushed, dilated, collapsed, spin casted, reaction injection molded, surgically implanted, installed with non invasive surgery techniques, positioned among others. When inserted, a guide wire, cable, catheter, or other deployment system is optionally utilized to pull or push the expanded material 12, reinforcement 68, or combinations thereof into the supporting member 64. The expanded material 12 (such as the expanded tubular profile 10), reinforcement 68, or combinations thereof are optionally inserted at an open end, trench, incision, or other opening. The supporting member 64, expanded material 12 (such as the expanded tubular profile 10), reinforcement 68, or combinations thereof can be pressurized or unpressurized. They can be empty, full or partially full of the contents 26. The contents 26 can also be flowing or static during insertion. The flow can be at least partially stopped in the area of insertion by valves, squeezing-off, pinching, inflatable devices, or by other means if necessary.

The deployment system can optionally include means for attaching or anchoring the expanded material 12, reinforcement 68, or combinations thereof to the supporting member 64 or another object. For example, it can adhere, fuse, graft, sew, interference fit, weld, hook, staple, mechanically attach, or otherwise fully or partially interconnect the expanded material 12, reinforcement 68, or combinations thereof to the supporting member 64. Furthermore, the deployment system can optionally include means for dilating the expanded material 12 (such as the expanded tubular profile 10), reinforcement 68, or combinations thereof once they are in final position. The expanded material 12 (such as the expanded tubular profile 10) can be, for example, mechanically expanded, self expanding, or combinations thereof. If the expanded material 12 (such as the expanded tubular profile 10), reinforcement 68, or combinations thereof are at first size and shape the deployment system can change them to second size and shape so that their bore 18 is partially or fully open when in final installed position. The deployment system can optionally adjust the second size and shape so that, for example, the final size and shape of the expanded material 12 (such as the expanded tubular profile 10), reinforcement 68, or combinations thereof are optimized for fit such as variable in size from first end to second end. The deployment system can also deform the expanded material 12, reinforcement 68, or combinations thereof so that when changed from first size and shape to second size and shape the expanded material 12, reinforcement 68, or combinations thereof substantially maintains the second size and shape after removal of the deployment system. Alternatively, the deployment system can position the expanded material 12, reinforcement 68, or combinations thereof and remove a constraint such as a sleeve, sheath, filament, thread, ribbon and so on that keeps the expanded material 12, reinforcement 68, or combinations thereof in first size and shape until they are released of the constraint thereby enabling the shape memory of the expanded material 12, reinforcement 68, or combinations thereof to change to a second size and shape in a way that that the expanded material 12, reinforcement 68, or combinations thereof are positioned against the bore of the supporting member 64 in such a way that a radial expansion force of the expanded material 12, reinforcement 68, or combinations thereof maintains the installed position after removal of the deployment system. An inflatable device (e.g., balloon), internal pressurization, mechanical device, or other means are useful for dilating the expanded material 12 (such as the expanded tubular profile 10), reinforcement 68, or combinations thereof within the supporting member 64. The deployment device can also be optionally adapted with a camera or another device which allows the operator to visualize the insertion process. It is also possible for the deployment system to be optionally adapted with aerosol, drip, spray, pneumatic, flow, hydraulic, lighting, laser, mechanical, ultrasonic, pumping, radiation, electric discharge, dispensing, magnetic field, stapler, or thermal modification capabilities. The deployment system can also optionally be capable of partially or fully removing scale, biological growth, deposits, lesions, etc. located in the supporting member 64. The deployment system can, for example, optionally perform angioplasty. The deployment system can also optionally assemble multiple expanded tubular profiles 10, reinforcements 68, or combinations thereof, for example, in branch, bifurcated, or tee configuration.

The supporting member 64 can be new or used. A used supporting member 64 could be, for example, one that previously served as a piping system, passageway, or vessel that carried, processed, transported or stored any gas, liquid or solid before the installation the expanded material 12, reinforcement 68, or combinations thereof. A used supporting member 64 can have a uniformly sized bore or the bore can be partially or fully bowed, enlarged, deformed, bent, bifurcated, constricted, curved, swollen, or combinations thereof. Moreover, the bore, inside surface, outside surface, or combination thereof of the supporting member 64 can have scale, biological growth, or other forms of obstructions.

The supporting member 64 is comprised of any material that meets the requirements of the end-use application. Without intent on limiting, a few examples of useful materials for partial or full composition of the supporting member 64 include, for example, acrylonitrile butadiene (ABS); alloys; aluminum; animal or human organs; animal or human cells or tissue; arteries; animal or human passageways; biocompatible materials; bladder; blood carrying vessels; body fluid carrying vessels; bone; biliary duct; biological tissue; brass; breast; bronze; carbon; carbon steel; cast iron; biological cells; ceramics; chlorinated polyvinyl chloride (CPVC); clay; colon (or digestive tract); concrete; copper; ductile iron; elastomers; ethylene propylene diene monomer (EPDM); fabric; fiberglass; galvanized steel; glass; gold; graphite; gums; human or animal body vessels; lead; ligaments; lung; lumen; natural rubber; neoprene; neoprene; nonwovens; nylon; organs; passageways; palladium; partially or fully digested food carrying vessels; particle reinforced plastic; plant cells or tissue; plastic; platinum; polyamide; polyester; polyether keytone (PEK); polyethylene (PE); polyisoprene; polypropylene (PP); polysulfones; polyvinyl chloride (PVC); resin; rubber; scalp; skin; stainless steel; steel; tantalum; tendons; tissue; titanium; tungsten; urinary tract; veins; wood; zirconium; their precursors or derivatives, or combinations thereof. In some cases the supporting member 64 has holes, corrosion, scale, biological growth, lesions, plaque, cracks, weak spots, joints, etc.

The supporting member 64 can be any size or shape that meets the requirements of the end-use application. The clearance between the supporting member 64 and the expanded material 12, reinforcement 68, or combinations thereof can range from zero clearance to substantial clearance. It is also possible that the expanded material 12 (such as the expanded tubular profile 10, sheet 42, fiber 58), reinforcement 68, or combinations thereof can be shorter or longer than the supporting member 64.

In cases where the expanded material 12 (such as the expanded tubular profile 10, sheet 42, or fiber 58), reinforcement 68, or combinations thereof are employed to, for example, line or re-line the interior of the supporting member 64, the preferred embodiment of the expanded material 12, reinforcement 68, or combinations thereof can be optionally at least partially flexible to facilitate installation. Flexibility allows the expanded material 12 (such as the expanded tubular profile 10, sheet 42, or fiber 58), reinforcement 68, or combinations thereof to be optionally at least temporarily collapsed, reduced in size, folded, flattened, pleated, converted into a U-shape, or combinations thereof for easy insertion into the supporting member 64. Flexibility also enables the expanded material 12, reinforcement 68, or combinations thereof to navigate multiple bends in one or more planes if needed.

The expanded material 12, reinforcement 68, or combinations thereof can also be optionally relatively or absolutely rigid or inflexible. A rigid or substantially inflexible expanded material 12 (such as an expanded tubular profile 10), reinforcement 68, or combinations thereof can be optionally, for example, swaged to reduce its size prior to insertion to provide at least a temporary clearance with supporting member 64 just prior to or during insertion.

The expanded material 12, reinforcement 68, or combinations thereof can optionally have shape memory or superelasticity. One way of providing the expanded material 12, reinforcement 68, or combinations thereof with shape memory is to include one or more materials in these components with shape memory characteristics. Shape memory materials like, for example, Nitinol (available from Nitinol Devices & Components, Fremont, Calif. or Memry®, Bethel, Conn.) or alloys of nickel and titanium enable the expanded material 12, reinforcement 68, or combinations thereof to be self expanding. Self expansion, for example, enables the expanded material 12, reinforcement 68, or combinations thereof to change from first size and shape to second size and shape substantially without mechanical deformation. A self expanding expanded material 12, reinforcement 68, or combination thereof can be, for example, constricted to a smaller size when positioned on a catheter, constrained in size, inserted into a supporting member 64 such as a blood carrying passageway, and upon deployment increase in size to fit the bore of the supporting member 64 by release of the constraint. A shape memory alloy is capable of remembering a previously memorized shape. Nitinol alloys are sometimes, for example, given shape memory by deforming the material in its low temperature phase Martensite and subsequently heating to the high temperature phase Austenite, e.g. in hot water or with an electrical current. The shape memory characteristics can be fine tuned by composition of the alloys.

The expanded material 12, reinforcement 68, or combinations thereof can optionally include one or more materials having different properties at different conditions. For example, a material that is substantially flexible and pliable at a first condition can transform into a substantially stiffer material at a second condition. Moreover, it is sometimes useful in the present invention to utilize materials which exhibit a martensite phase wherein the material has relatively low tensile strength and an austenite phase wherein the material exhibits a relatively high tensile strength. It is useful in the present invention to modify the transition temperature of the alloy from Martensite to Austenite to improve the deliverability, adjustability, or functionality of the expanded material 12, reinforcement 68, or combinations thereof.

If the supporting member 64 is somewhat pliable, it is possible to somewhat enlarge or modify the size and/or shape of the supporting member 64 during deployment of the expanded material 12, reinforcement 68, or combinations thereof. The expanded material 12 (such as the expanded tubular profile 10, sheet 42, or fiber 58), reinforcement 68, or combinations thereof can also be modified to fit, for example, multiple curves of the supporting member 64 or other objects. They can also bend without substantially kinking or closing the bore 18. Upon positioning of the expanded material 12, reinforcement 68, or combinations thereof they can optionally somewhat relax to minimize stress imposed on the supporting member 64.

It is optionally possible to install the expanded material 12, reinforcement 68, or combinations thereof with the constraining or deforming means and sell the assembly as a unit which can be subsequently combined with the deployment system used to install the expanded material 12, reinforcement 68, or combinations thereof. For example, the reinforcement 68 that is used as a stent can be assembled on a balloon catheter and sold as a unit.

If the wall thickness 24 of the expanded material 12 is porous, the voids 28 can be optionally designed to partially or fully prevent leakage of the contents 24 through the voids. Leakage can be prevented by, for example, hydrophobicity of the material 14, hydrophobicity of the covering 56, void 28 size, multiple layers of expanded material 12, densification of the expanded material 12, thermal treatment, or combinations thereof.

The reinforcement 68 of the present invention provides many possible functions. The need for the reinforcement 68, for example, could be due to a supporting member 64 having a hole, an enlarged bore, a reduced bore, a crack or tear, a weakened spot (e.g., from aging, disease, corrosion, etc.). The reinforcement 68 may also be desirable to increase the strength of thin or insufficiently strong expanded material 12 or a thin or low strength supporting members 64. The reinforcement 68 is also useful for opening, enlarging, or holding open the bore of the supporting member 64 (especially those that have been restricted in size from aging, disease or other reasons) or for compressing or holding the expanded material 12 against the supporting member 64. The reinforcement 68 is also useful for enabling the expanded material 12 to have shape or size memory (e.g. open the bore 18 of a self-expanding expanded tubular profile 10 after removal of a constraint) or to make it self supporting (e.g. hold open bore 18). The reinforcement 68 also has utility for partially or fully eliminating the damage of occlusion caused by "flaps" or fissuring from intimal tears associated with angioplasty.

The reinforcement 68 can be, for example, optionally modified in size and/or shape circumferentially (e.g., from first diameter to second diameter), axially (e.g. from first length to second length), transversely (e.g. from first width to second width), multi-axially, or combinations thereof. The change in size and/or shape can be temporary or permanent. The change in size and shape from first size and shape to second size and shape can be achieved through deformation (e.g. mechanically like with a balloon catheter) or through self-expansion. To deploy the reinforcement 68, for example, into the supporting member 64, the reinforcement 68 can be temporarily in a somewhat smaller size so that there is clearance between the outside surface of reinforcement 68 and the inside surface of the supporting member 64 until reaching its location of installation. The reinforcement 68 of the present invention 68 can be incrementally modified or adjusted in size and shape to achieve the desired end size and shape during or after positioning. If the size of the supporting member 64 is miscalculated the reinforcement 68 of the present invention can be adjusted in size and shape to more precisely fit the supporting member 64. The second size and shape of the reinforcement 68 of the present invention can optionally be variable in size and shape from first end 20 to second end 22 to achieve the best fit with the supporting member 64. These capabilities minimize the risk of the reinforcement 68 migrating from its installed position if under-dilated or from exerting excessive stress on the supporting member 64 if over-dilated.

The optional ability of the expanded material 12, reinforcement 68, or combinations thereof of the present invention to be modified in size axially, circumferentially, transversely, multi-axially, or combinations thereof also permits easier insertion into the supporting member 64. In addition, it permits insertion of longer lengths that need to be strategically positioned and/or to navigate one or more bends without substantially damaging the supporting member 64. This unique feature is especially beneficial when inserting into supporting members 64 that are vessels in the human body wherein installation damage can be detrimental, slow the healing process, interfere with treatment, cause another ailment, or result in lingering pain, for example.

The reinforcement 68 of the present invention can be of any size and configuration. As shown in FIG. 5, the reinforcement 68 can have a substantially solid wall thickness. Alternatively, as shown in FIGS. 33 and 34 the reinforcement 68 can have a configuration comprised of a wall thickness including solid and open portions. The solid portions can optionally be partially or fully porous, fibrous, or combinations thereof. An infinite range of possibilities exist for the configuration of the reinforcement 68. For example, there are many suitable configurations used by those skilled in the art of manufacturing braided tubing, stents, coils, or composites.

The reinforcement 68 comprising a wall thickness of solid and open portions can have, for example, member segments 67 that are angled member segments 74, radial member segments 72, longitudinal member segments 70, or combinations thereof. FIG. 33 shows one embodiment of the reinforcement 68 wherein it is comprised of a plurality of the angled member segments 74 (or struts) crisscrossing other angled member segments 74, the radial member segments 72, and the longitudinal member segments 70. FIG. 34 shows a second embodiment wherein the radial member segments 72 and longitudinal member segments 70 have been eliminated. The plurality of member segments 67 such as 70, 72, 74 can be connected, one-piece, multi-pieces, looped, welded, thermally bonded, contain linkages, glued, or disconnected at crossover points or junctures. To substantially reduce failure during installation or while flexing, the reinforcement 68 can optionally include one or more stress relief features. A few examples of stress relief features include radiuses, bends, curved sections, or expansion joints. The member segments 67 of the reinforcement 68 can also be continuous, discontinuous, randomly oriented or systematically oriented. The reinforcement 68 can be optionally deburred or polished.

The optional open area between the member segments 67 is an open cell 75. The open cells 75 can be optionally partially or fully covered or closed with a membrane that is solid, fibrous, porous, or combinations thereof material. The open cells 75 can be of any size and shape as several examples are schematically shown in FIGS. 38-47. The size and shape of the open cells 75 can be uniform or varied within one embodiment or from embodiment-to-embodiment to customize the flexibility, manage the longitudinal shrinkage or expansion upon changing size and shape, minimize drag within a passageway during insertion, modify other properties, or combinations thereof. There can be any number of open cells 75 in the present invention so long as the reinforcement 68 provides the functionality described herein. The open cells 75 can, for example, be in the range of about 0-99% of the surface area of the reinforcement 68. As shown in FIGS. 48-51, the open cells 75 are typically organized in groups of the open cells 75 that are in repeating, non-repeating, meandering, or combinations thereof patterns down the length, circumference, width, or combinations thereof of the reinforcement 68. As also shown, in FIGS. 48-51, the open cells 75 are optionally interconnected with other open cells 75 with one or more other member segments 67 or connecting members 77. The open cells 75 are generally partially or fully surrounded by the member segments 67. FIG. 48 illustrates an example of wherein all the open cells 75 are fully surrounded with the member segments 67 and FIG. 51 shows an example wherein few of the open cells 75 are partially surrounded by the member segments 67 so that there is at least one open member segment 81.

The member segments 67 of the reinforcement 68 can be of any cross sectional shape of uniform or varying thickness such as amorphous-shaped, angular-shaped, circular-shaped, concave polygon-shaped, curved-shaped, decagon-shaped, diamond-shaped, dodecagon-shaped, elliptical-shaped, hexagon-shaped; I-beam shaped, isogon-shaped, L-shaped, multilobal, nonagon-shaped, octagonal-shaped, parallelogram-shaped, pentagon-shaped, polygonal-shaped, quadrangle-shaped, quadrilateral-shaped, rectangular-shaped, rhombus-shaped, round-shaped, spherical polygon-shaped, square-shaped, star-shaped, trapezoid-shaped, triangular-shaped, T-shaped, tubular-shaped, undecagon-shaped, U-shaped, V-shaped, zig-zag shaped, or combinations thereof, to name a few. The length of the member segments 67 or connecting members 77 can be any shape such as straight, curved, twisted, helical, hoop, loop, bent, serpentine, semicircular, zigzag, or whatever shape necessary to obtain the functionality described herein. The length of the member segment 67 can be of any size that meets the functionality described herein. The length and thickness of the member segment 67 can be of uniform length and thickness around a cell 75 or there can be varying lengths and thicknesses utilized around a cell 75.

The member segments 67 can be optionally single or multiple strands such as wire or fiber of one or more materials. The strands are optionally woven, nonwoven, knitted, zigzagged, twisted, braided, curved, serpentine, helical, wound, or combinations thereof. The reinforcement 68 or the strands that comprise the member segments 67 can be continuous or discontinuous.

As shown in FIGS. 54 and 55, the reinforcement 68 in first size has first shaped cells 75 and first size internal angles 79. As shown in FIGS. 56 and 57, upon deformation or self-expansion the reinforcement 68 optionally changes to second size and shape resulting in the cells 75 and internal angels 79 also changing to a second size and shape. In this example of the inventive functionality, the reinforcement 68 is increased in size from first diameter to second diameter that results in the first internal angles 79 changing to the second internal angels 79'. Sometimes additional internal angles 79" are formed after expansion wherein the member segments 67 bend to take on the second size and shape of the reinforcement 68. In addition, the shape of the cells 75 changes from a rectangular shape to a polygonal shape.

The reinforcement 68 can be installed independently or it can be installed unattached or attached to the expanded material 12 (such as the expanded tubular profile 10, expanded sheet 42, or expanded fiber 58). It can be of any size or cross section that meets the requirements of the end-use application. For example, the reinforcement 68, expanded material 12, or combinations thereof can be thicker at the center portion and thinner at the ends to reduce the stress at the juncture of the reinforcement 68 and the supporting member 64. The reinforcement 68 can be of one or more materials. The reinforcement 68 can optionally also be spring-like, spring loaded, or have memory so that when modified in size and/or shape it can partially or fully spring back to about a predetermined size or range of sizes and/or shapes. The reinforcement 68 can also be mechanically enlarged and substantially hold its second size and shape after removal of the enlarging device.

It is also possible for the reinforcement 68 to optionally include snap-fit connections and/or hinges. Suitable snap-fit connections include: annular snap-fit, tapered-arm snap-fit, straight beam snap-fit, cantilever snap-fit, u-shaped cantilever snap-fit, L-shaped cantilever snap-fit, or any interlocking mechanical joint especially those that feature a locate and locking design.

The reinforcement 68 in some cases must be flexible to facilitate navigating one or more bends of one or more planes when being inserted into, for example, the supporting member 64. For instance, when the expanded material 12 (such as the expanded tubular profile 10), reinforcement 68, or combinations thereof are inserted into the supporting member 64 that is a human blood carrying artery or other vessel, it is usually important for the reinforcement 68 to be flexible so that it can be positioned without causing damage, injury or unnecessary pain to the patient. Moreover, when installed in a piping system flexibility facilitates insertion through elbows, tees and other fittings. As shown in FIG. 64, to improve flexibility, the reinforcement 68 can optionally include multiple segments or sections like an articulated stent. These sections can be attached or unattached to each other. The optional member segments 67 or connecting members 77 that connect one section to another can be of any configuration such as straight, bent, spiral, zigzag, arcuate, angled, helical, curved, or combinations thereof in shape or orientation to achieve the greatest flexibility. The separation between sections permits the reinforcement 68 to bend more easily especially around tighter turns than one long section.

The reinforcement 68 can also be optionally applied to the outside surface 16, the inside surface 17, or combinations thereof of the expanded material 12 by forming in place. It is possible, for example, to apply the reinforcement 68 in a fluid-like state and partially or fully cure or otherwise transform the form-in-place reinforcement 68 from a liquid to a gel, foam, solid, or combination thereof. Preferably the liquid cures into an elastomeric, plastic, or metallic material of sufficiently high strength to meet the requirements of the end-use application.

The expanded material 12 can be optionally temperature controlled during application of the reinforcement 68. The controlling of temperature can, for example, prevent the form-in-place reinforcement 68 from melting through the wall thickness 24 or causing a hole in wall thickness 24. A low temperature expanded material 12 that has been, for example, partially or fully frozen prior to or during application of a form-in-place reinforcement 68 thereby provides it with more tolerance to high temperature applied form-in-place reinforcements 68. Moreover, it is possible, for example, to use temporary contents 26 in bore 18 that are static or flowing to conduct or convect heat away from wall thickness 24 by serving as a heat sink.

A temperature differential between the expanded material 12 and the reinforcement 68 during assembly can also build in stress between the different components. Stress can also be built into the assembly by selecting materials of differing rates of thermal expansion. This built-in stress, for example, can be useful for size and shape maintenance or recovery.

The form-in-place reinforcement 68 can be applied by any way that meets the requirements of the end-use application. For example, it can be two or more components, thermally-cured, UV-cured, chemical reaction cured, radiation-cured, light cured, moisture cured, metals, a formable composite 73, alloy, biodegradable materials, etc., or combinations thereof. The material of the form-in-place reinforcement 68 can optionally include additives 60, nano size articles 62, deformable elements 71, or combinations thereof. The additives 60, nano size articles 62, or combinations thereof are optionally a particle, tube, or fiber shape. The additives 60, nano size articles 62, or combinations thereof are optionally partially or fully an active ingredient. The nano size articles 62 are optionally useful in delivering the active ingredients. The additives 60, nano size articles 62, or combinations thereof such as the active ingredients are optionally microencapsulated. Inactive ingredients, reinforcement 68 material concentration, or combinations thereof are sometimes employed to dilute the active ingredients to achieve the desired dosage or dosage distribution. The additives 60, nano size articles 62, or combinations thereof such as the active ingredient are optionally delivered to the surroundings by, for example, releasing, eluting, emitting, diffusing, dissolving, leaching, reacting, associating, or combinations thereof. The delivery is, for example, constant rate, ascending rate, descending rate, changing rate, or combinations thereof. The delivery is, for example, immediate, time delayed, modified release, sustained, or combinations thereof.

The form-in-place reinforcement 68 can be applied in any way such as molded, extruded, printed, painted, rolled, wrapped, sprayed, electrostatically transferred to name a few. One way to apply the form-in-place reinforcement 68 to the expanded material 12 such as the expanded tubular profile 10, for example, involves at least partially holding open its bore 18 by, for example, inflating its bore 18 by sealing off its first end 20 and second end 22 and partially or fully pressurizing. One or more elastomeric, polymeric, metallic, or other materials described herein bead is applied to the outside surface 16 of the inflated expanded tubular profile 10. The inflated expanded tubular profile 10 is optionally rotated while a bead is applied in, for example, radial, zigzag, linear, helical, spiral, dot, or matrix patterns. Although not necessary, the ideal fluid material for a for mn-in-place reinforcement 68 has a viscosity that permits it to penetrate into and bond to the surface and/or structure of the expanded material 12. The outside surface 16, the inside surface 17, or combinations thereof can also be treated, for example, as described herein or primed to improve the adhesion of the form-in-place reinforcement 68. Furthermore, the form-in-place material preferably has sufficient strength and elasticity upon setting up to partially or fully hold open the bore 18 of the expanded tubular profile 10. In the most preferred embodiment, the expanded tubular profile 10 having a form-in-place reinforcement 68 is able to be collapsed in size and restored partially or fully to its original shape and/or size once the collapsing force is removed. The form-in-place reinforcement 68 is optionally covered with one or more layers of the expanded material 12 of the same or different structure.

If the form-in-place reinforcement 68 is at least partially cured during fabrication, it can be additionally cured after reaching its ultimate installed location and shape. For example, if a vascular graft is inserted into a vein or artery, it can be collapsed in size for insertion, dilated to open its bore 18 once positioned, and then additionally cured in final position. Curing in its final position can be achieved in any way but it is preferred to do so thermally, chemically, electrically, or through use of light (e.g. UV), radiation, or moisture, for example.

The expanded tubular profile 10 can optionally be turned inside out prior to the application of the reinforcement 68 and then inverted so that the reinforcement 68 is positioned on the inside surface 17. Conversely, the reinforcement 68 can be applied to the inside surface 17 and then inverted so that the reinforcement 68 is on the outside surface 16.

Another method of positioning the reinforcement 68 on the expanded material 12 such as a tubular profile is to assemble one or more layers of the expanded material 12 of the same or different structure with the reinforcement 68 on a core and bake the assembly at an elevated temperature. The reinforcement 68 can be positioned on the outside surface 16, inside surface 17, or combinations thereof. The connecting material 66 can be optionally utilized to hold the components together. Upon cooling the core is removed.

The end or ends of the reinforcement 68 can be optionally blunted, welded, looped or otherwise adapted to prevent snagging, scratching, penetrating or other damage to the supporting member 64 or any other object with a blunt-end 86. Alternatively, there can be, for example, loops, rings (e.g., eyelets) or other blunted objects fabricated on the end or ends of reinforcement 68. The blunted-ends 86 can also be utilized as gripping locations for placing the expanded material 12, reinforcement 68, or combinations thereof in axial, circumferential, or multi-axial tension or compression. Axial, circumferential, or multi-axial tension or compression can be utilized to reduce or increase the size of the expanded material 12, reinforcement 68, or combinations thereof so that they can be inserted having enough clearance with the supporting member 64. When the reinforcement 68 is spring loaded the expanded material 12, reinforcement 68, or combinations thereof can return partially or fully to their original or predetermined size or range of sizes and/or shapes when the tension or compression is removed.

Although not shown, the reinforcement 68 or expanded material 12 can optionally contain somewhat sharp edges that grip the supporting member 64 or other nearby structures upon being located in their final position. The sharp edges are capable of preventing the expanded material 12, reinforcement 68, or combinations thereof from substantially moving out of the desired position upon locating. The reinforcement 68, expanded material 12, or combinations thereof can also optionally contain screens, filters, or hooks to collect debris in the contents 26. The reinforcement 68 can, for example, serve as a blood clot filter.

The reinforcement 68 can also optionally be a partially or fully hollow structure. The hollow reinforcement 68 can be filled with any gas, liquid or solid. The hollow reinforcement 68, for example, can be optionally filled with additives 60, nano size articles 62, or combinations thereof such as active ingredients to provide structure to the expanded material 12 while simultaneously delivering active ingredients such as one or more medications. When implanted these additives 60, nano size articles 62, or combinations thereof such as the active ingredients in the hollow space can, for example, be optionally delivered by releasing, migrating, eluting, emitting, diffusing, dissolving, leaching, reacting, associating, or combinations thereof through, for example, the voids 28. The delivery is, for example, immediate release, modified release, sustained release, extended release, or combinations thereof. The delivery is, for example, constant, ascending, descending, or changing rate into the patient or other surroundings.

Any natural or synthetic material that can be converted into a sufficiently strong strand, arrangement, bead, wire, wall thickness, member, strut, fiber, filament, or yarn is suitable for the fabrication of the reinforcement 68 of the present invention so long as it meets the requirements of the end-use application. The strand, arrangement, bead, wire, member, strut, fiber, filament, wall thickness, or yarn can be optionally further processed into a variety of configurations such as woven, fabric, non-woven, knitted, straight, spiral, coil, serpentine, curved, zigzagged, mesh, lattice, random orientation, loops, mat, foam, lattice, twisted, braided, mesh, or combination thereof to name a few. Without intent on limiting, the reinforcement 68 of the present invention can be, for example, partially or fully fabricated from one or more of the following materials: acetate; acrylic; acrylonitrile (AN); acrylonitrile styrene acrylate (ASA); acrylonitrile butadiene styrene (ABS); aliphatic polyesters; aliphatic-aromatic poly (esteramides); aliphatic-aromatic polyamides; aliphatic-aromatic polyazomethines; aliphatic-aromatic polyesters; alloys; alloys of nickel, alloys of nickel and titanium; alumina; aluminum; aluminum oxide; anidex; aramid (eg. Kevlar® or Nomex®); aromatic poly (esteramides); aromatic poly (estercarbonates); aromatic poly (esterimides); aromatic polyamide; aromatic polyester; biodegradable polymers, bioabsorbable materials; biocompatible materials; biodissolvable materials; boron; boron carbide (B4C); boron nitride; calcium metaphosphate; calcium stearate; carbides; carbon; carboxide; cellulose acetate; cellulose nitrate; ceramics; chromium alloys; cobalt; cobalt alloys; cobalt-chromium-nickel alloys; cobalt alloys with coating of boron nitride, titanium nitride, or diamonds; cobolt-chromium alloys [Stellite™]; copolymers; copolymers of PGA/GLA; cotton; deformable elements 71; elastic materials; elastomeric polyester; elastomers; ethylene vinyl acetate; extended chain polyethylene; extended chain polypropylene; formable composite 73; glass; gold; glycolide; glycolide:lactide; graphite; high MW polylactide; homopolymer of glycolic acid; iridium; inconel; lactide; lastrile; latex; liquid crystal copolyesters; liquid crystal polymers; lyocel; MP35N alloy; metals; metal alloys; minerals; modacrylic; modal; natural-based (animal, vegetable, mineral) materials; niobium alloys; nickel titanium alloy [NiTi, NITINOL™]; nitrides; nitrile; nylons (e.g., 6, 66, 46, 6-3, 610, 612, 11, 12, etc.); olefins; palladium; parylene; plastics; platinum; poly (alkylen naphthalates); poly (arylen sulfides); poly alkylene terephthalates; poly (butylene terephthalate); poly (ethylene naphthalate); poly (ethylene terephthalate); poly (phenylen sulfide); poly acrylonitrile (PAN); poly alkylene terephthalates; poly amides; poly arylene sulfide; poly (butylene terephthalate); poly (ethylene naphthalate); poly (ethylene terephthalate); poly (phenylen sulfide); poly acrylonitrile (PAN); poly alkylene terephthalates; poly amides; poly arylene sulfide; poly benzothiazole (PBT); poly dioxanone; poly (DL-lactide); poly(lactideglycolide) copolymers; poly(p-phenylene benzobisthiazole) (PBZT); polyacrylonitrile; polyamide (nylon); polyarylene sulfide; polyarylethersulfone; polybenzazole (PBO); polybenzimidazole (PBI); polybenzoxazole; polybisbenzimidazobenzophenananthroline; polybutylene terephthalate; polycaprolactone; polycarbonate; polydioxanone; polyesters; polyester containing glycolate ester linkages; polyetheretherketone (PEEK); polyethers; poly(ether-b-amide) [Pebax™ available from Arkema]; polyether block amides [PEBA]; poletherimide (PEI); polyetherketone (PEK); polyethermide; polyethersulfone; polyethylenes (PE, LDPE, MDPE, HDPE, UHMWPE, etc); polyethylene naphthalate (PEN); polyethylene terephthalate (PET); polyglycolic acid; polyhydroxybutyrate; polyimides; polylactic acid (PLA); poly-1-lactic acid [PLLA]; polycaprolactone [PCL]; poly(methyl methacrylate [PMMA]; polymers; polymers containing enzymes; polynosic; polyolefins; polyoxyamide; polyphenylenebenzobisoxazole (PBO); polyphthalamide; polypropylene (PP); polystyrenes (PS); polysulfide (or sulfar); polysulfone (PES); polytetrafluoroethylene (PTFE); polyurethanes (or spandex); polyvinyl; polyvinyl acetate [PVAC]; polyvinyl alcohol; polyvinyl chloride (PVC); polyvinyl dichloride; polyvinylidene chloride (PVDC or saran); polyvinylidinefluoride (PVDF); quartz; rayon; reconstituted refractory; refractory; rubber; semimetals; silicon carbide (SiC); silicon carboxide; silicon dioxide (quartz); silicone; silver; silicone rubber; silk; sisal; stainless steel; steel; styrenes; sulfides; synthetic materials; tantalum; tetrafluoroethylene; thermoplastic urethanes; thermoplastics; thermosets; thermotropic liquid crystalline polymers; titanium; titanium alloys; titanium and aluminum alloys; triacetate; tungsten; vinal; vinyls; vanadium; vulcanized materials; zirconium, zirconium oxides, their substantially functional equivalents, or combinations thereof.

It is preferred that the reinforcement 68 is comprised of a formable composite 73 that includes a plurality of deformable elements 71 that are partially or fully interconnected as shown in FIG. 52 or encapsulated as shown in FIG. 53 with one or more binders 69. The binder 69 optionally includes additives 60, nano size articles 62, or combinations thereof. The binder 69 partially or fully holds the deformable elements 71 substantially together as a pair or group of deformable elements 71. The deformable elements can be in the range of 0-99 volume percent of the formable composite 73. The deformable elements 71 are preferably a plurality of discontinuous elements. The deformable elements 71 for the most part retain the first size and shape until after deformation or self-expansion wherein they retain the second size shape. Having a reinforcement 68 comprised of a formable composite 73 provides substantially superior flexibility and less drag against the supporting member 64 during installation when compared to the prior art reinforcements which are generally manufactured of a single metallic material. The reinforcement 68 made of a formable composite 73 is manufactured, for example, by injection molding, extrusion, EDM, laser, weaving, stamping, melt spinning, electrospinning, or any other process capable of producing the configurations described herein.

The binder 69 of the present invention can be any material that partially or fully connects or encapsulates two or more deformable elements 71. For example, and without intent on limiting, one or more of the following materials can be selected for partial or full fabrication of binder 69: 1,3propanediol terephthalate (3GT); 1,3-propanediol [PDO] (Sorona™—available from DuPont); acetal; acetate; acrylates; acrylics; acrylonitrile (AN); acrylonitrile butadiene styrene (ABS); acrylonitrile styrene acrylate (ASA); aldehyde polymers; alginic polymers; aliphatic polyesters; aliphatic-aromatic poly (esteramides); aliphatic-aromatic polyamides; aliphatic-aromatic polyazomethines; aliphatic-aromatic polyesters; anhydride modified polyethylene; anhydride modified polypropylene; anhydride modified vinyl acetate; aramids; aromatic poly (esteramides); aromatic poly (estercarbonates); aromatic poly (esterimides); aromatic polyamide; aromatic polyester; bioabsorbable materials; bio-based polymers; biocompatible materials; bioabsorbable materials; bioadsorbable materials; biodegradable polymers; biodissolvable materials; biopolymers; carbonized polymeric materials; cellulose acetate; cellulose nitrate; chitosan; chlorinated polyvinyl chloride [CPVC]; condensation polymers; copolymers; copolymers of ethylene-tetrafluoroethylene [ETFE]; copolymers of PGA/GLA; copolymers of tetrafluoroethylene (TFE) and perfluoromethyl vinyl ether (PMVE); copolymers of tetrafluoroethylene [TFE]; copolymers of tetrafluoroethylene [TFE] and per fluoro (propyl vinyl ether) [PFA]; corn-based polymers; cross-linkable polymers; degradable poly carbonates; degradable polycarboxylates; degradable polymers; elastic materials; elastomeric polyester; elastomers; ethylene butyl acrylates; ethylene chlorotrifluoroethylene [ECTFE]; ethylene methyl acrylates; ethylene tetrafluoroethylenes [ETFE]; ethylene vinyl acetates [EVA]; ethylene vinyl alcohols; ethylene-chlorotrifluoroethylene (ECTFE); ethylene-chlorotrifluoroethylene copolymers; ethylene-tetrafluoroethylene [ETFE]; extended chain polyethylene;

extended chain polypropylene; fluorinated ethylene propylene [FEP]; fluorocarbons; fluoroelastomers FKM [Viton™]; fluoropolymers; fruit-based polymers; glutens; glycolide; glycolide:lactide; high M W polylactide; homopolymer of glycolic acid; homopolymers; homopolymers of polychlorotrifluoroethylene [PCTFE]; hydrolysable polyesters [e.g. polyactic acid and polyglycolic acid]; lactide; lastrile; latex; liquid crystal copolyesters; liquid crystal polymers [LCP]; lyocel; materials having low coefficient of friction; methacrylates; modacrylic; modal; modified polyphenylene oxides [PPO]; natural-based (animal, vegetable, mineral) materials; nitrile; non highly cross-linked hyaluronic acid; non-highly cross-linked collagen; nylons [e.g., 6, 46, 66, 6-3, 69, 610, 612, 11, 12, etc.]; olefins; parylene; per fluoro (alkyl vinyl ethers) [PAVE]; per fluoro methyl vinyl ether; perfluoro (propyl vinyl ethers) [PPVE]; perfluoroalkoxyethylene [PFA]; perfluoroelastomers FFKM (Kalrez™); perfluoroethylene-propylene copolymers; phenolics; plant-based polymers (capable of substantially maintaining structure greater than 24 hours after installation); plastics; poletherimide (PEI); poly (alkylen naphthalates); poly (arylen sulfides); poly (butylene terephthalate); poly (DL-lactide); poly(L-lactide-co-glycolide); poly (ethylene naphthalate); poly (ethylene oxide); poly (ethylene terephthalate); poly (phenylen sulfide); poly acrylonitrile (PAN); poly alkylene terephthalates; poly amides; poly arylene sulfide; poly benzothiazole (PBT); poly dioxanone; poly glycolide:trimethylene carbonate [PGA:TMC]; poly(alkyl-p-hydroxybenzoate)s; poly(benzimidazole)s; poly(benzoxazole)s; poly(benzthiazole)s; poly(ethylene glycol)-terephthalate-poly(butylene terephthalate) [PEGT/PBT] block co-polymer; poly(lactideglycolide) copolymers; poly-(p-phenylene benzbisoxazole)s; poly-(p-phenylene benzbis-thiazole)s; poly(p-phenylene benzo-bisthiazole) (PBZT); poly-3-hydroxybutrate; polyacetals; polyacrylamides; polyacrylonitrile; polyamide (nylon); polyamide imide; polyamids; polyanhydrides; polyarylamides; polyarylate; polyarylene ether; polyarylene sulfide; polyaryletherketone [PAEK]; polyarylethersulfone; polyarylsulfone [PAS]; polybenzazole (PBO); polybenzimidazole; polybenzoates; polybenzoxazole; polybisbenzimidazobenzophenananthroline; polybutylene; polybutylene terephthalate [PBT]; polycaprolactone; polycarbonate; polychlal; polychlorotrifluoroethylene [PCTFE]; polydioxanone; polyester containing glycolate ester linkages; polyester thermoplastic elastomer; polyesters; polyesters [Dacron™]; polyether block amide [PEBA]; poly(ether-b-amide); polyether ester elastomer; polyetheretherketone [PEEK]; polyetherimide; polyetherketone (PEK); polyetherketoneetherketoneketone [PEKEKK]; polyethermide; polyethersulfone [PES]; polyethylene ethyl acrylate; polyethylene naphthalate (PEN); polyethylene terephthalates (PET); polyethylenes [PE, LDPE, LLDPE, VLDPE, MDPE, HDPE, UHMWPE, HDXLPE, PEX, etc]; polyglycolic acid [PGLA]; polyhydroxybutyrate; polyimide; polyketone; polylactic acid (PLA); polymers; polymers based on corn-derived chemical; polymers containing enzymes; polymethyl-pentene [PMP]; polynosic; polyolefins; polyorthoesters; polyoxyamide; polyperfluoroalkoxyethylene; polyphenols; polyphenylene ether; polyphenylene sulfide (PPS); polyphenylenebenzobisoxazole (PBO); polyphenylsulfone; polyphthalamide; polypropylenes; polypropylenes (PP); polysaccharides; polysiloxanes; polystyrenes; polysulfide (or sulfar); polysulfides; polysulfones (PES); polytetrafluoroethylenes [PTFE]; polytrimethylene terephthalate [PTT]; polyureas; polyurethanes (or spandex); polyvinyl acetates, polyvinyl alcohol; polyvinyl dichloride [PVDC]; polyvinyl fluoride [PVF]; polyvinylidene fluoride [PVDF]; polyvinylchlorides [PVC]; polyvinylidene chloride (PVDC or saran); polyvinylidene fluoride [PVDF]; polyvinyls; rayon; rubber; silicone; silicone polyurethane; silicone rubber; siloxane-based aromatic polyurethanes; styrene; styrene acrylonitrile [SAN]; styrene butadiene; styrene butadienestyrene [SBS]; styrene maleic anhydride [SMA]; styrenes; styrenic elastomers [TES]; sulfides; syndiotactic polystyrene [SPS]; synthetic materials; tetrafluoroethylene [TFE]; thermoplastic olefinic elastomer [TPO]; thermoplastic polyurethane [TPUR]; thermoplastic urethanes; thermoplastics; thermosets; thermotropic liquid crystalline polymers; triacetates; urethanes; vegetable oil-based polymers; vegetable-based polymers; vinyl; vinylon; vulcanized materialsl; their substantially functional equivalents, copolymers, precursors, derivatives, or combinations thereof.

Without intent on limiting, other examples of suitable materials, for partial or full composition of the binder 69 of the present invention include, for example,: acrylate-based adhesives; 2-hydroxyethyl methacrylate (HEMA); acrylates; acrylic rubber (ACM); acrylic-based adhesives; acrylics; acrylonitrile methyl acrylate; adhesives; alkyds; allyl derivatives; allyl polydiallyphthalate plastics; amino plastics; biocurable materials; biocompatible resins; bis-acrylic resins; bisphenol glycidyl methacrylate; bisphenol-A-glycidymethacrylate (bisGMA); butadiene rubber; butyl rubber (IIR, CIIR, BIIR); carbamoylisocyanurates; carboxylate cement; chemical reaction curable materials; casein plastics (CS); cationically polymerizable epoxy; cationically polymerizable epoxy, compound or resin; cement; chlorobutyl (CIIR); chloronated polyethylene (CPE); chlorosulfonated polyethylene rubber (CM, CSM); collagen (Types 1-13); copolymerizable mixtures of acrylated monomers such as those in U.S. Pat. No. 4,652,274; crystalline polyglycolic acid; cure in place polymers; cyanoacrylate; cyclic acetals; diallyl phthalate (DAP); elastomeric materials; elastomeric silicones; elastomeric urethanes; electron beam cured resins; emulsions; encapsulating compounds; encapsulating gels; epichlorhydrin (CO, ECO); epoxies (EP); epoxy compounds; epoxy-based adhesives; ethylene acrylic (AEM); ethylene propylene rubber (EPM, EPDM); ethylene vinyl acetate; FDA approved resins; fluorocarbon rubber (FPM); fluorosilicone rubber (FMQ, FVMQ); foam; furan plastics; glue; hardenable resins; heat cured acrylics; heat cured resins; heat cured silicone; heat cured urethanes; hyaluronic acid; hydrogenated nitrile rubber (HNBR); hydroxyapatite ceramic; isophthalic resin; isoprene rubber (IR); lactams; lactones; latex; light activated adhesives; light activated resins; light curable acrylics; light curable epoxies; light curable oligomers; light curable polymers; light curable resins; light curable silicone; light curable urethanes; light-cured urethane-dimethacrylate (UDMA) resins; materials curable with argon-ion laser; materials curable with by way of an irradiation source; materials curable with edge emitting laser chips; materials curable with high intensity blue light; materials curable with laser based radiation; materials curable with laser chip array; materials curable with laser chips; materials curable with light; materials curable with light emitting diode chip array; materials curable with light emitting diode chips; materials curable with light emitting diodes; materials curable with metal halide lamps; materials curable with moisture; materials curable with plasma ark lamps; materials curable with surface emitting laser chips; materials curable with tungsten halogen lamps; materials curable with ultraviolet (UV) light; materials curable with VCSEL chips; materials curable with visible light; melamine; melamine formaldehyde; melamine phenolics; methacrylates; methyl a-cyanoacrylate; moisture curable acrylates; moisture curable acrylics; moisture curable epoxies; moisture curable polymers; moisture curable polysiloxanes; moisture curable resins; moisture curable silicone; monomer, oligomers and polymers with grafted adhesion promoters; monomers, oligomers and polymers with dissolved adhesion promoters; monomers, oligomers and polymers with dissolved photoinitiators; monomers, oligomers and polymers with grafted photoinitiators; monomers, oligomers, and polymers containing cationically active functional groups; monomers, oligomers, and polymers having one or more ethylenically unsaturated groups; monomers,oligomers and polymers prepared by the reaction of isophorone diisocyanate (D) with polyol polypropylene glycol (P) and a subsequent endcapping of non-reacted terminal isocyanato groups with 2-hydroxyethyl acrylate (A); mortar; multi part resins; natural rubber (NR, IR, polyisoprene); neoprene; nitrile rubber (NBR); oligomers; ortho diallyl phthalate; orthophthalic polyester; oxetanes; oxolanes; perfluoroelastomers (FFKM); peroxide cured fluoroelastomers; phenol formaldehydes; phenolics; photocatalytic acrylates; photocatalytic materials; photocatalytic resins; photocurable acrylics; photocurable epoxies; photocurable materials; photocurable polymers; photocurable resins; photocurable urethanes; photopolymerizable compositions; polyacrylates; polyacrylonitrides; polyamides; polybutadiene rubbers (BR); polychloroprene rubbers (CR); polycyanoethylenes; polyesters; polyethylenes; polyimides; polyisoprene rubber; polymerizable 1,2,4-butanetriol trimethacrylate; (polymerizable) 1,3-propanediol di(meth)acrylate; polymerizable 1,4-cyclohexanediol diacrylate; (polymerizable) acrylated oligomers such as those of U.S. Pat. No. 4,642,126; (polymerizable) allyl acrylate; (polymerizable) bis-(meth)acrylates of polyethylene glycols of molecular weight 200 to 500; (polymerizable) bis[1-(2-acryloxy)]-p-ethoxyphenyldimethyl bis[1-(3-acryloxy-2-hydroxy)]-p-propoxyphenyldimethylmethane, and trishydroxyethylisocyanurate trimethacrylate; (polymerizable) diethyleneglycol diacrylate; (polymerizable) diglycidyl methacrylate of bis-phenol A ("bis-GMA"); (polymerizable) ethyl acrylate; (polymerizable) ethyleneglycol diacrylate; (polymerizable) glycerol diacrylate; (polymerizable) glycerol triacrylate; (polymerizable) isopropyl methacrylate; (polymerizable) methyl (meth)acrylate; (polymerizable) mono-, di-or poly-(meth)acrylates; (polymerizable) n-hexyl acrylate; (polymerizable) pentaerythritol tetra(meth)acrylate; (polymerizable) pentaerythritol triacrylate; (polymerizable) sorbitol hexacrylate; (polymerizable) stearyl acrylate; (polymerizable) triethyleneglycol dimethacrylate; (polymerizable) trimethylolpropane triacrylate; (polymerizable) vinyl compounds such as styrene, diallyl phthalate, divinyl succinate, divinyl adipate and divinylphthalate; polymers; polymers with leachable additives; polymethyl methacrylates; polynorbornene rubbers (PNR); poly phosphazene rubbers (PZ, FZ); polypropylenes; polysulfones; polysulphide rubbers (TR); polyurethanes; polyurethane foams; polyurethane resins; polyurethane rubbers (AU, EU); polyurethane-based adhesives; polyvinyl acetates; polyvinyl butyrals; polyvinyl chloride resins; pottings; propylene oxide rubbers (GPO); purified serum albumin (BSA) and glutaraldehyde; radiation curable acrylics; radiation curable epoxies; radiation curable oligomers; radiation curable polymers; radiation curable polyurethane; resins; radiation curable polyurethanes acrylates; radiation curable urethanes; radiation-curable polyurethane acrylate oligomers (or prepolymers); radiation-curable polyurethanes; resins containing at least one ethylenically unsaturated bond, and are capable of undergoing addition polymerization; resins containing both cationically curable and free radically curable resins; resins containing photocatalysts; resins cured with electron beam ; resins that polymerize under irradiation with visible light; resins whose reaction mechanism is free-radical based on acrylates, methacrylates, vinyl, and allyl compounds; RTV; rubber-based adhesives; rubbers, sealants; silicones; silicone elastomers; silicone foams; silicone plastics (SI); silicone polycarbonate urethanes; silicone polyether urethanes; silicone rubbers (MQ, VMQ, PMQ, FMQ); single-component or multiple-component polyelectrolyte cements; styrene block copolymers; styrene butadiene rubbers (SBR); styrene-acrylics; styrene-butadiene block copolymer; styrene butadiene latexes; styrene isoprene block polymers; synthetic rubbers; tar; tetraflouroethylene-propylenes (FEPM); tetra-hydrofurfuryl methacrylates; thermoplastics; thermoset fluoroelastomers; thermoset plastics; thermoset polyurethanes; thermosetting resins; thermosetting unsaturated polyesters; triethyleneglycol methacrylate (TEGDMA); two part adhesives; ultraviolet light (UV) cured acrylates; ultraviolet light (UV) resins; ultraviolet light (UV)/visible light cured resins; unsaturated polyesters (UP); urethanes; urethane rubbers; urethane-acrylates; UV-curable urethane acrylates; UV-cured epoxies; UV-light sensitive urethane acrylate oligomers; vinyl benzene derivatives; vinyl esters; vinyl ethers; vinyl ketones; vinyl-acrylics; vinyl-based adhesives; vinyls; visible light curing resins; their substantially functional equivalents, copolymers, precursors, derivatives, or combinations thereof. The resins or other materials can be uncured or partially cured at time of installation.

Without intent on limiting, still more materials suitable for use in the present invention as partial or full compositon of binder 69 include, for example, one or more of the following: acrylate-based adhesives; 2-hydroxyethyl methacrylate (HEMA); acrylic rubber (ACM); acrylic-based adhesives; acrylonitrile methyl acrylate; adhesives; alkyds; allyl derivatives; allyl polydiallyphthalate plastics; amino plastics; biocurable materials; biocompatible resins; bis-acrylic resins; bisphenol glycidyl methacrylate; bisphenol-A-glycidymethacrylate (bisGMA); butadiene rubber; butyl rubber (IIR, CIIR, BIIR); carbamoylisocyanurates; carboxylate cement; chemical reaction curable materials; casein plastics (CS); cationically polymerizable epoxy; cationically polymerizable epoxy, compound or resin; caulks; cement; chlorobutyl (CIIR); chlorinated polyethylene (CPE); chlorosulfonated polyethylene rubber (CM, CSM); collagen (Types 1-13); copolymerizable mixtures of acrylated monomers such as those in U.S. Pat. No. 4,652,274; crystalline polyglycolic acid; cure in place polymers; cyanoacrylate; cyclic acetals; diallyl phthalate (DAP); elastomeric materials; elastomeric silicones; elastomeric urethanes; electron beam cured resins; emulsions; encapsulating compounds; encapsulating gels; epichlorhydrin (CO, ECO); epoxies (EP); epoxy compounds; epoxy-based adhesives; ethylene acrylic (AEM); ethylene propylene rubber (EPM, EPDM); FDA approved resins; fluorocarbon rubber (FPM); fluoroelastomers (FKM); fluorosilicone rubber (FMQ, FVMQ); foam; furan plastics; glue; hardenable resins; heat cured acrylics; heat cured resins; heat cured silicone; heat cured urethanes; hyaluronic acid; hydrogenated nitrile rubber (HNBR); hydroxyapatite ceramic; isophthalic resin; isoprene rubber (IR); lactams; lactones; light activated adhesives; light activated resins; light curable acrylics; light curable epoxies; light curable oligomers; light curable polymers; light curable resins; light curable silicone; light curable urethanes; light-cured urethane-dimethacrylate (UDMA) resins; materials curable with argon-ion laser; materials curable with by way of an irradiation source; materials curable with edge emitting laser chips; materials curable with high intensity blue light; materials curable with laser based radiation; materials curable with laser chip array; materials curable with laser chips; materials curable with light; materials curable with light emitting diode chip array; materials curable with light emitting diode chips; materials curable with light emitting diodes; materials curable with metal halide lamps; materials curable with moisture; materials curable with plasma ark lamps; materials curable with surface emitting laser chips; materials curable with tungsten halogen lamps; materials curable with ultraviolet (UV) light; materials curable with VCSEL chips; materials curable with visible light; melamine; melamine formaldehyde; melamine phenolics; methyl a-cyanoacrylate; moisture curable acrylates; moisture curable acrylics; moisture curable epoxies; moisture curable polymers; moisture curable polysiloxanes; moisture curable resins; moisture curable silicone; monomer, oligomers and polymers with grafted adhesion promoters; monomers, oligomers and polymers with dissolved adhesion promoters; monomers, oligomers and polymers with dissolved photoinitiators; monomers, oligomers and polymers with grafted photoinitiators; monomers, oligomers, and polymers containing cationically active functional groups; monomers, oligomers, and polymers having one or more ethylenically unsaturated groups; monomers, oligomers and polymers prepared by the reaction of isophorone diisocyanate (D) with polyol polypropylene glycol (P) and a subsequent endcapping of non-reacted terminal isocyanato groups with 2-hydroxyethyl acrylate (A); multi part resins; natural rubber (NR, IR, polyisoprene); neoprene; nitrile rubber (NBR); oligomers; ortho diallyl phthalate; orthophthalic polyester; oxetanes; oxolanes; peroxide cured fluoroelastomers; phenol formaldehydes; photocatalytic acrylates; photocatalytic materials; photocatalytic resins; photocurable acrylics; photocurable epoxies; photocurable materials; photocurable polymers; photocurable resins; photocurable urethanes; photopolymerizable compositions; polyacrylates; polyacrylonitrides; polybutadiene rubbers (BR); polychloroprene rubbers (CR); polycyanoethylenes; polyimides; polyisoprene rubber; polymerizable 1,2,4-butanetriol trimethacrylate; (polymerizable) 1,3-propanediol di(meth)acrylate; polymerizable 1,4-cyclohexanediol diacrylate; (polymerizable) acrylated oligomers such as those of U.S. Pat. No. 4,642,126; (polymerizable) allyl acrylate; (polymerizable) bis-(meth)acrylates of polyethylene glycols of molecular weight 200 to 500; (polymerizable) bis[1-(2-acryloxy)]-p-ethoxyphenyldimethyl bis[1-(3-acryloxy-2-hydroxy)]-p-propoxyphenyldimethylmethane, and trishydroxyethyl-isocyanurate trimethacrylate; (polymerizable) diethyleneglycol diacrylate; (polymerizable) diglycidyl methacrylate of bis-phenol A ("bis-GMA"); (polymerizable) ethyl acrylate; (polymerizable) ethyleneglycol diacrylate; (polymerizable) glycerol diacrylate; (polymerizable) glycerol triacrylate; (polymerizable) isopropyl methacrylate; (polymerizable) methyl (meth)acrylate; (polymerizable) mono-, di-or poly-(meth)acrylates; (polymerizable) n-hexyl acrylate; (polymerizable) pentaerythritol tetra(meth)acrylate; (polymerizable) pentaerythritol triacrylate; (polymerizable) sorbitol hexacrylate; (polymerizable) stearyl acrylate; (polymerizable) triethyleneglycol dimethacrylate; (polymerizable) trimethylolpropane triacrylate; (polymerizable) vinyl compounds such as styrene, diallyl phthalate, divinyl succinate, divinyl adipate and divinylphthalate; polymers with leachable additives; polymethyl methacrylates; polynorbornene rubbers (PNR); poly phosphazene rubbers (PZ, FZ); polysulphide rubbers (TR); polyurethane foams; polyurethane resins; polyurethane rubbers (AU, EU); polyurethane-based adhesives; polyvinyl butyrals; polyvinyl chloride resins; pottings; propylene oxide rubbers (GPO); purified serum albumin (BSA) and glutaraldehyde; radiation curable acrylics; radiation curable epoxies; radiation curable oligomers; radiation curable polymers; radiation curable polyurethane; resins; radiation curable polyurethanes acrylates; radiation curable urethanes; radiation-curable polyurethane acrylate oligomers (or prepolymers); radiation-curable polyurethanes; resins containing at least one ethylenically unsaturated bond, and are capable of undergoing addition polymerization; resins containing both cationically curable and free radically curable resins; resins containing photocatalysts; resins cured with electron beam ; resins that polymerize under irradiation with visible light; resins whose reaction mechanism is free-radical based on acrylates, methacrylates, vinyl, and allyl compounds; RTV; rubber-based adhesives; rubbers, sealants; silicones; silicone elastomers; silicone foams; silicone plastics (SI); silicone polycarbonate urethanes; silicone polyether urethanes; silicone rubbers (MQ, VMQ, PMQ, FMQ); single-component or multiple-component polyelectrolyte cements; styrene block copolymers; styrene butadiene rubbers (SBR); styrene-acrylics; styrene-butadiene block copolymer; styrene butadiene latexes; styrene isoprene block polymers; synthetic rubbers; tetraflouroethylene-propylenes (FEPM); tetra-hydrofurfuryl methacrylates; thermoset fluoroelastomers; thermoset plastics; thermoset polyurethanes; thermosetting resins; thermosetting unsaturated polyesters; triethyleneglycol methacrylate (TEGDMA); two part adhesives; ultraviolet light (UV) cured acrylates; ultraviolet light (UV) resins; ultraviolet light (UV)/visible light cured resins; unsaturated polyesters (UP); urethane rubbers; urethane-acrylates; UV-curable urethane acrylates; UV-cured epoxies; UV-light sensitive urethane acrylate oligomers; vinyl benzene derivatives; vinyl esters; vinyl ethers; vinyl ketones; vinyl-acrylics; vinyl-based adhesives; visible light curing resins; their substantially functional equivalents, copolymers, precursors, derivatives, or combinations thereof.

If the binder 69 of the present invention is partially or fully biodegradable, bioabsorbable, or bioadsorbable in any way, it is possible to leave the deformable elements 71 partially or fully behind so that they are attached or unattached to the supporting member 64. Likewise, if the deformable elements 71 are partially or fully biodegradable, bioabsorbable, or bioadsorbable in any way, it is possible to leave the binder 69 partially or fully behind so that it is attached or unattached to the supporting member 64. Finally, it is possible if the binder 69 and deformable elements 71 are partially or fully biodegradable, bioabsorbable, or bioadsorbable in any way, it is possible to have the binder 69 and deformable elements 71 partially or fully dissolve or otherwise disappear at different times or rates of time. For example, if a reinforcement 68 used as an endovascular stent is comprised of a formable composite 73 having a bio-dissolvable binder 69 and a plurality of stainless steel deformable elements 71, the binder 69 can dissolve and leave behind the deformable elements 71 that are held in place by tissue that has grown within the matrix of deformable elements 71. These remaining deformable elements 71 can keep a blood carrying vessel propped open so that blood flows through the substantially unrestricted passageway.

The deformable elements 71 of the present invention are preferably comprised of any material capable of substantially maintaining the desired first size and shape prior to and during installation while substantially maintaining second size and shape after installation. Without intent on limiting, examples of suitable materials, for partial or full composition of the deformable elements 71 of the present invention include: alloys; alloys of 50.5 atomic % Nickel (Ni)/49.5 atomic % Titanium (Ti); alloys of 50-60 atomic % Nickel (Ni)/40-50 atomic % Titanium (Ti); alloys of nickel; alloys of nickel and titanium; alumina; aluminum; aluminum oxide; anidex; annealed metals; annealed stainless steel; aramid (e.g. Kevlar® or Nomex®)); boron; boron carbide (B4C); boron nitride; brass; calcium metaphosphate; calcium stearate; carbides; carbon; carbon fibers; carboxide; ceramics; chromium alloys; coated metals; cobalt; cobalt alloys; cobalt alloys containing tungsten; cobalt-chromium-nickel alloys; copper; cotton; deformable materials; ductile metal or alloy plated with stainless steel, platinum, tantalum, titanium, or tungsten; ductile metals; elastic materials; fibers; filaments; formable materials; glass; gold; graphite; hafnium; heat treated metals; iron; MP 35N alloy; malleable materials; malleable metals; material or alloy that contains a ternary element; material or alloy that contains a ternary element between 1 atomic % to 30 atomic %; material or alloy that has a ratio of stress on loading to stress on unloading of 1:5 to 5:1; materials 20-80% cold worked; materials capable of plastic deformation; materials or alloys that are super elastic; materials plated with biocompatible material; materials plated with stainless steel, platinum, tantalum, titanium, or tungsten; materials that are super elastic at body temperature (98.6° F.); materials that are plastic at body temperature (98.6° F.); materials that can undergo a transformation from martensite to austenite state or reverse; materials that have been cold worked; materials that return to a defined shape or size when subjected to a certain thermal or stress condition; materials with austenite phase (Af temperature) in range of 1-80° C.; materials with austenite phase (Af temperature) in range of 24-37° C.; metals; metal alloys; metallic material; metals having thermal hyseresis; minerals; natural fibers; Ni44Ti47Nb9; nickel titanium alloy [NiTi, NITINOL™]; niobium; niobium alloys; Nitinol® wire; nitrides; plastic materials; plated materials; platinum; quartz; radiopaque materials; reconstituted refractory; refractory; semimetals; shape memory materials and alloys; silicon carbide (SiC); silicon carboxide; silicon dioxide (quartz); silk; silver; sisal; stainless steels; stainless steel AISI 316 alloy; stainless steel AISI 316L alloy; stainless steel wire; steel; tantalum; titanium; titanium alloys; tungsten; vinal; zirconium; zirconium oxides; their substantially functional equivalents, or combinations thereof.

The deformable elements 71 can be of any length, longitudinal shape, or cross sectional shape that provides the functionality described herein. The most preferred deformable elements 71 are small enough to be easily injection molded or extruded into shapes and configurations described herein. The deformable elements 71 are preferably less than about one diameter or width of the reinforcement 68, more preferably less than about one quarter of one diameter or width of the reinforcement 68, and most preferably less than about one tenth the diameter or width of the reinforcement 68. The deformable elements 71 can be of uniform or variable thickness. Without intent on limiting, the cross sectional shape of the deformable elements 71, for example, can be one or more of the following shapes: amorphous-shaped, angular-shaped, circular-shaped, concave polygon-shaped, curved-shaped, decagon-shaped, diamond-shaped, dodecagon-shaped, elliptical-shaped, hexagon-shaped; I-beamshaped, isogon-shaped, L-shaped, multilobal, nonagon-shaped, octagonal-shaped, parallelogram-shaped, pentagon-shaped, polygonal-shaped, quadrangle-shaped, quadrilateral-shaped, rectangular-shaped, rhombus-shaped, round-shaped, spherical polygon-shaped, square-shaped, star-shaped, trapezoid-shaped, triangular-shaped, T-shaped, tubular-shaped, undecagon-shaped, U-shaped, V-shaped, zig-zag shaped, or combinations thereof, to name a few. The longitudinal shape of the deformable elements can be, for example, straight, curved, twisted, helical, hoop, loop, bent, serpentine, semi-circular, zigzag, or whatever shape necessary to obtain the functionality described herein.

The reinforcement 68 can also be manufactured of a metal that is malleable and has been punctured, molded, or machined with slits, slots, or open spaces. The metal can be any shape such as cylindrical shape or flat shape. When the metal is dilated or lengthened the slits or hole pattern (e.g. open cell 75) open and form, for example, a diamond-like repeating pattern such as that produced by those skilled in the art of expanded metal. If the expanded metal is in sheet configuration it can be rolled or otherwise converted into a tubular or cylindrical shape. The edges can be welded or otherwise connected to form a tube or cylinder.

The slit or hole pattern (e.g. open cell 75) of the reinforcement 68 including those made of a formable composite 73 can be, for example, formed in the tube or sheet through machining, lasers, electrical discharge milling [EDM], waterjet cut, or chemical etching. The burrs can be removed and the surface polished.

The optional connecting material 66 is any natural or synthetic material that is capable of partially or fully interconnecting or attaching the expanded material 12, reinforcement 68, supporting member 64, backing material, additives 60, nano size articles 62, or combinations thereof. The connecting material 66 can be applied before or after the expanded material 12, reinforcement 68, or combinations thereof are positioned with supporting member 64. A layer or layers of foam, felt, fabric, absorbent material, or other material capable of holding or transporting the connecting material 66 (not shown) can be optionally applied to expanded material 12, reinforcement 68, or combinations thereof to carry the connecting material 66 to supporting member 64 or other components during assembly. In addition to attaching the various components of the present invention, the connecting material 66 can also serve as a sealant to fill a crack, hole or thin spot that may exist in the supporting member 64. The connecting material 66 can optionally include reinforcements, fillers, additives 60, nano size articles 62, or other materials as known by those skilled in the art of manufacturing composites, fiber reinforced plastics, or fiber reinforced concrete. The connecting material 66 optionally can be in the form of a thread, fiber, ribbon, filament, wire staple, coupling material, suture, or any other material capable of partially or fully connecting the expanded material 12, reinforcement 68, supporting member 66, or combinations thereof. It is also possible in the present invention to make the connections thermally or through the use of ultrasonics.

The optional connecting member 66 of the present invention is any material capable of partially or fully holding two or more items together. Without intent on limiting, examples of suitable materials, for partial or full composition of the connecting material 66 of the present invention include: acrylate-based adhesives; 2-hydroxyethyl methacrylate (HEMA); acrylates; acrylic rubber (ACM); acrylic-based adhesives; acrylics; acrylonitrile methyl acrylate; adhesives; alkyds; allyl derivatives; allyl polydiallyphthalate plastics; amino plastics; asphalt; biocurable materials; biocompatible resins; biological growth; bis-acrylic resins; bisphenol glycidyl methacrylate; bisphenol-A-glycidymethacrylate (bisGMA); butadiene rubber; butyl rubber (IIR, CIR, BIIR); carbamoyl-isocyanurates; carboxylate cement; chemical reaction curable materials; casein plastics (CS); cationically polymerizable epoxy; compound or resin; caulks; cement; chlorobutyl (CIIR); chlorinated polyethylene (CPE); chlorosulfonated polyethylene rubber (CM, CSM); coatings; collagen (Types 1-13); concrete; copolymerizable mixtures of acrylated monomers such as those in U.S. Pat. No. 4,652,274; crystalline polyglycolic acid; cure in place polymers; cyanoacrylate; cyclic acetals; diallyl phthalate (DAP); elastomeric materials; elastomeric silicones; elastomeric urethanes; elastomers; electron beam cured resins; emulsions; encapsulating compounds; encapsulating gels; epichlorhydrin (CO, ECO); epoxies (EP); epoxy compounds; epoxy-based adhesives; ethylene acrylic (AEM); ethylene propylene rubber (EPM, EPDM); ethylene vinyl acetate; FDA approved resins; fibronectin; film; film containing adhesive; fluoro surfactants; fluorinated ethylene propylene (FEP); fluorocarbon rubber (FPM); fluoroelastomers (FKM); fluoropolymers; fluorosilicone rubber (FMQ, FVMQ); fusion; foam; furan plastics; glue; gelatin; grease; hardenable resins; heat cured acrylics; heat cured resins; heat cured silicone; heat cured urethanes; homopolymers; hyaluronic acid; hydrogenated nitrile rubber (HNBR); hydroxyapatite ceramic; isophthalic resin; isoprene rubber (IR); lactams; lactones; latex; laminin; light activated adhesives; light activated resins; light curable acrylics; light curable epoxies; light curable oligomers; light curable polymers; light curable resins; light curable silicone; light curable urethanes; light-cured urethane-dimethacrylate (UDMA) resins; materials that minimize or prevent leakage of the contents 26 through the wall thickness. 24; materials that initiate a blood clotting response; materials curable with argon-ion laser; materials curable with by way of an irradiation source; materials curable with edge emitting laser chips; materials curable with high intensity blue light; materials curable with laser based radiation; materials curable with laser chip array; materials curable with laser chips; materials curable with light; materials curable with light emitting diode chip array; materials curable with light emitting diode chips; materials curable with light emitting diodes; materials curable with metal halide lamps; materials curable with moisture; materials curable with plasma ark lamps; materials curable with surface emitting laser chips; materials curable with tungsten halogen lamps; materials curable with ultraviolet (UV) light; materials curable with VCSEL chips; materials curable with visible light; melamine; melamine formaldehyde; melamine phenolics; methacrylates; methyl α-cyanoacrylate; moisture curable acrylates; moisture curable acrylics; moisture curable epoxies; moisture curable polymers; moisture curable polysiloxanes; moisture curable resins; moisture curable silicone; monomer, oligomers and polymers with grafted adhesion promoters; monomers, oligomers and polymers with dissolved adhesion promoters; monomers, oligomers and polymers with dissolved photoinitiators; monomers, oligomers and polymers with grafted photoinitiators; monomers, oligomers, and polymers containing cationically active functional groups; monomers, oligomers, and polymers having one or more ethylenically unsaturated groups; monomers,oligomers and polymers prepared by the reaction of isophorone diisocyanate (D) with polyol polypropylene glycol (P) and a subsequent endcapping of non-reacted terminal isocyanato groups with 2-hydroxyethyl acrylate (A); mortar; multi part resins; natural rubber (NR, IR, polyisoprene); neoprene; nitrile rubber (NBR); oligomers; ortho diallyl phthalate; orthophthalic polyester; oxetanes; oxolanes; perfluoroelastomers (FFKM); peroxide cured fluoroelastomers; phenol formaldehydes; phenolics; photocatalytic acrylates; photocatalytic materials; photocatalytic resins; photocurable acrylics; photocurable epoxies; photocurable materials; photocurable polymers; photocurable resins; photocurable urethanes; photopolymerizable compositions; polyacrylates; polyacrylonitrides; polyamides; pluronics; polybutadiene rubbers (BR); polychloroprene rubbers (CR); polycyanoethylenes; polyesters; polyethylenes; polyimides; polyisoprene rubber; polymerizable 1,2,4-butanetriol trimethacrylate; (polymerizable) 1,3-propanediol di(meth)acrylate; polymerizable 1,4-cyclohexanediol diacrylate; (polymerizable) acrylated oligomers such as those of U.S. Pat. No. 4,642,126; (polymerizable) allyl acrylate; (polymerizable) bis-(meth)acrylates of polyethylene glycols of molecular weight 200 to 500; (polymerizable) bis[1-(2-acryloxy)]-p-ethoxyphenyldimethyl bis[1-(3-acryloxy-2-hydroxy)]-p-propoxyphenyldimethylmethane, and trishydroxyethyl-isocyanurate trimethacrylate; (polymerizable) diethyleneglycol diacrylate; (polymerizable) diglycidyl methacrylate of bis-phenol A ("bis-GMA"); (polymerizable) ethyl acrylate; (polymerizable) ethyleneglycol diacrylate; (polymerizable) glycerol diacrylate; (polymerizable) glycerol triacrylate; (polymerizable) isopropyl methacrylate; (polymerizable) methyl (meth)acrylate; (polymerizable) mono-, di-or poly-(meth)acrylates; (polymerizable) n-hexyl acrylate; (polymerizable) pentaerythritol tetra(meth)acrylate; (polymerizable) pentaerythritol triacrylate; (polymerizable) sorbitol hexacrylate; (polymerizable) stearyl acrylate; (polymerizable) triethyleneglycol dimethacrylate; (polymerizable) trimethylolpropane triacrylate; (polymerizable) vinyl compounds such as styrene, diallyl phthalate, divinyl succinate, divinyl adipate and divinylphthalate; polymers; polymers with leachable additives; polymethyl methacrylates; polynorbornene rubbers (PNR); poly phosphazene rubbers (PZ, FZ); polypropylenes; polysulfones; polysulphide rubbers (TR); polyurethanes; polyurethane foams; polyurethane resins; polyurethane rubbers (AU, EU); polyurethane-based adhesives; polyvinyl acetates; polyvinyl alcohol (PVA); poly (tetrafluoroethylene-co-vinyl alcohol); polyacrylic acid; polyethylenimine; polyethylene glycol; polyvinyl butyrals; polyvinyl chloride resins; pottings; propylene oxide rubbers (GPO); purified serum albumin (BSA) and glutaraldehyde; radiation curable acrylics; radiation curable epoxies; radiation curable oligomers; radiation curable polymers; radiation curable polyurethane; resins; radiation curable polyurethanes acrylates; radiation curable urethanes; radiation-curable polyurethane acrylate oligomers (or prepolymers); radiation-curable polyurethanes; resins containing at least one ethylenically unsaturated bond, and are capable of undergoing addition polymerization; resins containing both cationically curable and free radically curable resins; resins containing photocatalysts; resins cured with electron beam; resins that polymerize under irradiation with visible light; resins whose reaction mechanism is free-radical based on acrylates, methacrylates, vinyl, and allyl compounds; RTV; ribbon; rubber-based adhesives; rubbers, saline; sealants; sodium dodecyl sulfate; silicones; silicone elastomers; silicone foams; silicone plastics (SI); silicone polycarbonate urethanes; silicone polyether urethanes; silicone rubbers (MQ, VMQ, PMQ, FMQ); single-component or multiple-component polyelectrolyte cements; styrene block copolymers; styrene butadiene rubbers (SBR); styrene-acrylics; styrene-butadiene block copolymer; styrene butadiene latexes; styrene isoprene block polymers; synthetic rubbers; tar; tape; tetraflouroethylene-propylenes (FEPM); tetra-hydrofurfuryl methacrylates; thermoplastics; thermoset fluoroelastomers; thermoset plastics; thermoset polyurethanes; thermosetting resins; thermosetting unsaturated polyesters; triethyleneglycol methacrylate (TEGDMA); two part adhesives; ultraviolet light (UV) cured acrylates; ultraviolet light (UV) resins; ultraviolet light (UV)/visible light cured resins; unsaturated polyesters (UP); urethanes; urethane rubbers; urethane-acrylates; UV-curable urethane acrylates; UV-cured epoxies; UV-light sensitive urethane acrylate oligomers; vinyl benzene derivatives; vinyl esters; vinyl ethers; vinyl ketones; vinyl-acrylics; vinyl-based adhesives; vinyls; visible light curing resins; vitronectin;

welds; their substantially functional equivalents, or combinations thereof. The resins or other materials can be uncured or partially cured at time of assembly.

The connecting material 66 of the present invention can optionally contain reinforcement materials, fillers, additives 60, nano size articles 62, deformable elements 71, or combinations thereof. By way of example, and without intending on limiting, these can be in the following configurations: axial, biaxial, carded, chopped, chopped mat strand, chopped strand, circumferential, continuous, crimped fiber, crisscross, discontinuous, fabric, felt, fiber bundles, fibers, filament, fleece, helical pattern, hoop, hybrids, honeycomb, inner layer, interlacing, interlocking, intermediate, knitted fabric, knitted unidirectional fabrics, mat, knitted multidirectional fabrics, matrix, milled fiber, natural fiber, needled, non-woven, outer layer, randomly oriented fiber, rigid, scrim, spun yarns, stitched, stretched or unstretched, synthetic fibers, textile sheet, thread, triaxial, twisted filament yarns, unidirectional fabrics, warp, weft, web, wire, or yarn, or combinations thereof.

Without intent on limiting, useful fibers for use with connecting material 66 can be comprised of materials known by those skilled in the art of manufacturing composites or that meets the requirements of the end-use application such as, for example, acrylic, acrylonitrile-butadiene-styrene copolymers (ABS), aluminum, aluminum oxide, aramid (Kevlar® and Nomex®), aromatic polyester, boron, boron carbide, boron nitride, carbide, carbon, carboxide, ceramic, co-polymers, elastic resin, elastomer, elastomeric polyester, extended chain polyethylene, ethylene vinyl acetate, glass, hybrids, liquid crystal polymers (LCP), metal, metal alloys, natural, nitrides, olefin polymers, polyacrylonitrile, polyamide (nylon), polyarylene sulfide, polybenzimidazoles (PBI), polybisbenzimidazobenzophenananthroline, polybutylene terephthalate, polyester, polyether keytone (PEK), polyethermide, polyethermide, polyethersulfone, polyethylene (PE), polyethylene naphthalate (PEN), polethyleneterphthalate (PET), polymers, polyolefin, polyphenylenebenzobisoxazole (PBO), polyphenylenebenzobisthiazole (PBZT), polypropylene, polystyrene (PS), polysulfone, polyurethane, polyvinylchloride (PVC), rubber, semimetals, silicon carbide, silicon dioxide (quartz), stainless steel, steel, synthetic, thermoplastic urethane, tungsten, urethane, zirconium oxide or combinations thereof.

In cases wherein the expanded material 12 has poor adhesion to supporting member 64 or a thin wall thickness 24 that is incapable of holding a shape, the connecting material 66 of the present invention can make the expanded material 12 substantially self-supporting. For the purposes of the present invention, the definition of self-supporting means that even if the expanded material 12 is flexible it for the most part does not collapse and it substantially retains its shape if it is not adhered to a supporting member 64. Therefore, the connecting material 66 of the present invention can provide structure to the material 12 as well as adhesion or an attachment mechanism.

If necessary, the surface of the supporting member 64 is optionally adapted to deliver a good surface, size, shape, or combinations thereof for adhesion or attachment between the supporting member 64 and the expanded material 12, reinforcement 68, connecting material 66, or combinations thereof. For example, the surface of supporting member 64 can be abraded, cleaned, sized or adapted with additives 60, nano size articles 62, or coverings 56. Other surface treatments known by those skilled in the art of adhesion are also suitable in the present invention. It is also possible to perform angioplasty on the supporting member 64 prior to, during, or after positioning the expanded material 12, reinforcement 68, or combinations thereof.

The expanded material 12 (such as the expanded tubular profile 10, expanded sheet 42, expanded fiber 58), reinforcement 68, connecting material 66, additives 60, nano size articles 62, supporting member 64, covering 56, or combinations thereof can be individually or collectively sterilized. The assembly or the individual parts can be, for example, subjected to radiation sterilization, elevated temperature, treated with ethylene oxide, etc. In addition, the assembly and its components can be optionally manufactured in a clean room environment that utilizes high efficiency filtration and other practices know by those skilled in the art of clean rooms.

Ramifications and Scope

While it is preferred to utilize the expanded material 12 that has been at least partially stretched in the present invention, and more preferred to utilize expanded material 12 that has been at least partially stretched circumferentially, and most preferred to utilize a uniformly expanded material 12, it is possible within the scope of the present invention for embodiments described herein to utilize unexpanded or unstretched material 14 or to utilize material 14 only stretched axially, transversely, or stretched in sheet, film, rod, tape configurations. For example, materials manufactured according to U.S. Pat. Nos. 3,953,566; 3,962,153; 4,187,390; 4,110,392; 4,482,516; 4,596,837; 5,234,739, 5,476,589; 5,026,513 and the like which are herein incorporated in their entirety as a reference can be substituted for the preferred uniform expanded material 12 of the present invention. In particular, it is possible to use these less preferred materials or expanded materials and/or processes when utilizing the additives 60; nano size articles 62; positions of additives 60, nano size articles 62 or combinations thereof; active ingredients; positions of active ingredients; inactive ingredients; delivery of active ingredients; delivery of active ingredients by releasing, eluting, emitting, diffusing, dissolving, leaching, reacting, associating, or combinations thereof; delivery of active ingredients at constant rate, ascending rate, descending rate, changing rate, or combinations thereof; delivery of active ingredients that are immediate, time delayed, modified release, sustained, or combinations thereof; contents 26; shells 92; casings 90; reinforcements 68; reinforcements 68 comprised of formable composites 73; supporting members 64; woven tubular profiles 144; nonwoven tubular profiles 146; pockets 88; pleated, folded, or corrugated expanded material 12; multilayer tubular profiles 46; cure-in-place tubular profiles; perforated tubular profiles 15 (e.g. expanded material including thru holes); coil shaped reinforcements; form-in-place reinforcements; self supporting tubular profiles 82; coverings 56; flattened tubular profiles 78; layered flat profiles 80; microencapsulated or nano encapsulated active ingredients; or combinations thereof as described herein. The trade off in doing this, however, is producing a less consistent product at a higher cost of manufacture due to wasted raw materials, less uniform administration of active ingredients when applicable, less consistent delivery of active ingredients, and use of larger manufacturing facilities with more energy consumption. It is also possible in some cases like when using fibers in the present invention to use polymer processed by melt spinning or electrospinning.

The expanded material 12 (such as the expanded tubular profile 10, expanded sheet 42, expanded fiber 58), reinforcement 68, or combinations thereof of the present invention is very versatile and useful in any end-use application. Without intent on limiting, some additional examples of end-use applications in which the expanded material 12, reinforcement 68, covering 56, or combinations thereof of the present invention are useful in include, for example,: abrasives; additives; aerators; aerospace; air fresheners; air purification; antennas; antiseptics; appliances; armor; architectural fabric or coverings; automobiles; baby bibs; bags; bakeware; basins; batteries; bearings; bedding (sheets; pillows; cases; blankets; comforters); bell & spigot connections; beverage storage & processing; boating (sailing) clothing & equipment; boots; boot liner; bores; bike clothing; breathable clothing; buildings; bullet proof clothing and armor; cable covers; cable jackets; cables; capsules; camping clothing & equipment; candy; casings; catalysts; catalytic converters; ceilings; chairs; chemical storage and processing; chemical-mechanical polishing; chewing gum; clean room filters; clean room garments; clothing; coated surfaces; coatings; coats; coaxial cables; coffee pouches; compressors; computer equipment & accessories; concrete floors; conductors; conduits; construction materials; consumer products; contact lenses; containers; containment linings; controlled release articles; cooking surfaces; corrosion prevention; cosmetics; couplings; coverings; culverts; cushions; cut resistant gloves; cycling clothing; deck covers; decontamination; desalinization units; diapers; diaphragms; dispensers; distillation systems; drains; ducts; dust masks; elbows; electro-conductive articles; electrodes; electronic cables; electronics; electrostatic articles; end caps; energy generation; energy sources; equipment; evaporators; fabrics; factories; fashion clothing & accessories; felts; fiber optic cables; fibers; filaments; filter bags; filter cartridges; filter socks; filters; filtration medias; fire resistant clothing; fire retardants; fittings; fixtures; flange connections; floor coverings; floors; food; food storage & processing; fold & form pipe; forensics; fragrances; fuel cells; fragrances containing clothing, personal care items, and household items; fungicides; furnaces; furnace filters; furniture; fusions; gaskets; geomembranes; glass; gloves; glove liners; golf balls; golf clothing & equipment; golf club grip covers; guitar strings; hats; healthcare; heat exchangers; heat resistant fabric; heat resistant gloves; heavy machinery; herbicides; high temperature applications; high flex cables; hiking clothing; hoses; hospitals; hot water heater liners; hot water/radiator hoses; housings; house wrap; humidification; hydrants; hygiene; immersion tank linings; implantable global positioning devices; implantable identification devices; interior architectural wall coverings; intumescent siding and roofing for buildings; information storage; ingredients; insulators; intake filters; jackets; laminates; laundry products; lawn mowers; lenses; ligaments; lighting; lines; locating devices; low temperature applications; low temperature fabric; lozenges; lubricants; lumber; luminous fabrics; machines; magnetic articles; magnetic resonance imaging devices; magnets; mammal implants; manholes; manufacturing processes; marine applications; mechanical connections; medias; medical applications; medical treatments; membranes; memory devices; mesh; meter risers; mittens; modifiers; modified release articles; moisture barriers; moisture barriers on buildings; mold releases; musical instruments; needles; non-wovens; odor killing clothing, personal care items, or industrial/household products; office equipment; optical fibers; oxygen generators; packaging; paint; panel filters; pants; passageways; patches; pathways; permeable articles; personal protection; petrochemical exploration and processing; pharmaceuticals; pharmaceutical storage and processing; pipe covers; pipe liners; pipes; plant grafts; plenums; plugs; polishing; prevention or containment of dust mites; printed circuit boards and materials; printers and components; printing; proofs; protective layer or surface on wood surfaces; protective layer or surface or surface on storage tanks, buildings, utilities, etc.; protective apparel; protective clothing; protective fabrics; protective layers; protective surfaces; pumps; radiation; railroad ties; rain coats; reagents; recording; reflective articles; reflective fabric; refractories; remediation; respirators; roads; ropes; rollers; roofing; moveable joints or connections; running clothing & equipment; sanitary products (napkins); scaffolds; screens; sea vessels; sealants; seals; separators; sewers; shafts; shock absorption; shoes; shrinkable tubes; shingles; siding on buildings; side walks; silos; skiing clothing & equipment; socks; sofas; solar energy; solar panels; sound absorption; space exploration; spool pieces; sporting clothing and equipment; stain resistant fabric; storage; structural members; surgical gowns; tables; tanks; tapping tees; tea bags; targeted delivery; tees; telephones and equipment; threads for weaving, knitting, and sewing; tires; tooling; tracing (e.g. steam or electric); transmission; transition fittings; transportation; treatments; trucks; tubes; tunnels; underground; underwater (submerged); U.V. protection; valves; vaporization processes; vents; vessels; vests; walls; water purification; water resistant articles; water proof articles; welds; wells; windows; wood floors; wound dressings; x-ray film; yarn, or combinations thereof.

The expanded material 12, reinforcement 68, or combinations thereof can also be useful in improving the flame retardancy of adjacent materials. The preferred additives 60, nano size articles 62, or combinations thereof that are suitable for any end-use application but preferably for optionally improving the flame retardancy of the material 14, expanded material 12, reinforcement 68, covering 56, connecting material 66, or combinations thereof partially or fully include, for example,: alumina, alumina trihydrate, antimony compounds; antimony oxide, bromide based additives, chlorine based additives, phosphorous based additives, magnesium hydroxide, red phosphorous, melamine cyanurate, and polybrominated diphenylethers (PBDE), polyphosphazenes, hydrated minerals, hologenated organics, organo-phosphates, organohalogen; melamine salts, inorganic compounds such as aluminum trihydroxide $Al(OH)_3$ and boric acid; organic compounds such as phosphoric and phosphonic acid esters, such as long-chain ammonium polyphosphate products, and halogenated compounds such as chlorinated paraffins, dibromoneopentyl glycol, tetrabromophthalic acid anhydride, brominated diphenyl, chlorine and bromine containing polyols or diphenyl oxide compounds together with antimony trioxide, zinc borate, barium metaborates, chlorowax, chlorinated paraffins, their substantially functional equivalents, or combinations thereof. Other useful additives 60 that also enhance flame retardation include compounds that will cause char formation, particularly those with a large number of carbon-carbon double bonds or those that swell (tumescent systems) such as cellulose, sugar derivatives, and melamines. A flame retardant embodiment is useful for production of sidings on buildings, structural member in buildings, protective clothing, etc.

The expanded material 12, reinforcement 68, or combinations thereof can also be useful in marine applications as an antifouling material. The preferred additives 60, nano size articles 62, or combinations thereof that are suitable for any end-use application but preferably to optionally adapt the material 14, expanded material 12, reinforcement 68, covering 56, connecting material 66, or combinations thereof with anti fouling agents partially or fully include, for example,: tributyltin (TBT), cuprous oxide, zinc, copper pyrithione, isothiazolinone (4,5-dichloro-2-n-octyl-4-isothiazolin-3-one) based products, their substantially functional equivalents, or combinations thereof. Anti fouling agent keep algae, slime, barnacles, muscles, and other organisms from attaching to ship bottoms and pipes, for example. An antifouling embodiment can be, for example, employed on the hull of a ship or other marine application.

The expanded material 12, reinforcement 68, or combinations thereof can also be useful in decontamination. The preferred additives 60, nano size articles 62, or combinations thereof that are suitable for any end-use application but preferably to optionally adapt the material 14, expanded material 12, covering 56, reinforcement 68, or combinations thereof for the decontamination of insecticide or chemical warfare agents such as organophosphorus agents (tabun, soman, sarin, cyclosarin, VX, etc.) partially or fully include, for example, enzymes or hydrolases such as organophosphorus hydrolase, their substantially functional equivalents, or combinations thereof.

The expanded material 12, reinforcement 68, or combinations thereof can also be useful in the prevention of decay or surface degradation of wood materials. The preferred additives 60, nano size articles 62, or combinations thereof that are suitable for any end-use application but preferably to optionally at least partially preventing the decomposition of wood or cellulose that are complementary to the material 14, expanded material 12, covering 56, reinforcement 68, or combinations thereof partially or fully include, for example, alkaline copper quat (ACQ types B and D), copper azole (CBA-A, CA-B), disodium octaborate tetrahydrate (DOT), acid copper chromate (ACC), or combinations thereof. Expanded material 12 including these additives are useful individually or in combinations with U.V. light absorbers to be wrapped around, for example, a board utilizing a connecting member to attach the expanded material to the board. The board can be, for example, converted into a variety of end uses such as railroad ties, boardwalks, decks, boat docks, floors, and exterior surfaces. The expanded material extends the life expectancy of the wood and sustains its original appearance longer than uncovered boards.

The expanded material 12, reinforcement 68, or combinations thereof can also be useful improving corrosion resistance. The preferred additives 60, nano size articles 62, or combinations thereof that are suitable for any end-use application but preferably for optionally improving the corrosion resistance of parts complementary to the material 14, expanded material 12, binder 69, covering 56, or combinations thereof partially or fully include, for example, any material that inhibits the oxidation of metals, corrosion inhibitors, azoles, amines, nitrides, phosphates, molybdates, phoshponates, silicates, chromates, borates, zinc salts, polyphosphates, 1,2,3 Benzotriazole, tolyltriazole, mercatobenzothiazole (MBT), metal salts of aminocarboxylates, salts of doecylnathalenesulfonic acids, zinc salts of cyanuric acid, zirconium or amine complexes of toluylpropionic acid, tridecylamine salts of thiosuccinic acid, sodium nitrite, organic zinc complexes, salts of dodecylnaphthalenesulfonic acid, ammonium benzoate, 2-aminomethyoxypropanol, amine neutralized thiosuccinic acid, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof anti static partially or fully include, for example, hydroscopic surfactants such as tertiary fatty amines and their quaternary ammonium salts, monoacyl glycerides, monoalkyl and dialkyl phosphates, alkane sulfonates, sulfonamides, antistatic surfactants, glycerol monostearate, stearyl phosphate, dodecylbenzene, conductive pigments; metal powders; carbon black; graphite fiber; barium titanate; potassium titanate; metal -doped silicas; TiO2; metallocenes such as bis (methyl) cyclopentadienyl cobalt; neoalkoxy titanates, zirconates; trineoalkloxy zirconates, quaternary ammonium salts (cationic) or alkyl sulfonates (anionic) based on fatty acid derivatives, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof with adhesion promoters partially or fully include, for example, zinc/iron phosphates, organo functional silanes, titanates (e.g. isopropyl tris-[N-ethylaminoethylaminoethylamino] titanate), zirconaluminates, zirconates, aryl/alkyl phosphate esters, epoxy/methoxy functional additives, neo-alkoxy products, methacrylate/methoxy functional additives, epoxy functional silanes, amine/methoxy functional additives, mercapto-silanes, amino-silanes, carboxyl/hydroxyl silanes, carboxyl-silanes, chlorinated polyolefin (CPO) with co-resins of acrylic, acrylic modified alkyds, polyesters, their substantially functional equivalents, or combinations thereof.

The preferred additives 60 nano size articles 62, or combinations thereof that are suitable for any end-use application but preferably to optionally adapt the material 14, expanded material 12, binder 69, covering 56, reinforcement 68, or combinations thereof with acid scavengers partially or fully include, for example, cycloaliphatic epoxides, soybean oil epoxides, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof with improved light stability partially or fully include: hindered amine light stabilizers (HALS) such as 2,2,6,6-tetrametylpiperidine chemical structures, bis (1,2,2,6,6-pentamethyl-4-piperidinyl) sebacate; non-reactive HALS (NOR-HALS); reactable HALS; carbon black, titanium dioxide (TiO2), ultraviolet light absorbers (UVAs) such as 2-hydroxy-phenyl benzotriazoles, hydroxyphenyl-s-triazines, 2-hydroxybenzophenones, oxalic anilides, their substantially functional equivalents, or combinations thereof.

The preferred additives 60, nano size articles 62, or combinations thereof that are suitable for any end-use application but preferably to optionally adapt the material 14, expanded material 12, binder 69, covering 56, reinforcement 68, or combinations thereof for improved plasticization partially or fully include, for example, dibutyl phthalates, dioctyl phthalate, abietates, adipates, benzoates, castor oil, epoxidized soybean oil, phosphates, phthalates, polymeric phthalates, sebacates, acrylic esters of aliphatic dicarboxylic acids, adipic acids, sebacic acids, derivatives of benzoic acid, toluene sulfonamide, dicyclohexyl phthalate, their substantially functional equivalents, or combinations thereof.

The preferred additives 60, nano size articles 62, or combinations thereof that are suitable for any end-use application but preferably to optionally adapt the material 14, expanded material 12, binder 69, covering 56, or combinations thereof with algaecide partially or fully include: gluteraldehyde, methylene bis (thiocyanate), guaternary ammonium compounds, zinc oxide, their substantially functional equivalents, or combinations thereof.

It is anticipated within the scope of the present invention that the expanded material 12 such as the expanded tubular profile 10, expanded sheet 42, expanded fiber 58, or combinations thereof, can serve as a protective surface on any substrate instead of coatings or in conjunction with coatings that are presently used. For example, siding on a home or a floor can include at least one layer of the expanded material 12 of the present invention to extend its useful life. Furthermore, sheet metal used to form body panels, hoods, trunk lids or other stamped or formed components on automobiles or other equipment can include at least one layer of the expanded material 12 of the present invention to extend its useful life and/or appearance. The expanded material 12 can be applied before, during, or after a part is formed. The expanded material 12 can also be utilized as a mold release for stamping, casting or molding parts. In addition, the expanded material 12 can be used as a pipe liner or to reline used, corroded, or leaking pipes. The most preferred expanded material 12 used for lining pipes includes abrasion resisting additives 60, nano size articles 62, or combinations thereof.

Positioning the expanded material 12 on the outside surface of the supporting member 64 such as a steel pipe is beneficial in highly corrosive atmospheres because it can extend service life. Furthermore, in contrast to a coating it provides a more environmentally sound solution to extending service life since volatile organic chemicals (VOC) that are common in coatings are minimized if not entirely eliminated. Moreover, the expanded material 12 can include or be impregnated with the previously mentioned additives 60, nano size articles 62, or combinations thereof that enhance adhesion, corrosion resistance, pigmentation or UV stability. The present invention offers superior UV light protection therefore significantly reducing external cracking, fading and other deterioration of the outside surface. When the expanded material 12 of the present invention is utilized in a structural support, an applied expanded material 12 such as the expanded tubular profile 10, expanded sheet 42, expanded fiber 58, or combinations thereof can extend the structural integrity in a fire especially when adapted with optional flame retardants.

The following examples are presented to more particularly illustrate our invention and are not to be construed as limitations thereon.

EXAMPLE 1

Expanded Material Used As Vascular Grafts

A thin wall, cylindrical shaped expanded tubular profile having a diameter of approximately 6 mm and a wall thickness of approximately 0.10 mm made of two layers of expanded material comprising polytetrafluoroethylene (PTFE) material having a structure including fibrils and voids that includes a plurality of glass nano fibers and nano size silicon dioxide crystals is converted into a prosthesis for a medical application. The fibrils of the expanded material have a mean length in the range of about 15-25 microns. The prosthesis is used as a coronary artery bypass graft (CABG) in a medical procedure. The prosthesis includes a microencapsulated active ingredient positioned between the two layers of expanded material that is delivered to the patient after installation over a period of 90 days in a descending rate to minimize the rejection of the prosthesis in the human body. Other examples were produced in diameters ranging in size from about 0.5 mm to 60 mm and wall thicknesses ranging in size from about 0.05 mm to 0.3 mm.

EXAMPLE 2

Reinforcements of Formable Composite Used in Stenting Procedures

A cylindrical shaped reinforcement having a diameter of 6 mm is comprised of a wall thickness having a plurality of rectangular shaped open cells surrounded by member segments having a rectangular cross section. The member segments having a thickness of about 0.0762 mm (0.003 inches) near the first and second ends and about 0.127 mm (0.005 inches) near middle are made of a formable composite including a plurality of deformable elements encapsulated in a binder of polytetrafluoroethylene (PTFE). Samples are produced using discontinuous deformable elements made of stainless steel and Nitinol®. Samples are produced wherein the deformable elements range in size from 10 to 500% the length of the member segments. Samples are produced wherein the ratio of first size to second size ranges from about 1:2 to 1:10. Other samples are prepared for neurological applications having a diameter of about 2 mm and larger sizes like 30 mm for placement in aorta. The reinforcements are coated with an non erodible covering containing an immunosuppressive and antiplatelet agents.

The cylindrical shaped prostheses are inserted into various blood carrying passageways of patients by non invasive surgery techniques using a catheter. There is sufficient clearance between the prostheses and the passageways. The samples containing the stainless steel deformable elements are dilated from a first size and shape to a second size and shape with a balloon catheter until the outside surfaces of the reinforcements are in substantial contact with the interior wall of the blood carrying passageways. The samples containing the Nitinol g deformable elements are dilated from first size and shape to second size and shape by removing a constraint that temporarily maintained the reinforcement in a reduced size. The shape memory of the Nitinol® deformable elements enable the reinforcements to be self-expanding so that they expand from a smaller first size to the larger second size so that the outside surface of the reinforcement is in substantial contact with the inside surface of the blood carrying passageway. The dilated reinforcements prop-open the passageways enabling blood to freely flow through its bore with a substantially normal pressure drop.

Other embodiments are prepared using a binder of perfluoroelastomers FFKM [Kalrez™—available from DuPont], perfluoroelastomers FKM [Viton™—available from DuPont], polyethylene, polypropylene, polyester, silicone, urethane, polyamides, bioabsorbable materials, and Sorona™[available from DuPont].

EXAMPLE 3

Expanded Material and Reinforcement Used as Stent-Graft

The expanded materials of Example 1 are combined with the reinforcements of Example 2 to produce stent-grafts. The stent-grafts are surgically implanted in a human body blood carrying passageway to repair an aneurismal vessel.

EXAMPLE 4

Generic Process for Manufacturing Uniform Expanded Materials

The expanded material 12 of the present invention can be made in a continuous process or a batch process. A batch process divides the manufacturing processes described into separate processes or groups of processes. It is advantageous, for example, to use a batch process when the processing rates of the upstream steps do not equal the rate of the downstream steps. Of course, in a continuous process differing rates can also be compensated for by storing partially manufactured products during the process.

FIG. 77 illustrates an overview of the preferred steps of a continuous process for manufacturing the expanded material 12 of the present invention. A material 14 to be converted into an expanded material 12 is stored in silo 98A. Optional solvents and optional additives 60, nano size articles 62, or combinations thereof are stored in silos 98B and 98C or other storage locations as necessary. The material 14 to be expanded is combined with the solvents, additives 60, nano size articles 62, or combinations thereof in optional blend tank 100. The combination, which is also known as a mixture, paste, slurry, dispersion, solution, damp powder, composition, or melt is transferred to the extruder 102 that converts the combination into an unexpanded tubular profile 104.

Any solvent capable of being combined with the material 14 that is capable of forming a mixture, paste, slurry, dispersion, solution, damp powder, composition, or combinations thereof is suitable in the present invention. Without intent on limiting, the preferred solvents of the present invention include acetone, paraffin oil, decalin (or dacahydronaphthlene), dodecane, xylene, toluene, trichlorobenzene, tetralin, cycloalkane, cycloalkene, carene, fluorene, camphene, menthane, dipentene, naphthalen, acenaphthene, methylcyclopentadien, tricyclodecane, 1,2,4,5-tetramethyl 1-1,4cyclohexadiene, fluorenone, naphthindane, tetramethyl-p-benzodiquinone, ethylfluorene, fluoranthene, naphthenone, glycols, mineral spirits, kerosene, naptha, chlorinated hydrocarbons, chlorofluorinated hydrocarbons, pentane, hexane, heptane, toluene, methylene chloride, carbon tetrachloride, trichlorotrifluoroethane (TCTFE), diethyle ether, ethanol ether, acetone, cyclohexanone, 2-methylpentanone, dichloromethane, n-hexane, heptane, diethyl ether, dioxane, and their derivatives and/or mixtures are examples of suitable solvents Any extruder 102 is useful in the process of the present invention so long as it is capable of converting the material 14 to be expanded into the unexpanded tubular profile 104 or other shape. It is, however, preferred to carefully control the ratio of solvent and material 14, temperature, and extrudate flow rate. It is also important to manage air entrainment, bubbles, lumps, and the like carefully in the previously mentioned solution, paste, slurry, damp powder, composition, mixture etc. before, during and after extrusion. As known by those skilled in the art of extrusion, the extruder 102 can optionally include screw(s), ram, die, pump, and controls. It is also preferable to have an optional adjustable die to make fine adjustments in the unexpanded tubular profile's 104 wall thickness 24 and uniformity.

In the process of the present invention, one or more orifices can be optionally utilized to produce a single or multiple unexpanded tubular profiles 104. These orifices optionally contain at least partially tapered sections preferably with optional temperature control. The multiple orifices optionally can extrude the same or different materials 14.

Additives 60, nano size articles 62, or combinations thereof can also be previously compounded with material 14 to be converted into the expanded material 12 for the convenience of handling fewer raw materials. Alternatively, the additives 60, nano size articles 62, or combinations thereof can be included in the material 14 to be expanded during polymerization of the material 14. The incorporation of the additives 60, nano size articles 62, or combinations thereof during polymerization of the material 14 can provide a more homogeneous distribution of the additives 60, nano size articles 62, or combinations thereof in the material 14.

As shown in FIG. 77, the optional solvent is removed from the unexpanded tubular profile 104 upon exiting the extruder 102 in extraction device 106. The solvent can be removed by any means such as elevated or reduced temperature, ventilation, use of a second solvent or any combinations of the preceding. Alternatively, the removal of the solvent can also occur at the middle or at the end of the conversion process.

The unexpanded tubular profile 104 or expanded tubular profile 10 can be optionally partially or fully calendered or sintered after extrusion. Moreover, calendaring and sintering can occur before or after stretching.

The unexpanded tubular profile 104 enters a temperature controlled area 108 by optional puller 128A. Another optional puller or support (not shown) located inside the bore 18 of the tubular profile can augment the feeding or stretching process. Depending on the choice of material 14, the pullers can be optionally temperature controlled or contain gripping devices to facilitate the stretching process. Furthermore, the pullers can be designed so that they do not damage the expanded material 12 during stretching. Moreover, the pullers can optionally move axially (e.g. in the machine direction) or rotate as needed to accommodate the stretching process.

In the temperature controlled area 108, the unexpanded tubular profile 104 is stretched or drawn either axially, circumferentially or both. For example, the unexpanded tubular profile 104 is stretched from first length L1 to second length L2, from first diameter D1 to second diameter D2 or both. One method of stretching the unexpanded tubular profile 104 axially is to have the puller 128B advance the unexpanded tubular profile 104 at a faster rate than the puller 128A. The unexpanded tubular profile 104 or the expanded tubular profile 10 can be optionally flattened during axial stretching. Care should be taken not to crease the edges of the expanded tubular profile 10 if a crease would interfere with the end-use application.

In the temperature controlled area 108 the temperature during stretching is preferably elevated to facilitate expansion. The preferred temperature can be experimentally determined for each material 14 to meet the requirements of the end-use application. Without intent on limiting, the elevated temperature can be optionally achieved through, for example, the use of a bath containing liquid, salt bath, liquid spray nozzles, a gas stream running transverse to the extrudate, radiant heater, steam, hot roll, hot chamber, or any other suitable methods for modifying the temperature of the unexpanded tubular profile 104 as it is expanded.

The unexpanded tubular profile 104 can be expanded circumferentially in temperature controlled area 108 in any way that produces a relatively precise expansion of first diameter D1 to second diameter D2. An uneven expansion of diameter or an unconstrained expansion will result in an inconsistent product. As previously mentioned, an inconsistent product has varying thickness, molecular orientation, structure, density, porosity, fibril size, node size, strength, permeability, specific gravity, and so on.

Upon expansion from the first diameter D1 to the second diameter D2, the expanded tubular profile 10 is optionally fed or pulled into thermal treatment zone 110 in its expanded state. The temperature in the thermal treatment zone 110 can be experimentally determined so that it substantially maintains the expanded structure of the expanded tubular profile 10. In the thermal treatment zone 110, the structure of the expanded material 12 created by stretching is locked-in, frozen, or made substantially permanent.

After thermal treating the expanded tubular profile 10, it is cooled and stored. The expanded tubular profile 10 can be stored in stick or coiled configuration. Furthermore, the expanded tubular profile 10 can be slit and stored in a expanded sheet 42 or the expanded fiber 58 configuration. The expanded sheet 42 or expanded fiber 58 can be stored in a roll. As previously mentioned, the expanded material 12 such as the expanded tubular profile 10, expanded sheet 42 or expanded fiber 58 can be further processed by flattening, densification, lamination, covering, adapted with additives 60 or nano size articles 62, or otherwise converting into its end-use product. These subsequent processes can be achieved in a continuous or batch -processes.

Referring to FIG. 78, which illustrates another more detailed side view of a process for manufacturing the present invention, the unexpanded tubular profile 104 enters temperature controlled area 108A and is stretched from first length L1 to second length L2. Having axial stretching preceding circumferential stretching reduces the specific gravity and or wall thickness 24 of the expanded material 12 and can make subsequent circumferential stretching easier. Next, the once stretched expanded tubular profile 10 is stretched from first diameter D1 to second diameter D2 in temperature controlled area 108B. The once expanded tubular profile 10 is stretched in any way that increases its diameter from first diameter D1 to second diameter D2 in a relatively precise manner. To achieve a uniformly expanded tubular profile 10, the second diameter D2 or subsequent diameters should preferably not have variation more than about 200 percent, more preferably less than the range of about 0-50 percent and most preferably less than the range of about 0-15 percent of the outside diameter of the expanded tubular profile 10 along its length from first end 20 to second end 22.

To achieve uniform circumferential stretching, it is possible to use the optional mandrel 114, as shown in FIG. 79 in side view and FIG. 80 in front view, that stretches the unexpanded tubular profile 104 or the expanded tubular profile 10 from first diameter D1 to second diameter D2. The mandrel 114 is preferably mounted so that it is positioned in the bore 18 of the expanded tubular profile 10. The mandrel 114 is optionally tapered or otherwise configured to stretch the expanded tubular profile 10 from first diameter D1 to second diameter D2 as the expanded tubular profile 10 passes over it. Furthermore, the mandrel 114 is optionally temperature controlled, for example, at an elevated or lower temperature to facilitate expansion. As shown in FIG. 79, which is a side view of one embodiment of the mandrel 114, the tapered mandrel 114 optionally has a first diameter of D1 on leading edge 116 and a second diameter of D2 on trailing edge 118. The mandrel 114 stretches the expanded tubular profile 10 by imparting an internal force on the bore 18 of the expanded tubular profile 10. The mandrel 114 stretches the expanded tubular profile 10 uniformly because it is relatively precisely stretched from first diameter D1 to second diameter D2. The mandrel 114 can be optionally polished or adapted with a substantially non-stick surface, lubricants or any other means that reduce the friction between inside surface 17 and mandrel 114. The mandrel 114 can also be optionally porous or contain a plurality of holes so that fluids, steam or gases can be introduced between bore 18 and the outside surface of the mandrel 114. Lubricants can also be optionally introduced by atomizers. It is also possible to have the mandrel 114 vibrate to impede adhesion. By pulling the expanded tubular profile 10 over the mandrel 114 it is common to also experience some axial stretching because the wall thickness 24 is usually in tension axially.

Referring to FIGS. 79-81, the mandrel 114 can optionally be any expandable device capable of stretching the unexpanded tubular profile 104 or expanded tubular profile 10 from first diameter D1 to second diameter D2. It can, for example, optionally contain a plurality of overlapping tabs 120 around its circumference between leading edge 116 and trailing edge 118. The overlapping tabs 120 allow the mandrel 114 to adjust from first diameter D1 to second diameter D2 in an incremental manner. To avoid the wall thickness 24 of the expanded tubular profile 10 from breaking or tearing due to an abrupt change in diameter, the overlapping tabs 120 permit the mandrel 114 to increase from first diameter D1 to second diameter D2 gradually until the process arrives at a steady state. The actual rate and degree of unfolding of the tabs 120 is experimentally determined for each unique material 14 and process conditions. The mandrel 114 can also optionally be an inflatable device. Differences in diameter, wall thickness, amount of stretch, rate of stretch require a different set of process conditions.

As shown in FIG. 78, in the thermal treatment zone 110 the expanded tubular profile 10 is optionally conveyed over a barrel 112, which is any means that substantially maintains the expanded tubular profile 10 in its approximate expanded size. The barrel 112 partially or fully prevents the expanded tubular profile 10 from shrinking back to its original size by serving as a constraint on the bore 18. The barrel 112 can be optionally temperature controlled, for example, at an elevated temperature. Furthermore, the barrel 112 can be optionally polished, have a substantially non-stick coating, or employ a lubricant to facilitate conveying the expanded tubular profile 10 over the barrel 112 with minimal to no friction. It is also possible that the barrel 112 be a porous material or contain a plurality of holes so that hot air or steam or any lubricating material can be fed through the barrel's outside surface to reduce friction between expanded tubular profile's 10 inside surface 17 and the barrel 112. Lubricants can also be optionally introduced with atomizers. The optional hot air, lubricant, or steam exiting the barrel 112 can also facilitate in the thermal treatment process. It is also possible to have the barrel 112 vibrate to impede adhesion between the barrel 112 and the expanded tubular profile 10. In the thermal treatment zone 110 any remaining solvents can also be substantially removed. It is alternatively possible to keep the expanded tubular profile 10 in expanded state through internal pressurization or a vacuum.

Once again referring to FIG. 78, the unexpanded tubular profile 104 of the present invention can also be optionally expanded circumferentially by pressurizing the bore 18 in the section between about puller 128C and about before puller 128B, preferably in the region of about temperature controlled area 108B. One or more pullers 128 can optionally temporarily or fully collapse or flatten the tubular profile to create a partial or full seal which is one way of enabling pressurization during processing. An optional material can be temporarily or permanently introduced to the bore 18 to prevent the top wall thickness 24 from permanently adhering to the bottom wall thickness 24 and facilitate sealing. To ensure substantially uniform expansion when pressurizing the bore 18, the wall thickness 24 of expanded tubular profile 10 is stretched circumferentially from first diameter D1 to second diameter D2 so that is grows in diameter up until it reaches a constraint 124 which limits expansion as it advances through the process. The constraint 124 limits the amount of stretching thereby delivering a uniformly stretched expanded material 12.

The constraint 124 can be optionally temperature controlled at an elevated or reduced temperature. The constraint can also be optionally polished or adapted with a substantially non-stick surface, lubricants or any other means that reduces the friction between the outside surface 16 and the constraint 124. Lubricating materials can also be optionally introduced through atomizers. Furthermore, the constraint 124 can also be optionally porous or contain a plurality of holes so that fluids, steam, or gases can be introduced between outside surface 16 and constraint 124. It is also optionally possible to have the constraint 124 vibrate to impede adhesion.

As shown in FIG. 78, one or more optional support seals 126 or internal pressure maintains the expanded tubular profile 10 at a relatively constant expanded diameter after stretching. The optional support seal 126 and optional internal pressure maintain a relatively open bore 18 and prevents the expanded tubular profile 10 from collapsing or sagging while processing. Optionally transferring the expanded tubular profile 10 through an liquid filled tank or bath can also assist a gas or liquid filled bore 18 from sagging by allowing it to more or less float through the process. Any gas or liquid can be used for pressurization.

It is also possible to use a combination of mandrel 114 and internal pressurization to achieve circumferential stretching.

As shown in FIGS. 82 and 83, the process of the present invention can contain multiple stretching steps that are circumferential, axial, or combinations thereof. Without intent on limiting, the expanded material 12 can be manufactured by, for example, stretching: axially-circumferentially-axially; circumferentially-axially-axially; axially-circumferentially-circumferentially; circumferentially-axially-circumferentially; circumferentially-circumferentially-circumferentially to illustrate a few of the possible combinations. In fact, the process of the present invention can have an infinite amount of stretching steps of any combination or be in any orientation required to meet the requirements of the end-use application or facilities. Furthermore, the process of the present invention can have any amount of stretch or rate of stretch in an infinite amount of combinations up to the point of substantially breaking the wall thickness 24. Like the composition, structure and dimensions of the expanded material 12 of the present invention, the process of the present invention is very flexible and can be adapted to meet the requirements of the end-use application. Moreover, the process can be oriented horizontally (as shown) or vertically (as not shown).

To further demonstrate the flexibility of the process of the present invention, FIG. 82 shows that the optional solvent can be extracted from the expanded material 12 at the end of the process in the extraction device 106 and that stretching can occur with the solvent partially or fully present in the wall thickness 24 of the expanded material 12. Moreover, the process can be optionally adapted to include an agitator 130 in blend tank 100; an intensive mix tank 132; a quench tank 134; or an air gap 136 after the extruder 102. The process can also include an adaptation zone 138. FIG. 82 also shows that multiple temperature controlled areas 108A, 108B and 108C where multiple stages of stretching or expansion takes place are possible. In fact, there can be an infinite number of temperature controlled areas 108 where stretching takes place in the present invention.

Although the figures illustrate the use of a continuous process to manufacture the present invention, it is often more practical to perform each step or group of steps of the process separately or in a batch process. A batch process provides the most flexibility for producing many structures to satisfy the large variety of end-use applications previously mentioned. A continuous process is most useful when manufacturing relatively long runs of the expanded material 12 that have substantially the same specifications.

An off-line or batch process is also preferred when at least one of the down stream processes operates at a different rate than an upstream process. For example, if the rate of stretching exceeds the rate of extrusion. A batch process can include at least one or more of the following sub-processes: polymerization, compounding, blending, mixing, extrusion, quenching, sintering, calendaring, extraction, heating, cooling, coating, stretching, thermal treatment, densification, assembly, reinforcement, lamination, surface modification, or other forms of adaptation.

FIG. 83 illustrates an embodiment of an off-line or batch stretching process. This off-line process can be utilized after extrusion of the unexpanded tubular profile 104 or after the expanded tubular profile 10 has been produced. The unexpanded tubular profile 104 or partially stretched expanded tubular profile 10 is stored on coiler 122B or in a partially or completely straight configuration. Optional puller 128F feeds the tubular profile into temperature controlled area 108D where it is stretched either axially or circumferentially or in both directions. Optionally, the partially stretched expanded tubular profile 10 is advanced to an optional second and third temperature controlled areas 108E and 108F with optional pullers 128G and 128H where it is stretched further either circumferentially, axially or both. Optional puller 128I feeds expanded tubular profile 10 to a coiler 122C. Alternatively, the expanded tubular profile 10 can be cut into straight lengths instead of wound up on a spool.

It is possible in the present invention to pre-assemble or nest multiple unexpanded tubular profiles 104 or expanded tubular profiles 10, for example of different diameters, and then run the assembly through the process of stretching either axially, circumferentially or both. The assembly process can be accomplished in line, for example, by co-extruding or off-line by sliding one unexpanded tubular profile 104 into the bore 18 of another unexpanded tubular profile 104' manually. These multiple unexpanded tubular profiles 104 can be optionally connected to one another before or after processing. The multiple wall thicknesses can also be optionally partially or fully calendered, sintered, or combinations thereof before stretching.

To achieve a uniformly expanded product it is also important to have control over the previously described process. Those skilled in the art of process engineering can experimentally determine using the guide in this specification the proper equipment such as pullers, motors, valves, heaters, control systems and so on to achieve relatively precise stretching from first diameter D1 to second diameter D2 and or from first length L1 to second length L2 when employing the process of the present invention.

Optionally, the expanded tubular profile 10 can be further modified in adaptation zone 138 by being partially or fully densified, covered, laminated, slit, surface modified, or impregnated, etc. Furthermore, the surface treatment or undercuts 76 on outside surface 16 or inside surface 17 are optionally included.

It has been recently discovered that the expanded material 12 can also be manufactured of any material 14 that includes a plurality of voids, inclusions, imperfections, or combinations thereof by stretching the material 14 while at an elevated temperature. It is preferred to heat the wall thickness 24 to around the melting point of the material 14 or to a temperature that lowers the tensile strength of the material 14 so that it yields in tension. Under these conditions it is also possible to produce the expanded material 12 that includes fibrils, voids, nodes or combinations thereof.

The expanded material 12 can also be formed of a material 14 comprised of a plurality of fine polymer particles having a different polymer on the core than on the outside shell. For example, the polymer comprising the core can have a higher melting point than the polymer comprising the outside shell. Therefore, when these particles are stretched in the presence of an elevated temperature, solvent or combinations thereof the fibrils are formed by stretching the at least partially melted or softened outside shell. It is also possible to form an expanded material 12 from polymer particles that have a more soluble outside shell than the core. When these particles are stretched in the presence of an elevated temperature, solvent or combinations thereof the fibrils are also formed by stretching the at least partially melted or softened outside shell.

EXAMPLE 5

Generic Process for Manufacturing Uniform Fluoropolymer Expanded Material

Fluoropolymers, polytetrafluoroethylene (PTFE), copolymers and other previously mentioned variations are the most preferred materials 14 of the expanded material 12 of the present invention. This polytetrafluoroethylene (PTFE) material 14 can be obtained under the trade name Teflon® from E.I. duPont de Nemours and Company, Inc., Wilmington, Del. (USA), under the trade name Fluon® from AGC Chemicals Americas, Inc., Bayonne, N.J. (USA), a wholly owned subsidiary of Asahi Glass, under the trade name Dyneon® from 3M, St. Paul Minn. (U.S.A), under the trade name Polyflon® from Daikin Industries, Ltd, Osaka, Japan, or under trade name Soreflon® from Ugine Kuhlmann Co, France. In addition, the material 14 can be manufactured according to the present invention including additives 60, nano size articles 62, or combinations thereof. Especially useful polytetrafluoroethylene (PTFE) material 14 copolymers include the following: (1) copolymers of tetrafluoroethylene and ethylene; (2) copolymers tetrafluoroethylene and chlorotrifluoroethylene; (3) copolymers of tetrafluoroethylene and hexafluoroporpylene. It is also preferred to use polytetrafluoroethylene (PTFE) that is known in the art as a fine powder and most preferably a relatively highly crystalline form.

Additives 60, nano size articles 62, or combinations thereof can also be optionally incorporated into the polytetrafluoroethylene (PTFE) material 14 during polymerization or through compounding. Very small additives 60 such as nano size articles 62 can be optionally predispersed, for example, in one or more of the monomers during polymerization or in the solvent prior to blending to facilitate handling.

As illustrated in FIG. 77, the polytetrafluoroethylene (PTFE) material 14 is stored in silo 98A and it is combined with a solvent (also known as liquid, lubricant, extrusion aid, etc.) stored in silo 98B and mixed in blend tank 100 to form a paste. It is recommended that the polytetrafluoroethylene (PTFE) material 14 is stored in a temperature controlled environment. Optionally, the previously mentioned additives 60, nano size articles 62, or combinations thereof are stored in silo 98C or in additional storage locations if necessary and combined with polytetrafluoroethylene (PTFE) material 14 and solvent. To improve handling of small size additives 60 like nano articles 62 it is helpful to predisperse the nano size articles 62 in a solvent or liquid prior to blending. It is useful to employ any solvent capable of enabling extrusion in the present invention. Hydrocarbon solvents are preferred and most preferred solvents are mineral spirits, kerosene and naphtha. Although it is not preferred and can sometimes produce lower quality results, it is also within the scope of the present invention to utilize thermoplastic or melt process-able polytetrafluoroethylene (PTFE) or dispersions of polytetrafluoroethylene (PTFE) with or without solvents.

The polytetrafluoroethylene (PTFE) material 14 and solvent paste or damp powder is formed into one of the previously mentioned tubular shapes with any extruder 102 capable of forming an unexpanded tubular profile 104.

Optionally, the polytetrafluoroethylene (PTFE) material 14, the paste or damp powder is compressed into a cylindrical pre-form slug and placed into a ram-type extruder. Under high pressure the composition is forced through a finishing die to produce an extrudate or unexpanded tubular profile 104. The unexpanded tubular profile 104 can be unsintered, partially sintered or fully sintered. Sintering can occur in the temperature range of about 300 to 400° C. (572 to 752° F.) to increase the specific gravity of the extrudate up to a maximum of about 2.2 if fully sintered when using polytetrafluoroethylene (PTFE) without additives. Furthermore, the extrudate of unexpanded tubular profile 104 can be optionally calendered prior to or after stretching. When calendering the unexpanded tubular profile 104 its specific gravity of the unexpanded tubular profile 104 can be increased up to about 2.2 when using polytetrafluoroethylene (PTFE) without additives.

The polytetrafluoroethylene (PTFE) material 14 can optionally be co-extruded with the same or dissimilar material 14 by feeding the supplemental material 14 or materials 14 through the axis of the extruder.

The solvent is removed from the unexpanded tubular profile 104 in extraction device 106 preferably by drying or the use of a second solvent. Drying can occur at any temperature, but it has been found to be practical to use temperatures for drying in the range of about 100 to 300° C. (212 to 572° F). Upon removal of the solvent, the first length L1 is stretched to a second length L2 or first diameter D1 is stretched to second diameter D2 or both in first temperature controlled area 108. First temperature controlled area 108 is at any temperature capable of producing one of the previously mentioned structures but preferably between about −100 to 380° C. (−148 to 716° F.) and more preferably between about 200 to 350° C. (392 to 662° F.) and most preferably between about 225 to 325 ° C. (437 to 617° F.). The length of the temperature controlled area 108 must be sufficiently long to condition the wall thickness 24 at about the specified temperature when taking into consideration the speed of the expanded material 12 as it passes through the temperature controlled area 108. The difference in first length L1 and second length L2 or first diameter D1 and second diameter D2 can be any change in dimension up to the point of substantially breaking the wall thickness 24, but preferably between about 0-20,000% and more preferably between about 10-10,000%.

The unexpanded tubular profile 104 can be stretched at any rate up to the point of breaking the wall thickness 24. To achieve an unbroken, fibrous wall thickness 24 as previously described, it is preferable to stretch unexpanded tubular profile 104 in the range of about 25%/sec to 2000%/sec, more preferably 50%/sec to 750%/sec and most preferably 120%/sec to 600%/sec. The temperature, rate and ratio of expansion can be varied to obtain the desired structure and properties of the expanded material 12 necessary for the targeted end-use application.

The amount of stretch and the rate of stretch can be experimentally determined using the process conditions described herein to meet the needs of the end-use application by those skilled in the art of engineering. These process conditions are dependent on wall thickness, temperature, and the material 14 being processed.

Next, the once stretched expanded tubular profile 10 is optionally held in its approximate stretched condition and it is optionally heated in thermal treatment zone 110. The expanded tubular profile 10 can be thermal treated at any temperature that substantially retains the structure of the wall thickness 24 that was imparted during stretching. However, it is preferred to thermal treat the expanded tubular profile 10 above the melting temperature of polytetrafluoroethylene (PTFE), more preferably at a temperature in the range of about 300 to 400° C. (572 to 752° F.), and most preferably in the range of about 325 to 375° C. (617 to 707° F.) for a duration sufficiently long that the expanded structure that is created in the article is retained. The once stretched expanded tubular profile 10 can be optionally partially or fully sintered during the thermal treatment stage.

Bent or wavy fibrils 38 are optionally formed by reducing the diameter of the expanded profile 10 to put the fibrils in partial or full compression after stretching but before thermal treatment. Alternatively the processing rate after stretching can be slowed to place the fibrils in a compressed condition before thermal treating.

Referring to FIG. 82, the previously mentioned process of stretching the unexpanded tubular profile 104 is adapted to have multiple temperature controlled areas 108A, 108B and 108C where stretching of the unexpanded tubular profile 104 or expanded tubular profile 10 occurs. The polytetrafluoroethylene (PTFE) material 14 is stored in silo 98A and combined with the solvent stored in silo 98B and mixed in blend tank 100 with optional agitator 130 to form a paste. The paste is converted into an unexpanded tubular profile 104 in the extruder 102.

The unexpanded tubular profile 104 is stretched from first length L1 to second length L2 and/or first diameter D1 to second diameter D2 in first temperature controlled area 108A. The optional puller 128B feeds the partially expanded tubular profile 10 of second length L2 and/or second diameter D2 into the second temperature controlled area 108B wherein it is stretched from second length L2 to third length L3 and/or second diameter D2 to third diameter D3. The optional puller 128C feeds the partially expanded tubular profile 10 of third length L and/or third diameter D3 into the third temperature controlled area 108C wherein it is stretched from third length L3 to fourth length L4 and/or from third diameter D3 to forth diameter D4. In the present invention there can be an infinite number of stretching steps of any combination to achieve the desired end-use product.

The process of the present invention can have unlimited temperature controlled areas 108 wherein stretching takes places. Moreover, there can be one long temperature controlled area 108 wherein the unexpanded tubular profile 104 or partially expanded tubular profile 10 goes through multiple stretching steps. The number of temperature controlled areas 108 and stretching zones are experimentally determined to achieve the requirements of the end-use application. Optionally, the amount and/or rate of stretching can be varied by, for example, sequentially increasing or decreasing these parameters along with temperature through the multiple stretching processes.

The residual solvent is substantially removed from the unexpanded tubular profile 104 in extraction device 106. In this example, the solvent is extracted at the end of the process, but as previously mentioned the solvent can also be extracted prior to stretching or between stretching operations.

The optional thermal treatment step can partially or fully occur at one time at the end of the process after all stretching has occurred or after all or some the stretching steps. Once the thermal treatment or stretching is complete, the expanded material 12 is cooled and stored.

EXAMPLE 6

Generic Process for Manufacturing Uniform Polyolefin Expanded Material

To produce an unusually strong expanded material 12 of the present invention, crystallizable polymer materials 14 such a polyolefins are preferred, polypropylene is more preferred, and polyethylene is most preferred. It is also possible, for example, to use the previously mentioned polymer materials 14 or polymethylpentene-1, polyocymethylene, polyvinylidenefluoride, polyvinyl alcohol, poly acrylonitrile, and polyamide (nylon). The polymer material 14 can be of any density, molecular weight, or molecular weight distribution. Preferably the molecular weight of polyethylene material 14 is in the range of about 100,000 to about 10,000,000.

Referring to FIG. 82, the polymer material 14 is stored in a silo 98A and is mixed in blend tank 100 with a first solvent that is stored in silo 98B. The first solvent is preferably nonvolatile under process conditions. The preferred first solvent for hydrocarbon polymers are aliphatic and aromatic hydrocarbons. Paraffin oil, decalin (or dacahydronaphthlene), dodecane, xylene, toluene, trichlorobenzene, tetralin, cycloalkane, cycloalkene, carene, fluorene, camphene, menthane, dipentene, naphthalen, acenaphthene, methylcyclopentadien, tricyclodecane, 1,2,4,5-tetramethyl 1-1,4cyclohexadiene, fluorenone, naphthindane, tetramethyl-p-benzodiquinone, ehtylfluorene, fluoranthene, naphthenone, and their derivatives and/or mixtures are examples of suitable solvents.

The polymer material 14 is combined with the solvent in the blend tank 100 at any ratio. Preferably, the polymer is dissolved in the solvent. However, it is possible to have the polymer undissolved, partially dissolved or fully dissolved. For polyethylene in paraffin oil it is preferred to have the polymer in first solvent at a ratio in the range of about 0.05 to 100 weight percent. To obtain a substantially fibril-free embodiment, it is preferred to have the ratio of polymer to solvent be less than about 15 weight percent polymer. To obtain a substantially void-free embodiment it is preferred to use a relatively low level of polymer in solvent in the range of about 5 to 8 weight percent polymer. To obtain a fibril-containing embodiment it is preferred to have a higher polymer concentration in the range of about 20 to 100 weight percent polymer. An optional agitator 130 as shown in FIG. 82 and/or elevated temperature can optionally facilitate dissolving the polymer material 14 in the solvent. It is desirable to sustain the polymer material 14 at a relatively constant concentration to achieve product uniformity. Furthermore, it is advantageous to manage air bubbles and/or lumps during agitation. For polyethylene material 14, the temperature during the blending or agitation stages is preferably in the range of about 60 to 350° C. (140 to 662° F.), more preferably in the range of about 200 to 250° C. (392 to 482° F.). Care should be taken not to degrade the polymer material 14. Blanketing the blend tank 100 or other process steps with an inert gas like nitrogen or by including antioxidants in the material 14 can prevent polymer degradation.

The previously mentioned additives 60, nano size articles 62, or combinations thereof can be optionally introduced to the blend tank 100. For ease of handling it is desirable to predisperse them in the solvent, compound them in the resin material 14, or incorporate them into the resin material 14 during polymerization.

As shown in FIG. 82, the polymer material 14, slurry, or solution of blend tank 100 is optionally transferred to an intensive mix tank 132. The intensive mixer further agitates the polymer material 14 in first solvent. The polymer material 14, slurry, or solution is then transferred to an extruder 102. The extruder 102 conveys the polymer material 14, slurry, or solution thru a die that forms an unexpanded tubular profile 104 of indefinite or finite length in any shape. The extruder 102 optionally includes a motor, gear pump, screw, barrel, metering pump to deliver the polymer material 14, solution, slurry, or melt to the die (or a plurality of dies) at a reasonably controlled rate.

Depending on the embodiment of the present invention, the unexpanded tubular profile 104 exits the die under pressure and passes through either an air gap 136, quench tank 134, or extraction device 106. For polyethylene material 14, nominally the temperature of the extrusion device and the die are in the range of about 100 to 350° C. (212 to 662° F.), preferably around about 200 ° C. (392° F.).

The unexpanded tubular profile 104 exits the die into an air gap 136. The air gap 136 can be optionally enclosed and filled with an inert gas like nitrogen. In addition, the air gap 136 can optionally have temperature control and/or cross ventilation to facilitate cooling of the extrudate. The unexpanded tubular profile 104 is optionally stretched axially from first length L1 to second length L2 or circumferentially from first diameter D1 to second diameter D2 or both when passing through the air gap 136. The amount of permissible stretching is dependent on the wall thickness of the unexpanded tubular profile 104, temperature of the extrudate, and rate of stretch. The upper limit of how much the extrudate can be stretched is up to the point wherein the extrudate breaks. The extrudate, for example, can be stretched up to and above about 200:1.

From the air gap 136 the unexpanded tubular profile 104 or once stretched expanded tubular profile 10 passes into a quench tank 134. It is not important how the unexpanded tubular profile 104 is conveyed, but pullers 128 or rollers are useful. In the quench tank 134 the temperature of the unexpanded tubular profile 104 or once stretched expanded tubular profile 10 is reduced to a second temperature. The second temperature is sufficiently low to convert the tubular profile in to a gel-extrudate. For polyethylene, the second temperature is nominally in the range of about −40° C. to +40° C. (−40 to 104° F.). The preferred liquid in quench tank 134 is water, but a second solvent may be utilized to extract the first solvent.

The partially expanded tubular profile 10 exits the quench tank 134 and enters temperature controlled area 108A which is at a temperature in a range of about 100 to 160° C. (212 to 320° F.). The partially expanded tubular profile 10 is heated by passing through a temperature controlled area 108A which is a heated chamber or sleeve, for example. The length of the chamber is dependent on the speed of the tubular article passing through it. The faster the speed, generally the longer the chamber needs to be. In this stretching process, the partially expanded tubular profile 10 is stretched from first length L1 to second length L2 or first diameter D1 to second diameter D2 or both in a range of about 0.001:1 to 15:1, preferably about 10:1. The upper limit of how much the extrudate can be stretched is up to the point wherein the extrudate breaks. The process is optionally repeated in temperature controlled areas 108B and 108C.

From the temperature controlled areas 108 the expanded tubular profile 10 of gel-extrudate passes into an extraction device 106. In the extraction device 106 the first solvent is at least partially replaced with a second solvent. It is preferred to replace the first solvent to less than one percent of the total solvent in the gel-extrudate. The second solvent preferably has a low boiling point. When first solvents are hydrocarbons, suitable second solvents include, for example, hydrocarbons, chlorinated hydrocarbons, chlorofluorinated hydrocarbons, and others such as pentane, hexane, heptane, toluene, methylene chloride, carbon tetrachloride, trichlorotrifluoroethane (TCTFE), diethyle ether, ethanol ether, acetone, cyclohexanone, 2-methylpentanone, dichloromethane, n-hexane, heptane, diethyl ether, dioxane, dioxane or mixtures thereof. The preferred solvents are methylene chloride and trichlorotrifluoroethane (TCTFE). In the extraction device some shrinkage or swelling may occur of the tubular article. Stretching of the gel-extrudate in the extraction device is optionally performed. As previously mentioned, it is also possible to extract the first solvent in the beginning of or during the process within the scope of the present invention.

Exiting the extraction device 106, the gel-extrudate optionally passes through a thermal treatment zone 110. In the thermal treatment zone 110 the second solvent is removed, typically through evaporation. The thermal treatment zone 110 can optionally be under a vacuum to facilitate removal of second solvent. There are numerous methods of drying the expanded tubular profile 10, but utilizing a hot gas (like air or nitrogen) or a heated cylinder or drum are especially useful in the present invention. Stretching of the expanded tubular profile 10 in the thermal treatment zone 110 is optionally performed.

From the thermal treatment zone 110, the expanded tubular profile 10 is optionally cooled and stored in coil(s) or cut into straight length(s) prior to optional additional stretching. This is sometimes desirable because the secondary stretching operation(s) can operate at a different line speed than the precursor line speed. The secondary stretching processes can, for example, operate slower.

EXAMPLE 7

Small Diameters Twice Stretched Thin Wall Expanded Tubular Profile

Fluon®V CD-123 polytetrafluoroethylene (PTFE) powder is mixed in blend tank with mineral spirits at a ratio of about 295 cc per 1 kg (2.2 pounds) of powder. The combination is extruded into a cylindrical shaped tubular profile of first inside diameter D1 of about 1.52 mm (0.06 inches). The unstretched tubular profile is rolled onto a spool for temporary storage.

The unstretched tubular profile is heated to about 315° C. (599° Fahrenheit) while stretching from a first length L1 of about 1 m (39.37 inches) to a second length L2 of about 5 m (196.85 inches) at a rate of about 500%/sec between two pullers.

The once axially stretched tubular profile is heated again to a temperature of about 315° C. (599° Fahrenheit) while stretching to a second inside diameter D2 of about 3.04 mm (0.12 inches) and a wall thickness of 0.10 mm (0.0039 inches) at a rate of about 500%/sec over a first mandrel mounted inside the bore of the tubular profile.

After stretching the tubular profile, its bore is moved over a barrel having its diameter sized to maintain the tubular profile about in its stretched configuration. The barrel is porous and hot air reduces friction between the outside surface of barrel and bore of tubular profile. The double stretched tubular profile is heated to about 365° C. (672.8° Fahrenheit) while moving over the barrel.

Upon cooling of the tubular profile that was first axially stretched at a ratio of about 5:1 and second circumferentially stretched at a ratio of about 2:1 is cooled to about 23° C. (73.4° Fahrenheit). The mean fibril length of the expanded material is about 5 microns long in the circumferential direction and about 10 microns in the axial direction.

EXAMPLE 8

Polytetrafluoroethylene (PTFE) Material Polymerized with Nano Tubes

Using an aqueous dispersion procedure, fine powder polytetrafluoroethylene (PTFE) resin is produced that contains single wall carbon nano tubes that are available from Thomas Swan & Co Ltd, Crookhall, Consett, County Durham DH8 7ND, UK under the trade name Elicarb™. Tetrafluoroethylene is combined with carbon nano tubes having a length from about 0.5 to 3.0 mm and diameter of about 2 nanometers. This combination is stirred in an aqueous medium in the presence of dissolved persulfate polymerization initiator and a dispersing agent under pressure of about 10 to 40 kg/cm2. The polymerization reaction is carried out at about 90-140° C. and the polymerization initiator (ammonium persulfate) is added to the reaction medium until about 65% of the amount of polytetrafluoroethylene has been formed. The resin obtained has an aqueous dispersion of polytetrafluoroethylene particles having a diameter generally within the range of about 0.005 to 400 microns. The dispersion is coagulated by diluting, bringing to a pH of 8 to 9, adding ammonium hydroxide, and stirring at a temperature in the range of about 20-30° C. until a jelly-like mass is produced. The resin is separated and dried for about 18 hours at about 120° C. The polytetrafluoroethylene (PTFE) resin is converted into expanded material.

EXAMPLE 9

High Molecular Weight Polyethylene Fibril Containing Expanded Material

Ultra high molecular weight polyethylene obtained from Chevron Phillips Chemical Co. (Woodlands, Tex., USA) is blended with Kaydol™ mineral spirits available from Chemtura Corporation (Middlebury, Conn., USA) at a ratio of about 40 weight percent polymer and 60 weight percent solvent. The solution is mixed at an elevated temperature so that it includes about 60 volume percent well dispersed micro air bubbles that have a mean diameter of about 0.5 microns. The blend also includes an antioxidant Irganox B-225 which is available from Ciba (Basel, Switzerland). The micro bubble containing polyethylene solution is extruded into an unexpanded tubular profile and stretched circumferentially and axially at an elevated temperature. The polyethylene between the micro air bubbles elongates to form fibrils between the voids in the wall thickness. The solvent is driven off and the expanded tubular profile is cooled. Additional samples are prepared in sheet and fiber configurations.

EXAMPLE 10

High Density Polyethylene Fibril Containing Expanded Material

High density polyethylene is formed into fine particles having a diameter ranging from about 0.05-500 microns. The fine particles of polyethylene are extruded into an unexpanded tubular profile having a wall thickness of about 0.38 mm (0.015 inches) at an elevated temperature and duration long enough to only melt the outside surface of the discrete particles while substantially leaving the core of each particle somewhat unmelted. The wall thickness is about 15 percent porous because there is some gas (air) located between the descrete polymer particles. The unexpanded tubular profile is cooled and transferred to a heat chamber where it is reheated to a temperature sufficiently high to remelt the outside surface of each particle while keeping the core of the discrete particles somewhat unmelted. The reheated unexpanded tubular profile is stretched to elongate the melted polymer on the outside surface of each particle to form fibrils between the nodes comprised of unmelted polymer. The expanded material is lowered in temperature to retain the expanded structure. Additional samples are made in sheet and fiber configurations. Additional samples are extruded including solvent.

EXAMPLE 11

Two Polymer Fibril Containing Expanded Material

Fine particles are formed having a nylon core and high density polyethylene shell. The fine particles are combined with a non volatile solvent and extruded into an unexpanded tubular profile having a wall thickness of about 0.38 mm (0.015 inches) at an elevated temperature of about 135° C. (275° F.) and duration long enough to only melt the very outside surface of polyethylene while leaving the core of nylon and part of the polyethylene on each particle somewhat unmelted. The wall thickness is about 15 percent porous because there is some gas (air) located between the descrete polymer particles. The somewhat porous unexpanded tubular profile is cooled and transferred to a heat chamber where it is reheated to a temperature sufficiently high to remelt the very outside surface of each particle while keeping the core of the discrete particles unmelted. The reheated unexpanded tubular profile is stretched to elongate the melted polymer of the outside surface of each particle to form fibrils between the nodes comprised of somewhat unmelted polymer. The expanded material is lowered in temperature to retain the expanded structure. Additional samples are made in sheet and fiber configurations with and without solvent.

EXAMPLE 12

Two Polymer Fibril Containing Expanded Material

Fine particles are formed having a polytetrafluoroethylene (PTFE) core and a high density polyethylene shell. The fine particles are blended with a solvent of paraffin oil and extruded into an unexpanded tubular profile having a wall thickness of about 0.76 mm (0.030 inches) at a temperature of around 200 to 250° C. (392 to 482° F.). The unexpanded tubular profile is transferred to a quench tank at temperature of about 23° C. (73.4° F.) and temporarily stored. The wall thickness is about 15 percent porous because there is some air located between the descrete polymer particles.

The unexpanded tubular profile is fed into a temperature controlled chamber at a temperature of about 200° C. (392° F.) and stretched first axially and then circumferentially. The melted polyethylene (HDPE) between the polytetrafluoroethylene (PTFE) particles elongates and produces fibrils inbetween. The solvent is removed with a more volatile solvent which is then driven off by heat. The expanded material is cooled. Additional samples are prepared of polyethylene-polypropylene, polyethylene-polyamide, and polyethylene-polyester. The samples are stretched in tubular, sheet, and fiber configurations.

EXAMPLE 13

Agent Coated Onto Nano Particles Attached to Surface of Expanded Material

An expanded tubular profile having an inside diameter of 6 mm (0.2362 inches) and a wall thickness of 0.15 mm (0.0059 inches) has glass nano particles applied to its outside surface while the expanded tubular profile is at a temperature of 260° C. (500° F.). The glass nano particles adhere to seventy percent (70%) of the surface of the outside surface. After cooling, the assembly of the expanded tubular profile and the glass nano particles is coated with an immunosuppressive agent. Samples were coated with are few representative immunosuppressive agents including sirolimus (Rapamune™) that is available from Wyeth, Madison, N.J., USA.; cyclosporine (Sandimmune™or Neoral™) that is available from Novartis International AG, Basel, Switzerland; leflunomide metabolite (Arava™, A77 1726, M1) that is available from Sanofi Aventis, Paris, France; and mycophenolate mofetil (CellCept™) available from Roche Pharmaceuticals, Nutley, N.J., USA. The coated expanded tubular profile is utilized as a vascular graft.

EXAMPLE 14

Active Ingredients Applied to Expanded Material Using Printing Process

A sheet of expanded material of approximately 1 m width (39.37 inches) by 0.0127 mm (0.0005 inches) thick and 25 m (82 feet) long that is made of polytetrafluoroethylene (PTFE) containing carbon nano tubes is coated with active ingredients using printing techniques. Samples are prepared so that active ingredients are applied by inkjet, laser, offset, gravure and flexographic techniques. Samples were prepared having active ingredients that are immunosuppressives including corticosteroids (Prednisone™) available from ZyF Pharm Chemical, Shanghai, China; azathioprine (6-mercaptopurine, Imuran™) available from Prometheus Laboratories Inc., San Diego, Calif., USA; cyclospoine (Sandimmune™, Neoral™) available from Novartis Pharmaceuticals, Basel, Switzerland; tacrolimus (Prograf™) available from Astellas Pharma U.S., Deerfield, Ill., USA; sirolimus (Rapamune™) available from Wyeth, Madison, N.J., USA; mycophenolate mofetil (CellCept™) available from Roche Pharmaceuticals, Nutley, N.J., USA; muromonabco3 (OKT3) available from Ortho Biotech, Bridgewater, N.J., USA; lymphocyle immune globulin (ATGAM) available from Pfizer-Pharmacia, New York, N.Y., USA & UpJohn, Kalamazoo, Mich., USA; basiliximab (Simulect™) available from Novartis Pharmaceutical Corporation, East Hanover, N.J., USA; daclizamab (Zenapax™) available from Roche Pharmaceuticals, Nutley, N.J., USA; ISAtx247 (a calcineurin inhibitor) available from Isotechnika of Edmonton, Alberta, Canada and Hoffman LaRoche; gusperimus (15-deoxyspergualin, Spanidin™) available from Nippon Kayaku Co. Ltd, Tokyo, Japan; Medi-500 (formerly T10B9, murine IgM anti-human CD3/TCR mAb T109B); FTY720 available from Cayman Chemical Company; siplizumab (Medi-507) available from Medimmune, Gaithersburg, Md., USA; HLA-B2702 peptide and combinations thereof. Sections of the sheet are implanted in the human body. The immunosuppressive active ingredients mitigate the rejection of the implant by the human body.

EXAMPLE 15

Multi-Layer Covering of Active Ingredients On Expanded Material

An expanded tubular profile of polytetrafluoroethylene (PTFE) material including nanocrystalline and microcrystalline silicon is coated with active ingredients that are immunosuppresives. Samples were prepared by dipping the expanded tubular profile in a solution and dispersion containing corticosteroids (Prednisone™) available from ZyF Pharm Chemical, Shanghai, China; azathioprine (6-mercaptopurine, Imuran™) available from Prometheus Laboratories Inc., San Diego, Calif., USA; cyclospoine (Sandimmune™, Neoral™) available from Novartis Pharmaceuticals, Basel, Switzerland; tacrolimus (Prograf™) available from Astellas Pharma U.S., Deerfield, Ill., USA; sirolimus (Rapamune™) available from Wyeth, Madison, N.J., USA; mycophenolate mofetil (CellCept™) available from Roche Pharmaceuticals, Nutley, N.J., USA; muromonabco3 (OKT3) available from Ortho Biotech, Bridgewater, N.J., USA; lymphocyle immune globulin (ATGAM) available from Pfizer-Pharmacia, New York, N.Y., USA & UpJohn, Kalamazoo, Mich., USA; basiliximab (Simulect™) available from Novartis Pharmaceutical Corporation, East Hanover, N.J., USA; daclizamab (Zenapax™) available from Roche Pharmaceuticals, Nutley, N.J., USA; ISAtx247 (a calcineurin inhibitor) available from Isotechnika of Edmonton, Alberta, Canada and Hoffinan LaRoche; gusperimus (15-deoxyspergualin, Spanidin™) available from Nippon Kayaku Co. Ltd, Tokyo, Japan; Medi-500 (formerly T10B9, murine IgM anti-human CD3/TCR mAb T109B); FTY720 available from Cayman Chemical Company; siplizumab (Medi-507) available from Medimmune, Gaithersburg, Md., USA; HLA-B2702 peptide and combinations thereof. The coated expanded tubular profile is dryed and recoated multiple times. The multi layer coated tubular profile is surgically implanted in a human body. Samples are prepared with and without non-erodible or erodible covering. Some samples are prepared with microencapsulated and nanoencapsulated active ingredients. The immunosuppressive active ingredients mitigate the rejection of the implant by the human body.

EXAMPLE 16

Extended Release of Active Ingredients Administered Orally in Shell

A bottom sheet of expanded material made of polytetrafluoroethylene (PTFE) material is placed over a form having a cavity 15.88 mm (⅝ inch) long by 7.94 mm (5/16 inch) wide by 4.76 mm (3/16 inch) deep. The bottom sheet is draped into the cavity and filled with an active ingredient of 500 mg of amoxicillin ($C_{16}H_{19}N_3O_5S \cdot 3H_2O$). Fifty percent (50%) of the active ingredient is micro encapsulated with a soluble covering to delay release of active ingredients. In addition, a variety of samples are prepared experimenting with different combinations of inactive ingredients consisting of colloidal silicon dioxide, crospovidone, hypromellose, magnesium stearate, microcrystalline cellulose, polyethylene glycol, sodium starch glycolate, and titanium dioxide are included. The cavity that is filled with active and inactive ingredients is covered with a top layer of expanded material made of polytetrafluoroethylene (PTFE) material. The top and bottom layers are substantially sealed closed and cut to form a shell. The shell is coated with a film of gelatin. The casing is administered to a patient orally. The contents are released into the digestive and intestinal tracts over a period of 24 hours at a descending rate through the voids in the expanded material. First the uncoated active ingredients are released and then the micro encapsulated active ingredients are released. The undigested expanded material is expelled by the human body through a bowel movement.

EXAMPLE 17

Cancer Eradicating Active Ingredients Diffused in Close Proximity of Tumor

The first end of one expanded tubular profile made of polytetrafluoroethylene (PTFE) material is substantially sealed closed. The tube is filled with an anti cancer agent and the second end is closed to form a casing that encapsulates the active ingredients. The casing is adapted with a device for refilling the casing while installed. The casing is implanted through noninvasive surgery in relatively close proximity to a metastic breast cancer. Samples are prepared with active ingredients that include fluorouracil/5-FU (Adracil™) which is available from Pharmacia and UpJohn, gemcitabine HCL (Gemzar™) which is available from Lilly, paclitaxel (Taxol™) which is available from Bristol-Meyers Squibb, bevacizumab (Avastin™) which is available from Genentech Inc., trastuzumab (Herceptin™) which is available from Genentech Inc., Abraxane™ which is available from Abraxis Oncology, Schaumburg, Ill., USA, and combinations thereof. Various inactive ingredients such as sterile water are combined with the active ingredients to facilitate delivery of the dosage. The active ingredients elute or diffuse through the voids in the wall thickness of the expanded material. The treatments permit higher localized dosage to more quickly kill and/or mitigate the growth of cancer cells with less adverse side effects on the patient.

EXAMPLE 18

Woven Stent

The voids of an expanded sheet made of polytetrafluoroethylene (PTFE) material are partially filled with an active ingredient that is an immunosuppressive called ISAtx247 (a calcineurin inhibitor) available from Isotechnika of Edmonton, Alberta, Canada and Hoffman LaRoche. The expanded sheet is densified and cut into expanded fibers. The densified expanded fiber containing ISAtx247 is woven with Nitinol® wire into a woven tube. The woven tube is compressed in size and inserted into a human sinus cavity with a catheter. When the compressive force is released the woven tube expands to open the previously narrowed sinus cavity. Upon installation the sinus cavity is open and mucus freely drains preventing infection. The tube can be periodically removed and replaced. Other samples are prepared to hold open blood carrying vessels and tubes that drain ears. The embedded active ingredient has no covering that can flake-off like embodiments using coatings to secure active ingredients onto substrate.

EXAMPLE 19

Non-Woven Stent

An expanded sheet made of polytetrafluoroethylene (PTFE) material is densified and cut into expanded fibers of random length having an approximate mean length of 10 mm (0.3937 inches). The densified expanded fiber is randomly wrapped around a 2.5 mm (0.0984 inches) core with random length Nitinol® wire of approximately the same mean length to form a non-woven tube having approximately thirty percent (30%) void space. Fluorinated ethylene propylene (FEP) is used as a binder to hold the fiber and wire in tubular form. The assembly is heated in an oven at a temperature around the melting temperature of polytetrafluoroethylene (PTFE) for sufficient time to bind the fibers. The non-woven tube is cooled, removed from the core, surface treated to improve adhesion with etching, and cut to length of approximately 8 mm. The luminal and abluminal surfaces of the non-woven tube are coated with an immunosuppressive called siplizumab (Medi-507) available from Medimmune, Gaithersburg, Md., USA. The siplizumab is held in place with a non-erodible polymer. The examples were prepared using a combination of polyethylene-co-vinyl acetate (PEVA) and poly n-butyl methacrylate (PBMA). The covering remains securely attached to the expanded material as a result of the etching surface treatment.

The non-woven tube is compressed in size and inserted into a human blood carrying vessel with a catheter. When the compressive force is released the non-woven tubular profile expands to open the previously narrowed vessel.

EXAMPLE 20

Highly Abrasion Resistant Gum Graft

Expanded sheet made of polytetrafluoroethylene (PTFE) material including glass particles is grafted onto a gum in a human mouth to repair a gum that has receded. The graft is abrasion resistant against the bristles of a tooth brush.

EXAMPLE 21

Drug Containing Oral Implant

An expanded tubular profile including glass nano fiber is filled with an active ingredient that is an antibiotic called (trimethoprim/sulfamethoxazole, TMP/SMZ, Batrin™) that is available from Roche Pharmaceuticals, Nutley, N.J., USA. The filled expanded material is utilized in an oral surgical procedure.

EXAMPLE 22

High Tensile Strength Hernia Patch

Expanded sheets including carbon nano tubes, glass fibers, and combinations thereof are surgically positioned to repair a hernia in a human body. Other examples are produced containing titanium dioxide, boron nitride nanotubes, and manganese oxide nanotubes.

EXAMPLE 23

Skin Graft

Expanded sheet made of polytetrafluoroethylene (PTFE) is grafted onto a human leg that was burned. The expanded sheet serves as a synthetic skin graft. A pressure bandage is applied over the graft until healing occurs.

EXAMPLE 24

Lab-Grown Organ Graft

Undifferentiated stem cells are positioned with an expanded tubular profile made of polytetrafluoroethylene (PTFE) material. Human colon cells and DNA are introduced to the expanded tubular profile to grow new colon cells on and within the expanded material. The expanded material serves as a scaffold for growing new cells and/or organs outside the body. The expanded tubular profile containing transformed cells is surgically implanted in a human body after removal of a like-size section of colon destroyed by cancer. The repaired colon restores for the most part normal functionality of the colon avoiding the necessity of an ostomy procedure.

EXAMPLE 25

Lab-Grown Blood Vessels

Skin cells and blood vessel cells are placed with expanded tubular profile made of polytetrafluoroethylene (PTFE) material in environment providing conditions for cell proliferation. Collagen and elastin are produced and form within the scaffold of expanded material to generate lab-grown blood vessels. The vessels are suitable for transplantation into diabetic patients that require dialysis. The lab-grown vessels having an expanded material backbone serve as a shut enabling multiple punctures without failing. Alternatively, the polytetrafluoroethylene (PTFE) material includes carbon nanotubes.

EXAMPLE 26

Cancer Drug Eluting, Expanded Tubular Profile Used as Suppository

The first end of the expanded tubular profile made of polytetrafluoroethylene (PTFE) material including carbon nano tubes is sealed and its bore is filled with an anti cancer drug. Samples are prepared with bevacizumab (Avastin™) and retuximab (Erbitux™) which are effective active ingredients against colon cancer. The second end of expanded tubular profile is sealed to form a suppository. The expanded tubular profile containing these contents has its outside surface coated with a water soluble covering, is lubricated and inserted into the rectum of a patient so that it is positioned nearby a cancerous tumor. The anti cancer agents that are active ingredients elute or diffuse through the voids in the wall thickness of the expanded tubular profile dispensing the active ingredients in close proximity of the tumor. The patient's tumor reduces in size more readily due to a higher localized dosage of active ingredients with minimized side effects on the patient vs. an infusion.

EXAMPLE 27

Expanded Material Used as Transdermal Birth Control Patch

An expanded sheet made of polytetrafluoroethylene (PTFE) material includes adhesive and active ingredients that are effective in birth control. The active ingredients consist of norelgestromin and ethinyl estradiol. The combination is converted into a transdermal patch that is applied to the skin of a human patient. The active ingredients elute through the pores in the expanded material into the skin of the patient to provide the correct dosage of active materials to prevent pregnancy. The hydrophobic surface facing away from the patient's skin prevents water from diluting or increasing the dosage. The patch is long lasting requiring less frequent replacements. Furthermore, it provides an accurate dosage significantly reducing the risk of overdosage.

EXAMPLE 28

Expanded Material Used as Transdermal Smoking Cessation Patch

An expanded sheet made of polytetrafluoroethylene (PTFE) material includes adhesive and an active ingredient that prevents or minimizes the desire to smoke cigarettes. The active ingredient is varenicline tartrate (Champix®, varenicline) which is available from Pfizer, New York, N.Y. (USA). The combination is converted into a transdermal patch that is applied to the skin of a human patient. The active ingredient elutes through the highly uniform voids in the expanded material into the skin of the patient to provide the correct dosage of active materials to allow the patients to gradually wean themselves off cigarettes. The patch is long lasting requiring less frequent replacements. Furthermore, it provides an accurate dosage significantly reducing the risk of overdosage.

EXAMPLE 29

Nitinol Reinforced Expanded Tubular Profile Used to Repair Aneurismal Vessel

A cylindrical shaped expanded tubular profile made of polytetrafluoroethylene (PTFE) including silicon dioxide nano size crystals that has an inside diameter of about 3.5 mm (0.1378 inches) and a length of 33 mm (1.299 inches) has a Nitinol® reinforcement attached to its outside surface. The reinforcement has a plurality of criss-cross members with spaces in-between like a lattice. The fabrication of the expanded tubular profile and reinforcement is coated on its luminal and abluminal surfaces with sirolimus available from Wyeth, Madison, N.J., USA so that the active ingredient is present on the fibrils, voids, and nodes of the expanded material. The covering is applied by dipping the fabrication in a solution of sirolimus and a binder comprised of a combination of polyethylene-co-vinyl acetate (PEVA) and poly n-butyl methacrylate (PBMA). The fabrication is coated and dried until it contains 315 micrograms of sirolimus. The fabrication is restrained so that its outside diameter is reduced by fifty percent (50%). The restrained fabrication is inserted by non invasive surgery utilizing the assistance of a catheter into a human blood carrying vessel. Upon positioning the restrained fabrication in the proximity of an aneurismal vessel, the restraint is released and the fabrication expands substantially to a second size and shape. The fabrication takes over for providing a fully operation bore capable of withstanding blood pressure and flow in the area of installation.

EXAMPLE 30

Stainless Steel Reinforced Expanded Tubular Profile Including Nano Crystals is Coated with Active Ingredients A cylindrical shaped expanded tubular profile of polytetrafluoroethylene (PTFE) as in example 29 wherein the Nitinol® reinforcement is substituted with a reinforcement made of 316L stainless steel member segments located on bore. Upon positioning the fabrication in the proximity of a lesion in a vessel, the fabrication is dilated with a balloon catheter so that it expands substantially against the host vessel where it is secured in place. The fabrication takes over for providing a fully operation bore capable of withstanding blood pressure and flow in the area of installation. Alternatively, the active ingredient is also positioned between layers of PTFE instead on surface.

EXAMPLE 31

Drug Eluting, Stent-Graft (Encapsulated Between Two Layers)

A stent-graft is formed of two tubes of porous expanded material made of polytetrafluoroethylene (PTFE) including titanium dioxide and a mechanically expandable Nitinol® reinforcement having member segments forming a lattice. The reinforcement is located between the two wall thicknesses of the expanded material. Prior to assembly, the outside surface of the interior tube of expanded material is coated with an anti-clotting active ingredient heparin that is available from Celsus, Cincinnati, Ohio, USA, the bore of the exterior tube of expanded material is coated with an immunosuppressive active ingredient paclitaxel (Taxol™) available from Bristol-Myers Squibb, New York, N.J., USA and the reinforcement is coated with an antibiotic active ingredient of trimethoprim/sulfamethoxazole, TMP/SMZ (Batrin™) that is available from Roche Pharmaceuticals, Nutley, N.J., USA. Sixty percent of the active ingredient is micro encapsulated to provide sustained release over a longer period of time. Furthermore, the bore of the interior tube is coated with an anti-platelet agent clopidogrel bisulfate (Plavix™) which is available from Bristo Meyers Squibb/Sanofi Pharmaceuticals. The first end and second end of the tubular profiles are substantially sealed closed to encapsulate the reinforcement and active ingredients.

The reinforcement has a first diameter that is approximately fifty percent (50%) smaller that the second diameter of the expanded tubular profiles. The excess circumference of the expanded tubular profiles is folded over and temporarily secured in place during assembly of the stent-graft.

The fabrication is inserted through a main artery in the groin (femoral artery) in a patient through noninvasive surgery utilizing a catheter. The fabrication is flexible and able to conform to the curvature of the artery. When in position, the fabrication is dilated by removal or a constraint that allows the shape memory Nitinol g wire to expand the stent-graft to the optimum diameter to permit sufficient blood flow without restriction. Once dilated, the expanded tubular profiles unfold to grow in circumference with the second size of the reinforcement. The sirolimus and heparin elute or diffuse into the proximity of the installed position through the voids in the wall thickness of the expanded material. The clopidogrel bisulfate assists in preventing blood clotting.

EXAMPLE 32

Drug Eluting Metallic Stent Covered with Expanded Material Containing Thru Holes The inside and outside surfaces of a metallic stent are covered with two tubes of expanded material having a wall thickness of about 0.08 mm. The two tubes of expanded material made of polytetrafluoroethylene (PTFE) cover a 316L stainless steel reinforcement having member segments forming a lattice. The expanded material in-between the members of the inner and outer tubes are attached or sealed to fully encapsulate each member of the reinforcement. The excess expanded material that is an interconnection between the pluralities of member segments is partially removed to make holes or pe forations in the two layers of expanded material like in FIG. 37.

The pockets between the tubular profiles are filled with a combination of sirolimus (Rapamune™) available from Wyeth, Madison, N.J., USA an anti-clotting agent (heparin) that is available from Celsus, Cincinnati, Ohio, USA. The pockets in the expanded material serve as reservoirs to hold the optimum dosage of active ingredients.

The covered stent in a reduced size is inserted through a main artery in the arm (brachial artery) of a patient through noninvasive surgery utilizing a tiny balloon catheter. The fabrication is flexible and able to conform to the curvature of the artery. Furthermore, the fabrication has sufficient strength so that its bore can withstand collapsing when positioned in a location such as a joint like near a movable joint. When in position, the fabrication is dilated using a balloon catheter to expand the fabrication to the optimum diameter to permit sufficient blood flow without restriction. The sirolimus and heparin elute or diffuse into the proximity of the installed position over time from the pockets. The endothelial cell grow through the thru holes in the expanded material and line the bore of the covered stent.

EXAMPLE 33

Drug Eluting, Kink-Resistant Stent-Graft (Installed in Flexible Artery)

Two cylindrical shaped expanded tubular profiles made of polytetrafluoroethylene (PTFE) material including carbon nanotubes having a mean fibril length of 20 microns have a cylindrical shaped reinforcement made of Nitinol® member segments positioned in-between the two wall thicknesses. The reinforcement is coated with an active ingredient that is an immunosuppressive called sirolimus (Rapamune™) that is available from Wyeth, Madison, N.J., USA. The space between the two wall thicknesses is filled with two active ingredients that are an anti-clotting agent (heparin) that is available from Celsus, Cincinnati, Ohio, USA and an anti-platelet agent clopidogrel bisulfate (Plavix™) which is available from Bristol Meyers Squibb/Sanofi Pharmaceuticals. The first end and second end are substantially sealed closed to encapsulate the reinforcement and active ingredients. The fabrication is utilized as a stent-graft in a human body.

The stent-graft is constrained in first size and inserted into an artery just below the back of the knee of a human body with a catheter. The stent-graft assumes the curvature of the artery and the bore of the stent-graft opens to its second diameter once the constraint is removed. The bore remains substantially open when the knee is straight and flexed. The active ingredients elute or diffuse through the voids in the wall of the expanded material into the localized area of the installation. Moreover, the active ingredients minimize the risk of rejection of the stent-graft by the human body and minimize the risk of blood clotting. Since the active ingredients are encased by the two wall thicknesses, there is no possibility of a coating flaking off into the blood stream.

EXAMPLE 34

One-Piece Stent-Graft and Procedure for Installing

Expanded tubular profiles having approximate dimensions ranging in size from about 2.5 to 30 mm inside diameter and 8 to 60 mm in length, which are made of polytetrafluoroethylene (PTFE) including a plurality of discontinuous stainless steel fibers positioned substantially within the wall thickness, is coated with approximately 70 micrograms sirolimus. The diameters of the expanded tubular profiles are temporarily reduced in size by 20% until deployment by pleating their wall thicknesses like the example shown in FIG. 8. The one-piece stent-grafts are sterilized with ethylene oxide gas during the manufacturing process and sealed in a f oil package. Examples are produced having stainless steel fibers having a length of 0.5, 0.75, 1, 2, 5, and combinations thereof times the diameter of the tubular profiles.

A catheter is rinsed with sterile heparinized normal saline solution (HepNS). In addition, the guidewire lumen is flushed with HepNS. The inflation device is prepared with diluted contrast medium. The lesion is predilated with a percutaneous transluminal coronary angioplasty (PTCA) catheter. One expanded tubular profile is advanced over the guidewire to the target lesion. Radiopaque balloon markers are used to position the one-piece stent-graft across a lesion. Angiography is performed to confirm position of the one-piece stent-graft.

The inflation device is attached and controlled via a 3-way stopcock. The inflation device is inflated for about 10 seconds under fluoroscopic visualization to a pressure sufficiently high enough (below about 1500 kPa) to place the expanded tubular profile in full contact with the artery or up to about 2.5 mm. Since the lesion is not fully covered, a second one-piece stent-graft is positioned by repeating the process taking care to sufficiently overlap the expanded tubular profiles. The balloon is deflated by pulling a vacuum on the inflation device and the catheter is removed. The bores of the one piece stent-grafts stay substantially dilated after removal of the expansion device without the use of a separate metallic stent. Alternative samples are made substituting the stainless steel fibers with Nitinol and tantalum alloy fibers.

The patient is administered clopidogrel bisulfate (Plavix ™) which is available from Bristol-Myers Squibb/Sanofi Pharmaceuticals or ticlopidine (Ticlid™) which is available from Roche Pharmaceuticals during pre and post procedure. In addition, the patient is administered aspirin to reduce the risk of thrombosis.

EXAMPLE 35

Perforated Expanded Tubular Profie for Use as Stent-Graft and Stent

A stent is produced from a 5 mm diameter expanded tubular profile made of polytetrafluoroethylene (PTFE) that includes a combination of stainless steel fibers and carbon nano tubes. Six thru holes having a rectangular shape are cut from the wall thickness around the circumference of the tube and repeated down the length of the tube to form a perforated tube like the example shown in FIG. 9. The perforated tube is coated with fluorinated ethylene propylene (FEP) and wrapped with expanded sheet. The assembly is thermally cured to substantially connect the perforated expanded tubular profile to the expanded sheet. There are folds in expanded sheet enabling dilation to a larger size. The assembly is coated with 10 micrograms of sirolimus and polymers of PEVA and PBMA at a ratio of about 70 percent polymer and 30 percent sirolimus. The assembly is inserted into a blood vessel of a human patient and dilated from first size of 5 mm to second size of 30 mm to repair an aneurismal vessel. The bore of the expanded tubular profile stays open and in proper position after it is installed without the aid of a separate or attached metallic stent. Additional samples are produced without the expanded sheet covering the perforated tubular profile to form just a stent.

EXAMPLE 36

Fiber Reinforced, Form-in-Place Stent-Graft

Two expanded tubular profiles made of polytetrafluoroethylene (PTFE) material including glass nano fibers are densified using a combination of elevated temperature and compression. The outside surface of the first tube and the inside surface of the second tube are treated to increase adhesion. The outside surface of the first expanded tubular profile is covered with randomly oriented and inter tangled carbon fibers that are impregnated with a curable epoxy, fluorinated ethylene propylene (FEP), or urethane connecting member. The second expanded tubular profile is slid over the first expanded tubular profile so that the combination of the carbon fiber and connecting member are located between the two profiles. The first ends and second ends of the two profiles are substantially sealed together to encapsulate the connecting member and carbon fiber between the two profiles.

The fabrication is reduced in size by pleating like in FIG. 8 and inserted into a lumen using a flexible shaft balloon catheter to repair an aneurismal vessel in a curved lumen using radiopaque markers to assist in positioning. The balloon expansion device is enlarged to dilate the bore of the fabrication so that the bore of the fabrication is sized to provide substantially the same diameter and curvature required to provide a relatively smooth and unrestricted transition from the healthy lumen leading into and out of the fabrication. In addition, the fabrication's wall thickness is sufficiently compressed against the bore of the host lumen to create a seal that substantially prevents flow around the fabrication. If necessary, the fabrication is anchored to the host lumen to prevent movement.

The connecting member encapsulated between the two expanded tubular profiles is cured after final positioning, sizing, and shaping using thermal treatment, radiation, moisture, or U.V. light. The balloon catheter is unpressurized and the catheter is removed.

The custom fit graft remains in position resisting kinking and allowing the blood contents to flow through the bore. The abrasion resistant graft provides pressure carrying service between the healthy lumens and thereby taking the host vessel in the area of the aneurism out of service. The cured resin containing carbon fibers sustains the fabrication in desired configuration without the use of a metallic stent.

Additional samples are produced wherein (1) the connecting member is partially cured before insertion and completely cured when in final position; (2) the connecting member is substantially flexible after curing; (3) the connecting member is substantially inflexible after curing; (4) the connecting member does not include fibers; (5) the expanded material is sufficiently translucent allowing the connecting member to be U.V. cured through the expanded material; (6) the connecting member is U.V. cured through the voids in the expanded material; (7) the outside surface of the inner tube and inside surface of outer tube are treated with plasma or etched to increase adhesion; (8) the expanded material is not densified; (9) the expanded material excludes glass nano fibers; and combinations thereof.

EXAMPLE 37

Coil Shaped Drug-Eluting Stent

A coil shaped reinforcement is coated with active ingredients that are immunosuppressant and anti-clotting agents.

The coil shaped reinforcement is covered with expanded material. The expanded material is coated to delay the release of the active ingredients. Once the covering erodes, the active ingredients escape, elute, or diffuse through the voids in the expanded material at a descending rate.

We claim:

1. A tubular-shaped prosthesis having a first size and a second different size configured to be in substantially secure position and alignment with an anatomical lumen in a living body without support from a separate structural component comprising:
   a tube including a plurality of strut patterns and connecting members configured to connect said strut patterns together,
   wherein the strut patterns and the connecting members include a wall thickness formed of one or more interconnected layers comprised of a plurality of interconnected fibril elements of the same or different cross-sectional thickness,
   wherein said fibril elements partially or fully extend a distance between two or more intersections or crossover points,
   wherein said fibril elements are at least partially separated by void spaces,
   wherein said fibril elements comprise one or more materials that are degradable within the living body,
   wherein said fibrils elements comprise said one or more degradable materials of the same or different molecular weight, and
   wherein said fibril elements comprise an average thickness of less than about 50 microns and an average length between intersections or cross over points of less than about 25,000 microns.

2. The prosthesis of claim 1 including said fibril elements comprising material having at least partially transitioned through a liquid, melt, paste, or gel state and solidified prior to, during, or after formation of said fibril elements.

3. The prosthesis of claim 1 including said fibril elements comprising material having been partially or fully dissolved in a solvent prior to or during formation of said fibril elements wherein said solvent partially or fully evaporates prior to, during, or after formation of said prosthesis.

4. The prosthesis of claim 1 including said fibril elements having undergone any amount of stretching, elongation, or deformation (strain) one or more times at any rate of deformation during formation of said fibril elements, said tube, or said prosthesis.

5. The prosthesis of claim 1 including said void spaces positioned in the wall thickness of said strut patterns and said connecting members having a size less than about 15 microns.

6. The prosthesis of claim 1 partially or fully disappears from said position in the anatomical lumen after implantation in the anatomical lumen.

7. The prosthesis of claim 1 including one or more layers of said fibril elements positioned on abluminal (outer) surface of said prosthesis.

8. The prosthesis of claim 1 including said fibril elements positioned within the wall thickness of said strut patterns and said connecting members in an axial direction (parallel to a central axis of the tubular-shaped prosthesis), in a circumferential direction (perpendicular to the central axis of the tubular-shaped prosthesis), in an angled direction (at any angle to the central axis of the tubular-shaped prosthesis), or combinations thereof.

9. The prosthesis of claim 1 including one or more layers of a deformed (strained) or un-deformed solid material positioned on luminal (inner) surface of said strut patterns and said connecting members.

10. The prosthesis of claim 1 including said void spaces and said fibril elements of any orientation throughout the entire wall thickness of said strut patterns and said connecting members.

11. The fibril elements of claim 1 include straight shape portions, curved shape portions, bent shape portions, or combinations thereof.

12. The prosthesis of claim 1 includes the wall thickness wherein the density of at least a portion of the wall thickness is increased from a lower density to a higher density by reducing a volume of said void spaces in said wall thickness.

13. The prosthesis of claim 1 includes one or more additives, nano sized additives, or combinations thereof.

14. The prosthesis of claim 1 at least temporarily including one or more additives or nano sized additives selected from the group of: materials that improve surface adhesion, inactive ingredients, active ingredients, alginates, albumin, amino acids, amorphous materials, antimicrobials, associative materials, bacteria, barium, barium sulfate, borides, alumina, degradable materials, degradable metals or alloys, drugs, carbides, carbon, carbon nano tubes, ceramics, chitosan, collagen, collagen (types 1-28), copper, crystalline materials, dextrans, dioxides, dispersants, elastin, enzymes, fibers, fibrin, fibrinogen, fibroin, fibroblast, gels, gelatin, glycoproteins, modified release drugs, encapsulated active ingredients, endothelial cells, fillers, fibronectin, gelatin, glycolipids, hydroxyapatite, hydrogels, insulin, iron, irradiation, modified release active ingredients, laminin, living cells, liposomes, lipoproteins, magnesium, magnesium alloys, materials enabling solidification of polymer (curing) in air, materials enabling solidification of polymer (curing) at elevated or low temperature, materials enabling solidification of polymer (curing) by radiation, materials enabling solidification of polymer (curing) by light, materials enabling solidification of polymer (curing) by laser, materials enabling solidification of polymer (curing) by moisture, metal alloys, minerals, nano tubes, nano wires, multi-wall nano tubes, nitrides, oxides, particles, peptides, pharmaceuticals, photo initiators, photo catalysts, parylene, polycaprolactone (PCL), poly (DL-Lactide), polydioxanone, polyethylene oxide, polyethylene glycol, poly vinyl alcohol, polyacrylamide, polyvinyl pyrrolidone, polyvinylamine, polysaccharides, powders, phosphates, polypeptides, proteins, genetic material, modified genetic material, nucleic acid, fillers, radiopaque materials, radiation, reactant materials, reinforcement materials, ribbons, salicylic acid, smooth muscle cells, strengthening materials, sodium, silica, silver, silicon, starch, sulfates, surfactants, tissue, pigments, locating or marking materials, iodine, virus, vitronectin, wax or combinations thereof.

15. The prosthesis of claim 1 includes one or more active ingredients or encapsulated active ingredients selected from the group of: agents that reduce vascular hyperplasia, anti-inflammatory agents, agents that inhibit smooth muscle cell proliferation, agents that modulate biological or chemical response, agents that promote endothelialization, agents for the treatment of malignant neoplasms, antimicrobials, antibiotics, bioactive materials, biological compounds, bio-catalysts, everolimus, heparin, limus-based drugs, immunosuppressive agents, phosphates, mTOR inhibitors, oncology drugs, paclitaxel, pimecrolimus, rapamycin derivatives, restenosis inhibiting drugs, sirolimus, sirolimus salicylate, tacrolimus, their analogs, derivatives, functional equivalents, and combinations thereof.

16. The prosthesis of claim 1 includes active ingredients delivered within the living body over a period of less than 10 years.

17. The prosthesis of claim 1 includes one or more layers of porous, non-porous, or porous and non-porous coatings of the same or different chemical composition having a position selected from the group of: partial or full coverage of external surfaces of said prosthesis; partial or full coverage between layers of said tubular-shaped layers; partial or full coverage of surfaces of active ingredients, partial or full coverage of surfaces of said fibril elements, partially or fully filling said void spaces, partial or full coverage of exterior of said intersections or said crossover points; or combinations thereof.

18. The prosthesis of claim 1 including a delivery of said prosthesis into the anatomical lumen using a catheter.

19. The prosthesis of claim 1 including one or more deformable additives of sufficient strength to overcome the natural viscoelastic properties of said degradable material wherein said prosthesis is securely crimped onto a balloon catheter from a larger size to a smaller size by deforming said deformable additives into a second size and shape and wherein said prosthesis is subsequently expanded from said smaller size to a second larger size by deforming said deformable additives into a third size and shape wherein an outer surface of said prosthesis is configured to be in secure position and in substantial alignment with an inner surface of the anatomical lumen without exerting a substantial chronic outward force other than what is required to substantially immobilize said prosthesis in anatomical lumen.

20. The prosthesis of claim 1 comprising said one or more degradable materials selected from the group of: bioabsorbable polymers, bioabsorbable materials, bioadsorbable materials, biodissolvable materials, biodegradable polymers, chitosan, degradable polycarbonates, hydrolysable materials, lactide-based polymers, polyethylene glycol, polylactic acid, polyglycolic acid, poly (L-lactide-co-glycolide), poly-DL-lactide (PDLLA), poly L-lactide (PLLA), polydiaoxanone, polycaprolactone (PCL), polyethersulfone (PES), degradable polycarboxylates, polyorthoesters, polyphosphoesters, polycarbonates, poly ether-esters, polyethylene oxide, polyphosphazenes, polyvinyl alcohol, hyaluronic acid, hydrolysable polyesters, natural polymers, polyanhydrides, poly-3-hydroxybutyrate, polyglycolide, poly glycolide:trimethylene, collagen, polyglycolide, poly lactide, poly L-lactide, high molecular weight polylactide, homopolymer of glycolic acid, polysaccharides, polymers containing enzymes, synthetic polymers, trimethylene carbonate, or combinations thereof.

21. The prosthesis of claim 1 including a tubular-shaped porous or non-porous, sheath comprised of biodegradable or non-biodegradable material partially or fully covering outer surface, inner surface, or inner and outer surfaces of said prosthesis.

22. The prosthesis of claim 1 including production by one or more manufacturing processes selected from the group of: extrusion; molding; casting; electrospinning; melt spinning; printing; encapsulation; sputtering; coating; spraying; plating; deposition; tumbling; stretching; deformation; heating; cooling; mixing; stirring; pressurization; chemical reaction; atomization; aerosolization; cutting; laser; surface treatment; fusion; evaporation; adhering; bonding; purification; thermal treatment; chemical bonding; dissolution; ablation; lamination, powder coating; sintering; electroplating; electrostatic coating; grafting; polymerization; co-polymerization; annealing; molecular orientation; wrapping; seaming; ultrasonics; welding; sewing; taping; calendaring; or combinations thereof.

23. The prosthesis of claim 1 includes a prosthesis-to-passageway coverage of less than 99%.

24. The prosthesis of claim 1 includes an application selected from the group of: treatment of any medical condition; treatment or repair of abdominal aortic aneurysms; treatment of aneurysms; delivery of drugs or therapeutic agents; angioplasty; tissue engineering (e.g. veins, arteries, organs); use with balloon expandable stent; autogenous grafts; auto grafts; bifurcated stents; bifurcated grafts; bioabsorbable grafts; bioabsorbable stents; treatment of biliary ducts; biliary stent; biliary graft; treatment of blood vessels; bowel stents; treatment of cancer; bypass grafts; treatment of cardiovascular disease; carotid artery stent; colon stent; colon grafts; coronary vascular stent; drug delivery stent; drug delivery graft; endovascular grafts; treatment of de novo lesions; treatment of diseases of the thoracic aorta; treatment of diseases of the superficial femoral artery; filters; esophageal stent; treatment of eustachian tube dysfunction; femoral-popliteal stent; gastric bypass; treatment of gastroepiploic artery; treatment of hemorrhoids; iliac stent; iliac grafts; treatment of bladder diseases; treatment of reproductive system; treatment of urinary tract; respiratory stent; treatment of injuries; thoracic artery graft; interventional devices; intestinal graft; intestinal stent; renal stent; renal graft; radiation delivery devices; tracheal stent; treatment of lesions; treatment of occluded passageways; reconstructive surgery; shunt; nasal graft; nasal stent; nerve repair; pancreatic stent; percutaneous coronary interventions; peripheral vascular stents and stent-grafts; treatment of popliteal aneurysms; scaffold; saphenous vein graft; sinus stent; sinus graft; tissue repair; stents; stent-grafts; tissue scaffolds; treatment of cancer in anatomical lumens; ureteral stenting; valves; vascular grafts; vascular stents; or combinations thereof.

25. The prosthesis of claim 1 includes one or more coatings including one or more therapeutic drugs.

26. The prosthesis of claim 1 includes a different or varying: fibril element length between intersections or cross over points wherein said fibril element length has a variation of less than about 25,000 microns; average fibril element thickness wherein said fibril element length has a variation of less than about 50 microns; average void size; said one or more degradable materials; or combinations thereof at different locations of said prosthesis.

27. The fibril elements of claim 1 are nonwoven.

28. The prosthesis of claim 1 wherein said tube wall thickness includes one or more slits.

29. The prosthesis of claim 1 includes one or more coatings having an erosion rate selected from the range of: less than one day; one to thirty days; greater than thirty days; or greater than forty-eight hours.

30. The fibril elements of claim 1 are woven.

31. The coating of claim 17 is hydrophobic, hydrophilic, or combination thereof.

* * * * *